US009938331B2

(12) United States Patent
Schellenberger et al.

(10) Patent No.: US 9,938,331 B2
(45) Date of Patent: Apr. 10, 2018

(54) BIOLOGICALLY ACTIVE PROTEINS HAVING INCREASED IN VIVO AND/OR IN VITRO STABILITY

(71) Applicant: Amunix Operating Inc., Mountain View, CA (US)

(72) Inventors: Volker Schellenberger, Palo Alto, CA (US); Willem P. Stemmer, Los Gatos, CA (US); Chia-Wei Wang, Santa Clara, CA (US); Michael D. Scholle, Mountain View, CA (US); Nathaniel C. Gordon, Campbell, CA (US); Andreas Crameri, Los Altos Hills, CA (US); Mikhail Popkov, San Diego, CA (US)

(73) Assignee: Amunix Operating Inc., Mountain View, CA (US)

( * ) Notice: Subject to any disclaimer, the term of this patent is extended or adjusted under 35 U.S.C. 154(b) by 0 days.

(21) Appl. No.: 14/970,723

(22) Filed: Dec. 16, 2015

(65) Prior Publication Data

US 2016/0280753 A1    Sep. 29, 2016

Related U.S. Application Data

(63) Continuation of application No. 14/102,297, filed on Dec. 10, 2013, now abandoned, which is a continuation of application No. 13/439,738, filed on Apr. 4, 2012, now abandoned, which is a continuation of application No. 13/396,403, filed on Feb. 14, 2012, now abandoned, which is a continuation of application No. 12/634,556, filed on Dec. 9, 2009, now abandoned, which is a continuation of application No. 11/715,276, filed on Mar. 6, 2007, now Pat. No. 7,855,279, which is a continuation-in-part of application No. 11/528,950, filed on Sep. 27, 2006, now abandoned, and a continuation-in-part of application No. 11/528,927, filed on Sep. 27, 2006, now abandoned.

(60) Provisional application No. 60/743,622, filed on Mar. 21, 2006, provisional application No. 60/743,410, filed on Mar. 6, 2006, provisional application No. 60/721,270, filed on Sep. 27, 2005, provisional application No. 60/721,188, filed on Sep. 27, 2005.

(51) Int. Cl.
| | |
|---|---|
| C07K 1/00 | (2006.01) |
| A61K 38/24 | (2006.01) |
| C07K 14/00 | (2006.01) |
| C07K 14/56 | (2006.01) |
| C07K 7/06 | (2006.01) |
| C07K 7/08 | (2006.01) |
| C07K 14/415 | (2006.01) |
| C12N 15/10 | (2006.01) |
| G01N 33/68 | (2006.01) |
| C07K 14/47 | (2006.01) |
| C07K 14/53 | (2006.01) |
| C07K 14/61 | (2006.01) |
| C07K 14/535 | (2006.01) |
| A61K 38/00 | (2006.01) |

(52) U.S. Cl.
CPC ............ *C07K 14/56* (2013.01); *C07K 7/06* (2013.01); *C07K 7/08* (2013.01); *C07K 14/001* (2013.01); *C07K 14/415* (2013.01); *C07K 14/47* (2013.01); *C07K 14/53* (2013.01); *C07K 14/535* (2013.01); *C07K 14/61* (2013.01); *C12N 15/1044* (2013.01); *G01N 33/6845* (2013.01); *A61K 38/00* (2013.01); *C07K 2319/31* (2013.01); *C07K 2319/35* (2013.01)

(58) Field of Classification Search
None
See application file for complete search history.

(56) References Cited

U.S. PATENT DOCUMENTS

| | | | |
|---|---|---|---|
| 3,992,518 | A | 11/1976 | Chien et al. |
| 4,088,864 | A | 5/1978 | Theeuwes et al. |
| 4,200,984 | A | 5/1980 | Fink |
| 4,284,444 | A | 8/1981 | Bernstein et al. |
| 4,398,908 | A | 8/1983 | Siposs |
| 4,435,173 | A | 3/1984 | Siposs et al. |
| 4,542,025 | A | 9/1985 | Tice et al. |
| 4,599,311 | A | 7/1986 | Kawasaki |

(Continued)

FOREIGN PATENT DOCUMENTS

| | | |
|---|---|---|
| CN | 1761684 A | 4/2006 |
| CN | 1933855 A | 3/2007 |

(Continued)

OTHER PUBLICATIONS

Kangueane et al 2005. Bioinformation 1:21-24.*
About this file: EP1971355—Extract from the Register of European Patent dated Jul. 29, 2015. In Opposition against EP-B1 2402754 of Amunix.
Zhu, et al. Molecular cloning and sequencing of two 'short chain' and two 'long chain' K(+) channel-blocking peptides from the Chinese scorpion Buthus martensii Karsch. FEBS Lett 1999; 457:509-514.
Ackerman et al. Ion Channels —Basic Science and Clinical Disease. New Engl. J. Med.1997; 336:1575-1587.
Adams, et al. High affinity restricts the localization and tumor penetration of single-chain fv antibody molecules. Cancer Res. 2001; 61(12):4750-5.
Adams, et al. Increased affinity leads to improved selective tumor delivery of single-chain Fv antibodies. Cancer Res. 1998; 58(3):485-90.

(Continued)

*Primary Examiner* — Shulamith H Shafer
(74) *Attorney, Agent, or Firm* — Wilson Sonsini Goodrich & Rosati

(57) ABSTRACT

The present invention provides unstructured recombinant polymers (URPs) and proteins containing one or more of the URPs. The present invention also provides microproteins, toxins and other related proteinaceous entities, as well as genetic packages displaying these entities. The present invention also provides recombinant polypeptides including vectors encoding the subject proteinaceous entities, as well as host cells comprising the vectors. The subject compositions have a variety of utilities including a range of pharmaceutical applications.

13 Claims, 47 Drawing Sheets

(56) References Cited

U.S. PATENT DOCUMENTS

| | | |
|---|---|---|
| 4,684,479 A | 8/1987 | D'Arrigo |
| 4,713,339 A | 12/1987 | Levinson et al. |
| 4,757,006 A | 7/1988 | Toole, Jr. et al. |
| 4,845,075 A | 7/1989 | Murray et al. |
| 4,861,800 A | 8/1989 | Buyske |
| 4,870,008 A | 9/1989 | Brake |
| 4,882,279 A | 11/1989 | Cregg |
| 4,897,268 A | 1/1990 | Tice et al. |
| 4,931,373 A | 6/1990 | Kawasaki et al. |
| 4,933,185 A | 6/1990 | Wheatley et al. |
| 4,965,199 A | 10/1990 | Capon et al. |
| 4,976,696 A | 12/1990 | Sanderson et al. |
| 4,988,337 A | 1/1991 | Ito |
| 5,004,804 A | 4/1991 | Kuo et al. |
| 5,017,378 A | 5/1991 | Turner et al. |
| 5,037,743 A | 8/1991 | Welch et al. |
| 5,089,474 A | 2/1992 | Castro et al. |
| 5,112,950 A | 5/1992 | Meulien et al. |
| 5,171,844 A | 12/1992 | Van Ooyen et al. |
| 5,176,502 A | 1/1993 | Sanderson et al. |
| 5,186,938 A | 2/1993 | Sablotsky et al. |
| 5,198,349 A | 3/1993 | Kaufman |
| 5,215,680 A | 6/1993 | D'Arrigo |
| 5,223,409 A | 6/1993 | Ladner et al. |
| 5,250,421 A | 10/1993 | Kaufman et al. |
| 5,270,176 A | 12/1993 | Doerschug et al. |
| 5,298,022 A | 3/1994 | Bernardi |
| 5,318,540 A | 6/1994 | Athayde et al. |
| 5,364,934 A | 11/1994 | Drayna et al. |
| 5,407,609 A | 4/1995 | Tice et al. |
| 5,492,534 A | 2/1996 | Athayde et al. |
| 5,534,617 A | 7/1996 | Cunningham et al. |
| 5,543,502 A | 8/1996 | Nordfang et al. |
| 5,554,730 A | 9/1996 | Woiszwillo et al. |
| 5,573,776 A | 11/1996 | Harrison et al. |
| 5,576,291 A | 11/1996 | Curtis et al. |
| 5,578,709 A | 11/1996 | Woiszwillo |
| 5,599,907 A | 2/1997 | Anderson et al. |
| 5,610,278 A | 3/1997 | Nordfang et al. |
| 5,660,848 A | 8/1997 | Moo-Young |
| 5,756,115 A | 5/1998 | Moo-Young et al. |
| 5,789,379 A | 8/1998 | Drucker et al. |
| 5,833,911 A | 11/1998 | Llort et al. |
| 5,833,991 A | 11/1998 | Masucci |
| 5,874,104 A | 2/1999 | Adler-Moore et al. |
| 5,916,588 A | 6/1999 | Popescu et al. |
| 5,919,766 A | 7/1999 | Oesterberg et al. |
| 5,942,252 A | 8/1999 | Tice et al. |
| 5,965,156 A | 10/1999 | Proffitt et al. |
| 5,972,885 A | 10/1999 | Spira et al. |
| 5,981,719 A | 11/1999 | Woiszwillo et al. |
| 6,024,983 A | 2/2000 | Tice et al. |
| 6,043,094 A | 3/2000 | Martin et al. |
| 6,048,720 A | 4/2000 | Dalborg et al. |
| 6,056,973 A | 5/2000 | Allen et al. |
| 6,060,447 A | 5/2000 | Chapman et al. |
| 6,090,925 A | 7/2000 | Woiszwillo et al. |
| 6,110,498 A | 8/2000 | Rudnic et al. |
| 6,126,966 A | 10/2000 | Abra et al. |
| 6,183,770 B1 | 2/2001 | Muchin et al. |
| 6,251,632 B1 | 6/2001 | Lillicrap et al. |
| 6,254,573 B1 | 7/2001 | Haim et al. |
| 6,268,053 B1 | 7/2001 | Woiszwillo et al. |
| 6,284,276 B1 | 9/2001 | Rudnic et al. |
| 6,294,170 B1 | 9/2001 | Boone et al. |
| 6,294,191 B1 | 9/2001 | Meers et al. |
| 6,294,201 B1 | 9/2001 | Kettelhoit et al. |
| 6,303,148 B1 | 10/2001 | Hennink et al. |
| 6,309,370 B1 | 10/2001 | Haim et al. |
| 6,316,024 B1 | 11/2001 | Allen et al. |
| 6,316,226 B1 | 11/2001 | Van Ooyen et al. |
| 6,329,186 B1 | 12/2001 | Nielsen et al. |
| 6,346,513 B1 | 2/2002 | Van Ooyen et al. |
| 6,352,716 B1 | 3/2002 | Janoff et al. |
| 6,352,721 B1 | 3/2002 | Faour |
| 6,361,796 B1 | 3/2002 | Rudnic et al. |
| 6,395,302 B1 | 5/2002 | Hennink et al. |
| 6,406,632 B1 | 6/2002 | Safir et al. |
| 6,406,713 B1 | 6/2002 | Janoff et al. |
| 6,458,387 B1 | 10/2002 | Scott et al. |
| 6,458,563 B1 | 10/2002 | Lollar |
| 6,514,532 B2 | 2/2003 | Rudnic et al. |
| 6,517,859 B1 | 2/2003 | Tice et al. |
| 6,534,090 B2 | 3/2003 | Puthli et al. |
| 6,572,585 B2 | 6/2003 | Choi |
| 6,669,961 B2 | 12/2003 | Kim et al. |
| 6,713,086 B2 | 3/2004 | Qiu et al. |
| 6,715,485 B1 | 4/2004 | Djupesland |
| 6,733,753 B2 | 5/2004 | Boone et al. |
| 6,743,211 B1 | 6/2004 | Prausnitz et al. |
| 6,759,057 B1 | 7/2004 | Weiner et al. |
| 6,814,979 B2 | 11/2004 | Rudnic et al. |
| 6,818,439 B1 | 11/2004 | Jolly et al. |
| 6,838,093 B2 | 1/2005 | Burnside et al. |
| 6,890,918 B2 | 5/2005 | Burnside et al. |
| 6,905,688 B2 | 6/2005 | Rosen et al. |
| 6,919,311 B2 | 7/2005 | Lenting et al. |
| 6,945,952 B2 | 9/2005 | Kwon |
| 7,045,318 B2 | 5/2006 | Ballance |
| 7,294,513 B2 | 11/2007 | Wyatt |
| 7,413,537 B2 | 8/2008 | Ladner et al. |
| 7,442,778 B2 | 10/2008 | Gegg et al. |
| 7,452,967 B2 | 11/2008 | Bertin |
| 7,514,257 B2 | 4/2009 | Lee et al. |
| 7,528,242 B2 | 5/2009 | Anderson et al. |
| 7,560,107 B2 | 7/2009 | Lollar |
| 7,709,605 B2 * | 5/2010 | Knopf .................. A61K 9/2072 530/350 |
| 7,846,445 B2 | 12/2010 | Schellenberger et al. |
| 7,855,279 B2 | 12/2010 | Schellenberger et al. |
| 8,129,348 B2 * | 3/2012 | Besman .................. C07K 14/47 514/20.9 |
| 8,178,495 B2 | 5/2012 | Chilkoti |
| 8,492,530 B2 | 7/2013 | Schellenberger et al. |
| 8,557,961 B2 | 10/2013 | Silverman et al. |
| 8,673,860 B2 | 3/2014 | Schellenberger et al. |
| 8,680,050 B2 | 3/2014 | Schellenberger et al. |
| 8,703,717 B2 | 4/2014 | Schellenberger et al. |
| 8,716,448 B2 | 5/2014 | Schellenberger et al. |
| 8,957,021 B2 | 2/2015 | Schellenberger et al. |
| 9,168,312 B2 | 10/2015 | Schellenberger et al. |
| 9,249,211 B2 | 2/2016 | Schellenberger et al. |
| 9,371,369 B2 | 6/2016 | Schellenberger et al. |
| 2002/0042079 A1 | 4/2002 | Simon et al. |
| 2002/0150881 A1 | 10/2002 | Ladner et al. |
| 2003/0049689 A1 | 3/2003 | Edwards et al. |
| 2003/0143694 A1 | 7/2003 | Lustbader |
| 2003/0181381 A1 | 9/2003 | Himmelspach et al. |
| 2003/0190740 A1 | 10/2003 | Altman |
| 2004/0043446 A1 | 3/2004 | Defrees et al. |
| 2004/0106118 A1 | 6/2004 | Kolmar et al. |
| 2004/0142870 A1 | 7/2004 | Finn |
| 2004/0234609 A1 | 11/2004 | Collier et al. |
| 2004/0259780 A1 | 12/2004 | Glasebrook et al. |
| 2005/0032081 A1 | 2/2005 | Ju et al. |
| 2005/0042721 A1 | 2/2005 | Fang et al. |
| 2005/0048512 A1 | 3/2005 | Kolkman et al. |
| 2005/0118136 A1 | 6/2005 | Leung et al. |
| 2005/0123997 A1 | 6/2005 | Lollar |
| 2005/0260605 A1 | 11/2005 | Punnonen et al. |
| 2005/0287153 A1 | 12/2005 | Dennis |
| 2006/0026719 A1 | 2/2006 | Kieliszewski et al. |
| 2006/0040856 A1 | 2/2006 | DeFrees et al. |
| 2006/0084113 A1 | 4/2006 | Ladner et al. |
| 2006/0122376 A1 | 6/2006 | Chapman et al. |
| 2006/0211621 A1 | 9/2006 | Knudsen et al. |
| 2006/0287220 A1 | 12/2006 | Li et al. |
| 2006/0293232 A1 | 12/2006 | Levy et al. |
| 2007/0048282 A1 | 3/2007 | Rosen et al. |
| 2007/0161087 A1 | 7/2007 | Glaesner et al. |
| 2007/0191272 A1 | 8/2007 | Stemmer et al. |
| 2007/0203058 A1 | 8/2007 | Lau et al. |
| 2007/0212703 A1 | 9/2007 | Stemmer et al. |
| 2007/0244301 A1 | 10/2007 | Siekmann et al. |

(56) References Cited

U.S. PATENT DOCUMENTS

| | | |
|---|---|---|
| 2008/0039341 A1 | 2/2008 | Schellenberger et al. |
| 2008/0167238 A1 | 7/2008 | Rosen et al. |
| 2008/0176288 A1 | 7/2008 | Leung et al. |
| 2008/0227691 A1 | 9/2008 | Ostergaard et al. |
| 2008/0286808 A1 | 11/2008 | Schellenberger et al. |
| 2008/0312157 A1 | 12/2008 | Levy et al. |
| 2009/0060862 A1 | 3/2009 | Chang et al. |
| 2009/0092582 A1 | 4/2009 | Bogin et al. |
| 2009/0099031 A1 | 4/2009 | Stemmer et al. |
| 2009/0169553 A1 | 7/2009 | Day |
| 2009/0239795 A1 | 9/2009 | Ballance et al. |
| 2009/0280056 A1 | 11/2009 | Dennis et al. |
| 2010/0081615 A1 | 4/2010 | Pan et al. |
| 2010/0189682 A1 | 7/2010 | Schellenberger et al. |
| 2010/0239554 A1 | 9/2010 | Schellenberger et al. |
| 2010/0292130 A1 | 11/2010 | Skerra et al. |
| 2011/0142859 A1 | 6/2011 | Ebens, Jr. et al. |
| 2011/0151433 A1 | 6/2011 | Schellenberger et al. |
| 2012/0178691 A1 | 7/2012 | Schellenberger et al. |
| 2012/0220011 A1 | 8/2012 | Schellenberger et al. |
| 2012/0230947 A1 | 9/2012 | Schellenberger et al. |
| 2012/0263701 A1 | 10/2012 | Schellenberger et al. |
| 2012/0263703 A1 | 10/2012 | Schellenberger et al. |
| 2013/0017997 A1 | 1/2013 | Schellenberger et al. |
| 2013/0039884 A1 | 2/2013 | Bogin et al. |
| 2013/0137763 A1 | 5/2013 | Van Delft et al. |
| 2013/0165389 A1 | 6/2013 | Schellenberger et al. |
| 2013/0183280 A1 | 7/2013 | Oestergaard et al. |
| 2014/0162949 A1 | 6/2014 | Cleland et al. |
| 2014/0186327 A1 | 7/2014 | Schellenberger et al. |
| 2014/0301974 A1 | 10/2014 | Schellenberger et al. |
| 2014/0356326 A1 | 12/2014 | Schellenberger et al. |
| 2017/0037088 A1 | 2/2017 | Schellenberger et al. |
| 2017/0095567 A1 | 4/2017 | Schellenberger et al. |

FOREIGN PATENT DOCUMENTS

| | | |
|---|---|---|
| CN | 101190945 A | 6/2008 |
| DE | 257197 A1 | 6/1988 |
| EP | 0036776 A2 | 9/1981 |
| EP | 0036776 A3 | 10/1982 |
| EP | 0184438 A2 | 6/1986 |
| EP | 0238023 A2 | 9/1987 |
| EP | 0244234 A2 | 11/1987 |
| EP | 0184438 A3 | 1/1988 |
| EP | 0244234 A3 | 10/1988 |
| EP | 0295597 A2 | 12/1988 |
| EP | 0238023 A3 | 2/1989 |
| EP | 0295597 A3 | 5/1990 |
| EP | 0272277 B1 | 9/1993 |
| EP | 0556171 B1 | 8/2000 |
| JP | 2000502901 A | 3/2000 |
| RU | 2005133665 A | 6/2006 |
| WO | WO-8704187 A1 | 7/1987 |
| WO | WO-8800831 A1 | 2/1988 |
| WO | WO-8909051 A1 | 10/1989 |
| WO | WO-9210576 A1 | 6/1992 |
| WO | WO-9306844 A1 | 4/1993 |
| WO | WO-9711178 A1 | 3/1997 |
| WO | WO-9733552 A1 | 9/1997 |
| WO | WO-9822577 A1 | 5/1998 |
| WO | WO-9852976 A1 | 11/1998 |
| WO | WO-9941383 A1 | 8/1999 |
| WO | WO-9949901 A1 | 10/1999 |
| WO | WO-0003317 A1 | 1/2000 |
| WO | WO-02077036 A2 | 10/2002 |
| WO | WO-02079232 A2 | 10/2002 |
| WO | WO-02079232 A3 | 12/2002 |
| WO | WO-2005025499 A2 | 3/2005 |
| WO | WO-2005025499 A3 | 5/2005 |
| WO | WO-2005069845 A2 | 8/2005 |
| WO | WO-2006024953 A2 | 3/2006 |
| WO | WO-2006081249 A2 | 8/2006 |
| WO | WO-2006081249 A3 | 2/2007 |
| WO | WO-2007073486 A2 | 6/2007 |
| WO | WO-2007103455 A2 | 9/2007 |
| WO | WO-2007103515 A2 | 9/2007 |
| WO | WO-2007103455 A3 | 11/2007 |
| WO | WO-2008012629 A2 | 1/2008 |
| WO | WO-2008049711 A1 | 5/2008 |
| WO | WO-2008049931 A1 | 5/2008 |
| WO | WO-2008155134 A1 | 12/2008 |
| WO | WO-2009023270 A2 | 2/2009 |
| WO | WO-2010091122 A1 | 8/2010 |
| WO | WO-2010144502 A2 | 12/2010 |
| WO | WO-2010144508 A1 | 12/2010 |
| WO | WO-2011028228 A1 | 3/2011 |
| WO | WO-2011028229 A1 | 3/2011 |
| WO | WO-2011069164 A2 | 6/2011 |
| WO | WO-2011084808 A2 | 7/2011 |
| WO | WO-2011123813 A2 | 10/2011 |
| WO | WO-2011123830 A2 | 10/2011 |
| WO | WO-2012006623 A1 | 1/2012 |
| WO | WO-2012006624 A2 | 1/2012 |
| WO | WO-2012006633 A1 | 1/2012 |

OTHER PUBLICATIONS

Alam, et al. Expression and purification of a mutant human growth hormone that is resistant to proteolytic cleavage by thrombin, plasmin and human plasma in vitro. J Biotechnol. 1998; 65(2-3):183-90.

Altschul et al. Basic local alignment search tool. J Mol Biol215(3):403-410 (1990).

Alvarez, et al. Improving Protein Pharmacokinetics by Genetic Fusion to Simple Amino Acid Sequences. J Biol Chem. 2004; 279:3375-81.

Amin, et al. Construction of stabilized proteins by combinatorial consensus mutagenesis. Protein Eng Des Sel. 2004; 17:787-93.

Annex 1: Overview for purposes of the assessment of Art. 123(2) EPC/76(1) EPC; Notice of opposition dated Aug. 18, 2015 by XL-protein GmbH for EP2402754.

Annex 2: Chou Fasman (1974) and Tepitope analyses of prior art sequences; Notice of opposition dated Aug. 18, 2015 by XL-protein GmbH for EP2402754.

Antcheva, et al. Proteins of circularly permuted sequence present within the same organism: the major serine proteinase inhibitor from Capsicum annuum seeds. Protein Sci. 2001; 10:2280-90.

Appendix 1. In Biopharmaceuticals Biochemistry and Biotechnology. Second Edition. Gary Walsh, ed. Wiley. 1998.

Araki, et al. Four disulfide bonds' allocation of Na+, K(+)-ATPase inhibitor (SPAI). Biochemical and biophysical research communications. 1990. 172(1):42-46. (Abstract Only).

Arap, et al. Steps toward mapping the human vasculature by phage display. Nat Med. 2002; 8:121-7.

Arnau, et al. Current strategies for the use of affinity tags and tag removal for the purification of recombinant proteins. Protein Expr Purif. 2006; 48(1):1-13.

Arndt, et al. Factors influencing the dimer to monomer transition of an antibody single-chain Fv fragment. Biochemistry. 1998; 37(37):12918-26.

Assadi-Porter, et al. Sweetness determinant sites of brazzein, a small, heat-stable, sweet-tasting protein. Arch Biochem Biophys. 2000; 376:259-265.

Aster, et al. The Folding and Structural Integrity of the first LIN-12 Module of Human Notch1 are Calcium-Dependent. Biochemistry 1999; 38:4736-4742.

Ausubel, et al. eds. Current Protocols in Molecular Biology. Wiley. 1987.

Bailon, et al. Rational design of a potent, long-lasting form of interferon: a 40 kDa branched polyethylene glycol-conjugated interferon alpha-2a for the treatment of hepatitis C. Bioconjug Chem. Mar.-Apr. 2001;12(2):195-202.

Baneyx, et al. Recombinant protein folding and misfolding in *Escherichia coli*. Nat Biotechnol. 2004; 22(11):1399-408.

Baron, et al. From cloning to a commercial realization: human alpha interferon. Crit Rev Biotechnol. 1990; 10(3):179-90.

Barta, et al. Repeats with variations: accelerated evolution of the Pin2 family of proteinase inhibitors. Trends Genet. 2002; 18: 600-3.

(56) References Cited

OTHER PUBLICATIONS

Bateman, et al. Granulins: the structure and function of an emerging family of growth factors. J Endocrinol. 1998; 158: 145-151.
Beissinger, et al. How chaperones fold proteins. Biol Chem. 1998; 379(3):245-59.
Belew, et al. Purification of recombinant human granulocyte-macrophage colony-stimulating factor from the inclusion bodies produced by transformed *Escherichia coli* cells. J Chromatogr A. 1994; 679(1):67-83.
Bensch et al. hBD-1: a novel beta-defensin from human plasma. FEBS Lett 1995; 368:331-335.
Berger, et al. Phoenix mutagenesis: one-step reassembly of multiply cleaved plasmids with mixtures of mutant and wild-type fragments. Anal Biochem. 1993; 214: 571-9.
Beste, et al. Small antibody-like proteins with prescribed ligand specificities derived from the lipocalin fold. Proc Natl Acad Sci U S A. 1999; 96: 1898-1903.
Binz, et al. Engineering novel binding proteins from nonimmunoglobulin domains. Nature Biotechnology 2005; 23:1257-68.
Bird, et al. Single-chain antigen-binding proteins. Science. 1988; 242(4877):423-6.
Bittner, et al. Recombinant human erythropoietin (rhEPO) loaded poly(lactide-co-glycolide) microspheres: influence of the encapsulation technique and polymer purity on microsphere characteristics. Eur J Pharm Biopharm. 1998; 45(3):295-305.
Blanchette, et al. Principles of transmucosal delivery of therapeutic agents, Biomedicine & Pharmacotherapy. 2004; 58:142-152.
Bloch, Jr., et al. H NMR structure of an antifungal gamma-thionin protein SI alpha 1: Similarity to scorpion toxins. Proteins. 1998; 32:334-49.
Bodenmuller, et al. The Neuropeptide Head Activator Loses Its Biological Acitivity by Dimerization. EMBO J. Aug. 1986; 5(8):1825-1829.
Boder, et al. Directed evolution of antibody fragments with monovalent femtomolar antigen-binding affinity. Proc Natl Acad Sci U S A. 2000; 97(20):10701-5.
Brooks, et al. Evolution of amino acid frequencies in proteins over deep time: inferred order of introduction of amino acids into the genetic code. Mol Biol Evol. 2002; 19, 1645-1655.
Buchner. Supervising the fold: functional principles of molecular chaperones. FASEB J. 1996; 10(1):10-19.
Bulaj, et al. Efficient oxidative folding of conotoxins and the radiation of venomous cone snails. Proc Natl Acad Sci U S A. 2003; 100 Suppl 2:14562-8.
Buscaglia, et al. Tandem amino acid repeats from Trypanosoma cruzi shed antigens increase the half-life of proteins in blood. Blood. Mar. 15, 1999;93(6):2025-32.
Calabrese, et al. Crystal Structure of Phenylalanine Ammonia Lyase: Multiple Helix Dipoles Implicated in Catalysis. Biochemistry. 2004; 43: 11403-16.
Calvete, et al. Disulfide-bond pattern and molecular modelling of the dimeric disintegrin EMF-10, a potent and selective integrin alpha5beta1 antagonist from Eristocophis macmahoni venom. Biochem J. Feb. 1, 2000;345 Pt 3:573-81.
Calvete, et al. Snake venom disintegrins: Evolution of structure and function. Toxicon 2005; 45:1063-1074.
Calvete, et al. Snake venom disintegrins: Novel dimeric disintegrins and structural diversification by disulfphide bond engineering. Biochem J. 2003; 372:725-734.
Campbell, et al. Ed. Chapter 5: The structure and function of large biological molecules, p. 81. In Biology. Pearson; 7th edition (Dec. 23, 2004).
Campbell, et al. Ed. Chapter 5: The structure and function of large biological molecules, p. 81. In Biology. Pearson; 8th edition (Dec. 7, 2007).
Cao, et al. Development of a compact anti-BAFF antibody in *Escherichia coli*. Appl Microbiol Biotechnol. 2006; 73(1):151-7.
Carr, et al. Solution structure of a trefoil-motif-containing cell growth factor, porcine spasmolytic protein. PNAS 1994; 91:2206-2210.

Castor, et al. Septic cutaneous lesions caused by *Mycobacterium malmoense* in a patient with hairy cell leukemia. Eur. J. Clin. Microbiol. Infect. Dis. 1994; 13(2):145-148.
Chen, et al. Crystal structure of a bovine neurophysin II dipeptide complex at 2.8 A determined from the single-wavelength anomalous scattering signal of an incorporated iodine atom. Proc Natl Acad Sci U S A. 1991; 88: 4240-4.
Chen, et al. Expression, purification, and in vitro refolding of a humanized single-chain Fv antibody against human CTLA4 (CD152). Protein Expr Purif. 2006; 46(2):495-502.
Chen, et al. Site-directed mutations in a highly conserved region of Bacillus thuringiensis delta-endotoxin affect inhibition of short circuit current across Bombyx mori midguts. Proc Natl Acad Sci U S A. 1993; 90(19):9041-5.
Chirino, et al. Minimizing the immunogenicity of protein therapeutics. Drug Discovery Today. 2004; 9:82-90.
Chong, et al. Determination of Disulfide Bond Assignments and N-Glycosylation Sites of the Human Gastrointestinal Carcinoma Antigen GA733-2 (CO17-1A, EGP, KS1-4, KSA, and Ep-CAM). J. Biol. Chem. 2001; 276:5804-5813.
Chong, et al. Disulfide Bond Assignments of Secreted Frizzled-related Protein-1 Provide Insights about Frizzled Homology and Netrin Modules. J. Biol. Chem. 2002; 277:5134-5144.
Chou, et al. Conformational parameters for amino acids in helical, β-sheet, and random coil regions calculated from proteins. Biochemistry 13.2 (1974): 211-222.
Chou, et al. Empirical predictions of protein conformation. Annual review of biochemistry 47.1 (1978): 251-276.
Chou, et al. Prediction of Protein Conformation. Biochemistry. 1974; 13: 222-245.
Chou, et al. Prediction of the secondary structure of proteins from their amino acid sequence. Adv Enzymol Relat Areas Mol Biol. 1978;47:45-148.
Chou; et al., "Prediction of the Secondary Structure of Proteins from Their Amino Acid Sequence, from Advances in Enzymology vol. 47, John Wiley and Sons. Published 1978, p. 60.".
Chou-Fasman values for random 200mer sequences composed of the amino acids GADSTEP; Reply to notice of opposition dated Apr. 8, 2016 for EP2402754.
Chowdhury, et al. Improving antibody affinity by mimicking somatic hypermutation in vitro. Nat Biotechnol. 1999; 17(6):568-72.
Christmann, et al. The cystine knot of a squash-type protease inhibitor as a structural scaffold for *Escherichia coli* cell surface display of conformationally constrained peptides. Protein Eng. 1999; 12:797-806.
Clark, et al. Long-acting growth hormones produced by conjugation with polyethylene glycol. J Biol Chem. 1996; 271(36):21969-77.
Clark, et al. Recombinant human growth hormone (GH)-binding protein enhances the growth-promoting activity of human GH in the rat. Endocrinology. 1996; 137(10):4308-15.
Cleland, et al. Emerging protein delivery methods. Current Opinion in Biotechnology. 2001; 12:212-219.
Coia, et al. Use of mutator cells as a means for increasing production levels of a recombinant antibody directed against Hepatitis B. Gene. 1997; 201: 203-9.
Collen, et al. Polyethylene Glycol-Derivatized Cysteine-Substitution Variants of Recombinant Staphylokinase for Single-Bolus Treatment of Acute Myocardial Infarction. Circulation. 2000; 102: 1766-72.
Composition and properties of some URPs according to the invention; Reply to notice of opposition dated Apr. 8, 2016 for EP2402754.
Conticello, et al. Mechanisms for evolving hypervariability: the case of conopeptides. Mol. Biol. Evol. 2001; 18:120-131.
Corisdeo, et al. Functional expression and display of an antibody Fab fragment in *Escherichia coli*: study of vector designs and culture conditions. Protein Expr Purif. 2004; 34(2):270-9.
Corrected version of "Exhibit 1" (D23) without cut and paste error; Reply to notice of opposition dated Apr. 8, 2016 for EP2402754.
Craik, et al. Plant cyclotides: A unique family of cyclic and knotted proteins that defines the cyclic cystine knot structural motif. J Mol Biol. 1999; 294: 1327-1336.

(56) References Cited

OTHER PUBLICATIONS

Crameri, et al. Improved Green Fluorescent Protein by Molecular Evolution Using DNA Shuffling. Nature Biotechnology. 1996; 14: 315-319.
Cull, et al. Screening for receptor ligands using large libraries of peptides linked to the C terminus of the lac repressor. Proc. Natl. Acad. Sci. USA. 1992; 89: 1865-1869.
Daley, et al. Structure and dynamics of a beta-helical antifreeze protein. Biochemistry. 2002; 41: 5515-25.
Daniel et al. Screening for potassium channel modulators by a high through-put 86-rubidium efflux assay in a 96-well microtiter plate. J. Pharmacol. Meth. 1991; 25:185-193.
Danner, et al. T7 phage display: a novel genetic selection system for cloning RNA-binding proteins from cDNA libraries. Proc Natl Acad Sci U S A. 2001; 98: 12954-9.
D'Aquino, et al. The magnitude of the backbone conformational entropy change in protein folding. Proteins. 1996; 25: 143-56.
Dattani, et al. An investigation into the lability of the bioactivity of human growth hormone using the ESTA bioassay. Horm Res. 1996; 46(2):64-73.
Dauplais, et al. On the convergent evolution of animal toxins. Conservation of a diad of functional residues in potassium channel-blocking toxins with unrelated structures. J Biol Chem. 1997; 272: 4302-9.
De, et al. Crystal Structure of a disulfide-linked "trefoil" motif found in a large family of putative growth factors. PNAS 1994; 91:1084-1088.
De Kruif, et al. Selection and application of human single chain Fv antibody fragments from a semi-synthetic phage antibody display library with designed CDR3 regions. J Mol Biol. 1995; 248: 97-105.
De Rosa, et al. Influence of the co-encapsulation of different non-ionic surfactants on the properties of PLGA insulin-loaded microspheres. J Control Release. 2000; 69(2):283-95.
Deckert, et al. Pharmacokinetics and microdistribution of polyethylene glycol-modified humanized A33 antibody targeting colon cancer xenografts. Int J Cancer. 2000; 87: 382-90.
Der Maur, et al. Direct in vivo screening of intrabody libraries constructed on a highly stable single-chain framework. J Biol Chem. 2002; 277(47):45075-85.
Desplancq, et al. Multimerization behaviour of single chain Fv variants for the tumour-binding antibody B72.3. Protein Eng. 1994; 7(8):1027-33.
Devlin, Thomas M. Ed. Textbook of Biochemistry with Clinical Correlations. Sixth Edition. 2006. p. 92.
Dhalluin, et al. Structural and biophysical characterization of the 40 kDa PEG-interferon-alpha2a and its individual positional isomers. Bioconjug Chem. 2005; 16: 504-17.
Di Lullo, et al. Mapping the ligand-binding sites and disease-associated mutations on the most abundant protein in the human, type I collagen. J Biol Chem. 2002; 277(6):4223-31.
Dietrich, et al. ; ABC of oral bioavailability: transporters as gate-keepers in the gut. Gut. 2005; 52:1788-1795.
Dolezal, et al. ScFv multimers of the anti-neuraminidase antibody NC10: shortening of the linker in single-chain Fv fragment assembled in V(L) to V(H) orientation drives the formation of dimers, trimers, tetramers and higher molecular mass multimers. Protein Eng. 2000; 13(8):565-74.
Dooley, et al. Stabilization of antibody fragments in adverse environments. Biotechnol Appl Biochem. 1998; 28 ( Pt 1):77-83.
Doyle, et al. Crystal structures of a complexed and peptide-free membrane protein-binding domain: molecular basis of peptide recognition by PDZ. Cell. Jun. 28, 1996;85(7):1067-76.
Dufton. Classification of elapid snake neurotoxins and cytotoxins according to chain length: evolutionary implications. J. Mol. Evol. 1984; 20:128-134.
Dumoulin, et al. Single-domain antibody fragments with high conformational stability. Protein Sci. 2002; 11(3):500-15.

Dutton, et al. A New Level of Conotoxin Diversity, a Non-native Disulfide Bond Connectivity in -Conotoxin AulB Reduces Structural Definition but Increases Biological Activity. J. Biol Chem. 2002; 277: 48849-48857.
Dyson, et al. Production of soluble mammalian proteins in *Escherichia coli*: identification of protein features that correlate with successful expression. BMC Biotechnol. 2004; 4:32.
Ellis, et al. Valid and invalid implementations of GOR secondary structure predictions. Comput Appl Biosci. Jun. 1994;10(3):341-8.
European search report dated Feb. 4, 2010 for Application No. 6804210.
European search report dated Mar. 26, 2009 for Application No. 7752636.6.
European search report dated Mar. 5, 2009 for Application No. 7752549.1.
Evidence that length of URP according to the invention correlates with serum half-life improvement, and that results can be allometrically scaled; Reply to notice of opposition dated Apr. 8, 2016 for EP2402754.
Fajloun, et al. Maurotoxin Versus Pi1/HsTx1 Scorpion Toxins. Toward New Insights in the Understanding of Their Distinct Disulfide Bridge Patterns J. Biol. Chem. 2000; 275:39394-402.
Felici, et al. Selection of antibody ligands from a large library of oligopeptides expressed on a multivalent exposition vector. J Mol Biol. 1991; 222: 301-310.
Fisher, et al. Genetic selection for protein solubility enabled by the folding quatliy control feature of the twin-arginin translocation pathway. Protein Sci. Mar. 2006;15(3):449-58.
Fitzgerald, et al. Interchangeability of Caenorhabditis elegans DSL proteins and intrinsic signalling activity of their extracellular domains in vivo Development. 1995; 121:4275-82.
Fonar, et al. NMR structure of the water soluble Aβ17-34 peptide. Bioscience reports 34.6 (2014): e00155.
Franz, et al. Percutaneous absorption on the relevance of in vitro data. J Invest Dermatol. 1975; 64(3):190-5.
Frenal, et al. Exploring structural features of the interaction between the scorpion toxinCnErg1 and ERG K+ channels. Proteins. 2004; 56:367-375.
Freshney, R.I. Culture of Animal Cells. Second Edition. Alan R. Liss, Inc. 1987.
Gamez, et al. Development of pegylated forms of recombinant Rhodosporidium toruloides phenylalanine ammonia-lyase for the treatment of classical phenylketonuria. Mol Ther. 2005; 11: 986-9.
Geething, et al. Gcg-XTEN: an improved glucagon capable of preventing hypoglycemia without increasing baseline blood glucose. PLoS One. Apr. 14, 2010;5(4):e10175. doi: 10.1371/journal.pone.0010175.
Gilkes, et al. Domains in microbial beta-1, 4-glycanases: sequence conservation, function, and enzyme families. Microbiol Rev. 1991; 55: 303-15.
Gomez-Duarte, et al. Expression of fragment C of tetanus toxin fused to a carboxyl-terminal fragment of diphtheria toxin in *Salmonella typhi* CVD 908 vaccine strain. Vaccine. 1995; 13(16):1596-602.
Graff, et al. Theoretical analysis of antibody targeting of tumor spheroids: importance of dosage for penetration, and affinity for retention. Cancer Res. 2003; 63(6):1288-96.
Gray, et al. Peptide Toxins From Venomous Conus Snails. Annu Rev Biochem 1988; 57:665-700.
Greenbaum, et al. Functional classification of class II human leukocyte antigen (HLA) molecules reveals seven different supertypes and a surprising degree of repertoire sharing across supertypes. Immunogenetics 63.6 (2011): 325-335.
Greenwald, et al. Effective drug delivery by PEGylated drug conjugates. Adv Drug Deliv Rev. 2003; 55: 217-50.
Guncar, et al. Crystal structure of MHC class II-associated p41 Ii fragment bound to cathepsin L reveals the structural basis for differentiation between cathepsins L and S EMBO J 1999; 18:793-803.
Guo, et al. Crystal Structure of the Cysteine-rich Secretory Protein Stecrisp Reveals That the Cysteine-rich Domain Has a K+ Channel Inhibitor-like Fold. J Biol Chem. 2005; 280: 12405-12.

(56) References Cited

OTHER PUBLICATIONS

Gupta, et al. A classification of disulfide patterns and its relationship to protein structure and function. Protein Sci. 2004; 13: 2045-2058.
Gustafsson, et al. Codon bias and heterologous protein expression. Trends Biotechnol. Jul. 2004;22(7):346-53.
Hamers-Casterman, et al. Naturally occurring antibodies devoid of light chains. Nature. 1993; 363(6428):446-8.
Hammer. New methods to predict MHC-binding sequences within protein antigens. Curr Opin Immunol 1995; 7: 263-9.
Harlow, et al. Antibodies: a Laboratory Manual. Cold Spring Harbor Laboratory, Cold Spring Harbor, NY. 1988.
Harris, et al. Effect of pegylation on pharmaceuticals. Nat Rev Drug Discov. 2003; 2: 214-21.
Henninghausen, et al. Mouse whey acidic protein is a novel member of the family of 'four-disulfide core' proteins. Nucleic Acids Res. 1982; 10:2677-2684.
Hermeling, et al. Structure-immunogenicty relationships of therapeutic proteins. Pharm. Res. 2004; 21: 897-903.
Higgins, et al. Polyclonal and clonal analysis of human CD4+ T-lymphocyte responses to nut extracts. J. Immunol. 1995; 155:5777-85.
Hill, et al. Conotoxin TVIIA, a novel peptide from the venom of Conus tulipa 1. Isolation, characterization and chemical synthesis. Eur J Biochem. 2000; 267: 4642-8.
Hinds, et al. PEGylated insulin in PLGA microparticles. In vivo and in vitro analysis. J Control Release. Jun. 2, 2005;104(3):447-60.
Hirel, et al. Extent of N-terminal methionine excision from *Escherichia coli* proteins is governed by the side-chain length of the penultimate amino acid. Proc Natl Acad Sci U S A. 1989; 86(21):8247-51.
Hogg. Dislfide Bonds as Switches for Protein Function. Trends Biochem Sci, 2003; 28: 210-4.
Holevinsky et al. ATP-sensitive K+ channel opener acts as a potent Cl-channel inhibitor in vascular smooth muscle cells. J. Membrane Biology. 1994; 137:59-70.
Hopp, et al. Prediction of protein antigenic determinants from amino acid sequences. Proc Natl Acad Sci U S A 1981; 78, 3824-3828, #3232.
Hsu, et al. Vaccination against gonadotropin-releasing hormone (GnRH) using toxin receptor-binding domain-conjugated GnRH repeats. Cancer Res. Jul. 15, 2000;60(14):3701-5.
Hudson, et al. High avidity scFv multimers; diabodies and triabodies. J Immunol Methods. 1999; 231(1-2):177-89.
Hugli. Structure and function of C3a anaphylatoxin. Curr Topics Microbiol Immunol. 1990; 153:181-208.
Huston, et al. Protein engineering of antibody binding sites: recovery of specific activity in an anti-digoxin single-chain Fv analogue produced in *Escherichia coli*. Proc Natl Acad Sci U S A. 1988; 85(16):5879-83.
IEDB Analysis Resource; MHC-II Binding Prediction Results. Available at http://tools.immuneepitope.org/mhcii/result. Accessed Jul. 13, 2015: 10:34.
IEDB Analysis Resource; MHC-II Binding Prediction Results. Available at http://tools.immuneepitope.org/mhcii/result. Accessed Jul. 13, 2015: 10:51.
IEDB Analysis Resource; MHC-II Binding Prediction Results. Available at http://tools.immuneepitope.org/mhcii/result. Accessed Jul. 13, 2015: 14:17.
IEDB Analysis Resource; MHC-II Binding Prediction Results. Available at http://tools.immuneepitope.org/mhcii/result. Accessed Jul. 13, 2015: 15:45.
IEDB Analysis Resource; MHC-II Binding Prediction Results. Available at http://tools.immuneepitope.org/mhcii/result. Accessed Jul. 16, 2015: 11:03.
IEDB Analysis Resource; MHC-II Binding Prediction Results. Available at http://tools.immuneepitope.org/mhcii/result. Accessed Aug. 28, 2015.
International search report and written opinion dated Dec. 20, 2010 for PCT Application No. US10/02147.
International search report dated Jul. 12, 2011 for PCT Application No. US10/61590.
International search report dated Jan. 17, 2008 for PCT Application No. US2006/37713.
International search report dated Dec. 26, 2007 for PCT Application No. US2007/05952.
International search report dated Mar. 16, 2009 for PCT Application No. US2008/09787.
International search report dated Apr. 20, 2010 for PCT Application No. US10/23106.
International search report dated Sep. 26, 2007 for PCT Application No. US2007/05857.
IUPAC-IUB Commission on biochemical Nomenclature (CBN)—Abbreviations and Symbols for the Description of the Conformation of Polypeptide Chains. Tentative Rules (1969): 4. Side Chains.
Iwasaki, et al. Solution structure of midkine, a new heparin-binding growth factor. Embo J. 1997; 16: 6936-6946.
Jackson, et al. The characterization of paclitaxel-loaded microspheres manufactured from blends of poly(lactic-co-glycolic acid) (PLGA) and low molecular weight diblock copolymers. Int J Pharm. Sep. 5, 2007;342(1-2):6-17.
Johansson, et al. Modifications increasing the efficacy of recombinant vaccines; marked increase in antibody titers with moderately repetitive variants of a therapeutic allergy vaccine. Vaccine. 2007; 25(9):1676-82.
Jonassen, et al. Finding flexible patterns in unaligned protein sequences. Protein Sci 1995; 4:1587-1595.
Jones, et al. Determination of Tumor Necrosis Factor Binding Protein Disulfide Structure: Deviation of the Fourth Domain Structure from the TNFR/NGFR Family Cysteine-Rich Region Signature Biochemistry. 1997; 36: 14914-23.
Jones, et al. Replacing the complementarity-determining regions in a human antibody with those from a mouse. Nature. 1986; 321(6069):522-5.
Jonsson, et al. Quantitative sequence-activity models (QSAM)—tools for sequence design. Nucleic Acids Res. 1993; 21: 733-9.
Jung, et al. Improving in vivo folding and stability of a single-chain Fv antibody fragment by loop grafting. Protein Eng. 1997; 10(8):959-66.
Kamikubo, et al. Disulfide bonding arrangements in active forms of the somatomedin B domain of human vitronectin. Biochemistry. 2004; 43: 6519-6534.
Kay, et al. An M13 phage library displaying random 38-amino-acid peptides as a source of novel sequences with affinity to selected targets. Gene. 1993; 128: 59-65.
Kelly, et al. Isolation of a Colon Tumor Specific Binding Peptide Using Phage Display Selection Neoplasia, 2003; 5: 437-44.
Khan, et al. Solubilization of recombinant ovine growth hormone with retention of native-like secondary structure and its refolding from the inclusion bodies of *Escherichia coli*. Biotechnol Prog. 1998; 14(5):722-8.
Kim, et al. Three-dimensional Solution Structure of the Calcium Channel Antagonist ω-Agatoxin IVA: Consensus Molecular Folding of Calcium Channel Blockers. J. Mol. Biol.1995; 250:659-671.
Kimble, et al. The LIN12/Notch signaling pathway and its regulation. Annu Rev Cell Dev Biol 1997; 13:333-361.
Kissel, et al. ABA-triblock copolymers from biodegradable polyester A-blocks and hydrophilic poly(ethylene oxide) B-blocks as a candidate for in situ forming hydrogel delivery systems for proteins. Adv Drug Deliv Rev. 2002; 54(1):99-134.
Kochendoerfer. Chemical and biological properties of polymer-modified proteins. Expert Opin Biol Ther. 2003; 3: 1253-61.
Kohn, et al. Random-coil behavior and the dimensions of chemically unfolded proteins. Proc Natl Acad Sci U S A. Aug. 24, 2004;101(34):12491-6.
Koide, et al. The fibronectin type III domain as a scaffold for novel binding proteins. J Mol Biol. 1998; 284: 1141-51.
Kornblatt, et al. Cross-linking of cytochrome oxidase subunits with difluorodinitrobenzene. Can J Biochem. 1980; 58: 219-224.
Kortt, et al. Single-chain Fv fragments of anti-neuraminidase antibody NC10 containing five- and ten-residue linkers form dimers and with zero-residue linker a trimer. Protein Eng. 1997; 10(4):423-33.

(56) References Cited

OTHER PUBLICATIONS

Kou, et al. Preparation and characterization of recombinant protein ScFv(CD11c)-TRP2 for tumor therapy from inclusion bodies in *Escherichia coli*. Protein Expr Purif. 2007; 52(1):131-8.

Kratzner, et al. Structure of Ecballium elaterium trypsin inhibitor II (EETI-II): a rigid molecular scaffold. Acta Crystallogr D Biol Crystallogr. Sep. 2005;61(Pt 9):1255-62.

Kristensen, et al. Proteolytic selection for protein folding using filamentous bacteriophages. Fold Des. 1998; 3: 321-8.

Kubetzko, et al. Protein PEGylation decreases observed target association rates via a dual blocking mechanism. Mol Pharmacol. 2005; 68: 1439-54.

Kwon, et al. Biodegradable triblock copolymer microspheres based on thermosensitive sol-gel transition. Pharm Res. 2004; 21(2):339-43.

Kyngas, et al. Unreliability of the Chou-Fasman parameters in predicting protein secondary structure. Protein Eng. May 1998;11(5):345-8.

Lane, et al. Influence of post-emulsification drying processes on the microencapsulation of human serum albumin. Int J Pharm. 2006; 307(1):16-22.

Lapatto, et al. X-ray structure of antistasin at 1.9 Å resolution and its modelled complex with blood coagulation factor Xa. Embo J. 1997; 16: 5151-61.

Lauber, et al. Homologous Proteins with Different Folds: The Three-dimensional Structures of Domains 1 and 6 of the Multiple Kazal-type Inhibitor LEKTI. J. Mol. Biol. 2003; 328:205-219.

Le Gall, et al. Di-, tri- and tetrameric single chain Fv antibody fragments against human CD19: effect of valency on cell binding. FEBS Lett. 1999; 453(1-2):164-8.

Lee, et al. A recombinant human G-CSF/GM-CSF fusion protein from *E. coli* showing colony stimulating activity on human bone marrow cells. Biotechnol Lett. 2003; 25(3):205-11.

Lee, Vhl. Mucosal drug delivery. J Natl Cancer Inst Monogr. 2001; 29:41-44.

Lehninger, A. Chapter 6: Proteins: Three-dimensional conformation, pp. 130-131. In Biochemistry. Worth Publishers. 2nd Edition 1970.

Leong, et al. Adapting pharmacokinetic properties of a humanized anti-interleukin-8 antibody for therapeutic applications using site-specific pegylation. Cytokine. 2001; 16(3):106-19.

Leong, et al. Optimized expression and specific activity of IL-12 by directed molecular evolution. Proc. Natl. Acad. Sci. USA 2003; 100:1163-1168.

Leung, et al. A method for random mutagenesis of a defined DNA segment using a modified polymerase chain reaction. Technique. 1989; 1: 11-15.

Leung-Hagesteijn, et al. UNC-5, a transmembrane protein with immunoglobulin and thrombospondin type 1 domains, guides cell and pioneer axon migrations in C. elegans. Cell 1992; 71:289-99.

Levitt, M. A simplified representation of protein conformations for rapid simulation of protein folding. J Mol Biol. Jun. 14, 1976;104(1):59-107.

Levy, et al. Isolation of trans-acting genes that enhance soluble expression of scFv antibodies in the *E. coli* cytoplasm by lambda phage display. J Immunol Methods. 2007; 321(1-2):164-73.

Lin, et al. Metal-chelating affinity hydrogels for sustained protein release. J Biomed Mater Res A. 2007; 83(4):954-64.

Lirazan, et al. The Spasmodic Peptide Defines a New Conotoxin Superfamily. Biochemistry. 2000; 39: 1583-8.

Liu et al. The Human beta-Defensin-1 and alpha-Defensins Are Encoded by Adjacent Genes: Two Peptide Families with Differing Disulfide Topology Share a Common Ancestry. Genomics. 1997; 43:316-320.

Lowman, et al. Selecting high-affinity binding proteins by monovalent phage display. Biochemistry. 1991; 30: 10832-10838.

Maggio. Intravail™: highly effective intranasal delivery of peptide and protein drugs Expert Opinion in Drug Delivery 2006; 3: 529-539.

Maggio. A Renaissance in Peptide Therapeutics in Underway. Drug Delivery Reports. 2006; 23-26.

Maillere, et al. Immunogenicity of a disulphide-containing neurotoxin: presentation to T-cells requires a reduction step. Toxicon, 1995; 33(4): 475-482.

Maillere et al. Role of thiols in the presentation of a snake toxin to murine T cells. J. Immunol. 1993; 150, 5270-5280.

Marshall, et al. Enhancing the activity of a beta-helical antifreeze protein by the engineered addition of coils. Biochemistry, 2004; 43: 11637-11646.

Marshall, et al. Rational design and engineering of therapeutic proteins. Drug discovery today 8.5 (2003): 212-221.

Martin, et al. Rational design of a CD4 mimic that inhabits HIV-1 entry and exposes cryptic neutralization epitopes. Nat. Biotechnol. 2003; 21: 71-76.

Martineau, et al. Expression of an antibody fragment at high levels in the bacterial cytoplasm. J Mol Biol. 1998; 280(1):117-27.

Matthews, et al. Comparison of the predicted and observed secondary structure of T4 phage lysozyme. Biochimica et Biophysica Acta (BBA)—Protein Structure 405.2 (1975): 442-451.

McDonald, et al. Significance of blood vessel leakiness in cancer. Cancer Res. 2002; 62: 5381-5.

McNulty, et al. High-resolution NMR structure of the chemically-synthesized melanocortin receptor binding domain AGRP(87-132) of the Agouti-Related Protein. Biochemistry. 2001; 40: 15520-7.

McPherson, et al. eds. PCR 2: a practical approach. Oxford University Press. 1995.

Meier, et al. Determination of a high-precision NMR structure of the minicollagen cysteine rich domain from Hydra and characterization of its disulfide bond formation. FEBS Lett. 2004; 569: 112-6.

Menez, A. Immunology of snake toxins. In: Snake Toxins. A. L. Harvey (Ed). Pergamon Press, Inc. New York. 1991. (Table of contents only).

Miljanich. Ziconotide: neuronal calcium channel blocker for treating severe chronic pain. Curr. Med. Chem. 2004; 23: 3029.

Misenheimer, et al. Biophysical Characterization of the Signature Domains of Thrombospondin-4 and Thrombospondin-2. J. Biol. Chem. 2005; 280:41229-41235.

Misenheimer, et al. Disulfide Connectivity of Recombinant C-terminal Region of Human Thrombospondin 2 J. Biol. Chem. 2001; 276:45882-7.

Mitraki, et al. Protein Folding Intermediates and Inclusion Body Formation. Bio/Technology. 1989; 7:690-697.

Mogk, et al. Mechanisms of protein folding: molecular chaperones and their application in biotechnology. Chembiochem. Sep. 2, 2002;3(9):807-14.

Morgan, et al. The amino acid sequence of human chorionic gonadotropin. The alpha subunit and beta subunit. Journal of Biological Chemistry 250.13 (1975): 5247-5258.

Mrsny, et al. Bacterial toxins as tools for mucosal vaccination. Drug Discovery Today. 2002; 4:247-258.

Muller, O. Kayser, R. Ed. Pharmaceutical biotechnology. Drug Discovery and Clinical Applications. Wiley-VCH. 2004. pp. 114-116.

Murtuza, et al. Transplantation of skeletal myoblasts secreting an IL-1 inhibitor modulates adverse remodeling in infarcted murine myocardium. Proc Natl Acad Sci U S A. Mar. 23, 2004;101(12):4216-21.

Name of the sequences is 486. In CFSSP: Chou & Fasman Secondary Structure Prediction Server. Available at http://cho-fas.sourceforge.net/index.php. Accessed Jul. 13, 2015.

Name of the sequences is Gpp67. In CFSSP: Chou & Fasman Secondary Structure Prediction Server. Available at http://www.biogem.org/tool/chou-fasman. Accessed Aug. 28, 2015.

Name of the sequences is HRM. In CFSSP: Chou & Fasman Secondary Structure Prediction Server. Available at http://cho-fas.sourceforge.net/index.php. Accessed Jul. 13, 2015.

Name of the sequences is Randoml. In CFSSP: Chou & Fasman Secondary Structure Prediction Server. Available at http://cho-fas.sourceforge.net/index.php. Accessed Jul. 15, 2015.

Name of the sequences is Rndl. In CFSSP: Chou & Fasman Secondary Structure Prediction Server. Available at http://www.biogem.org/tool/chou-fasman. Accessed Aug. 26, 2015.

(56) References Cited

OTHER PUBLICATIONS

Name of the sequences is SAPA. In CFSSP: Chou & Fasman Secondary Structure Prediction Server. Available at http://cho-fas.sourceforge.net/index.php. Accessed Jul. 13, 2015.
Narmoneva, et al. Self-assembling short oligopeptides and the promotion of angiogenesis. Biomaterials. 2005; 26:4837-4846.
Nielsen, et al. Di-/Tri-peptide transporters as drug delivery targets: Regulation of transport under physiological and patho-physiological conditions. Current Drug Targets. 2003; 4:373-388.
Nielsen, et al. Solution Structure of μ-Conotoxin PIIIA, a Preferential Inhibitor of Persistent Tetrodotoxin-sensitive Sodium Channels. J. Biol. Chem 2002; 277: 27247-27255.
Nord, et al. Binding proteins selected from combinatorial libraries of an α-helical bacterial receptor domain. Nat Biotechnol, 1997; 15: 772-777.
O'Connell, et al. Phage versus phagemid libraries for generation of human monoclonal antibodies. J Mol Biol. 2002; 321: 49-56.
Office action dated Apr. 29, 2013 for U.S. Appl. No. 12/939,129.
Office action dated Jun. 6, 2012 for U.S. Appl. No. 12/939,129.
Ofir, et al. Versatile protein microarray based on carbohydrate-binding modules. Proteomics. 2005; 5(7):1806-14.
Okten, et al. Myosin VI walks hand-over-hand along actin. Nat Struct Mol Biol. 2004; 11(9):884-7.
O'Leary, et al. Solution Structure and Dynamics of a Prototypical Chordin-like Cysteine-rich Repeat (von Willebrand Factor Type C Module) from Collagen IIA. J Biol Chem. 2004; 279: 53857-66.
Oslo, ed. Remington's Pharmaceutical Sciences. 16th edition. 1980.
Padiolleau-Lefevre, et al. Expression and detection strategies for an scFv fragment retaining the same high affinity than Fab and whole antibody: Implications for therapeutic use in prion diseases. Mol Immunol. 2007; 44(8):1888-96.
Pallaghy, et al. A common structural motif incorporating a cystine knot and a triple-stranded beta-sheet in toxic and inhibitory polypeptides. Protein Sci 1994; 3:1833-1839.
Pallaghy, et al. Three-dimensional Structure in Solution of the Calcium Channel Blocker ω-Conotoxin. J Mol Biol 1993; 234:405-420.
Pan, et al. Structure and expression of fibulin-2, a novel extracellular matrix protein with multiple EGF-like repeats and consensus motifs for calcium binding. J. Cell. Biol. 1993; 123: 1269-127.
Panda. Bioprocessing of therapeutic proteins from the inclusion bodies of *Escherichia coli*. Adv Biochem Eng Biotechnol. 2003; 85:43-93.
Patra, et al. Optimization of inclusion body solubilization and renaturation of recombinant human growth hormone from *Escherichia coli*. Protein Expr Purif. 2000; 18(2):182-92.
Pelegrini, et al. Plant gamma-thionins: novel insights on the mechanism of action of a multi-functional class of defense proteins. Int J Biochem Cell Biol. 2005; 37: 2239-53.
Pepinsky, et al. Improved pharmacokinetic properties of a polyethylene glycol-modified form of interferon-beta-1a with preserved in vitro bioactivity. J Pharmacol Exp Ther. 2001; 297: 1059-66.
Petersen, et al. The dual nature of human extracellular superoxide dismutase: one sequence and two structures. Proc. Natl. Acad. Sci. USA 2003; 100:13875-80.
Pi, et al. Analysis of expressed sequence tags from the venom ducts of Conus striatus: focusing on the expression profile of conotoxins. Biochimie. 2006; 88(2):131-40.
Pimanda, et al. The von Willebrand factor-reducing activity of thrombospondin-1 is located in the calcium-binding/C-terminal sequence and requires a free thiol at position 974. Blood. 2002; 100: 2832-2838.
Pokidysheva, et al. The Structure of the Cys-rich Terminal Domain of Hydra Minicollagen, Which Is Involved in Disulfide Networks of the Nematocyst Wall. J Biol Chem. 2004; 279: 30395-401.
Popkov, et al. Isolation of human prostate cancer cell reactive antibodies using phage display technology. J. Immunol. Methods. 2004; 291:137-151.
Prinz, et al. The Role of the Thioredoxin and Glutaredoxin Pathways in Reducing Protein Disulfide Bonds in the *Escherichia coli* Cytoplasm. J Biol Chem. 1997; 272(25):15661-7.
Qi, et al. Structural Features and Molecular Evolution of Bowman-Birk Protease Inhibitors and Their Potential Application (283-292). Act Biochim Biophys Sin. (Shanghai) 2005; 37:283-292.
Rao, et al. Molecular and Biotechnological Aspects of Microbial Proteases. Microbiol Mol Biol Rev. 1998; 62(3): 597-635.
Rasmussen, et al. Tumor cell-targeting by phage-displayed peptides. Cancer Gene Ther. 2002; 9: 606-12.
Rawlings, et al. Evolutionary families of peptidase inhibitors. Biochem J. 2004; 378: 705-16.
Rebay, et al. Specific EGF repeats of Notch mediate interactions with Delta and serrate: Implications for notch as a multifunctional receptor. Cell 1991; 67:687-699.
Roberge, et al. Construction and optimization of a CC49-based scFv-beta-lactamase fusion protein for ADEPT. Protein Eng Des Sel. 2006; 19(4):141-5.
Rosenfeld, et al. Biochemical, Biophysical, and Pharmacological Characterization of Bacterially Expressed Human Agouti-Related Protein. Biochemistry. 1998; 37: 16041-52.
Roussel, et al. Complexation of Two Proteic Insect Inhibitors to the Active Site of Chymotrypsin Suggests Decoupled Roles for Binding and Selectivity. J Biol Chem. 2001; 276: 38893-8.
Rudensky, et al. Sequence analysis of peptides bound to MHC class II molecules. Nature a-z index 353.6345 (1991): 622-627.
Sahdev, et al. Production of active eukaryotic proteins through bacterial expression systems: a review of the existing biotechnology strategies. Mol Cell Biochem. Jan. 2008;307(1-2):249-64.
Salloum, et al. Anakinra in experimental acute myocardial infarction—does dosage or duration of treatment matter? Cardiovasc Drugs Ther. Apr. 2009;23(2):129-35.
Salvador, et al. Parasite-derived neurotrophic factor/trans-sialidase of Trypanosoma cruzi links neurotrophic signaling to cardiac innate immune response. Infection and immunity 82.9 (2014): 3687-3696.
Sambrook, et al. Molecular Cloning: A Laboratory Manual, 2nd Edition; Current Protocols in Molecular Biology. 1989.
Schellenberger, et al., U.S. Appl. No. 11/715,296.
Schellenberger, et al., U.S. Appl. No. 11/715,300.
Schlapschy, et al. Fusion of a recombinant antibody fragment with a homo-amino-acid polymer: effects on biophysical properties and prolonged plasma half-life. Protein Eng Des Sel. Jun. 2007;20(6):273-84. Epub Jun. 26, 2007.
Scholle, et al. Efficient construction of a large collection of phage-displayed combinatorial peptide libraries. Comb. Chem. & HTP Screening. 2005; 8:545-551.
Schultz-Cherry, et al. Regulation of Transforming Growth Factor-beta Activation by Discrete Sequences of Thrombospondin. J. Biol. Chem. 1995; 270:7304-7310.
Schultz-Cherry, et al. The type 1 repeats of thrombospondin 1 activate latent transforming growth factor-beta. J. Biol. Chem. 1994; 269:26783-8.
Schulz, et al. Potential of NIR-FT-Raman spectroscopy in natural carotenoid analysis. Biopolymers 2005; 80:34-49.
Scopes. Protein Purification: Principles and Practice. Castor, ed. Springer-Verlag. 1994.
Shen, et al. A Type I Peritrophic Matrix Protein from the Malaria Vector Anopheles gambiae Binds to Chitin. Cloning, Expression, and Characterization. J Biol Chem. 1998; 273: 17665-70.
Sidhu, et al. Phage display for selection of novel binding peptides. Methods Enzymol. 2000; 328: 333-63.
Silverman, et al. Multivalent avimer proteins evolved by exon shuffling of a family of human receptor domains. Nat Biotechnol 2005; 23:1556-1561.
Simonet, et al. Structural and functional properties of a novel serine protease inhibiting peptide family in arthropods. Comp Biochem Physiol B Biochem Mol Biol. 2002; 132: 247-55.
Singh, et al. ProPred: Prediction of HLA-DR binding sites. Bioinformatics. 2001; 17: 1236-1237.
Skinner, et al. Purification and characterization of two classes of neurotoxins from the funnel web spider, *Agelenopsis aperta*. J. Biol. Chem. 1989; 264:2150-2155.

(56) References Cited

OTHER PUBLICATIONS

Smith, et al. Phage Display. Chem Rev. 1997; 97: 391-410.
Smith, et al. Single-step purification of polypeptides expressed in *Escherichia coli* as fusions with glutathione S-transferase. Gene. 1988; 67(1):31-40.
So, et al. Contribution of conformational stability of hen lysozyme to induction of type 2 T-helper immune responses. Immunology. 2001; 104: 259-268.
Srivastava, et al. Application of self-assembled ultra-thin film coatings to stabilize macromolecule encapsulation in alginate microspheres. J Microencapsul. 2005; 22(4):397-411.
Stamos, et al. Crystal structure of the HGF beta-chain in complex with the Sema domain of the Met receptor. Embo J. 2004; 23: 2325-35.
Steipe, et al. Sequence statistics reliably predict stabilizing mutations in a protein domain. J Mol Biol. 1994; 240(3):188-92.
Stemmer, et al. Single-step assembly of a gene and entire plasmid from large numbers of oligodeoxyribonucleotides. Gene 1995; 164(1):49-53.
Stemmer, W. Rapid evolution of a protein in vitro by DNA shuffling Nature. 1994; 370: 389-391.
Sternberg, Michael. Declaration dated Jan. 6, 2016. London, England.
Stickler, et al. Human population-based identification of CD4(+) T-cell peptide epitope determinants. J Immunol Methods. 2003; 281: 95-108.
Stites, et al. Empirical evaluation of the influence of side chains on the conformational entropy of the polypeptide backbone. Proteins. 1995; 22: 132-140.
Stoll, et al. A mechanistic analysis of carrier-mediated oral delivery of protein therapeutics. J Control Release. 2000; 64: 217-28.
Sturniolo, et al. Generation of tissue-specific and promiscuous HLA ligand databases using DNA microarrays and virtual HLA class II matrices. Natural Biotechnol. 1999; 17: 555-561.
Suetake, et al. Chitin-binding Proteins in Invertebrates and Plants Comprise a Common Chitin-binding Structural Motif. J Biol Chem. 2000; 275: 17929-32.
Suetake, et al. Production and characterization of recombinant tachycitin, the Cys-rich chitin-binding protein. Protein Eng. 2002; 15: 763-9.
Summers, et al. Baculovirus structural polypeptides. Virology. 1978; 84(2):390-402.
Summons to attend oral proceedings from European Patent Office dated May 26, 2015 regarding EP Application No. 07752636.6.
Takahashi, et al. Solution structure of hanatoxin1, a gating modifier of voltage-dependent K+ channels: common surface features of gating modifier toxins. J Mol Biol. 2000; 297: 771-80.
Takenobu, et al. Development of p53 protein transduction therapy using membrane-permeable peptides and the application to oral cancer cells. Mol Cancer Ther. 2002; 1: 1043-9.
Tam, et al. A biomimetic strategy in the synthesis and fragmentation of cyclic protein. Protein Sci. 1998; 7:1583.
Tavladoraki, et al. A single-chain antibody fragment is functionally expressed in the cytoplasm of both *Escherichia coli* and transgenic plants. Eur J Biochem. 1999; 262(2):617-24.
Tax, et al. Sequence of C. elegans lag-2 reveals a cell-signalling domain shared with Delta and Serrate of *Drosophila*. Nature 1994; 368: 150-154.
Tepitope values for random 200mer sequences composed of the amino acids GADSTEP; Reply to notice of opposition dated Apr. 8, 2016 for EP2402754.
Terpe, K. Overview of tag protein fusions: from molecular and biochemical fundamentals to commercial systems. Appl Microbiol Biotechnol. Jan. 2003;60(5):523-33.
Thai, et al. Antigen stability controls antigen presentation. J. Biol. Chem. 2004; 279: 50257-50266.
The Oxford Paperback Dictionary, pp. 536-537 and 742-743. Third Edition, Joyce M. Hawkins, Ed. Oxford University Press. 1988.

Tolkatchev, et al. Design and Solution Structure of a Well-Folded Stack of Two beta-Hairpins Based on the Amino-Terminal Fragment of Human Granulin A. Biochemistry. 2000; 39: 2878-86.
Torres, et al. Solution structure of a defensin-like peptide from platypus venom. Biochem J. 1999; 341 ( Pt 3): 785-794.
Tur, et al. A novel approach for immunization, screening and characterization of selected scFv libraries using membrane fractions of tumor cells. Int J Mol Med. 2003; 11: 523-7.
Uversky, et al. Why are "natively unfolded" proteins unstructured under physiologic conditions? Proteins. Nov. 15, 2000;41(3):415-27.
Valente, et al. Optimization of the primary recovery of human interferon alpha2b from *Escherichia coli* inclusion bodies. Protein Expr Purif. 2006; 45(1):226-34.
Van Den Hooven, et al. Disulfide Bond Structure of the AVR9 Elicitor of the Fungal Tomato Pathogen *Cladosporium fulvum*: Evidence for a Cystine Knot. Biochemistry 2001; 40:3458-3466.
Van Vlijmen, et al. A novel database of disulfide patterns and its application to the discovery of distantly related homologs. J Mol. Biol. 2004; 335:1083-1092.
Vanhercke, et al. Reducing mutational bias in random protein libraries. Anal Biochem. 2005; 339: 9-14.
Vardar, et al. Nuclear Magnetic Resonance Structure of a Prototype Lin12-Notch Repeat Module from Human Notch1. Biochemistry 2003; 42:7061-7067.
Venkatachalam, et al. Conformation of polypeptide chains. Annu Rev Biochem. 1969; 38: 45-82.
Ventura. Sequence determinants of protein aggregation: tools to increase protein solubility. Microb Cell Fact. 2005; 4(1):11.
Vestergaard-Bogind, et al. Single-file diffusion through the Ca2+-activated K+ channel of human red cells. J. Membrane Biol. 1985; 88:67-75.
Voet; et al., "Biochemistry (3rd Ed.). John Wiley and Sons. Published 2004, p. 230.".
Zaveckas, et al. Effect of surface histidine mutations and their number on the partitioning and refolding of recombinant human granulocyte-colony stimulating factor (Cys17Ser) in aqueous two-phase systems containing chelated metal ions. J Chromatogr B Analyt Technol Biomed Life Sci. 2007; 852(1-2):409-19.
Voisey, et al. Agouti: from Mouse to Man, from Skin to Fat Pigment Cell Res. 2002; 15: 10-18.
Vranken, et al. A 30 residue fragment of the carp granulin 1 protein folds into a stack of two β hairpins similar to that found in the native protein J Pept Res. 1999; 53: 590-7.
Walker, et al. Using protein-based motifs to stabilize peptides. J Pept Res. Nov. 2003;62(5):214-26.
Wang, et al. Structure-function studies of omega-atracotoxin, a potent antagonist of insect voltage-gated calcium channels. Eur J Biochem. 1999; 264: 488-494.
Ward et al. Binding activities of a repertoire of single immunoglobulin variable domains secreted from *Escherichia coli*. Nature. 341(6242):544-546 (1989).
Weiss, et al. A cooperative model for receptor recognition and cell adhesion: evidence from the molecular packing in the 1.6-A crystal structure of the pheromone Er-1 from the ciliated protozoan *Euplotes raikovi*. Proc Natl Acad Sci U SA 1995; 92: 10172-6.
Wentzel, et al. Sequence requirements of the GPNG beta-turn of the Ecballium elaterium trypsin inhibitor II explored by combinatorial library screening. J Biol Chem. Jul. 23, 1999;274(30):21037-43.
Werle, et al. The potential of cystine-knot microproteins as novel pharmacophoric scaffolds in oral peptide drug delivery. J. Drug Targeting 2006; 14:137-146.
Werther, et al. Humanization of an anti-lymphocyte function-associated antigen (LFA)-1 monoclonal antibody and reengineering of the humanized antibody for binding to rhesus LFA-1. J Immunol. 1996; 157(11):4986-95.
Whitlow, et al. Multivalent Fvs: characterization of single-chain Fv oligomers and preparation of a bispecific Fv. Protein Eng. 1994; 7(8):1017-26.
Winter, et al. Humanized antibodies. Trends Pharmacol Sci. May 1993;14(5):139-43.
Wittrup. Protein engineering by cell-surface display. Curr Opin Biotechnol. 2001; 12: 395-9.

(56) References Cited

OTHER PUBLICATIONS

Worn, et al. Correlation between in vitro stability and in vivo performance of anti-GCN4 intrabodies as cytoplasmic inhibitors. J Biol Chem. 2000; 275(4):2795-803.
Worn, et al. Stability engineering of antibody single-chain Fv fragments. J Mol Biol. 2001; 305(5):989-1010.
Wrammert, et al. Rapid cloning of high-affinity human monoclonal antibodies against influenza virus. Nature. 2008; 453(7195):667-71.
Wright, et al. Intrinsically unstructured proteins: re-assessing the protein structure-function paradigm. J Mol Biol. Oct. 22, 1999;293(2):321-31.
Xiong, et al. A Novel Adaptation of the Integrin PSI Domain Revealed from Its Crystal Structure. J Biol Chem. 2004; 279: 40252-4.
Xu, et al. Solution Structure of BmP02, a New Potassium Channel Blocker from the Venom of the Chinese Scorpion *Buthus martensi* Karsch Biochemistry 2000; 39:13669-13675.
Yamazaki, et al. A possible physiological function and the tertiary structure of a 4-kDa peptide in legumes. Eur J Biochem. 2003; 270: 1269-1276.
Yang, et al. CDR walking mutagenesis for the affinity maturation of a potent human anti-HIV-1 antibody into the picomolar range. J Mol Biol. 1995; 254:392-403.
Yang, et al. Intestinal Peptide transport systems and oral drug availability. Pharmaceutical Research. 1999; 16: 1331-1343.
Yang, et al. Tailoring structure-function and pharmacokinetic properties of single-chain Fv proteins by site-specific PEGylation. Protein Eng. 2003; 16: 761-70.
Yankai, et al. Ten tandem repeats of beta-hCG 109-118 enhance immunogenicity and anti-tumor effects of beta-hCG C-terminal peptide carried by mycobacterial heat-shock protein HSP65. Biochem Biophys Res Commun. 2006; 345(4):1365-71.
Yuan, et al. Solution structure of the transforming growth factor beta-binding protein-like module, a domain associated with matrix fibrils. Embo J. 1997; 16: 6659-66.
About this file: EP2081958—Extract from the Register of European Patent dated Jul. 29, 2015. In Opposition against EP-B1 2402754 of Amunix.
Ahmad, et al. ASAView: database and tool for solvent accessibility representation in proteins. BMC Bioinformatics. May 1, 2004;5:51.
Alber, et al. Nucleotide sequence of the triose phosphate isomerase gene of *Saccharomyces cerevisiae*. J Mol Appl Genet. 1982;1(5):419-34.
Alters; et al., "GLP2-2G-XTEN: A Pharmaceutical Protein with Improved Serum Half-Life and Efficacy in a Rat Crohn's Disease Model. PLOS One, vol. 7, No. 11, Nov. 26, 2012, p. e50630.".
Ansong, et al. Epitope mapping factor VIII A2 domain by affinity-directed mass spectrometry: residues 497-510 and 584-593 comprise a discontinuous epitope for the monoclonal antibody R8B12. J Thromb Haemost. Apr. 2006;4(4):842-7.
Bachmann, et al. T helper cell-independent neutralizing B cell response against vesicular stomatitis virus: role of antigen patterns in B cell induction? Eur J Immunol. Dec. 1995;25(12):3445-51.
Barrowcliffe, et al. Coagulation and chromogenic assays of factor VIII activity: general aspects, standardization, and recommendations. Semin Thromb Hemost. Jun. 2002;28(3):247-56.
Belaaouaj, et al. Matrix metalloproteinases cleave tissue factor pathway inhibitor. Effects on coagulation. J Biol Chem. Sep. 1, 2000;275(35):27123-8.
Bengtsson, et al. The amino-terminal part of PRELP binds to heparin and heparan sulfate. J Biol Chem. Dec. 29, 2000;275(52):40695-702.
Bjorkman, et al. Pharmacokinetics of coagulation factors: clinical relevance for patients with haemophilia. Clin Pharmacokinet. 2001;40(11):815-32.
Bobrow, RS. Excess factor VIII: a common cause of hypercoagulability. J Am Board Fam Pract. Mar.-Apr. 2005;18(2):147-9.
Boshart, et al. A very strong enhancer is located upstream of an immediate early gene of human cytomegalovirus. Cell. Jun. 1985;41(2):521-30.
Briet, et al. High titer inhibitors in severe haemophilia A. A meta-analysis based on eight long-term follow-up studies concerning inhibitors associated with crude or intermediate purity factor VIII products. Thromb Haemost. Jul. 1994;72(1):162-4.
Caliceti, et al. Pharmacokinetic and biodistribution properties of poly(ethylene glycol)-protein conjugates. Adv Drug Deliv Rev. Sep. 26, 2003;55(10):1261-77.
Cameron, et al. The canine factor VIII cDNA and 5' flanking sequence. Thromb Haemost. Feb. 1998;79(2):317-22.
Casolaro, et al. Augmentation of lung antineutrophil elastase capacity with recombinant human alpha-1-antitrypsin. J Appl Physiol. Nov. 1987;63(5):2015-23.
Cell Therapeutics Press Reease. Cell Therapeutics Inc.'s Polyglutamate (PG) Technology Highlighted at International Polymer Therapeutics Meeting; Novel Recombinant Technology Extends PG Platform to G-CSF. Jan. 4, 2002. PR Newswire.
Chang, et al. Phenotypic expression in *E. coli* of a DNA sequence coding for mouse dihydrofolate reductase. Nature. Oct. 19, 1978;275(5681):617-24.
"Schellenberger et al. "Online Supplementary material: A recombinant polypeptide extends the in vivo half-life of peptides and proteins in a tunable manner", Nature biotechnology, vol. 27, No. 12, Nov. 15, 2009 (Nov. 15, 2009), pp. 1186-1190, XP055190665, ISSN: 1087-0156, DOI: 10.1038/nb.1588".
Chou, Fasman Analyses of prior art sequences. 1974.
Cleland, et al. An Extended Half-Life Glucagon Construct for the Prevention of Nocturnal Hypoglycemia. In DIABETES. 2009; 58:A513.
Cleland, et al. A Monthly Dosed GLP-1 Analog for Treatment of Type 2 Diabetes Mellitus. Diabetes, 2010; 59(1):A104. 70th Annual Meeting of the American Diabetes Association, Orland, FL, USA 2010.
Cleland, et al. A Novel Human Growth Hormone XTEN Construct (VRS-317) for Once-a-Month Subcutaneous Administration in a Phase la Study of Growth Hormone Deficient Adults. Endocr Rev, vol. 32 (03 Meeting Abstracts): P2-371. Jun. 2011, XP002697386.
Cleland, et al. A novel long-acting human growth hormone fusion protein (VRS-317): enhanced in vivo potency and half-life. J Pharm Sci. Aug. 2012;101(8):2744-54. doi: 10.1002/jps.23229. Epub Jun. 7, 2012.
Cleland, et al. An extended half-life exenatide construct for weekly administration in the treatment of diabetes mellitus. In DIABETES, vol. 58, pp. A511-A512. 1701 N Beauregard St, Alexandria, VA 22311-1717 USA: Amer Diabetes Assoc, 2009. Abstract only.
Clinicaltrials.gov archive. VRS-317 in Adult Subjects With Growth Hormone Deficiency. Updated May 23, 2011.
Conference abstracts: Antibodies and Beyond Antibodies. Loews Coronado Bay Resort, Coronado, CA. Jun. 1-2, 2006.
Co-pending U.S. Appl. No. 14/077,068, filed Nov. 11, 2013.
Corsaro, et al. Enhancing the efficiency of DNA-mediated gene transfer in mammalian cells. Somatic Cell Genet. Sep. 1981;7(5):603-16.
Cutler, et al. The identification and classification of 41 novel mutations in the factor VIII gene (F8C). Hum Mutat. Mar. 2002;19(3):274-8.
De Boer, et al. The tac promoter: a functional hybrid derived from the trp and lac promoters. Proc Natl Acad Sci U S A. Jan. 1983;80(1):21-5.
Denoto, et al. Human growth hormone DNA sequence and mRNA structure: possible alternative splicing. Nucleic Acids Res. Aug. 11, 1981;9(15):3719-30.
Diaz-Collier, et al. Refold and characterization of recombinant tissue factor pathway inhibitor expressed in *Escherichia coli*. Thromb Haemost. Mar. 1994;71(3):339-46.
Eaton, et al. Construction and characterization of an active factor VIII variant lacking the central one-third of the molecule. Biochemistry. Dec. 30, 1986;25(26):8343-7.
El-Manzalawy, Y. M. Machine learning approaches for epitope prediction. Graduate Theses and Dissertations. Iowa State University. Graduate College. 2008.

(56) References Cited

OTHER PUBLICATIONS

Engels, et al. Gene Synthesis. Agnew. Chem. Int. Ed. Engl.; 1989; 28:716-734.
Exhibit 1: Percentage Secondary Structure of Random Sequence URP by Chou-Fasman Analysis. Date unknown.
Extract from USPTO with regard to assignment of U.S. Appl. No. 60/743,410. Assignment Data not available.
Extract from USPTO with regard to assignment of U.S. Appl. No. 60/743,622. Assignment Data not available.
Garnier, et al. GOR method for predicting protein secondary structure from amino acid sequence. Methods Enzymol. 1996;266:540-53.
GenBank: EIW63862.1. hypothetical protein TRAVEDRAFT_138159 [Trametes versicolor FP-101664 SS1]. Available at http://www.ncbi.nlm.nih.gov/protein/392570690?report=genbank&log$=protalign&blast_rank=1&RID=3ERS0M7501R. Accessed on Sep. 16, 2013.
George, et al. An analysis of protein domain linkers: their classification and role in protein folding. Protein Eng. Nov. 2002;15(11):871-9.
Gleeson, et al. Transformation of the Methylotrophic Yeast *Hansenula polymorpha*. J. Gen. Microbiology. Dec. 1986; 132(12):3459-3465.
Goeddel, et al. Direct expression in *Escherichia coli* of a DNA sequence coding for human growth hormone. Nature. Oct. 18, 1979;281(5732):544-8.
Goeddel, et al. Synthesis of human fibroblast interferon by *E. coli*. Nucleic Acids Res. Sep. 25, 1980;8(18):4057-74.
Graham, et al. A new technique for the assay of infectivity of human adenovirus 5 DNA. Virology. Apr. 1973;52(2):456-67.
Harris, et al. Rapid and general profiling of protease specificity by using combinatorial fluorogenic substrate libraries. Proc Natl Acad Sci U S A. Jul. 5, 2000;97(14):7754-9.
Hoeben, et al. Expression of functional factor VIII in primary human skin fibroblasts after retrovirus-mediated gene transfer. J Biol Chem. May 5, 1990;265(13):7318-23.
Huang, et al. Preparation and characterization of a novel exendin-4 human serum albumin fusion protein expressed in Pichia pastoris. J Pept Sci. May 2008;14(5):588-95.
Internet printout for Chou Fasman algorithm, 1974. Available at www.biogem.org/tool/chou-fasman.
Kabsch, et al. How good are predictions of protein secondary structure? FEBS Lett. May 8, 1983;155(2):179-82.
Kaufman, et al. Amplification and expression of sequences cotransfected with a modular dihydrofolate reductase complementary dna gene. J Mol Biol. Aug. 25, 1982;159(4):601-21.
Kaufman, et al. Construction of a modular dihydrofolate reductase cDNA gene: analysis of signals utilized for efficient expression. Mol Cell Biol. Nov. 1982;2(11):1304-19.
Kemball-Cook G, et al. The factor VIII Structure and Mutation Resource Site: HAMSTeRS version 4. Nucleic Acids Res. Jan. 1, 1998;26(1):216-9.
Law, et al. Peptide-based biomaterials for protease-enhanced drug delivery. Biomacromolecules. Apr. 2006;7(4):1261-5.
Lee, et al. Stabilizing peptide fusion for solving the stability and solubility problems of therapeutic proteins. Pharm Res. Oct. 2005;22(10):1735-46. Epub Sep. 22, 2005.
Lee, et al. Synthesis, characterization, and pharmacokinetic studies of PEGylated glucagon-like peptide-1. Bioconjug Chem. Mar.-Apr. 2005;16(2):377-82.
Lenting, et al. Clearance mechanisms of von Willebrand factor and factor VIII. J Thromb Haemost. Jul. 2007;5(7):1353-60. Epub Apr. 7, 2007.
Lenting, et al. The light chain of factor VIII comprises a binding site for low density lipoprotein receptor-related protein. J Biol Chem. Aug. 20, 1999;274(34):23734-9.
Lethagen, et al. Clinical application of the chromogenic assay of factor VIII in haemophilia A, and different variants of von Willebrand's disease. Scand J Haematol. Nov. 1986;37(5):448-53.
Leyte, et al. Sulfation of Tyr1680 of human blood coagulation factor VIII is essential for the interaction of factor VIII with von Willebrand factor. J Biol Chem. Jan. 15, 1991;266(2):740-6.
Leyte, et al. The interaction between human blood-coagulation factor VIII and von Willebrand factor. Characterization of a high-affinity binding site on factor VIII. Biochem J. Feb. 1, 1989;257(3):679-83.
Lind, et al. Novel forms of B-domain-deleted recombinant factor VIII molecules. Construction and biochemical characterization. Eur J Biochem. Aug. 15, 1995;232(1):19-27.
Lines labeled D represents multiple predictions of order that were calculated using the respective programs FoldIndex found on the World-Wide web site bip.weizmann.ac.il/fldbin/findex. Accessed Jun. 7, 2012.
London, et al. Zymogen factor IX potentiates factor IXa-catalyzed factor X activation. Biochemistry. Aug. 15, 2000;39(32):9850-8.
Loyter, et al. Mechanisms of DNA uptake by mammalian cells: fate of exogenously added DNA monitored by the use of fluorescent dyes. oc Natl Acad Sci U S A. Jan. 1982;79(2):422-6.
Malardier, et al. Cloning of the nitrate reductase gene (niaD) of Aspergillus nidulans and its use for transformation of Fusarium oxysporum. Gene. May 15, 1989;78(1):147-56.
Matthews, et al. Substrate phage: selection of protease substrates by monovalent phage display. Science. May 21, 1993;260(5111):1113-7.
McKnight, et al. Identification and molecular analysis of a third Aspergillus nidulans alcohol dehydrogenase gene. EMBO J. Aug. 1985;4(8):2093-9.
Mehvar, et al. Modulation of the pharmacokinetics and pharmacodynamics of proteins by polyethylene glycol conjugation. J Pharm Pharm Sci. Jan.-Apr. 2000;3(1):125-36.
Morfini, M. Secondary prophylaxis with factor IX concentrates: continuous infusion. Blood Transfus. Sep. 2008;6 Suppl 2:s21-5.
Mozdzanowski, et al. Protein Purification Protocols. Ch 39, 2nd Ed. 2004, p. 402.
Narita, et al. The low-density lipoprotein receptor-related protein (LRP) mediates clearance of coagulation factor Xa in vivo. Blood. Jan. 15, 1998;91(2):555-60.
NCBI Reference Sequence: WP_005158338.1. Serine phosphatase RsbU, regulator of sigma subunit [Amycolatopsis azurea]. Available at http://www.ncbi.nlm.nih.gov/protein/491300334?report=genbank&log$=protalign&blast_rank=1&RID=3ERSOM7501R. Accessed on Sep. 16, 2013.
NCBI Reference Sequence: XP_003746909.1. PREDICTED: electron transfer flavoprotein subunit alpha, mitochondrial-like [Metaseiulus occidentalis]. Available at http://www.ncbi.nlm.nih.gov/protein/391345263?report=genbank&log$=protalign&blast_rank=1&RID=3ERS0M7501R. Accessed on Sep. 16, 2013.
Needleman, et al. A general method applicable to the search for similarities in the amino acid sequence of two proteins. J Mol Biol. Mar. 1970;48(3):443-53.
Neumann, et al. Gene transfer into mouse lyoma cells by electroporation in high electric fields. EMBO J. 1982;1(7):841-5.
Ngo JC, et al. Crystal structure of human factorVII: implications for the formation of the factor IXa-factor VIIIa complex. Structure (2008)16(4):597-606).
Noe, et al. A mathematical model of coagulation factor VIII kinetics. Haemostasis. Nov.-Dec. 1996;26(6):289-303.
O'Brien, et al. Purification and characterization of factor VIII 372-Cys: a hypofunctional cofactor from a patient with moderately severe hemophilia A. Blood. Apr. 15, 1990;75(8):1664-72.
Opposition dated Feb. 13, 2014 by Novo Nordisk against EP Application No. 07752636.6.
Opposition dated Feb. 17, 2014 by XL-Protein GmBH against EP Application No. 07752636.6.
Palmiter, et al. Metallothionein-human GH fusion genes stimulate growth of mice. Science. Nov. 18, 1983;222(4625):809-14.
Pipe, S. W. Functional roles of the factor VIII B domain. Haemophilia. Nov. 2009;15(6):1187-96. Epub Apr. 7, 2009.
Pipe, SW. The promise and challenges of bioengineered recombinant clotting factors. J Thromb Haemost. Aug. 2005;3(8):1692-701.

(56) References Cited

OTHER PUBLICATIONS

Pool, et al. Ineffectiveness of intramuscularly injected Factor 8 concentrate in two hemophilic patients. N Engl J Med. Sep. 8, 1966;275(10):547-8.

Rawlings, et al. MEROPS: the peptidase database. Nucleic Acids Res. Jan. 2008;36(Database issue):D320-5. Epub Nov. 8, 2007.

Rodriguez, et al. Does trypsin cut before proline? J Proteome Res. Jan. 2008;7(1):300-5. Epub Dec. 8, 2007.

Rychkov, et al. Joint neighbors approximation of macromolecular solvent accessible surface area. J Comput Chem. Sep. 2007;28(12):1974-89.

Saenko, et al. Role of the low density lipoprotein-related protein receptor in mediation of factor VIII catabolism. J Biol Chem. Dec. 31, 1999;274(53):37685-92.

Saenko, et al. Strategies towards a longer acting factor VIII. Haemophilia. Jul. 2006;12 Suppl 3:42-51.

Sarver, et al. Stable expression of recombinant factor VIII molecules using a bovine papillomavirus vector. DNA. Dec. 1987;6(6):553-64.

Scandella, et al. Localization of epitopes for human factor VIII inhibitor antibodies by immunoblotting and antibody neutralization. Blood. Oct. 1989;74(5):1618-26.

Schellenberger; et al., "A recombinant polypeptide extends the in vivo half-life of peptides and proteins in a tunable manner. Nature Biotechnology, Nature Publishing Group, US, vol. 27, No. 2, Nov. 15, 2009, pp. 1186-1190.".

Schellenberger, et al. Analysis of enzyme specificity by multiple substrate kinetics. Biochemistry. Apr. 27, 1993;32(16):4344-8.

Schellenberger, V. Engineering of Microproteins for Pharmaceutical Applications. PowerPoint Presentation. Date unknown.

Schulte, et al. Prolonged In-Vivo Half-Life of FVIIa by fusion to Albumin. Blood (ASH Annual Meeting Abstracts). 2007, 110: Abstract 3142.

Schulte, S. Use of albumin fusion technology to prolong the half-life of recombinant factor VIIa. Thromb Res. 2008;122 Suppl 4:S14-9. doi: 10.1016/S0049-3848(08)70029-X.

Sheffield, et al. Effects of genetic fusion of factor IX to albumin on in vivo clearance in mice and rabbits. Br J Haematol. Aug. 2004;126(4):565-73.

Shen, et al. The tertiary structure and domain organization of coagulation factor VIII. Blood. Feb. 1, 2008;111(3):1240-7. Epub Oct. 26, 2007.

Smith, et al. Comparison of Biosequences. Advances in Applied Mathematics. 1981;2: 482-489.

Tepitope analyses of prior art sequences. Date unknown.

The Chou-Fasman tool was provided by William R. Pearson and the University of Virginia, at the "Biosupport" internet site, URL located on the World Wide Web at .fasta.bioch.virginia.edu/fasta_www2/fasta_www.cgi?rm=misc1 as it existed on Jun. 19, 2009.

The GOR tool was provided by Pole Informatique Lyonnais at the Network Protein Sequence Analysis Internet site, URL located on the World Wide Web at .npsa-pbil.ibcp.fr/cgi-bin/secpred_gor4.pl as it existed on Jun. 19, 2008.

Thomson Pharma. Literature & News Report. Antibodies and Beyond Antibodies. Coronado, CA. Jun. 1-2, 2006.

Toole, et al. A large region (approximately equal to 95 kDa) of human factor VIII is dispensable for in vitro procoagulant activity. Proc Natl Acad Sci U S A. Aug. 1986;83(16):5939-42.

Towfighi, et al. Comparative measurement of anti-factor VIII antibody by Bethesda assay and ELISA reveals restricted isotype profile and epitope specificity. Acta Haematol. 2005;114(2):84-90.

Travis, et al. Isolation and properties of recombinant DNA produced variants of human alpha 1-proteinase inhibitor. J Biol Chem. Apr. 10, 1985;260(7):4384-9.

Watters, et al. An optimized method for cell-based phage display panning. Immunotechnology. 1997; 3: 21-29.

Weber, et al. Unglycosylated rat alpha 1-proteinase inhibitor has a six-fold shorter plasma half-life than the mature glycoprotein. Biochem Biophys Res Commun. Jan. 16, 1985;126(1):630-5. (abstract only).

Weimer, et al. Prolonged in-vivo half-life of factor VIIa by fusion to albumin. Thromb Haemost. Apr. 2008;99(4):659-67. (Abstract only).

Yang, et al. Ronn: the bio-basis function neural network technique applied to the detection of natively disordered regions in proteins. Bioinformatics. Aug. 15, 2005;21(16):3369-76. Epub Jun. 9, 2005.

Yuen; et al., "A long-acting human growth hormone with delayed clearance (VRS-317): results of a double-blind, placebo-controlled, single ascending dose study in growth hormone-deficient adults.", Jun. 2013, 98(6), 2595-2603.

Zhou, et al. Preparation and PEGylation of exendin-4 peptide secreted from yeast Pichia pastoris. Eur J Pharm Biopharm. Jun. 2009;72(2):412-7.

* cited by examiner

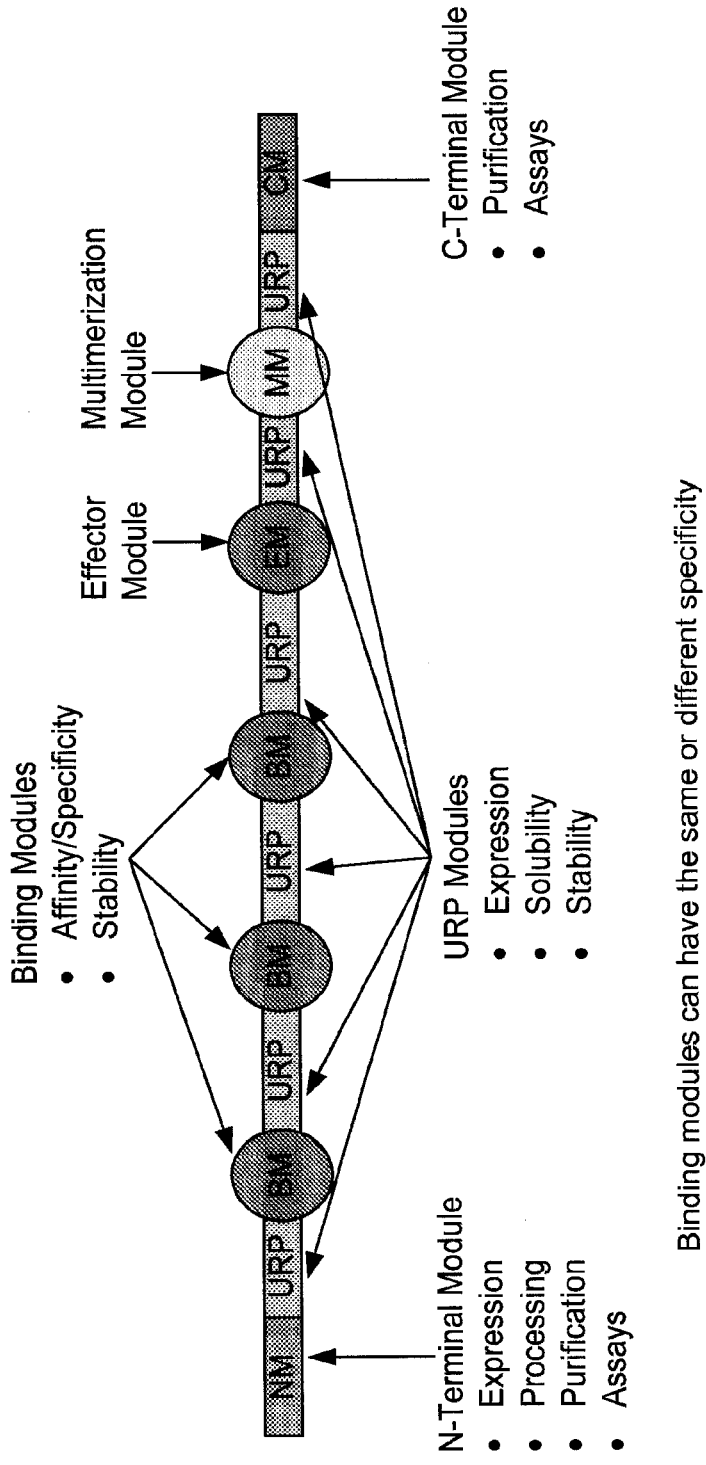
Fig. 1: Multifunctional Unstructured Recombinant Proteins (MURPs)

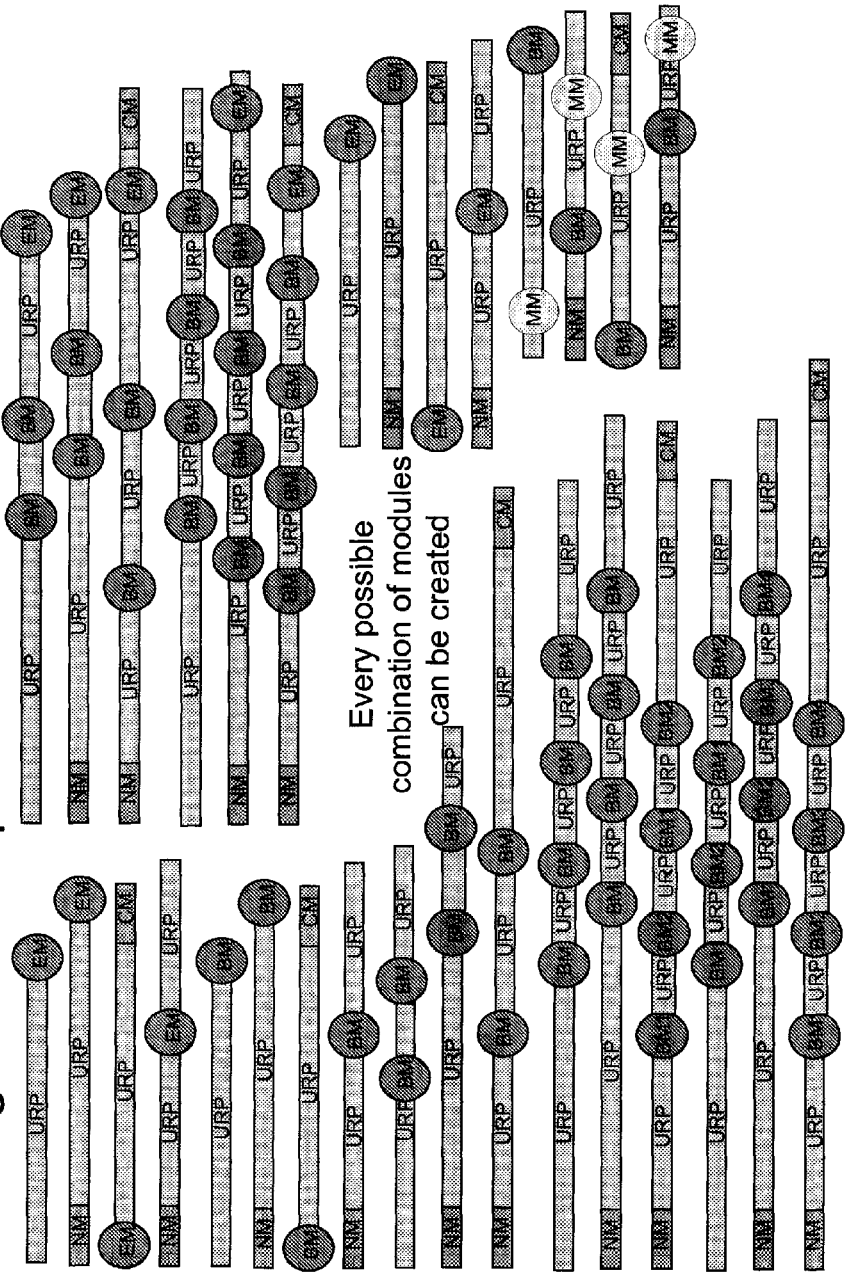

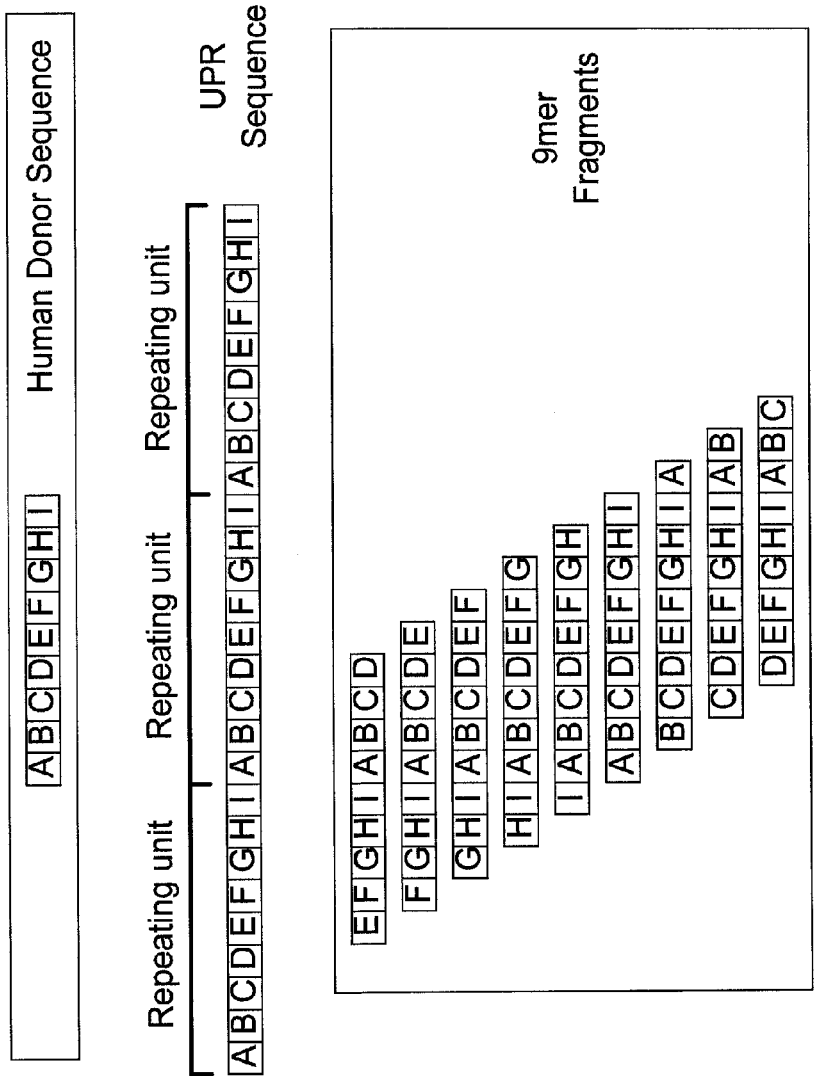
Fig. 3: URP sequences as oligomers of human sequences

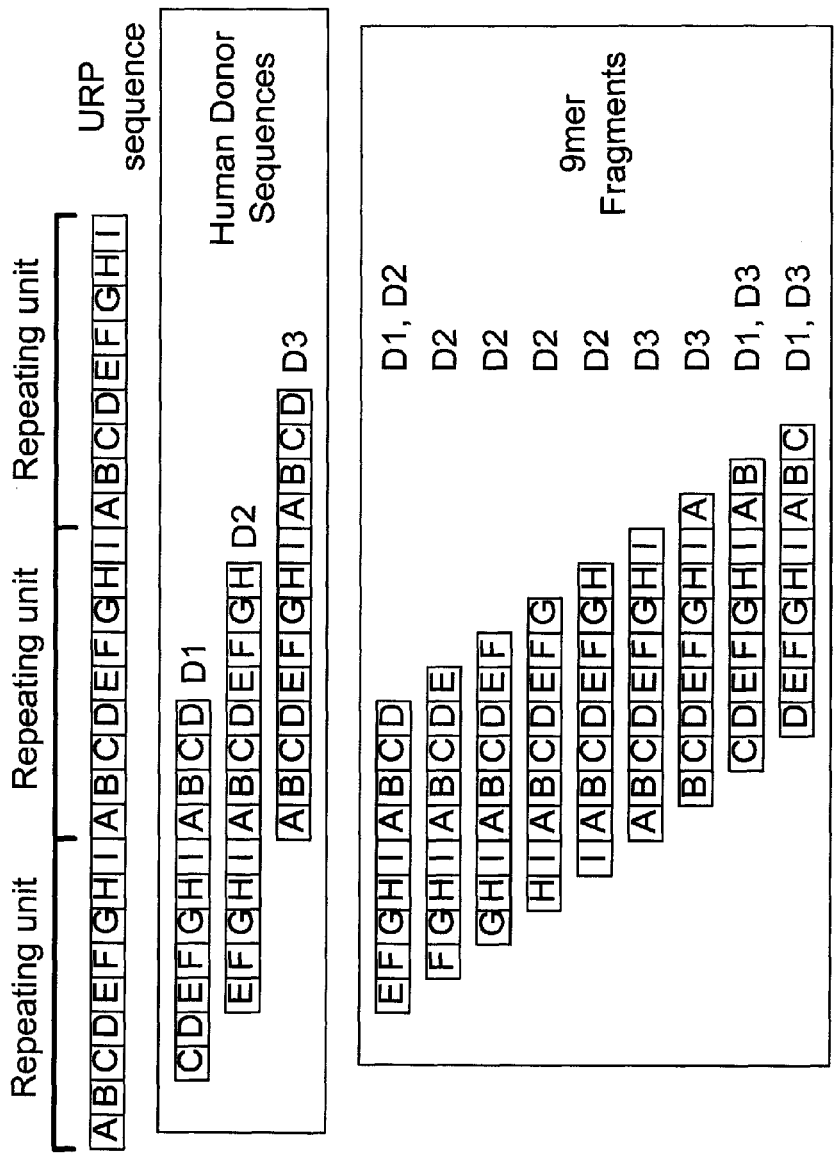
Fig. 4. URP sequences as oligomers of overlapping human sequences

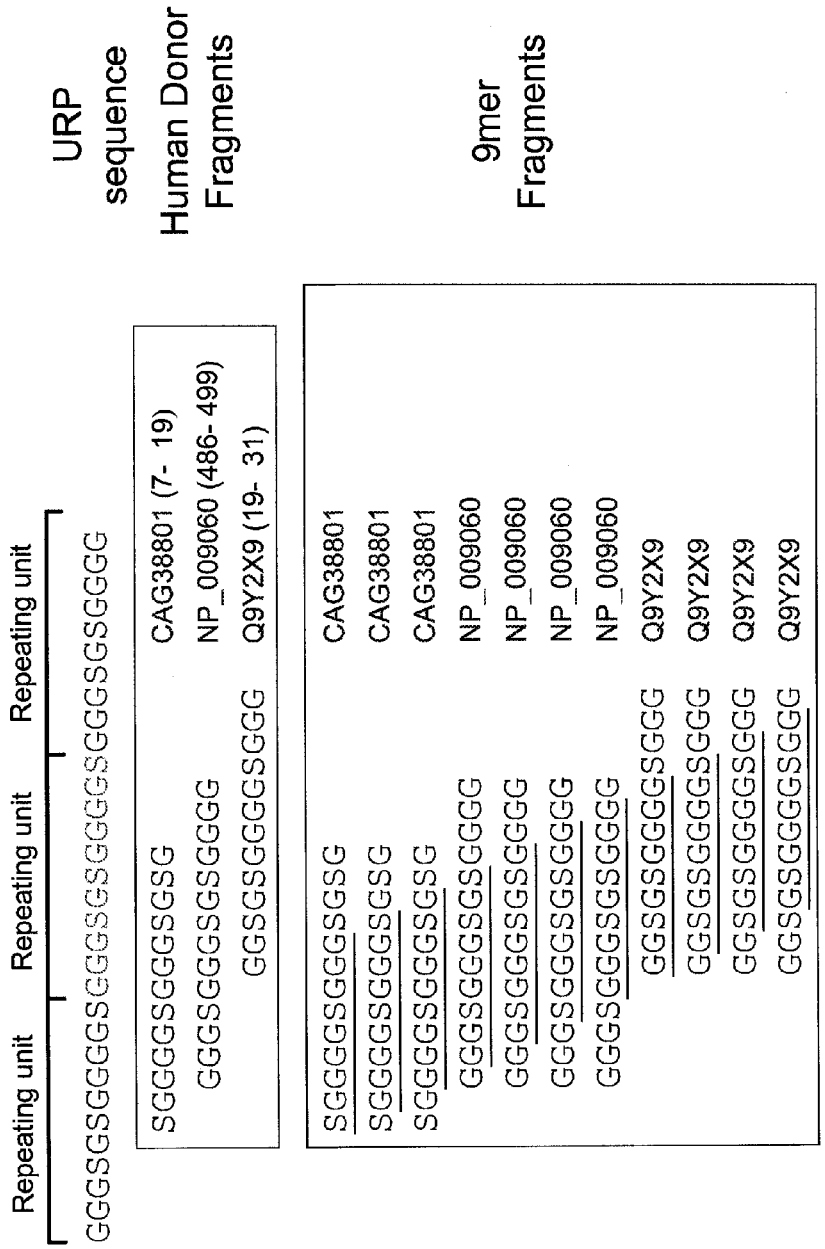
Fig. 5. Glycine/serine-rich URP sequences based on three overlapping human sequences

Fig. 6. Glycine/proline-rich URP sequences based on the sequence of human POU domain Repeating unit    Repeating unit    Repeating unit GGGGGPGGGGGPGGGGGPGGGGGP    URP sequence 9mer Fragments as part of POU (146-182)

GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG
GPGGGGGPGGGGGPGGGGGPGGGGGPGGG

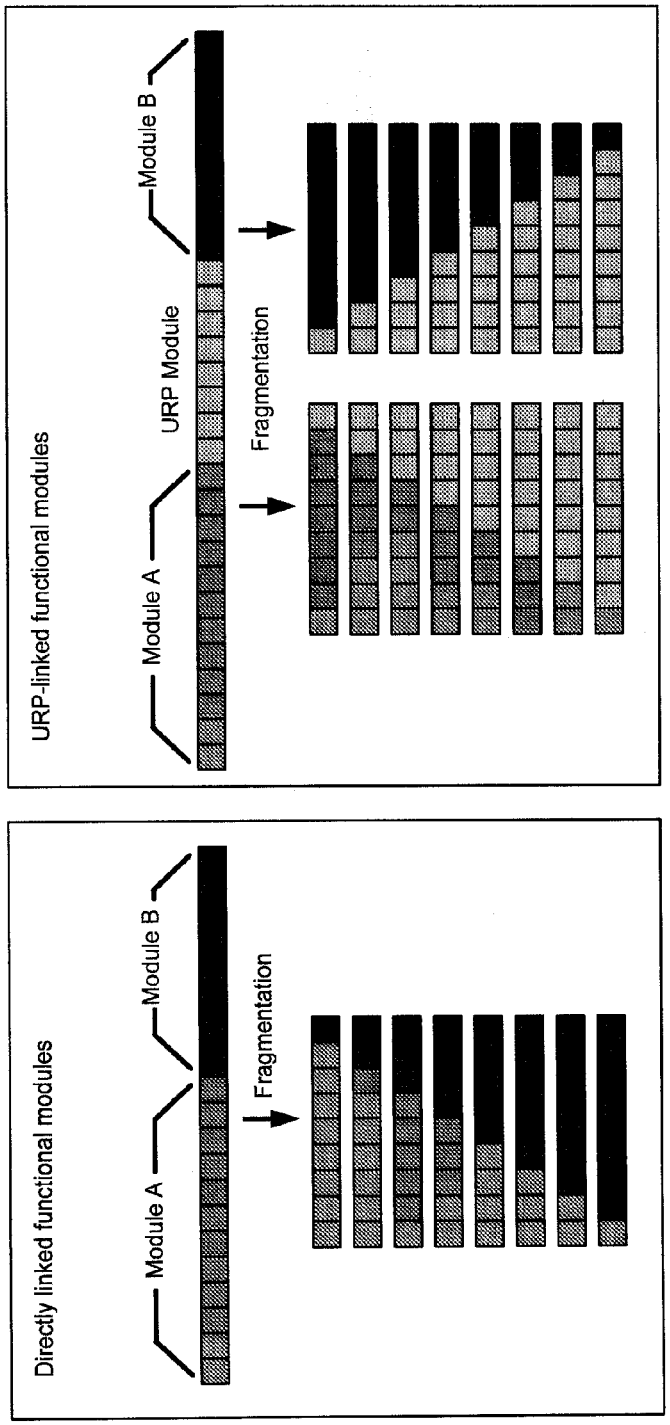
Fig. 7: Interruption of Module-Spanning T cell epitopes by URP Modules

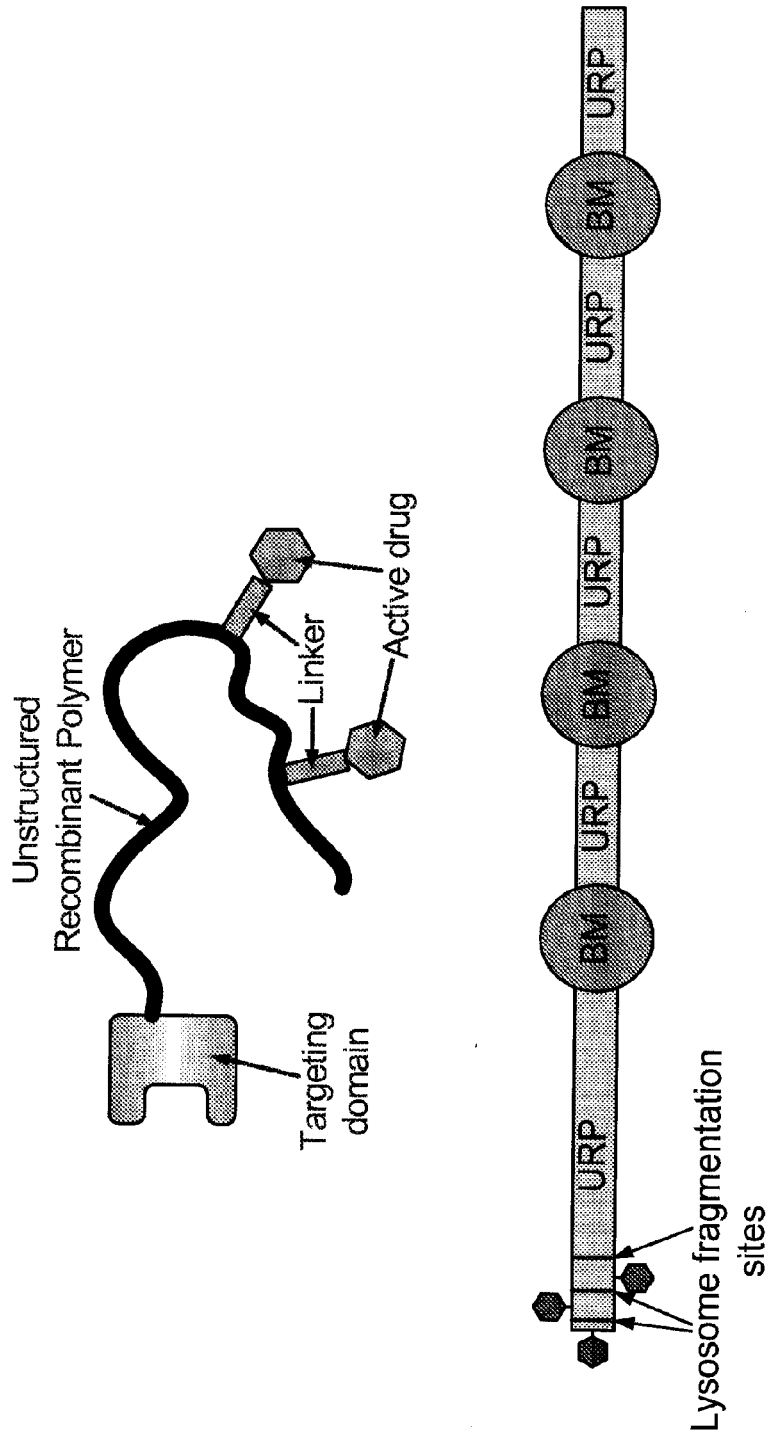
Figure 8. Drug Delivery Constructs

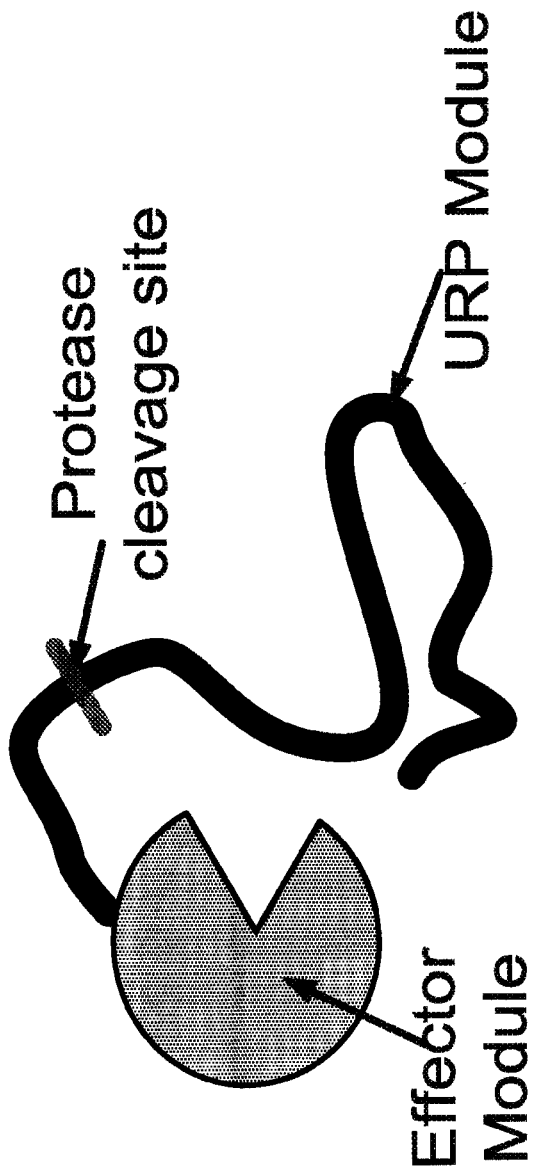
Figure 9. Example of a MURP containing a protease-sensitive site

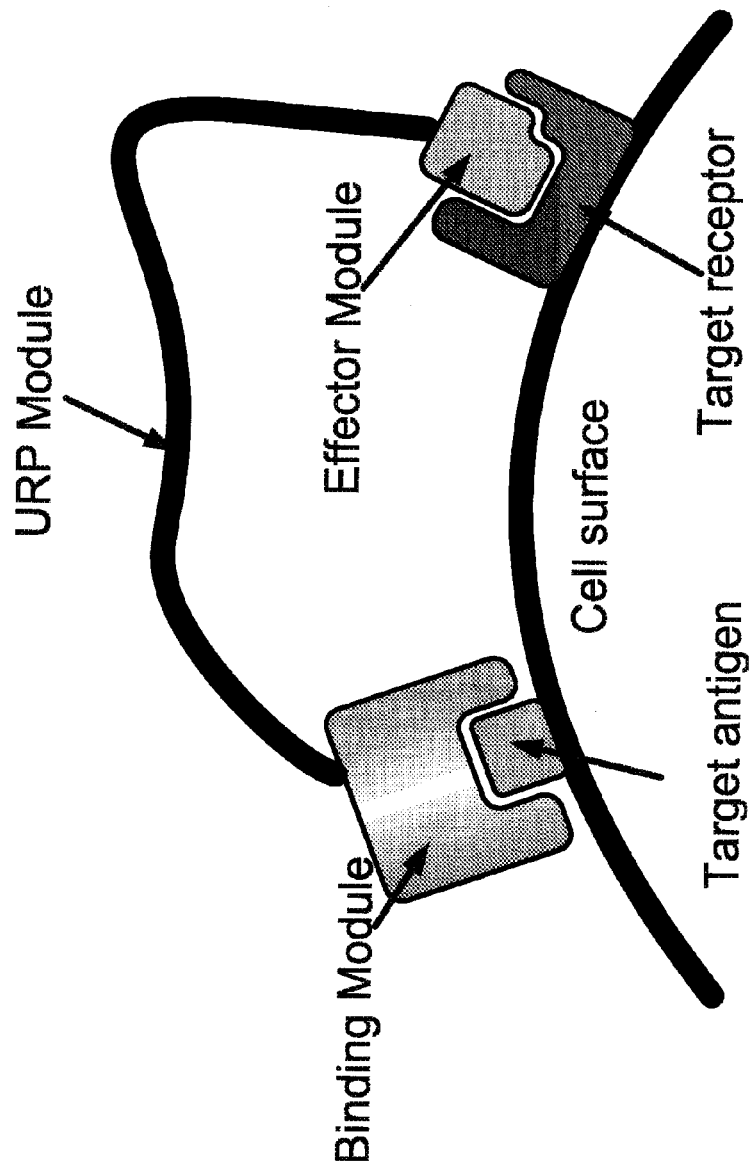
Figure 10. Increasing the local concentration of an effector module

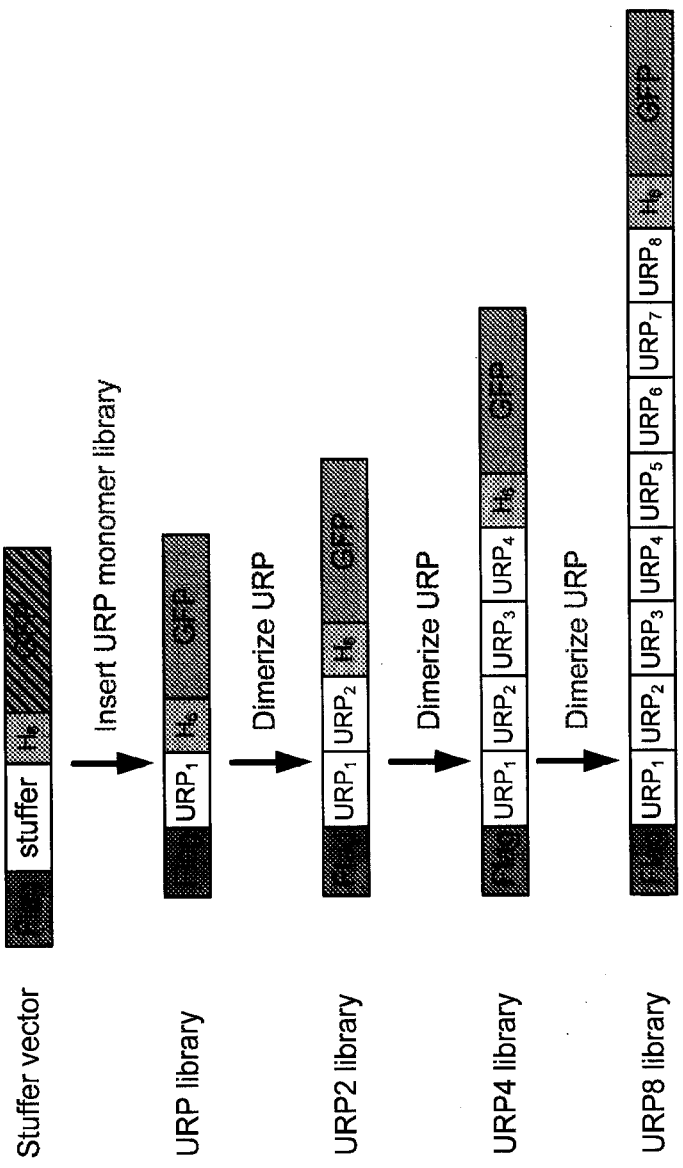
Fig. 11 Construction of URP Modules by iterative dimerization

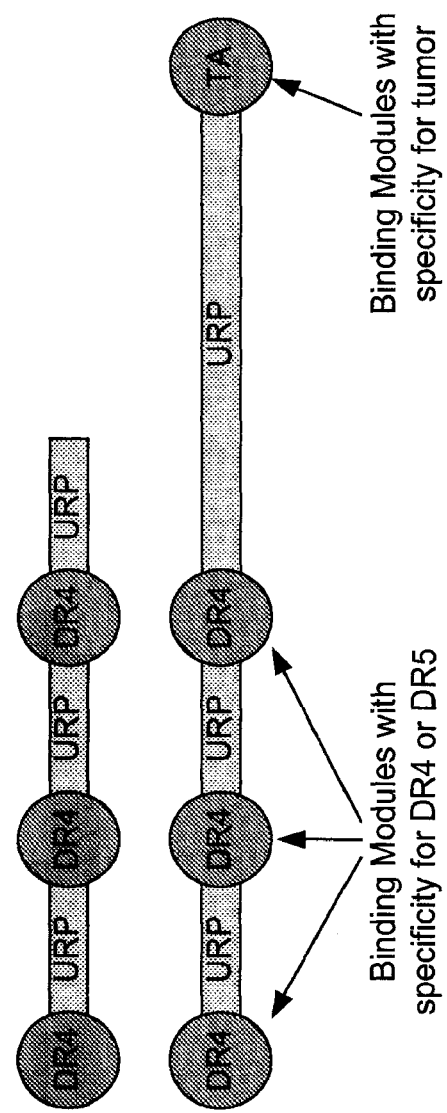
Fig. 12: Examples of MURPs with specificity for death receptors

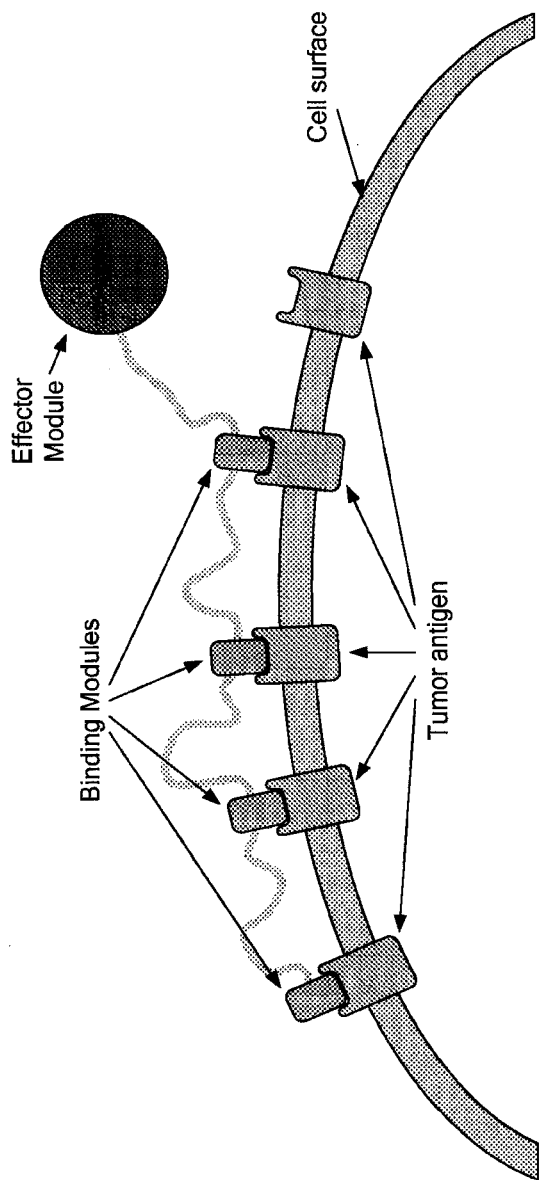
Fig. 13 Tumor antigen-targeted IL2

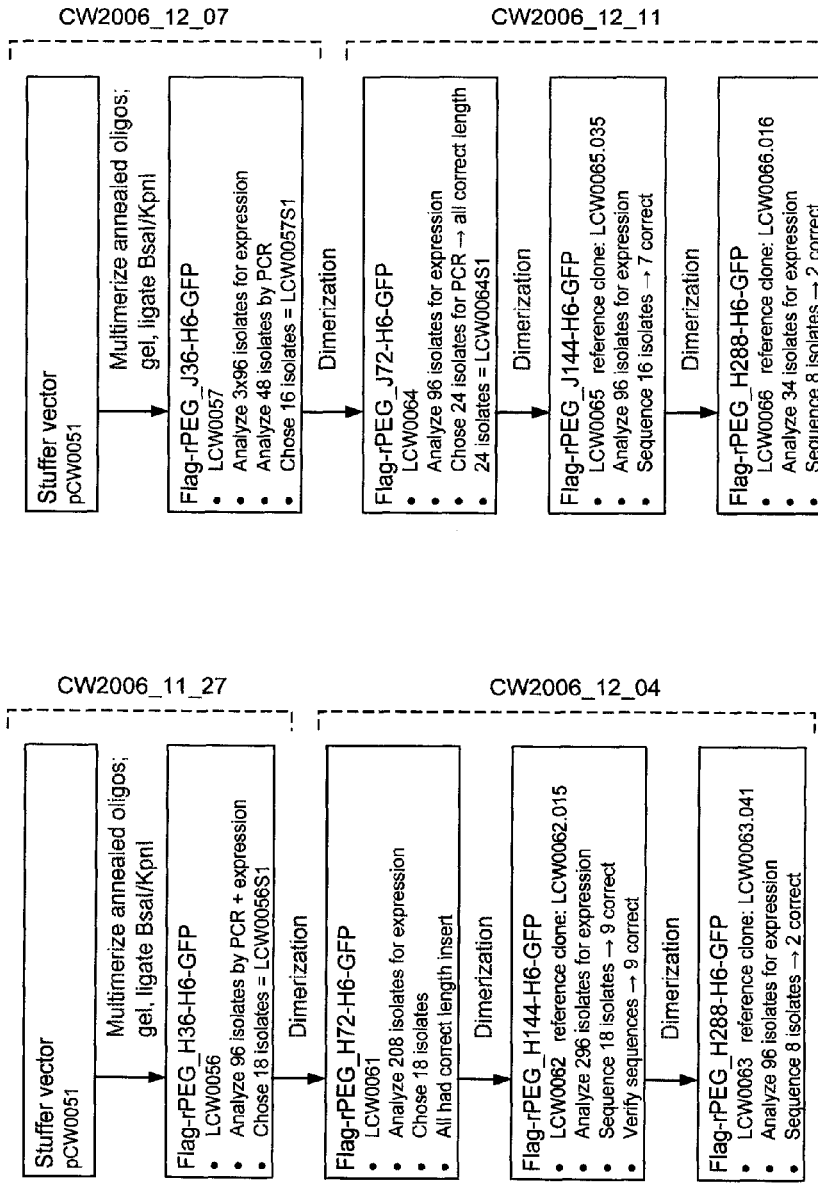
Fig. 14 Construction of rPEG_H288 and rPEG_J288

Fig. 15 Sequence of rPEG_J288

```
G  S  G  G  E  G  S  G  G  E  G  G  S  G  G  E  G  G  S  G  G  E  G  G  S
GGTAGTGGTGGTGAAGGAGGTTCTGGTGGAGGAGAAGGAGGTAGTGGTGGAGAAGGAGGTTCTGGTGGAGGAGAAGGAGGTAGT
 G  G  E  G  G  S  G  G  E  G  G  S  G  G  E  G  G  S  G  G  E  G  G  S  G  G
GGAGGTGAAGGAGGATCCGGAGGAGAAGGAGGTAGTGGTGGAGAAGGAGGTTCTGGTGGAGGAGAAGGAGGTAGTGGAGGT
  E  G  G  S  G  G  E  G  G  S  G  G  E  G  G  S  G  G  E  G  G  S  G  G  E
GAAGGTGGATCCGGAGGAGAAGGAGGTAGTGGTGGAGAAGGAGGTAGTGGTGGAGAAGGAGGTGGATCTGGAGGTGAAGGT
 G  S  G  G  E  G  G  S  G  G  E  G  G  S  G  G  E  G  G  S  G  G  E  G  G
GGATCCGGTGGAGAAGGAGGTTCCGGTGGAGAAGGAGGTAGTGGTGGAGAAGGAGGGTGGATCTGGAGGTGAAGGA
  S  G  G  E  G  G  S  G  G  E  G  G  S  G  G  E  G  G  S  G  G  E  G  G  S
GGAGGAGAAGGAGGTAGTGGTGGAGAAGGAGGTTCTGGTGGAGAAGGAGGTAGTGGTGGAGAAGGAGGTAGTGGAGGAGGT
 G  G  E  G  G  S  G  G  E  G  G  S  G  G  E  G  G  S  G  G  E  G  G  S  G  G
GGTAGTGGAGGTGAAGGTGAAGGTGGATCCGGAGGAGAAGGAGGTAGTGGAGGTGGAGAAGGAGGTAGTGGAGGTGGAGGT
  E  G  G  S  G  G  E  G  G  S  G  G  E  G  G  S  G  G  E  G  G  S  G  G  E
GGTGGTGAAGGAGGTTCTGGTGGAGGAGAAGGAGGTAGTGGAGGTGAAGGTGGAGGTGGAGGAGAAGGAGGTAGTGGAGGT
 G  G  S  G  G  E  G  G  S  G  G  E  G  G  S  G  G  E  G  G  S  G  G  E  G  G
GAAGGAGGATCCGGAGGAGAAGGAGGTAGTGGAGGTGAAGGTGGATCCGGAGGAGAAGGAGGTAGTGGAGGTGAAGGA
  S  G  G  E  G  G  S  G  G  E  G  G  S  G  G  E  G  G  S  G  G  E  G  G  S
GGTTCCGGTGGAGAAGGAGGTGGATCTGGAGGTGAAGAGGGTGGATCTGGAGGTGAAGAGGGTGGAGAAGGTGGTTCT
 G  G  E  G  G  S  G  G  E  G  G  S  G  G  E  G  G  S  G  G  E  G  G  S  G  G
GGAGGAGAAGGAGGTAGTGGAGGTGGAGAAGGAGGTAGTGGTGGAGAAGGTGGTTCTGGAGGA
  E  G
GAAGGA
```

Fig. 16 Sequence of rPEG_H288

```
G   S   G   G   E   G   S   G   G   S   G   E   G   G   S   G   G   S   G   G   S
GGTAGTGGTGGTGAGGGTGGATCCGGAGGTGGATCTGGTGAAGTGGAGGTAGT
G   G   E   G   G   S   G   G   S   G   G   E   G   G   S   G   G   S   G   G   G
GCAGGTGAGGGAGGATCTGGTGGAGAAGTGGAGGTAGTGGAGGTAGTGGAGGA
E   G   G   S   G   G   S   G   G   E   G   G   S   G   G   S   G   G   E   G
GAAGGTGGTTCCGGTGTGGAAGTGGAGGTAGTGGAGGTAGTGGTGGTGAGGGT
G   S   G   G   S   G   G   E   G   G   S   G   G   S   G   G   E   G   G   S
GGTTCCGGAGGAAGTGGAGGTAGTGGAGGAAGTGGTTCCGGTGAGAGGGTGATCT
G   G   S   G   G   S   G   G   E   G   G   S   G   G   S   G   G   G
GGAGGAAGTGGAGGTAGTGGAGGAGGATCTGGAGGAAGTGGAGGTAGTGGAGGTTCCGGTGAA
S   G   G   G   S   G   G   E   G   G   S   G   G   S   G   G   S
AGTGGAGGTAGTGGTGGTGAGAGGGAGGTTCTGGAGGAAGTGGAGGAGGATCTGGTGGAAGTGGA
G   G   E   G   G   S   G   G   S   G   G   E   G   G   S   G   G   S   G   G   S
GGCTAGTGGAGGTGGAGAAGGTTCTGGAGGAAGTGGAGGTAGTGGAGGAAGTGGAGGTAGTGGAGGA
E   G   G   S   G   G   S   G   G   E   G   G   S   G   G   S   G   G   E   G   G   S
GAAGGAGGATCTGGAGGAAGTGGAGGTAGTGGTGGTGAGGGTGGTTCCGGAGGAGAAGGT
G   G   S   G   G   S   G   G   E   G   G   S   G   G   S   G   G   G   S   G
GGTTCCGGTGAAGTGGAGGTAGTGGTGGTGGATCTGGTGGAGAGGGTGATCTGGTGAAGGAGGTTCC
G   G   S   G   G   E   G   G   S   G   G
GGTGAAGTGGAGGTAGTGGAGGTGAAGGTGTAGTGGAGGTGAGGGTGGTTCCGGAGGA
S   G
AGTGGA
```

Fig. 17 Examples of a human serine rich sequence dentin sialophosphoprotein preproprotein;
SDSSDSDSSDSSNSSDSSDSSDSSDSSNSSDSSDSSDSSDSSDSSDSSDSSDSSDSSDKSDS
SKSESDSSDSKSDSSDSNSSDNSDSSDSSNSNSSDSSDSSDSSSSDSSNSSDSSDSSDSNSSE
SSDSSDSSDSDSSDSSNSNSSDSSNSNSSDSSDSSDSSNSSDSSDSSNSSDSSDSSNSSDSN
DSSNSSDSSDSSNSSDSSDSSDSSDSSNESSNSSDSSDSSNSSDSSNSSDSSDSNRSDSNSSD
SDSSDSSNSSDSSNSSDSSNGDSSNSSDSSNSSDSSESSNSSDSSDSSDNSNSSDSSNSSD
SSDSSDSSNSSDDSSNSDSSNSSDSDSSNSSDSSDSSDSSNSSDSSDSSDSSNSSDSSN
SSDSSDSSDSSDSSNSSDSSNSSDSSDSSDSDSSGSSDSSDSSDSSDSSDSSESSDSSDSSDSS
DSSDSSDSSDSSDSSDSSDSSNSSDSSDSSDSSDSSDSSDSSDSSDSSDSSDSSDSSDSNES
SDSSDSSDSSDSSNSSDSSDSSDSTSDS Examples of URP sequences that are related to dentin sialophosphoprotein:
$(SSD)_n$, $(SSDSSN)_{n'}$ $(SSE)_n$

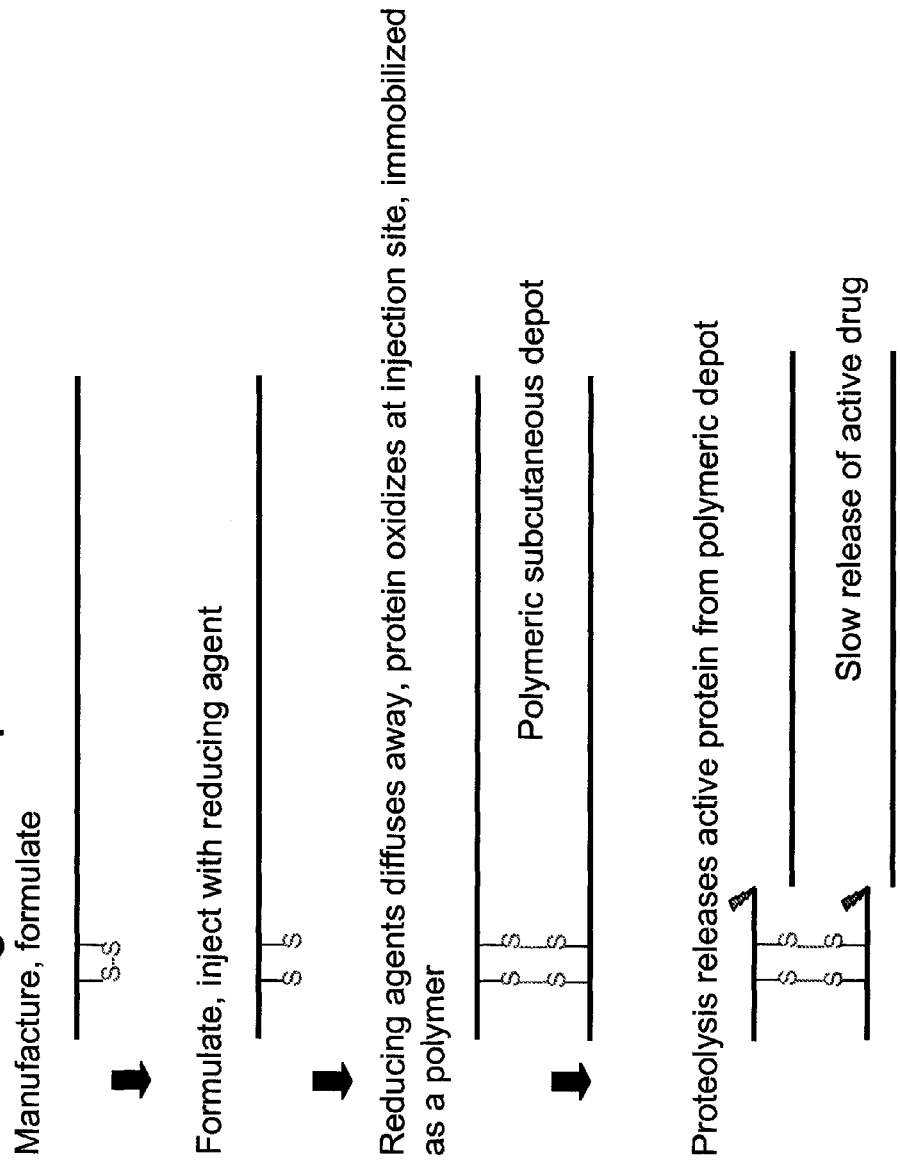

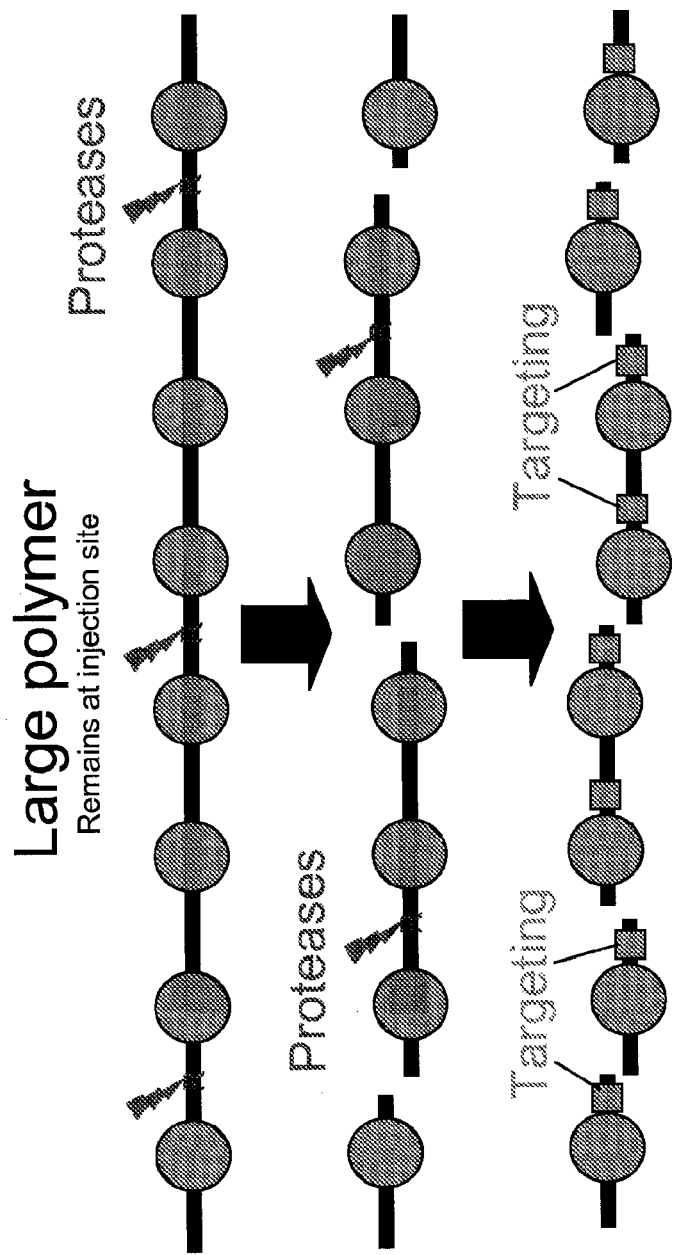
Fig. 19 MURP engineered for slow release

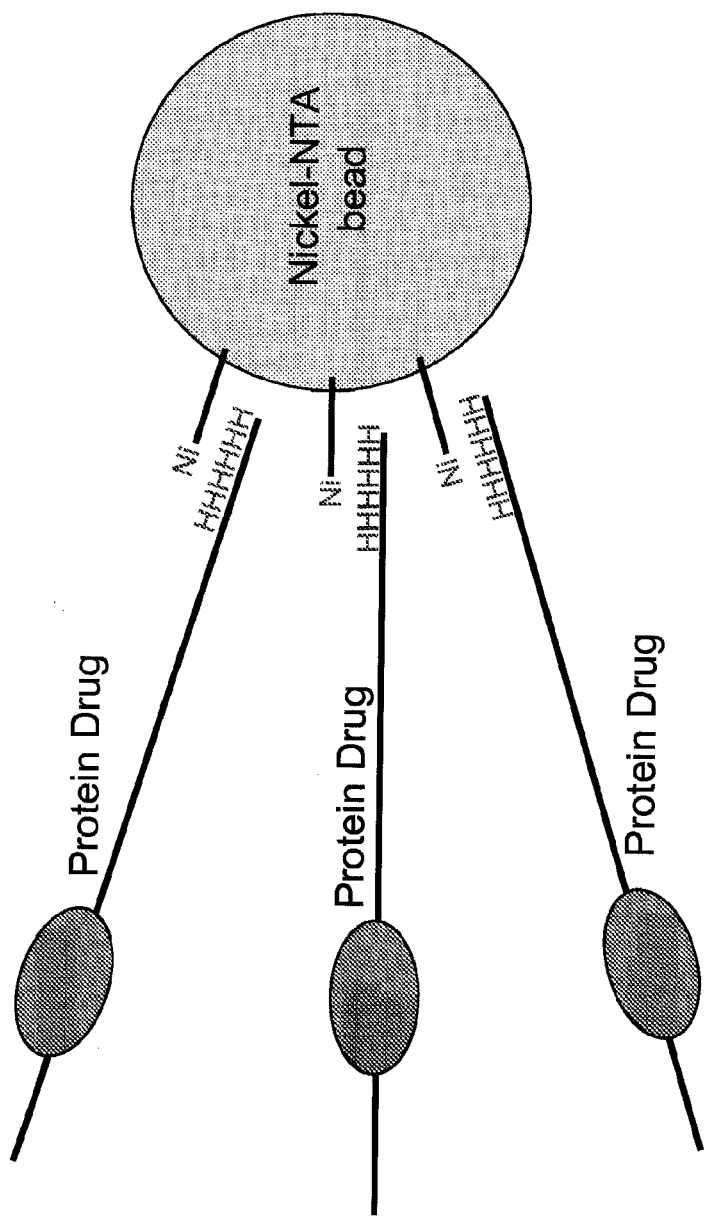
Fig. 20 Depot Derivatives of MURPs based on His-rich sequences

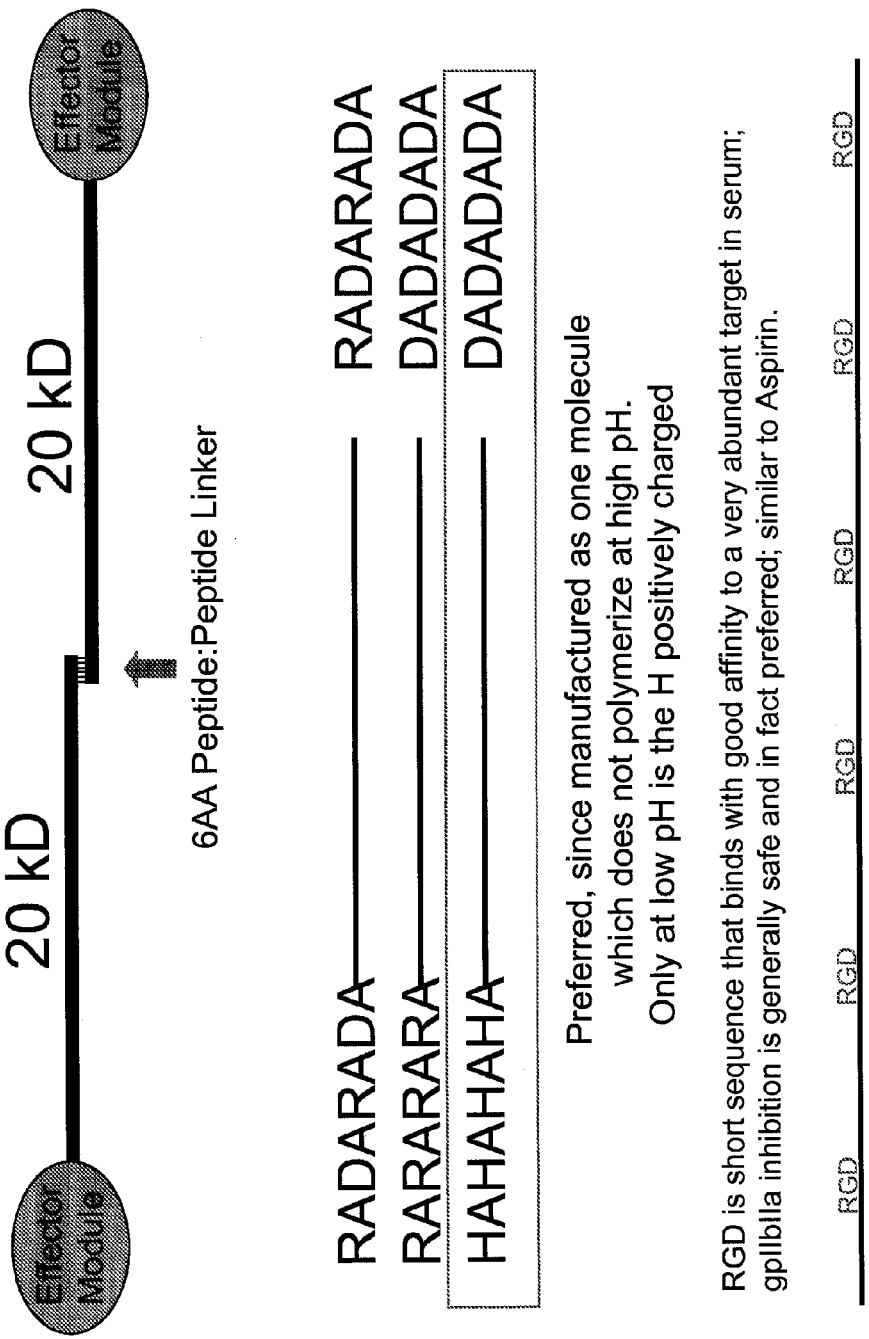
Fig. 21 Illustration of a MURP that forms a homodimer

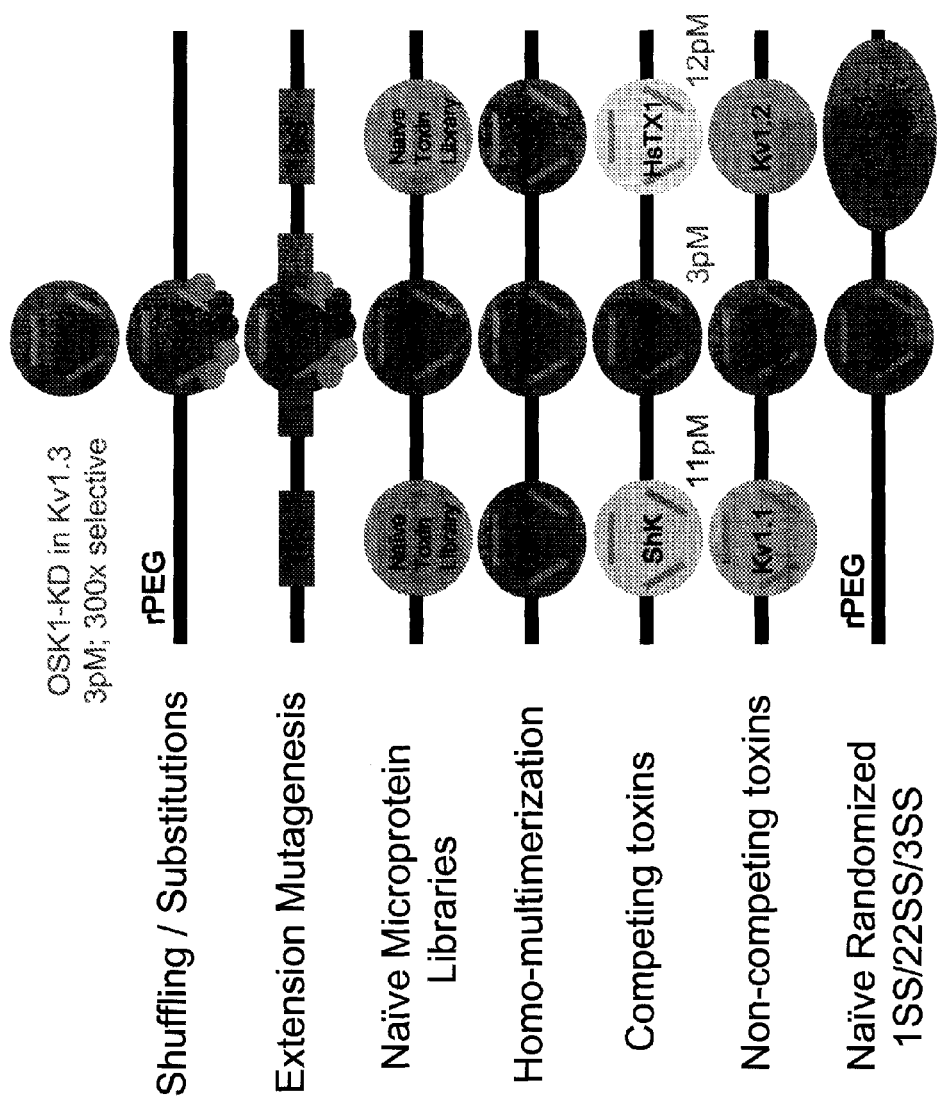
Fig. 22. Optimizing ion channel blockers

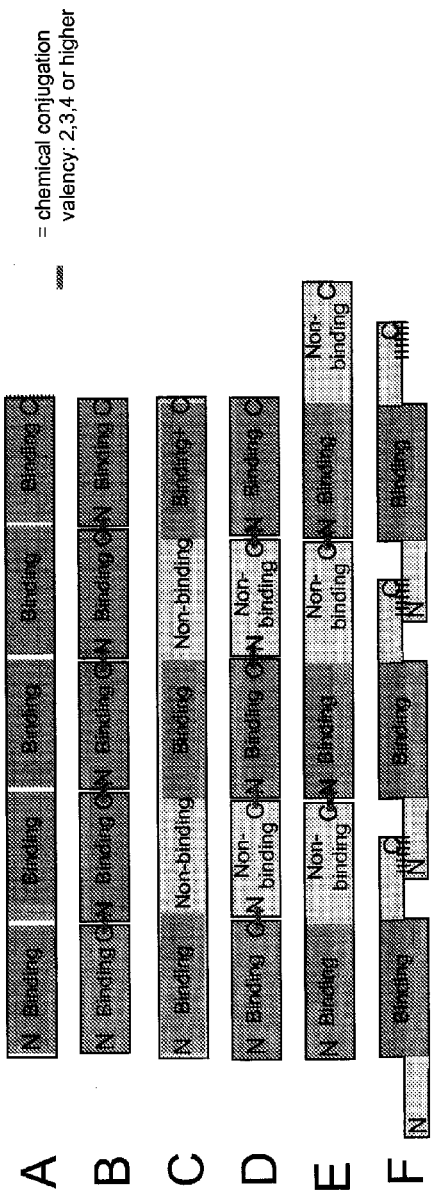

Fig. 23 Additional Halflife Concepts

A Multiple copies of the binding motif in a single protein chain. Copies can be same or different.

B Copies of a binding site are expressed as separate proteins and multimerized by chemical coupling. Various chemical coupling methods can be used (add Pierce list of coupling agents). Copies can be same or different.

C Multiple copies of a binding site in a single protein chain, but separated by non-binding linkers.

D Copies of a binding site and non-binding linker are expressed as separate proteins and multimerized by chemical coupling. Various chemical coupling methods can be used (add Pierce list of coupling agents). Copies can be same or different.

E Copies of a binding site and copies of a non-binding linker are each expressed as separate proteins and multimerized by chemical coupling. Various chemical coupling methods can be used (add Pierce list of coupling agents). Copies can be same or different.

F Copies of a binding site and a non-binding linker which contains a self-binding site are expressed as separate proteins and multimerized by self-binding of the peptides sequences. Various peptide sequences can be used (add list of peptide references). Copies can be same or different.

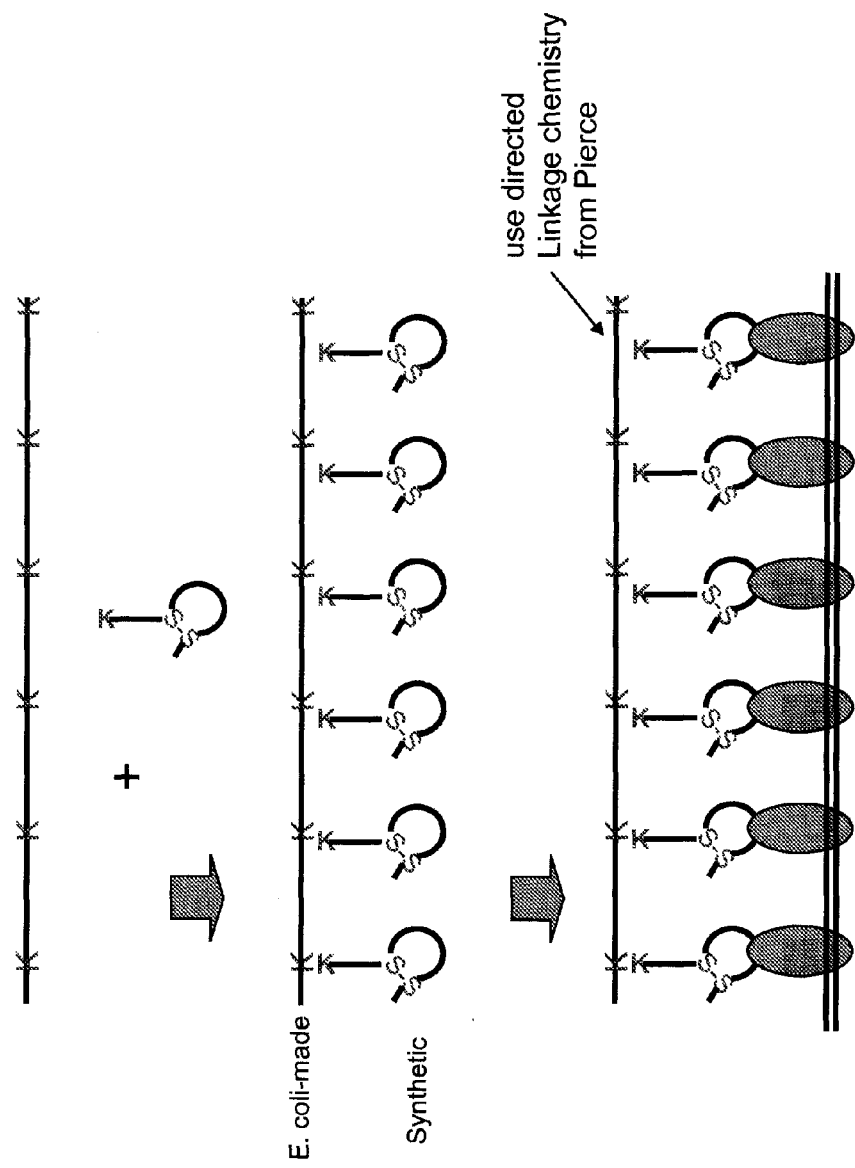

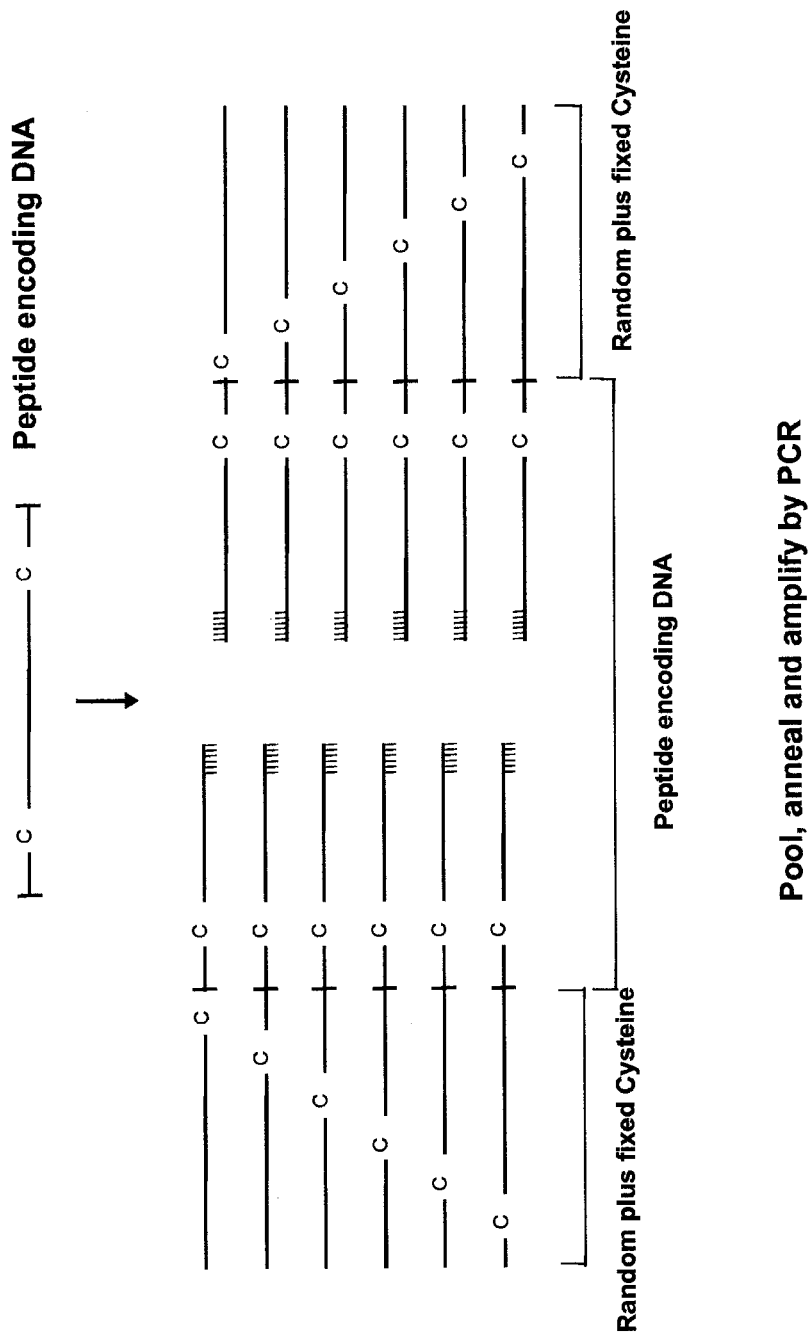
Fig. 25. Buildup of 2SS Binding Modules

Fig. 26. Buildup of 2SS Binding Modules

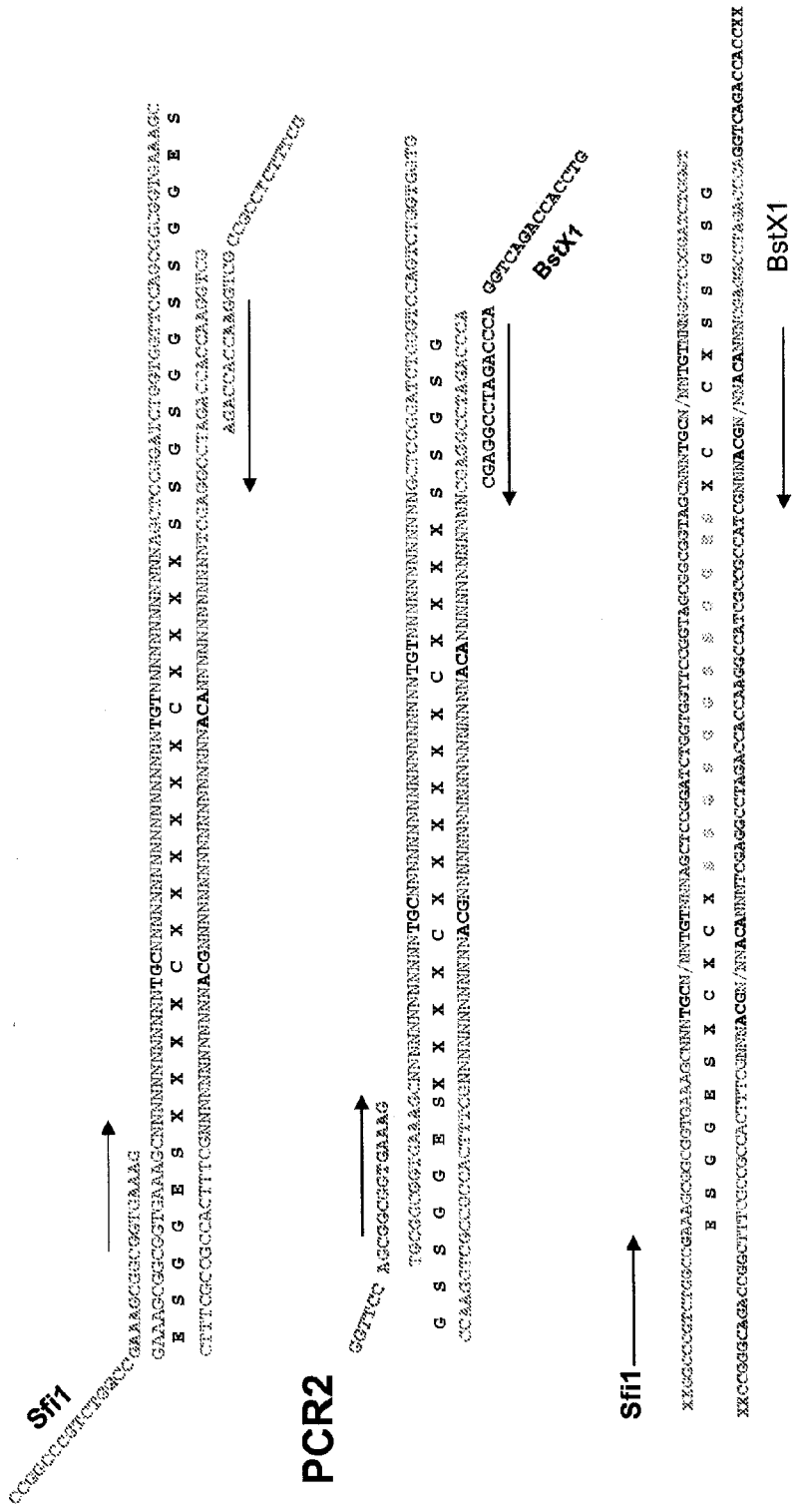
Fig. 27. Buildup by dimerization of 1SS peptides

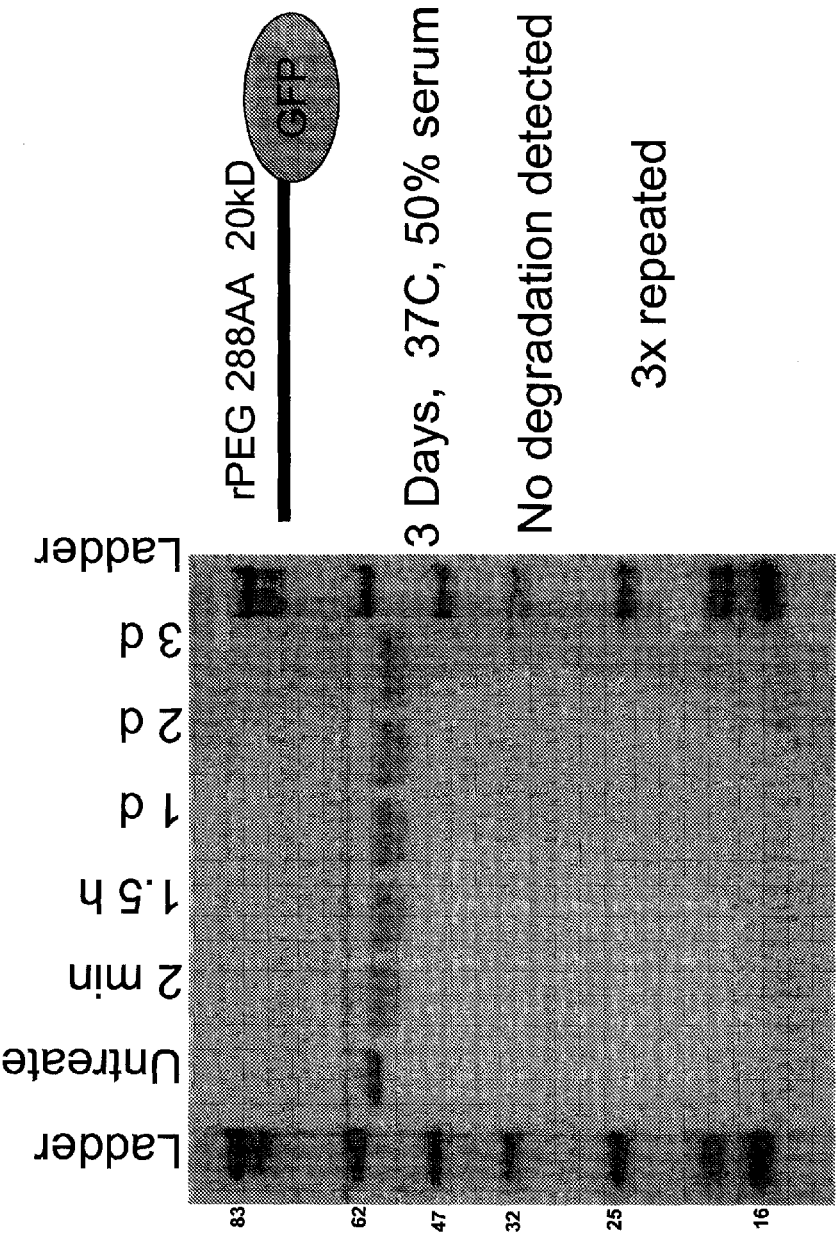
Fig. 28. Plasma stability of rPEG_J288

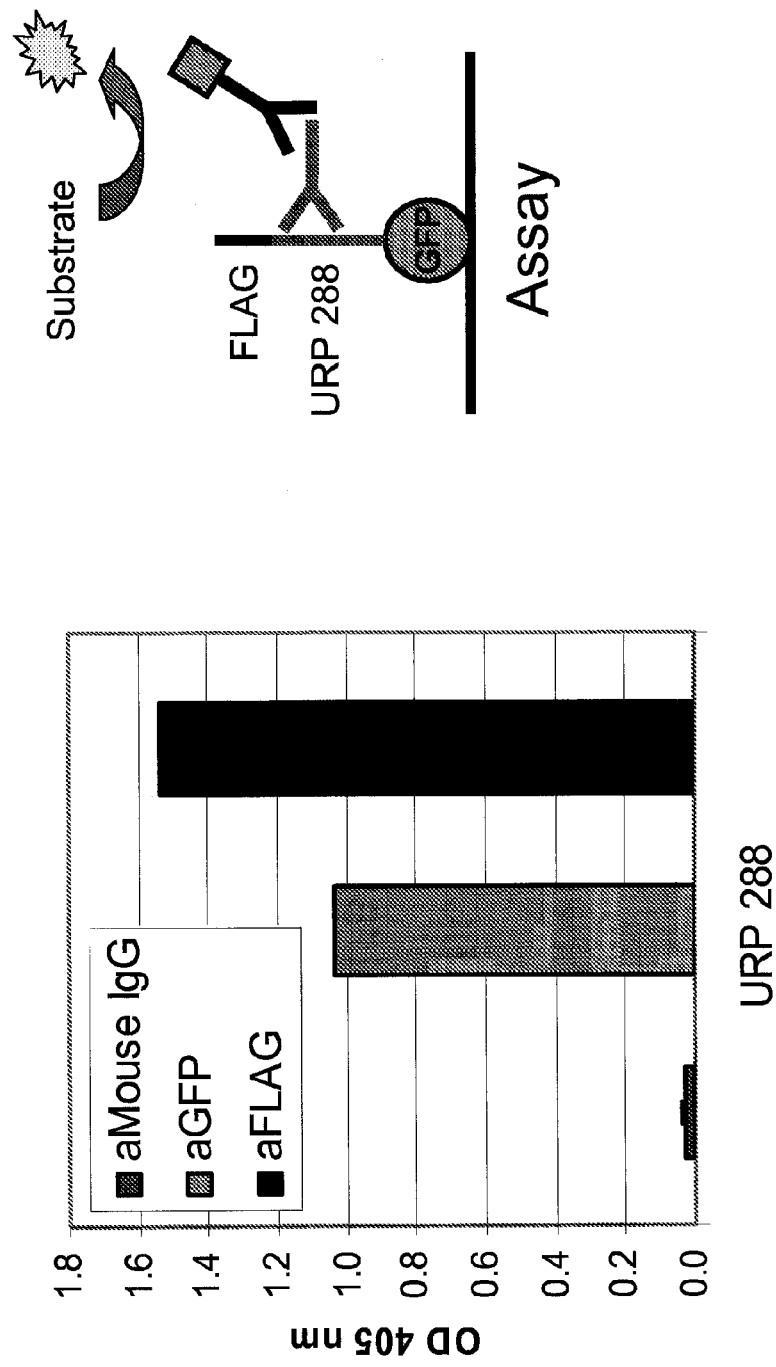
Fig. 29. Absence of pre-existing antibodies against URP

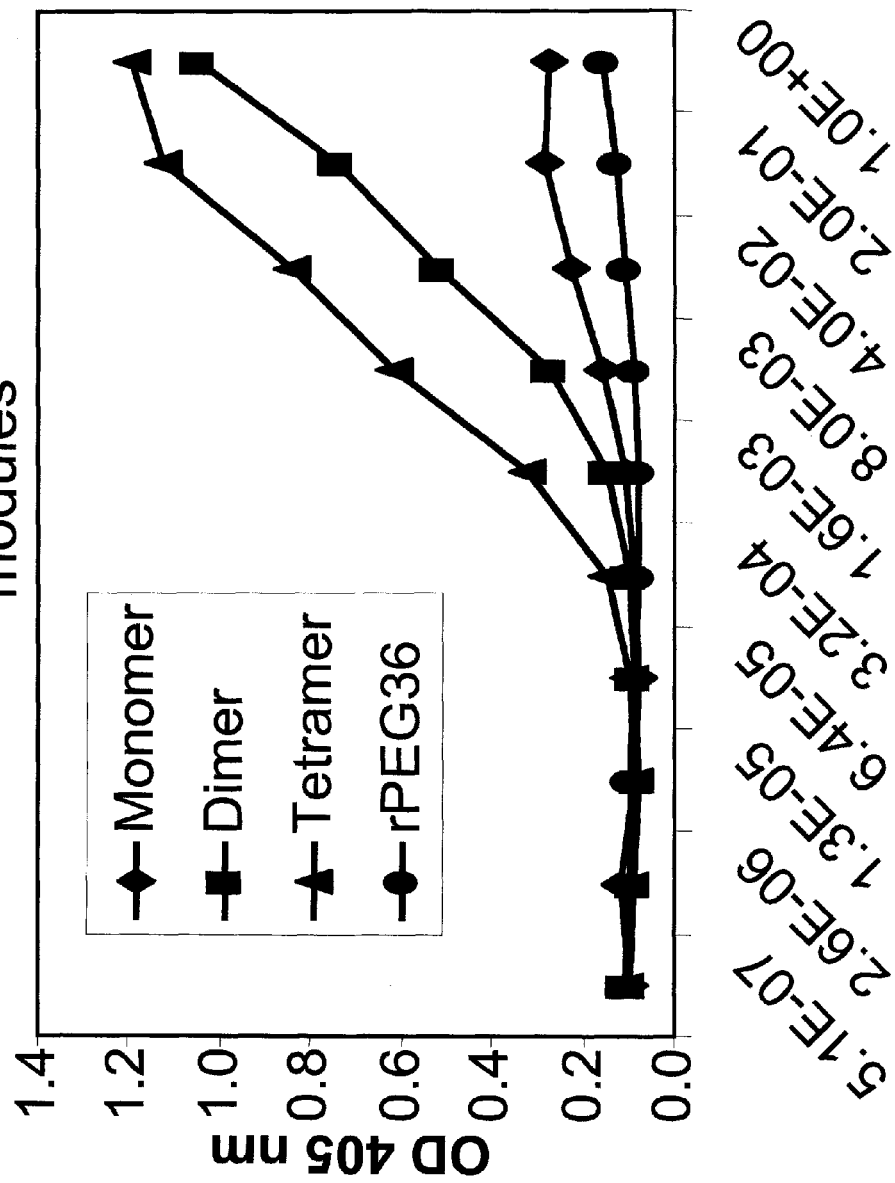
Fig. 30. Binding affinity of anti-VEGF binding modules

Fig. 31. MURP designed for drug conjugation with specificity for EpCAM

FLAG
MDYKDDDDKPGSPGSGGEGGSGGEGGSGGEGGSGGEGGSGGEGGSHTLECLGNICWVIN

URP 36                                                anti-EpCam

QGGEGGSGGEGGSGGEGGSGGEGGSGGEGGSGGEGGSHTLECLGNICWVINQGGEGGSGGEGGS

GGEGGSGGEGGSGGEGGSGGEGGSHTLECLGNICWVINQGGEGGSGGEGGSGGEGGSGGEGGSG

His tag
GEGGSGGEGGSHTLECLGNICWVINQSSLEGTHHHHHH

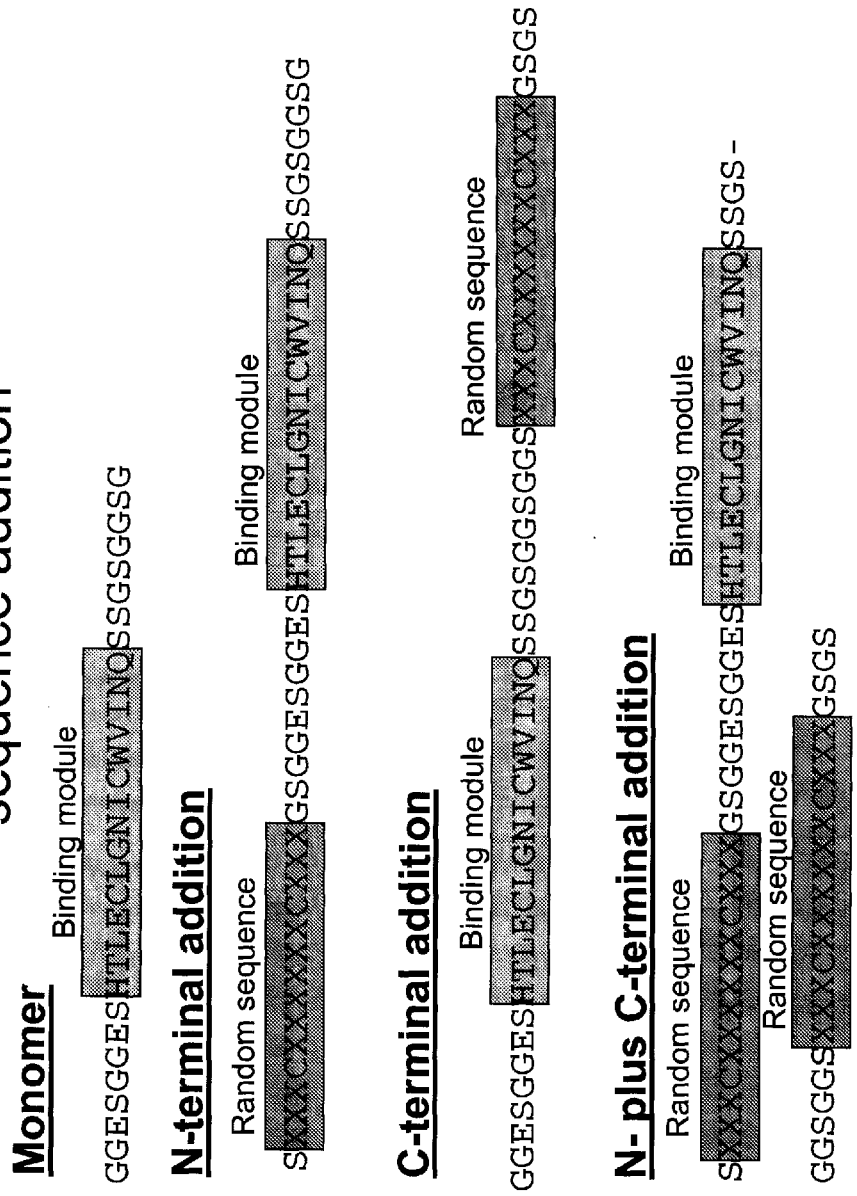

Fig. 33 Structure of Three Finger Toxin (3FT)

Short 3FT scaffold (NXSA_LATSE/22-83):
RICFNHQSSQPQTTKTCSPGESSCYNKQWSDFRGTIIERGCG
CPTVKPGIKLSCCESEVCNN

```
CFNHQSQPQTTKTCSPGESSCYNKQWSD---F-RGTIIERGCG--CPTVKPGIKLSCCESEVC
CHNQQSQPPTIKTCSEGQ--CYKKTWRD---H-RGTISERGCG--CPTVKPGIHISCCASDKC
CYKQRSQFPITTVCPGEKN-CYKKQWSG---H-RGTIIERGCG--CPSVKKGIEINCCTTDKC
CHNQQSQPPTTKSCPGDTN-CYNKRWRD---H-RGTIIERGCG--CPTVKPGINLKCCTTDRC
CYNQPSQHPTTKACPGEKN-CYRKQWSD---H-RGTIIERGCG--CPTVKPGVKLHCCTTEKC
CHNQQSQTPTTTGCSGGETNCYKKRWRD---H-RGYRTERGCG--CPIVKNGIESNCCTTDRC
CHNQMSQPPTTTRCSRWETNCYKKRWRD---H-RGYKTERGCG--CPTVKKGIQLHCCTSDNC
CFNQQSQPKTTKSCPPGENSCYNKQWRD---H-RGSITERGCG--CPKVKPGIKLRCCESEDC
CYNHQSTRATTKSC--EENSCYKKYWRD---H-RGTIIERGCG--CPKVKPGVGIHCCQSDKC
CYNHQSTPATTKSC--VENSCYKSIWAD---H-RGTIIKRGCG--CPRVKS--KIKCCKSDNC
CYNQQSEAKTTTTCSGGVSSCYKKTWSD---G-RGTIIERGCG--CPSVKKGIERICCRTDKC
CLKQEPQPETTTTCPEGEDACYNLFWSD---H-SEIKIEMGCG--CPKTEPYTNLYCCKIDSC
CYSHKLQAKTTKTC--BENSCY-KRSLP---KIPLIIIGRGCG--CPLTLPFLRIKCCTSDKC
CYSHKTQPSATITC--EEKTCY-KKSVR---KLPAIVAGRGCG--CPSKEMLVAIHCCRSDKC
CYIHKALPRATKTC--VENTCY-KMFIR---TQREYISERGCG--CPTAMWPYQTECCKGDRC
CYTHKSQAKTTKSC--EGNTCY-KMFIR---TSREYISERGCG--CPTAMWPYQTECCKGDRC
```

Fig. 34. Design of a 3FT library

SCHX$_1$X$_2$X$_3$X$_4$X$_5$X$_6$X$_7$X$_8$AVTCPPGENLCYRKMWX$_9$X$_{10}$X$_{11}$X$_{12}$X$_{13}$X$_{14}$X$_{15}$X$_{16}$X$_{17}$X$_{18}$X$_{19}$GCAATCPSVKPYEEVTCCSTDKC
G

X$_1$ – MNW (HIKLNPQRST)
X$_2$ – VVK (ADEGHKNPQRST)
X$_3$ – 50% MVA (KPQRT) and 50% KMT (ADSY)
X$_4$ – RVT (ADGNST)
X$_5$ – MVW (HKNPQRST)
X$_6$ – SCT (AP)
X$_7$ – MNA (IKLPQRT)
X$_8$ – RNM (ADEGIKNRSTV)
X$_9$ – VKT (GILRSV)

X$_{10}$ – SVT (ADGHPR)
X$_{11}$ – RST( (AGST)
X$_{12}$ – WYA (ILST)
X$_{13}$ – CST (PR)
X$_{14}$ – GVG (AEG)
X$_{15}$ – 50% RRG (EGKR) AND 50% WHT (FINSTY)
X$_{16}$ – RDA (EGIKRV)
X$_{17}$ – DYA (AILSTV)
X$_{18}$ – RDM (DEGIKNRSV)
X$_{19}$ – MKG (LMR)

Fig. 35. Alignment of Plexin sequences

```
CRHFQSCSQCLSAPPFVQCGWCHDKCVRSEECLSGTWTQQIC    MET_HUMAN/519-562
CEHFQSCSQCLSAPPFVQCGWCHNKCVRSEECPSGVWTQDVC    Q2IBC0_RHIFE/519-562
CEHFQSCSQCLSAPPFVQCGWCHDKCVRLETCPSGAWTQEIC    Q2QLD2_CARPS/119-162
CEHFQSCSQCLSAPPFVQCGWCHDKCVRSEECPSGSWTQETC    MET_OTOGA/520-563
CEHFQSCSQCLSAPPFVQCGWCQDKCVQLEECPSGTWTQEIC    Q2VHX7_PIG/519-562
CEHFQSCSQCLSAPPFVQCGWCHDRCVHLEECPTGAWTQEVC    MET_CANFA/520-563
CGHFQSCSQCLSPPYFIQCGWCHNRCVHSNECPSGTWTQEIC    MET_RAT/520-563
CHHFQSCSQCLLAPAFMRCGWCGQQCLRAPECNGGTWTQETC    Q90975_CHICK/519-562
CDHLTTCTSCLVSSRVTECGWCEGRCTRANQCPPSVWTQEYC    Q9YGM7_FUGRU/528-571
CQHFLTCAVCLTAPKFVGCGWCSGVCSWESDCDHHW-RNDSC    Q9YGN0_FUGRU/512-554
CQHFLTCAMCLMAPQFMGCGWCSGVCSWENQCDDRW-RNESC    Q4SR43_TETNG/490-532
CAHFRTCSMCLMAPRFMNCGWCSGVCSRQHECTSQW-TSASC    Q4RXB0_TETNG/431-473
CAHFRTCSMCLMAPRFMNCGWCSGVCSRQHQCDMQW-EKDSC    Q9YGM5_FUGRU/509-551
CRHFLTCGRCLRAWHFMGCGWCGNMCGQQKECPGSW-QQDHC    RON_HUMAN/526-568
CHHFLTCGSCLRAQRFMGCGWCGGMCGRQKECPGSW-QQDHC    Q6DTW4_CANFA/118-160
CRHFLTCWRCLRAQRFMGCGWCGDRCDRQKECPGSW-QQDHC    RON_MOUSE/528-570
CRHFSTCDRCLRAERFMGCGWCGNGCTRHHECAGPW-VQDSC    Q08757_CHICK/521-563
```

Fig. 36. Design of Plexin libraries

N-terminal library

SCX$_1$HX$_2$X$_3$X$_4$CX$_5$X$_6$CLX$_7$X$_8$X$_9$X$_{10}$X$_{11}$X$_{12}$X$_{13}$CGWCHDKCVRSEECLSGTWTQQICG

- X$_1$ – SRS (DEGHQR)
- X$_2$ – TTM (FL)
- X$_3$ – MNW (HIKLNPQRST)
- X$_4$ – AST (ST)
- X$_5$ – DSG (AGRSTW)
- X$_6$ – MDG (KLMQR)
- X$_7$ – VKS (GILMRSV)
- X$_8$ – KCT (AS)
- X$_9$ – 75% SMA (AEPQ) and 25% TSG (SW)
- X$_{10}$ – SVK (ADEGHPQR)
- X$_{11}$ – KKT (FV)
- X$_{12}$ – RYS (AIMTV)
- X$_{13}$ – VRS (DEGHKNQRS)

C-terminal library

SCRHFQSCSQCLSAPPFVQCGWCX$_1$X$_2$X$_3$X$_4$CX$_4$X$_5$X$_6$X$_7$X$_8$CX$_9$X$_{10}$X$_{11}$(X$_{12}$)WX$_{13}$X$_{14}$X$_{15}$X$_{16}$CG

- X$_1$ – VRT (DGHNRS)
- X$_2$ – RRT (DGNS)
- X$_3$ – RDG (EGKMRV)
- X$_4$ – RBT (AGISTV)
- X$_5$ – 75% CRM (HQR) and 25% TGG (W)
- X$_6$ – 50% KYH (SLA) and 50% SAM (DEHQ)
- X$_7$ – VAM (DEHKNQ)
- X$_8$ – SAM (DEHQ)
- X$_9$ – VMT (ADHNPT)
- X$_{10}$ – RVT (ADGNST)
- X$_{11}$ – VRS (DEGHKNQRS)
- Split with X$_{12}$ – DYT (AFISTV) and without
- X$_{13}$ – MVA (QRT)
- X$_{14}$ – MAM (HKNQ)
- X$_{15}$ – SAM (DEHQ)
- X$_{16}$ – NHT (ADFHILNPSTVY)

Fig. 37. Sequences of target-specific isolates from Plexin-based libraries

Library LMP031
SCXHXXXCXXCLXXXXXXXCGWCHDKCVRSEECLSGTWTQQICG
Library LMP032
SCRHFQSCSQCLSAPPFVQCGWCXXXCXXXXXCXXXXWXXXXCG Binders to DR4
SCHHFISCGRCLRSWHVVDCGWCHDKCVRSEECLSGTWTQQICG D4.09
SCRHFQSCSQCLSAPPFVQCGWCGDMCARVQQCHDR-WTHHACG D4.01
SCRHFQSCSQCLSAPPFVQCGWCHDKCGHQDECTAS-WRKEACG D4.03

Binders to ErbB2
SCRHFQSCSQCLSAPPFVQCGWCRNMCVQEKQCDDSIWKNQHCG E2.39
SCRHFQSCSQCLSAPPFVQCGWCRDRCSREDHCPTKIWRNHPCG E2.56
SCRHFQSCSQCLSAPPFVQCGWCNNVCSRHNDCDNN-WQHQNCG E2.57

Binders to HGFR
SCRHFQSCSQCLSAPPFVQCGWCNSMCGRAHDCTDH-WQKQHCG CM.33
SCRHFQSCSQCLSAPPFVQCGWCGNMCVRSERCHTD-WRHDTCG CM.39
SCRHFQSCSQCLSAPPFVQCGWCNSMCGRAQDCNDRIWKQHTCG CM.52

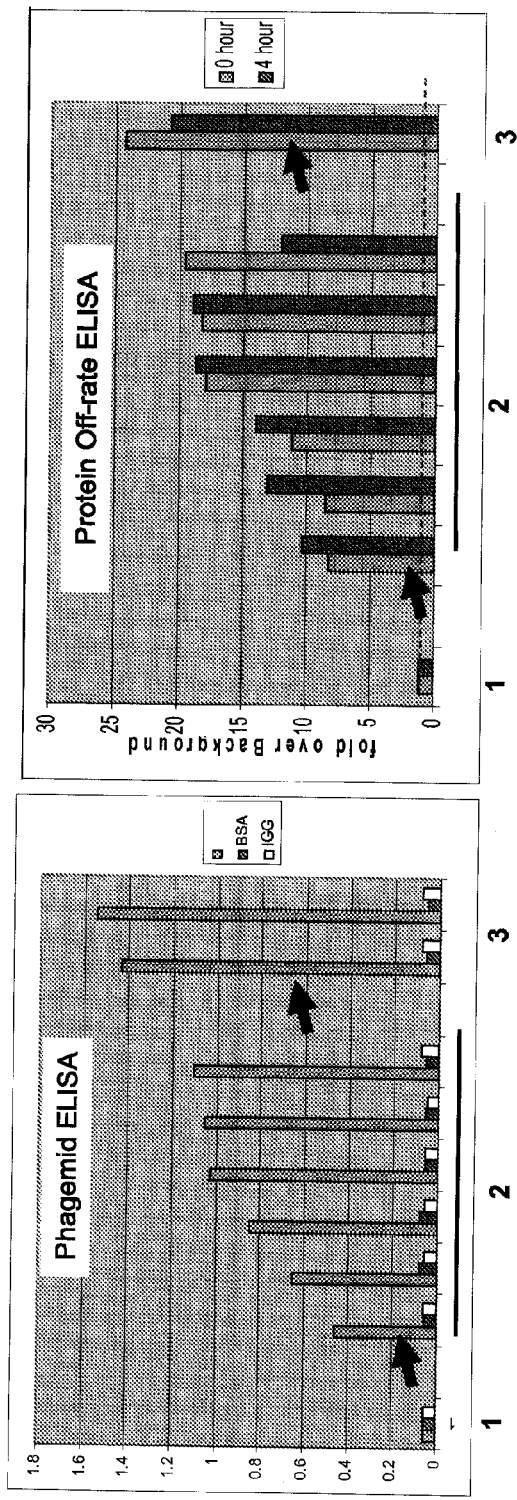
Fig. 38. Binding and expression of 2SS VEGF-binders resulting from buildup
Affinity Maturation yields improved affinity without loss of specificity

Fig. 39. Expression and sequences of 2SS VEGF binders resulting from buildup libraries
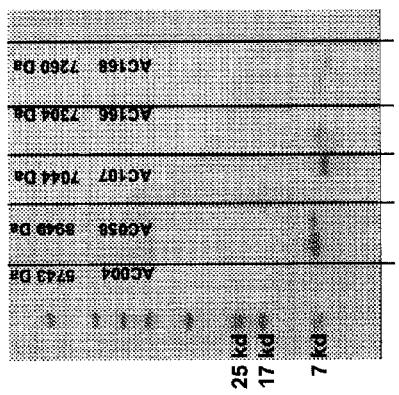
AC58
QAAGPSGPCSYYAYFTCTNHWCPSPPFAFTCTNHWCPSYYDSAYCGQSGGS
AC107
QAAGPSGPCAAYAYFTCTNHWCPSYYSAACGQSGGSG
AC166
QAAGPSGPCAYAYYFTCTNHWCPSYYAYYCGQSGGSG
AC168
QAAGPSGPCAYYSYFTCTNHW

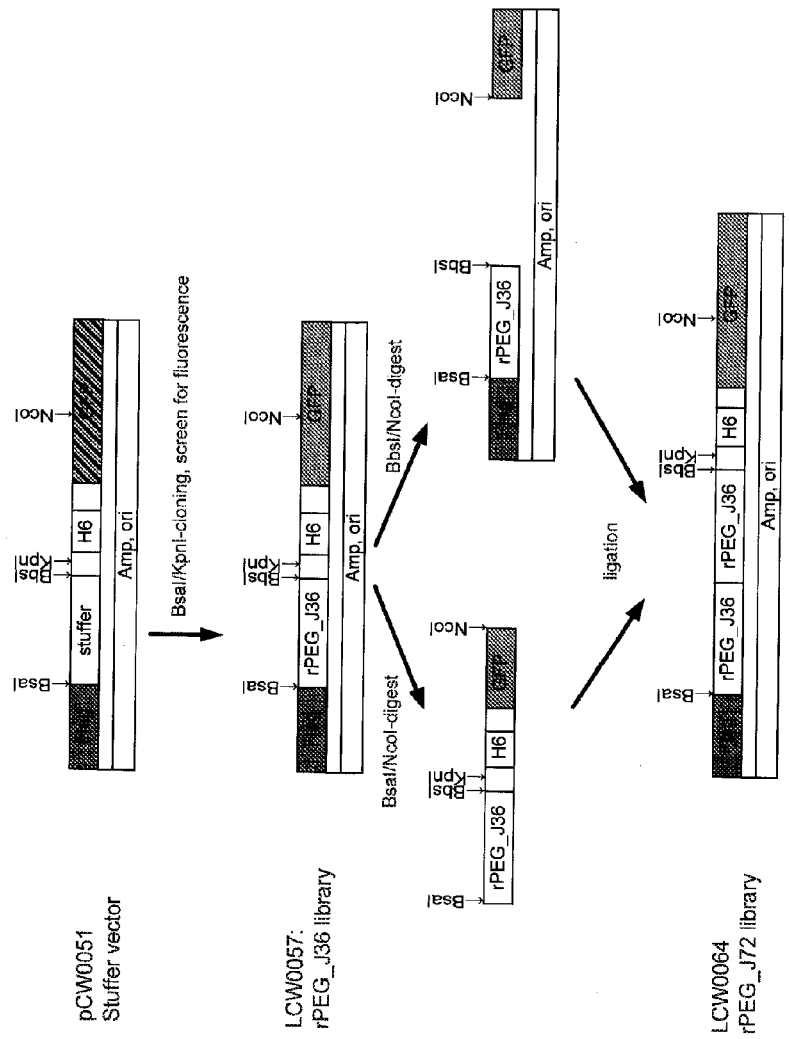
Fig. 40. Construction of rPEG_J72

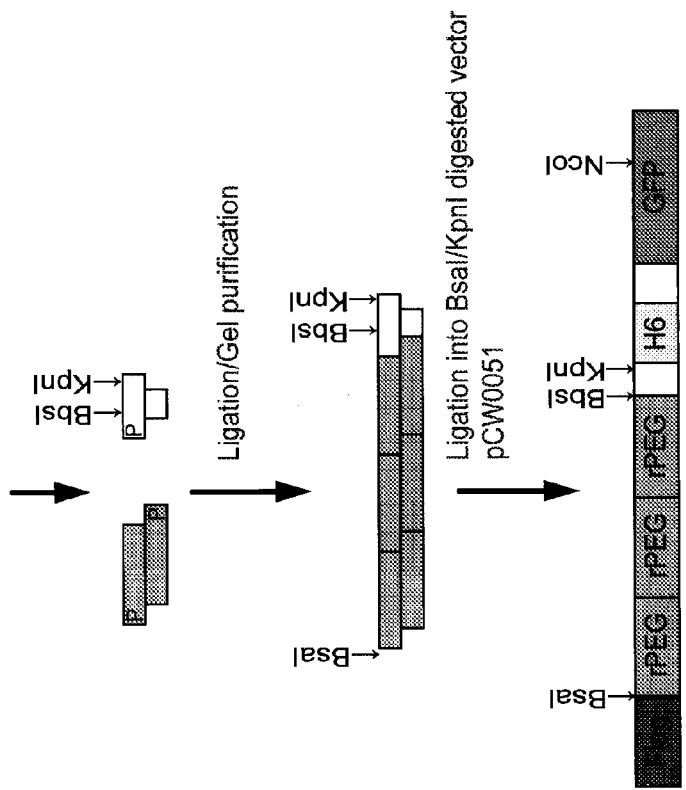
Fig. 41. Construction of an rPEG_J36 codon library

Fig. 42. Design of the pCW0051 stuffer vector

```
     Flag                          BsaI                                                                    BbsI
M  D  Y  K  D  D  D  D  K  G  S  P  G  *  *  P  R  *  *  G  G  S  S  S  L  E
ATGGATTATAAAGACGATGACGATAAAGGGTCTCCAGGTTAGTAACCTAGGTGATAGGGAGGTTCGTCTTCACTCGAG KpnI    6x His-tag
G  T  H  H  H  H  H  H  E  L  V  P  V  E  K  M
GGTACCCATCACCATCACCATCACGAGCTCGTACCGGTAGAAAAATG
```

Recognition sequences of the restriction sites are underlined. The overhangs that will be generated by BsaI and BbsI digest are shown in italics. The figure illustrates that BsaI and BbsI digest of pCW0051 generates compatible overhangs.

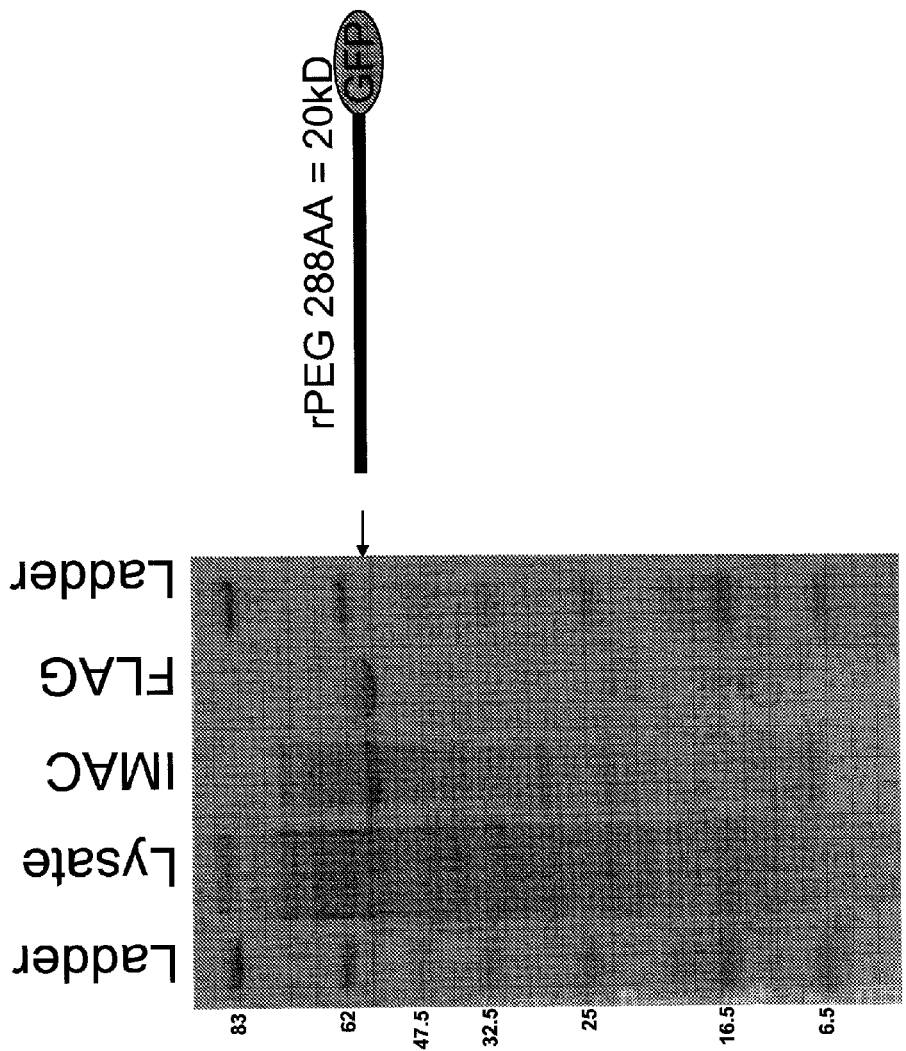
Fig. 43. Purification of Flag-rPEG_J288-H6-GFP

Fig. 44. Amino acid sequence of a fusion proteins between rPEG_J288 and effector modules

Interferon-alpha 2a: 463aa, pI=4.27, MW=41698.0 (pCW0084):

MGHHHHHHGGSGGEGGSGGEGGSGGEGGSGGEGGSGGEGGSGGEGGSGGEGGSGGEGGSGGEGGSGGEGGSGGEGGSGGEGG
SGGEGGSGGEGGSGGEGGSGGEGGSGGEGGSGGEGGSGGEGGSGGEGGSGGEGGSGGEGGSGGEGGSGGEGGSGGEGGSGGE
GGSGGEGGSGGEGGSGGEGGSGGEGGSGGEGGSGGEGGSGGEGGSGGEGGSGGEGGSGGEGGSGGEGGSGGEGGSGGEGGSG
GEGGSGGEGGSGGEGGSGGEGGSGGEGGSGGEGGSGGEGGSGGEGGSGGEGGCDLPQTHSLGSRRTLMLLAQMRKISLFSCL
KDRHDFGFPQEEFGNQFQKAETIPVLHEMIQQIFNLFSTKDSSAAWDETLLDKFYTELYQQLNDLEACVIQGVGVTETPLMK
EDSILAVRKYFQRITLYLKEKKYSPCAWEVVRAEIMRSFSLSTNLQESLRSKE*

G-CSF: 472aa, pI=4.11, MW=41128.67 (pCW0085):

MGHHHHHHGGSGGEGGSGGEGGSGGEGGSGGEGGSGGEGGSGGEGGSGGEGGSGGEGGSGGEGGSGGEGGSGGEGGSGGEGG
SGGEGGSGGEGGSGGEGGSGGEGGSGGEGGSGGEGGSGGEGGSGGEGGSGGEGGSGGEGGSGGEGGSGGEGGSGGEGGSGGE
GGSGGEGGSGGEGGSGGEGGSGGEGGSGGEGGSGGEGGSGGEGGSGGEGGSGGEGGSGGEGGSGGEGGSGGEGGSGGEGGSG
GEGGSGGEGGSGGEGGSGGEGGSGGEGGSGGEGGSGGEGGSGGEGGSGGEGGTPLGPASSLPQSFLLKCLEQVRKIQGDGAA
LQEKLCATYKLCHPEELVLLGHSLGIPWAPLSSCPSQALQLAGCLSQLHSGLFLYQGLLQALEGISPELGPTLDTLQLDVAD
FATTIWQQMEELGMAPALQPTQGAMPAFASAFQRRAGGVLVASHLQSFLEVSYRVLRHLAQP *

Human Growth Hormone: 489aa, pI=4.21, MW=44586.03 (pCW0083):

MGHHHHHHGGSGGEGGSGGEGGSGGEGGSGGEGGSGGEGGSGGEGGSGGEGGSGGEGGSGGEGGSGGEGGSGGEGGSGGEGG
SGGEGGSGGEGGSGGEGGSGGEGGSGGEGGSGGEGGSGGEGGSGGEGGSGGEGGSGGEGGSGGEGGSGGEGGSGGEGGSGGE
GGSGGEGGSGGEGGSGGEGGSGGEGGSGGEGGSGGEGGSGGEGGSGGEGGSGGEGGSGGEGGSGGEGGSGGEGGSGGEGGSG
GEGGSGGEGGSGGEGGSGGEGGSGGEGGSGGEGGSGGEGGSGGEGGSGGEGGFPTIPLSRLFDNAMLRAHRLHQLAFDTYQE
FEEAYIPKEQKYSFLQNPQTSLCFSESIPTPSNREETQQKSNLELLRISLLLIQSWLEPVQFLRSVFANSLVYGASDSNVYD
LLKDLEEGIQTLMGRLEDGSPRTGQIFKQTYSKFDTNSHNDDALLKNYGLLYCFRKDMDKVETFLRIVQCRSVEGSCGF*

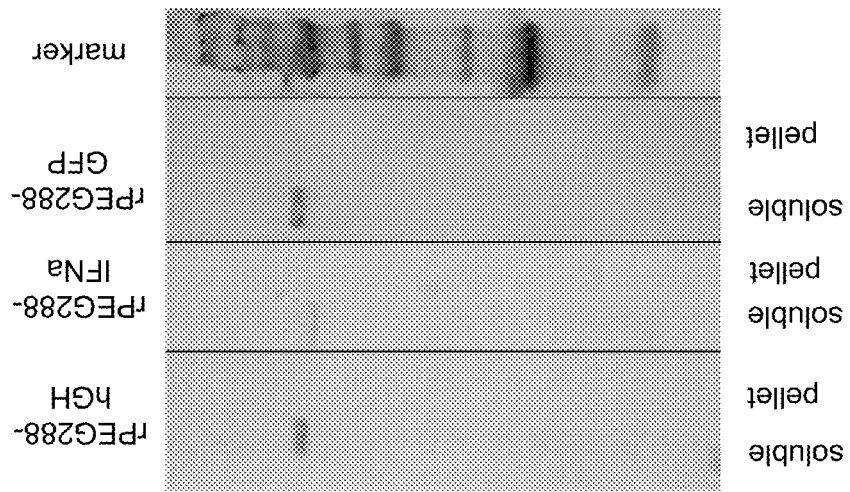
Fig. 45. Expresson of fusion proteins between rPEG_J288 and human effector modules

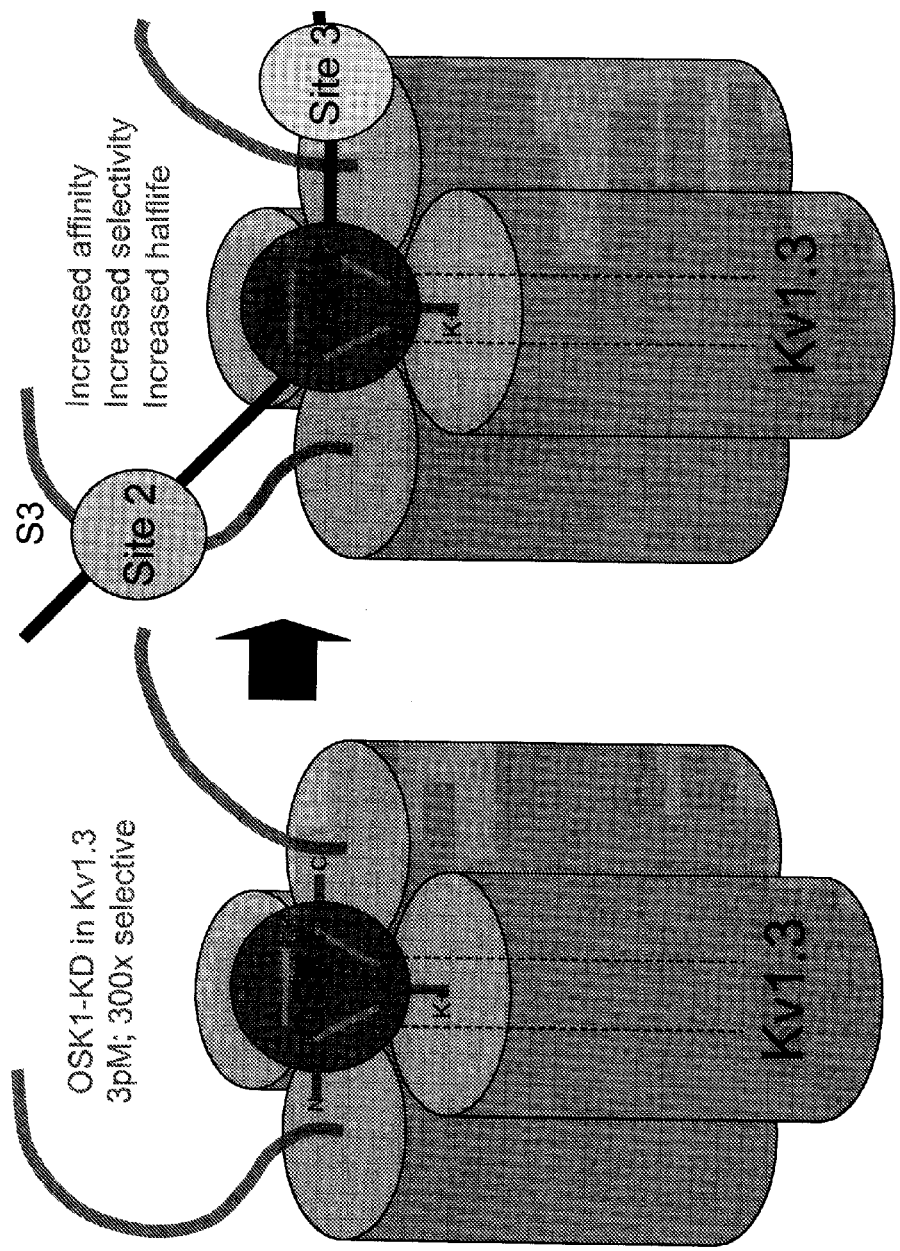
Fig. 46. Optimizing ion channel blockers

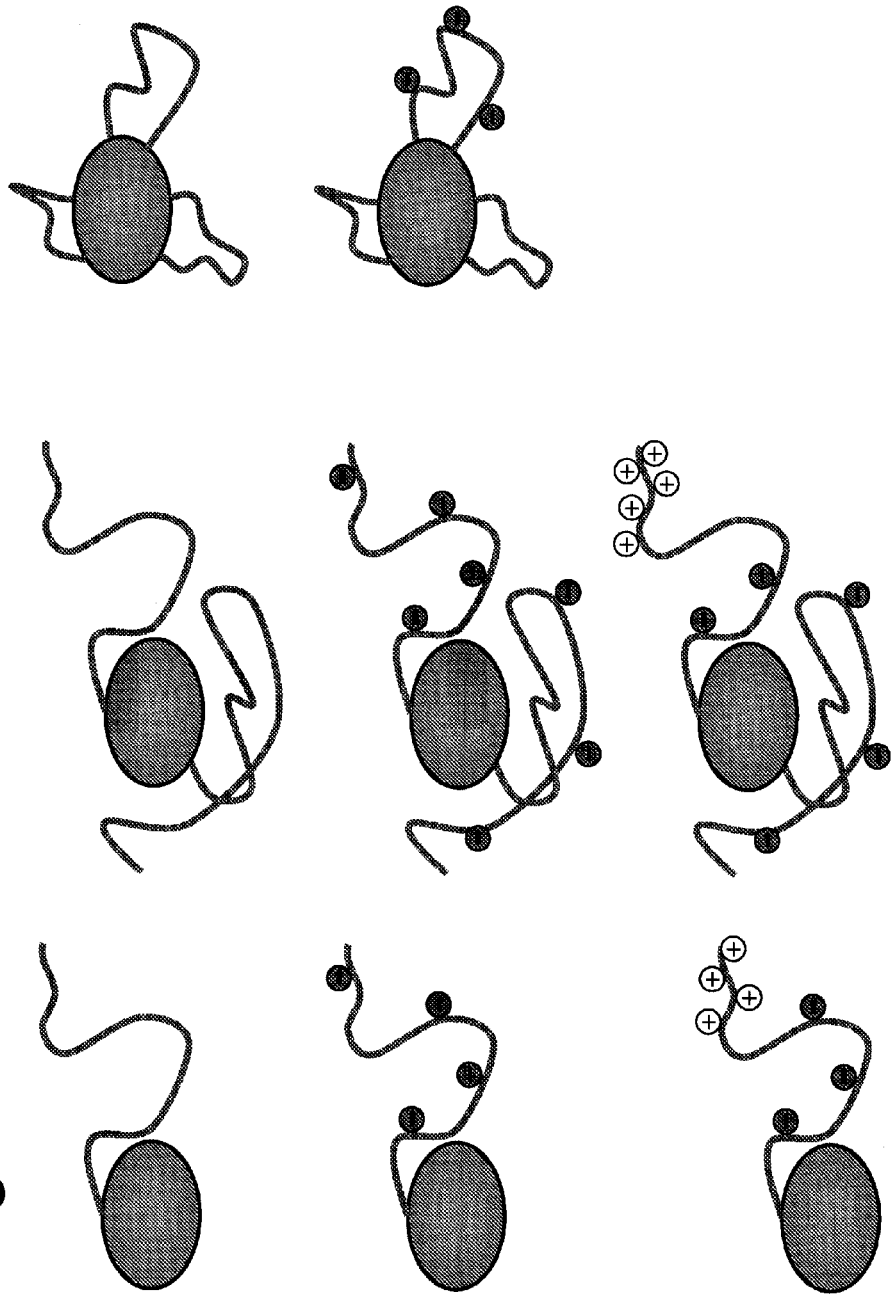
Figure 47. Product Formats

SEQUENCE LISTING

```
<160> NUMBER OF SEQ ID NOS: 366

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (9)..(11)
<223> OTHER INFORMATION: Any amino acid

<400> SEQUENCE: 1

Cys Xaa Xaa Xaa Xaa Xaa Cys Cys Xaa Xaa Xaa Cys
```

```
1               5                   10

<210> SEQ ID NO 2
<211> LENGTH: 15
<212> TYPE: PRT
<213> ORGANISM: Porcine Parvovirus

<400> SEQUENCE: 2

Ser Gly Gly Gly Gly Gly Gly Gly Gly Arg Gly Ala Gly Gly
1               5                   10                  15

<210> SEQ ID NO 3
<211> LENGTH: 17
<212> TYPE: PRT
<213> ORGANISM: Feline Panleukopenia Virus

<400> SEQUENCE: 3

Thr Gly Ser Gly Asn Gly Ser Gly Gly Gly Gly Gly Gly Ser Gly
1               5                   10                  15

Gly

<210> SEQ ID NO 4
<211> LENGTH: 17
<212> TYPE: PRT
<213> ORGANISM: Canine Parvovirus

<400> SEQUENCE: 4

Thr Gly Ser Gly Asn Gly Ser Gly Gly Gly Gly Gly Gly Ser Gly
1               5                   10                  15

Gly

<210> SEQ ID NO 5
<211> LENGTH: 12
<212> TYPE: PRT
<213> ORGANISM: Murine Minute Virus

<400> SEQUENCE: 5

Gly Gly Ser Gly Gly Gly Gly Ser Gly Gly Gly Gly
1               5                   10

<210> SEQ ID NO 6
<211> LENGTH: 37
<212> TYPE: PRT
<213> ORGANISM: Homo sapiens

<400> SEQUENCE: 6

Gly Pro Gly Gly Gly Gly Gly Pro Gly Gly Gly Gly Pro Gly Gly
1               5                   10                  15

Gly Gly Pro Gly Gly Gly Gly Gly Gly Pro Gly Gly Gly Gly
            20                  25                  30

Gly Pro Gly Gly Gly
        35

<210> SEQ ID NO 7
<211> LENGTH: 33
<212> TYPE: PRT
<213> ORGANISM: Homo sapiens

<400> SEQUENCE: 7

Gly Ala Gly Gly Gly Gly Gly Gly Gly Gly Gly Gly Gly Gly Ser
1               5                   10                  15

Gly Gly Gly Gly Gly Gly Gly Gly Ala Gly Ala Gly Gly Ala Gly Ala
```

```
                    20                  25                  30

Gly

<210> SEQ ID NO 8
<211> LENGTH: 32
<212> TYPE: PRT
<213> ORGANISM: Homo sapiens

<400> SEQUENCE: 8

Gly Gly Gly Ser Gly Ser Gly Gly Ala Gly Gly Ser Gly Gly Gly
1               5                   10                  15

Ser Gly Ser Gly Gly Gly Gly Gly Ala Gly Gly Gly Gly Gly
            20                  25                  30

<210> SEQ ID NO 9
<211> LENGTH: 27
<212> TYPE: PRT
<213> ORGANISM: Homo sapiens

<400> SEQUENCE: 9

Gly Asp Gly Gly Gly Ala Gly Gly Gly Gly Gly Gly Gly Ser Gly
1               5                   10                  15

Gly Gly Gly Ser Gly Gly Gly Gly Gly Gly
            20                  25

<210> SEQ ID NO 10
<211> LENGTH: 25
<212> TYPE: PRT
<213> ORGANISM: Homo sapiens

<400> SEQUENCE: 10

Gly Ser Gly Ser Gly Ser Gly Gly Gly Gly Gly Gly Gly Gly Gly
1               5                   10                  15

Gly Gly Ser Gly Gly Gly Gly Gly Gly
            20                  25

<210> SEQ ID NO 11
<211> LENGTH: 23
<212> TYPE: PRT
<213> ORGANISM: Homo sapiens

<400> SEQUENCE: 11

Gly Gly Gly Arg Gly Gly Arg Gly Gly Arg Gly Gly Gly Arg
1               5                   10                  15

Gly Gly Gly Arg Gly Gly Gly
            20

<210> SEQ ID NO 12
<211> LENGTH: 33
<212> TYPE: PRT
<213> ORGANISM: Homo sapiens

<400> SEQUENCE: 12

Gly Ala Gly Gly Gly Gly Gly Gly Gly Gly Gly Gly Gly Gly Ser
1               5                   10                  15

Gly Gly Gly Gly Gly Gly Gly Ala Gly Ala Gly Gly Ala Gly Ala
            20                  25                  30

Gly

<210> SEQ ID NO 13
<211> LENGTH: 32
```

```
<212> TYPE: PRT
<213> ORGANISM: Homo sapiens

<400> SEQUENCE: 13

Gly Gly Gly Ser Gly Ser Gly Gly Ala Gly Gly Ser Gly Gly
1               5                   10                  15

Ser Gly Ser Gly Gly Gly Gly Gly Ala Gly Gly Gly Gly Gly
            20                  25                  30

<210> SEQ ID NO 14
<211> LENGTH: 27
<212> TYPE: PRT
<213> ORGANISM: Homo sapiens

<400> SEQUENCE: 14

Gly Asp Gly Gly Gly Ala Gly Gly Gly Gly Gly Gly Ser Gly
1               5                   10                  15

Gly Gly Gly Ser Gly Gly Gly Gly Gly Gly
            20                  25

<210> SEQ ID NO 15
<211> LENGTH: 21
<212> TYPE: PRT
<213> ORGANISM: Homo sapiens

<400> SEQUENCE: 15

Gly Ser Gly Gly Ser Gly Ser Gly Gly Pro Gly Pro Gly Pro
1               5                   10                  15

Gly Gly Gly Gly Gly
            20

<210> SEQ ID NO 16
<211> LENGTH: 18
<212> TYPE: PRT
<213> ORGANISM: Homo sapiens

<400> SEQUENCE: 16

Gly Glu Gly Gly Gly Gly Gly Gly Glu Gly Gly Ala Gly Gly
1               5                   10                  15

Ser Gly

<210> SEQ ID NO 17
<211> LENGTH: 12
<212> TYPE: PRT
<213> ORGANISM: Homo sapiens

<400> SEQUENCE: 17

Gly Gly Gly Gly Gly Gly Gly Gly Asp Gly Gly Gly
1               5                   10

<210> SEQ ID NO 18
<211> LENGTH: 46
<212> TYPE: PRT
<213> ORGANISM: Homo sapiens

<400> SEQUENCE: 18

Gly Gly Gly Ser Gly Ser Gly Gly Ala Gly Gly Ser Gly Gly
1               5                   10                  15

Ser Gly Ser Gly Gly Gly Gly Gly Ala Gly Gly Gly Gly Gly
            20                  25                  30

Ser Ser Gly Gly Gly Ser Gly Thr Ala Gly Gly His Ser Gly
            35                  40                  45
```

```
<210> SEQ ID NO 19
<211> LENGTH: 37
<212> TYPE: PRT
<213> ORGANISM: Homo sapiens

<400> SEQUENCE: 19

Gly Pro Gly Gly Gly Gly Pro Gly Gly Gly Gly Pro Gly Gly
1               5                   10                  15

Gly Gly Pro Gly Gly Gly Gly Gly Gly Pro Gly Gly Gly Gly
            20                  25                  30

Gly Pro Gly Gly Gly
        35

<210> SEQ ID NO 20
<211> LENGTH: 35
<212> TYPE: PRT
<213> ORGANISM: Homo sapiens

<400> SEQUENCE: 20

Gly Gly Ser Gly Ala Gly Gly Gly Gly Gly Gly Gly Gly Gly
1               5                   10                  15

Ser Gly Ser Gly Gly Gly Ser Thr Gly Gly Gly Gly Thr Ala
            20                  25                  30

Gly Gly Gly
        35

<210> SEQ ID NO 21
<211> LENGTH: 33
<212> TYPE: PRT
<213> ORGANISM: Homo sapiens

<400> SEQUENCE: 21

Gly Ala Gly Gly Gly Gly Gly Gly Gly Gly Gly Gly Gly Ser
1               5                   10                  15

Gly Gly Gly Gly Gly Gly Gly Ala Gly Ala Gly Gly Ala Gly Ala
            20                  25                  30

Gly

<210> SEQ ID NO 22
<211> LENGTH: 33
<212> TYPE: PRT
<213> ORGANISM: Homo sapiens

<400> SEQUENCE: 22

Gly Ala Gly Gly Gly Gly Gly Gly Gly Gly Gly Gly Gly Ser
1               5                   10                  15

Gly Gly Gly Gly Gly Gly Gly Ala Gly Ala Gly Gly Ala Gly Ala
            20                  25                  30

Gly

<210> SEQ ID NO 23
<211> LENGTH: 33
<212> TYPE: PRT
<213> ORGANISM: Homo sapiens

<400> SEQUENCE: 23

Gly Ala Gly Gly Gly Gly Gly Gly Gly Gly Gly Gly Gly Ser
1               5                   10                  15

Gly Gly Gly Gly Gly Gly Gly Gly Ala Gly Ala Gly Gly Ala Gly Ala
```

-continued

```
                20                  25                  30

Gly

<210> SEQ ID NO 24
<211> LENGTH: 32
<212> TYPE: PRT
<213> ORGANISM: Homo sapiens

<400> SEQUENCE: 24

Gly His Pro Gly Ser Gly Ser Gly Ser Gly Gly Gly Gly Gly Gly Gly
1               5                   10                  15

Gly Gly Gly Gly Gly Ser Gly Gly Gly Gly Gly Ala Pro Gly Gly
            20                  25                  30

<210> SEQ ID NO 25
<211> LENGTH: 31
<212> TYPE: PRT
<213> ORGANISM: Homo sapiens

<400> SEQUENCE: 25

Gly Gly Gly Gly Ser Gly Gly Gly Gly Gly Gly Gly Gly Gly Gly Gly
1               5                   10                  15

Gly Gly Gly Ser Gly Ser Thr Gly Gly Gly Ser Gly Ala Gly
            20                  25                  30

<210> SEQ ID NO 26
<211> LENGTH: 31
<212> TYPE: PRT
<213> ORGANISM: Homo sapiens

<400> SEQUENCE: 26

Gly Gly Arg Gly Arg Gly Gly Arg Gly Arg Gly Ser Arg Gly Arg Gly
1               5                   10                  15

Gly Gly Gly Thr Arg Gly Arg Gly Arg Gly Arg Gly Gly Arg Gly
            20                  25                  30

<210> SEQ ID NO 27
<211> LENGTH: 30
<212> TYPE: PRT
<213> ORGANISM: Homo sapiens

<400> SEQUENCE: 27

Gly Ser Gly Gly Ser Gly Gly Ser Gly Gly Gly Pro Gly Pro Gly Pro
1               5                   10                  15

Gly Gly Gly Gly Gly Pro Ser Gly Ser Gly Ser Gly Pro Gly
            20                  25                  30

<210> SEQ ID NO 28
<211> LENGTH: 29
<212> TYPE: PRT
<213> ORGANISM: Homo sapiens

<400> SEQUENCE: 28

Gly Gly Gly Gly Gly Gly Gly Gly Gly Gly Arg Gly Gly Gly Gly Gly
1               5                   10                  15

Arg Gly Gly Gly Arg Gly Gly Gly Glu Gly Gly Gly
            20                  25

<210> SEQ ID NO 29
<211> LENGTH: 28
<212> TYPE: PRT
<213> ORGANISM: Homo sapiens
```

```
<400> SEQUENCE: 29

Gly Gly Gly Gly Thr Gly Ser Ser Gly Ser Gly Ser Gly Gly
1               5                   10                  15

Gly Ser Gly Gly Gly Gly Gly Gly Ser Ser Gly
                20                  25

<210> SEQ ID NO 30
<211> LENGTH: 27
<212> TYPE: PRT
<213> ORGANISM: Homo sapiens

<400> SEQUENCE: 30

Gly Asp Gly Gly Gly Ala Gly Gly Gly Gly Gly Gly Ser Gly
1               5                   10                  15

Gly Gly Gly Ser Gly Gly Gly Gly Gly Gly Gly
                20                  25

<210> SEQ ID NO 31
<211> LENGTH: 27
<212> TYPE: PRT
<213> ORGANISM: Homo sapiens

<400> SEQUENCE: 31

Gly Gly Gly Gly Gly Gly Ser Gly Gly Gly Gly Ser Gly Gly
1               5                   10                  15

Gly Gly Ser Gly Gly Gly Arg Gly Ala Gly Gly
                20                  25

<210> SEQ ID NO 32
<211> LENGTH: 27
<212> TYPE: PRT
<213> ORGANISM: Homo sapiens

<400> SEQUENCE: 32

Gly Gly Gly Ala Ala Gly Ala Gly Gly Gly Ser Gly Ala Gly Gly
1               5                   10                  15

Gly Ser Gly Gly Ser Gly Gly Arg Gly Thr Gly
                20                  25

<210> SEQ ID NO 33
<211> LENGTH: 27
<212> TYPE: PRT
<213> ORGANISM: Homo sapiens

<400> SEQUENCE: 33

Gly Ala Gly Gly Gly Arg Gly Gly Gly Ala Gly Gly Glu Gly Ala
1               5                   10                  15

Ser Gly Ala Glu Gly Gly Gly Gly Ala Gly Gly
                20                  25

<210> SEQ ID NO 34
<211> LENGTH: 27
<212> TYPE: PRT
<213> ORGANISM: Homo sapiens

<400> SEQUENCE: 34

Gly Asp Gly Gly Gly Ala Gly Gly Gly Gly Gly Gly Gly Ser Gly
1               5                   10                  15

Gly Gly Gly Ser Gly Gly Gly Gly Gly Gly
                20                  25
```

<210> SEQ ID NO 35
<211> LENGTH: 26
<212> TYPE: PRT
<213> ORGANISM: Homo sapiens

<400> SEQUENCE: 35

Gly Gly Gly Gly Gly Gly Gly Gly Gly Gly Gly Gly Gly Gly
1               5                   10                  15
Gly Gly Gly Gly Gly Gly Gly Glu Ala Gly
            20                  25

<210> SEQ ID NO 36
<211> LENGTH: 26
<212> TYPE: PRT
<213> ORGANISM: Homo sapiens

<400> SEQUENCE: 36

Gly Gly Gly Gly Gly Gly Ser Ala Gly Gly Ser Ser Gly Gly Gly
1               5                   10                  15
Pro Gly Gly Gly Gly Gly Gly Ala Gly Gly
            20                  25

<210> SEQ ID NO 37
<211> LENGTH: 25
<212> TYPE: PRT
<213> ORGANISM: Homo sapiens

<400> SEQUENCE: 37

Gly Gly Gly Gly Gly Pro Gly Gly Gly Gly Gly Gly Pro Gly Gly
1               5                   10                  15
Gly Gly Gly Pro Gly Gly Gly Gly Gly
            20                  25

<210> SEQ ID NO 38
<211> LENGTH: 25
<212> TYPE: PRT
<213> ORGANISM: Homo sapiens

<400> SEQUENCE: 38

Gly Arg Gly Gly Ala Gly Ser Gly Gly Ala Gly Ser Gly Ala Ala Gly
1               5                   10                  15
Gly Thr Gly Ser Ser Gly Gly Gly Gly
            20                  25

<210> SEQ ID NO 39
<211> LENGTH: 25
<212> TYPE: PRT
<213> ORGANISM: Homo sapiens

<400> SEQUENCE: 39

Gly Gly Gly Gly Gly Gly Gly Gly Gly Gly Ser Gly Gly Ser Gly
1               5                   10                  15
Gly Gly Gly Gly Gly Gly Gly Gly Gly
            20                  25

<210> SEQ ID NO 40
<211> LENGTH: 25
<212> TYPE: PRT
<213> ORGANISM: Homo sapiens

<400> SEQUENCE: 40

Gly Gly Ser Gly Gly Gly Arg Gly Gly Ala Ser Gly Pro Gly Ser Gly

```
                1               5                   10                  15
Ser Gly Gly Pro Gly Gly Pro Ala Gly
            20                  25

<210> SEQ ID NO 41
<211> LENGTH: 25
<212> TYPE: PRT
<213> ORGANISM: Homo sapiens

<400> SEQUENCE: 41

Gly Gly His His Gly Asp Arg Gly Gly Arg Gly Arg Gly Gly
1               5                   10                  15

Arg Gly Gly Arg Gly Gly Arg Ala Gly
            20                  25

<210> SEQ ID NO 42
<211> LENGTH: 25
<212> TYPE: PRT
<213> ORGANISM: Homo sapiens

<400> SEQUENCE: 42

Gly Ser Arg Gly Gly Gly Gly Gly Gly Gly Gly Gly Gly Gly
1               5                   10                  15

Gly Gly Gly Ala Gly Ala Gly Gly Gly
            20                  25

<210> SEQ ID NO 43
<211> LENGTH: 24
<212> TYPE: PRT
<213> ORGANISM: Homo sapiens

<400> SEQUENCE: 43

Gly Gly Arg Gly Gly Arg Gly Pro Gly Glu Pro Gly Arg Gly Arg
1               5                   10                  15

Ala Gly Gly Ala Glu Gly Arg Gly
            20

<210> SEQ ID NO 44
<211> LENGTH: 24
<212> TYPE: PRT
<213> ORGANISM: Homo sapiens

<400> SEQUENCE: 44

Gly Gly Gly Gly Gly Asp Ala Gly Ser Gly Asp Ala Gly Ala
1               5                   10                  15

Gly Gly Arg Ala Gly Arg Ala Gly
            20

<210> SEQ ID NO 45
<211> LENGTH: 23
<212> TYPE: PRT
<213> ORGANISM: Homo sapiens

<400> SEQUENCE: 45

Gly Gly Gly Arg Gly Gly Arg Gly Gly Arg Gly Gly Gly Arg
1               5                   10                  15

Gly Gly Gly Arg Gly Gly Gly
            20

<210> SEQ ID NO 46
<211> LENGTH: 23
<212> TYPE: PRT
```

<213> ORGANISM: Homo sapiens

<400> SEQUENCE: 46

Gly Gly Ser Gly Gly Gly Gly Gly Ser Ser Gly Gly Arg Gly Ser
1               5                   10                  15

Gly Gly Gly Ser Ser Gly Gly
            20

<210> SEQ ID NO 47
<211> LENGTH: 23
<212> TYPE: PRT
<213> ORGANISM: Homo sapiens

<400> SEQUENCE: 47

Gly Ser Gly Pro Gly Thr Gly Gly Gly Ser Gly Ser Gly Gly
1               5                   10                  15

Gly Gly Gly Ser Gly Gly Gly
            20

<210> SEQ ID NO 48
<211> LENGTH: 23
<212> TYPE: PRT
<213> ORGANISM: Homo sapiens

<400> SEQUENCE: 48

Gly Ala Arg Gly Gly Gly Ser Gly Gly Gly Gly Gly Gly Gly
1               5                   10                  15

Gly Gly Gly Gly Gly Pro Gly
            20

<210> SEQ ID NO 49
<211> LENGTH: 23
<212> TYPE: PRT
<213> ORGANISM: Homo sapiens

<400> SEQUENCE: 49

Gly Gly Gly Gly Gly Gly Gly Gly Gly Gly Gly Gly Gly Gly
1               5                   10                  15

Gly Gly Gly Gly Gly Asp Gly
            20

<210> SEQ ID NO 50
<211> LENGTH: 23
<212> TYPE: PRT
<213> ORGANISM: Homo sapiens

<400> SEQUENCE: 50

Gly Gly Thr Arg Gly Gly Thr Arg Gly Gly Thr Arg Gly Gly Asp Arg
1               5                   10                  15

Gly Arg Gly Arg Gly Ala Gly
            20

<210> SEQ ID NO 51
<211> LENGTH: 23
<212> TYPE: PRT
<213> ORGANISM: Homo sapiens

<400> SEQUENCE: 51

Gly Gly Thr Arg Gly Gly Thr Arg Gly Gly Thr Arg Gly Gly Asp Arg
1               5                   10                  15

Gly Arg Gly Arg Gly Ala Gly
            20

<210> SEQ ID NO 52
<211> LENGTH: 23
<212> TYPE: PRT
<213> ORGANISM: Homo sapiens

<400> SEQUENCE: 52

Gly Ala Gly Gly Gly Gly Gly Gly Gly Gly Gly Gly Gly Gly Gly
1               5                   10                  15

Ala Gly Gly Gly Gly Gly Gly
            20

<210> SEQ ID NO 53
<211> LENGTH: 23
<212> TYPE: PRT
<213> ORGANISM: Homo sapiens

<400> SEQUENCE: 53

Gly Gly Gly Arg Gly Gly Arg Gly Gly Arg Gly Gly Gly Arg
1               5                   10                  15

Gly Gly Gly Arg Gly Gly Gly
            20

<210> SEQ ID NO 54
<211> LENGTH: 22
<212> TYPE: PRT
<213> ORGANISM: Homo sapiens

<400> SEQUENCE: 54

Gly Arg Gly Arg Gly Gly Gly Gly Gly Gly Gly Gly Gly Gly Gly
1               5                   10                  15

Gly Arg Gly Gly Gly Gly
            20

<210> SEQ ID NO 55
<211> LENGTH: 22
<212> TYPE: PRT
<213> ORGANISM: Homo sapiens

<400> SEQUENCE: 55

Gly Arg Gly Arg Gly Arg Gly Arg Gly Arg Gly Arg Gly Arg Gly Arg
1               5                   10                  15

Gly Arg Gly Gly Ala Gly
            20

<210> SEQ ID NO 56
<211> LENGTH: 22
<212> TYPE: PRT
<213> ORGANISM: Homo sapiens

<400> SEQUENCE: 56

Gly Ala Gly Gly Gly Gly Gly Gly Gly Gly Gly Gly Gly Gly Gly Gly
1               5                   10                  15

Gly Gly Gly Gly Gly Gly
            20

<210> SEQ ID NO 57
<211> LENGTH: 22
<212> TYPE: PRT
<213> ORGANISM: Homo sapiens

<400> SEQUENCE: 57

Gly Gly Gly Ser Gly Gly His Ser Gly Ser Gly Gly His
1               5                   10                  15

Ser Gly Gly Ser Gly Gly
            20

<210> SEQ ID NO 58
<211> LENGTH: 22
<212> TYPE: PRT
<213> ORGANISM: Homo sapiens

<400> SEQUENCE: 58

Gly Ala Gly Ala Gly Gly Gly Gly Gly Gly Gly Ala Gly Gly
1               5                   10                  15

Gly Ser Ala Gly Ser Gly
            20

<210> SEQ ID NO 59
<211> LENGTH: 22
<212> TYPE: PRT
<213> ORGANISM: Homo sapiens

<400> SEQUENCE: 59

Gly Gly Pro Gly Thr Gly Ser Gly Gly Gly Ala Gly Thr Gly Gly
1               5                   10                  15

Gly Ala Gly Gly Pro Gly
            20

<210> SEQ ID NO 60
<211> LENGTH: 22
<212> TYPE: PRT
<213> ORGANISM: Homo sapiens

<400> SEQUENCE: 60

Gly Gly Gly Gly Gly Gly Gly Gly Ala Gly Gly Ala Gly Gly Ala
1               5                   10                  15

Gly Ser Ala Gly Gly Gly
            20

<210> SEQ ID NO 61
<211> LENGTH: 21
<212> TYPE: PRT
<213> ORGANISM: Homo sapiens

<400> SEQUENCE: 61

Gly Gly Asp Gly Gly Gly Ser Ala Gly Gly Ala Gly Gly Gly Ser
1               5                   10                  15

Gly Gly Gly Ala Gly
            20

<210> SEQ ID NO 62
<211> LENGTH: 21
<212> TYPE: PRT
<213> ORGANISM: Homo sapiens

<400> SEQUENCE: 62

Gly Gly Gly Gly Gly Gly Ser Gly Gly Gly Gly Gly Gly Gly
1               5                   10                  15

Gly Gly Gly Gly Gly
            20

<210> SEQ ID NO 63
<211> LENGTH: 21

```
<212> TYPE: PRT
<213> ORGANISM: Homo sapiens

<400> SEQUENCE: 63

Gly Pro Gly Ala Gly Ala Gly Ser Gly Ala Gly Gly Ser Ser Gly Gly
1               5                   10                  15

Gly Gly Gly Pro Gly
            20

<210> SEQ ID NO 64
<211> LENGTH: 21
<212> TYPE: PRT
<213> ORGANISM: Homo sapiens

<400> SEQUENCE: 64

Gly Gly Gly Gly Gly Gly Gly Gly Gly Gly Ser Ser Gly Gly Gly Gly
1               5                   10                  15

Gly Ser Ser Gly Gly
            20

<210> SEQ ID NO 65
<211> LENGTH: 21
<212> TYPE: PRT
<213> ORGANISM: Homo sapiens

<400> SEQUENCE: 65

Gly Ser Gly Ser Gly Pro Gly Pro Gly Ser Gly Pro Gly Ser Gly Pro
1               5                   10                  15

Gly His Gly Ser Gly
            20

<210> SEQ ID NO 66
<211> LENGTH: 21
<212> TYPE: PRT
<213> ORGANISM: Homo sapiens

<400> SEQUENCE: 66

Gly Pro Gly Pro Gly Pro Gly Pro Gly Pro Gly Pro Gly Pro Gly Pro
1               5                   10                  15

Gly Pro Gly Pro Gly
            20

<210> SEQ ID NO 67
<211> LENGTH: 21
<212> TYPE: PRT
<213> ORGANISM: Homo sapiens

<400> SEQUENCE: 67

Gly Ala Gly Ser Gly Gly Gly Ala Ala Gly Ala Gly Ala Gly Ala Ser
1               5                   10                  15

Ala Gly Gly Gly Gly
            20

<210> SEQ ID NO 68
<211> LENGTH: 21
<212> TYPE: PRT
<213> ORGANISM: Homo sapiens

<400> SEQUENCE: 68

Gly Ala Gly Ser Gly Gly Gly Ala Ala Gly Ala Gly Ala Gly Ala Ser
1               5                   10                  15

Ala Gly Gly Gly Gly
```

```
                    20

<210> SEQ ID NO 69
<211> LENGTH: 21
<212> TYPE: PRT
<213> ORGANISM: Homo sapiens

<400> SEQUENCE: 69

Gly Gly Gly Gly Gly Gly Gly Ser Gly Gly Gly Gly Gly Ser Gly
1               5                  10                  15

Gly Gly Gly Gly Gly
            20

<210> SEQ ID NO 70
<211> LENGTH: 21
<212> TYPE: PRT
<213> ORGANISM: Homo sapiens

<400> SEQUENCE: 70

Gly Arg Gly Arg Gly Arg Gly Arg Gly Arg Gly Arg Gly Arg Gly Arg
1               5                  10                  15

Gly Arg Gly Arg Gly
            20

<210> SEQ ID NO 71
<211> LENGTH: 21
<212> TYPE: PRT
<213> ORGANISM: Homo sapiens

<400> SEQUENCE: 71

Gly Gly Gly Gly Gly Gly Gly Ser Gly Ser Gly Gly Gly Gly
1               5                  10                  15

Ser Gly Gly Gly Gly
            20

<210> SEQ ID NO 72
<211> LENGTH: 21
<212> TYPE: PRT
<213> ORGANISM: Homo sapiens

<400> SEQUENCE: 72

Gly Gly Glu Glu Gly Gly Ala Ser Gly Gly Pro Gly Ala Gly Ser
1               5                  10                  15

Gly Ser Ala Gly Gly
            20

<210> SEQ ID NO 73
<211> LENGTH: 21
<212> TYPE: PRT
<213> ORGANISM: Homo sapiens

<400> SEQUENCE: 73

Gly Ser Gly Ser Gly Pro Gly Pro Gly Ser Gly Pro Gly Ser Gly Pro
1               5                  10                  15

Gly His Gly Ser Gly
            20

<210> SEQ ID NO 74
<211> LENGTH: 21
<212> TYPE: PRT
<213> ORGANISM: Homo sapiens

<400> SEQUENCE: 74
```

Gly Arg Gly Arg Gly Arg Gly Arg Gly Arg Gly Arg Gly Arg
1               5                   10                  15

Gly Arg Gly Arg Gly
            20

<210> SEQ ID NO 75
<211> LENGTH: 21
<212> TYPE: PRT
<213> ORGANISM: Homo sapiens

<400> SEQUENCE: 75

Gly Gly Gly Gly Gly Gly Gly Asp Gly Gly Gly Arg Arg Gly Arg
1               5                   10                  15

Gly Arg Gly Arg Gly
            20

<210> SEQ ID NO 76
<211> LENGTH: 20
<212> TYPE: PRT
<213> ORGANISM: Homo sapiens

<400> SEQUENCE: 76

Gly Gly Pro Gly Gly Pro Gly Gly Gly Ala Gly Gly Pro Gly Gly
1               5                   10                  15

Ala Gly Ala Gly
            20

<210> SEQ ID NO 77
<211> LENGTH: 20
<212> TYPE: PRT
<213> ORGANISM: Homo sapiens

<400> SEQUENCE: 77

Gly Thr Gly Gly Gly Gly Ser Thr Gly Gly Gly Gly Gly Gly Gly
1               5                   10                  15

Ser Gly His Gly
            20

<210> SEQ ID NO 78
<211> LENGTH: 20
<212> TYPE: PRT
<213> ORGANISM: Homo sapiens

<400> SEQUENCE: 78

Gly Pro Ala Gly Ala Gly Gly Gly Gly Gly Gly Gly Gly Gly Gly
1               5                   10                  15

Gly Gly Gly Gly
            20

<210> SEQ ID NO 79
<211> LENGTH: 20
<212> TYPE: PRT
<213> ORGANISM: Homo sapiens

<400> SEQUENCE: 79

Gly Gly Thr Gly Gly Ser Ser Gly Ser Ser Gly Ser Gly Ser Gly Gly
1               5                   10                  15

Gly Arg Arg Gly
            20

<210> SEQ ID NO 80

-continued

```
<211> LENGTH: 20
<212> TYPE: PRT
<213> ORGANISM: Homo sapiens

<400> SEQUENCE: 80

Gly Gly Thr Gly Gly Ser Ser Gly Ser Ser Gly Ser Gly Ser Gly Gly
1               5                   10                  15

Gly Arg Arg Gly
            20

<210> SEQ ID NO 81
<211> LENGTH: 20
<212> TYPE: PRT
<213> ORGANISM: Homo sapiens

<400> SEQUENCE: 81

Gly Ser Gly Thr Gly Thr Thr Gly Ser Ser Gly Ala Gly Gly Pro Gly
1               5                   10                  15

Thr Pro Gly Gly
            20

<210> SEQ ID NO 82
<211> LENGTH: 20
<212> TYPE: PRT
<213> ORGANISM: Homo sapiens

<400> SEQUENCE: 82

Gly Gly Ser Gly Gly Gly Ala Ala Gly Gly Ala Gly Gly Ala Ser Gly
1               5                   10                  15

Ala Gly Ala Gly
            20

<210> SEQ ID NO 83
<211> LENGTH: 20
<212> TYPE: PRT
<213> ORGANISM: Homo sapiens

<400> SEQUENCE: 83

Gly Gly Ser Gly Gly Gly Ala Ala Gly Gly Ala Gly Gly Ala Gly
1               5                   10                  15

Ala Gly Ala Gly
            20

<210> SEQ ID NO 84
<211> LENGTH: 20
<212> TYPE: PRT
<213> ORGANISM: Homo sapiens

<400> SEQUENCE: 84

Gly Ser Ser Gly Gly Gly Gly Gly Ala Gly Ala Ala Gly Gly Ala
1               5                   10                  15

Gly Gly Ala Gly
            20

<210> SEQ ID NO 85
<211> LENGTH: 20
<212> TYPE: PRT
<213> ORGANISM: Homo sapiens

<400> SEQUENCE: 85

Gly Pro Gly Pro Ser Gly Gly Pro Gly Gly Gly Gly Gly Gly Gly
1               5                   10                  15
```

```
Gly Gly Gly Gly
        20

<210> SEQ ID NO 86
<211> LENGTH: 20
<212> TYPE: PRT
<213> ORGANISM: Homo sapiens

<400> SEQUENCE: 86

Gly Gly Gly Gly Gly Gly Gly Gly Gly Gly Gly Gly Gly Gly Ala Ala
1               5                   10                  15

Gly Ala Gly Gly
        20

<210> SEQ ID NO 87
<211> LENGTH: 20
<212> TYPE: PRT
<213> ORGANISM: Homo sapiens

<400> SEQUENCE: 87

Gly Arg Gly Arg Gly Arg Gly Arg Gly Arg Gly Arg Gly Arg Gly Arg
1               5                   10                  15

Gly Arg Gly Gly
        20

<210> SEQ ID NO 88
<211> LENGTH: 20
<212> TYPE: PRT
<213> ORGANISM: Homo sapiens

<400> SEQUENCE: 88

Gly Ser Ala Gly Gly Ser Ser Gly Ala Ala Gly Ala Ala Gly Gly Gly
1               5                   10                  15

Ala Gly Ala Gly
        20

<210> SEQ ID NO 89
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 4 to 200
      "Ser-Ser-Asp" repeating units

<400> SEQUENCE: 89

Ser Ser Asp Ser Ser Asp Ser Ser Asp Ser Ser Asp Ser Ser Asp Ser
1               5                   10                  15

Ser Asp Ser Ser Asp Ser Ser Asp Ser Ser Asp Ser Ser Asp Ser Ser
                20                  25                  30

Asp Ser Ser Asp Ser Ser Asp Ser Ser Asp Ser Ser Asp Ser Ser Asp
            35                  40                  45

Ser Ser Asp Ser Ser Asp Ser Ser Asp Ser Ser Asp Ser Ser Asp Ser
        50                  55                  60

Ser Asp Ser Ser Asp Ser Ser Asp Ser Ser Asp Ser Ser Asp Ser Ser
65                  70                  75                  80

Asp Ser Ser Asp Ser Ser Asp Ser Ser Asp Ser Ser Asp Ser Ser Asp
                85                  90                  95

Ser Ser Asp Ser Ser Asp Ser Ser Asp Ser Ser Asp Ser Ser Asp Ser
                100                 105                 110
```

Ser Asp Ser Ser Asp Ser Ser Asp Ser Ser Asp Ser Ser Asp Ser Ser
            115                 120                 125

Asp Ser Ser Asp Ser Ser Asp Ser Ser Asp Ser Ser Asp Ser Ser Asp
        130                 135                 140

Ser Ser Asp Ser Ser Asp Ser Ser Asp Ser Ser Asp Ser Ser Asp Ser
145                 150                 155                 160

Ser Asp Ser Ser Asp Ser Ser Asp Ser Ser Asp Ser Ser Asp Ser Ser
            165                 170                 175

Asp Ser Ser Asp Ser Ser Asp Ser Ser Asp Ser Ser Asp Ser Ser Asp
        180                 185                 190

Ser Ser Asp Ser Ser Asp Ser Ser Asp Ser Ser Asp Ser Ser Asp Ser
            195                 200                 205

Ser Asp Ser Ser Asp Ser Ser Asp Ser Ser Asp Ser Ser Asp Ser Ser
            210                 215                 220

Asp Ser Ser Asp Ser Ser Asp Ser Ser Asp Ser Ser Asp Ser Ser Asp
225                 230                 235                 240

Ser Ser Asp Ser Ser Asp Ser Ser Asp Ser Ser Asp Ser Ser Asp Ser
            245                 250                 255

Ser Asp Ser Ser Asp Ser Ser Asp Ser Ser Asp Ser Ser Asp Ser Ser
            260                 265                 270

Asp Ser Ser Asp Ser Ser Asp Ser Ser Asp Ser Ser Asp Ser Ser Asp
        275                 280                 285

Ser Ser Asp Ser Ser Asp Ser Ser Asp Ser Ser Asp Ser Ser Asp Ser
        290                 295                 300

Ser Asp Ser Ser Asp Ser Ser Asp Ser Ser Asp Ser Ser Asp Ser Ser
305                 310                 315                 320

Asp Ser Ser Asp Ser Ser Asp Ser Ser Asp Ser Ser Asp Ser Ser Asp
            325                 330                 335

Ser Ser Asp Ser Ser Asp Ser Ser Asp Ser Ser Asp Ser Ser Asp Ser
            340                 345                 350

Ser Asp Ser Ser Asp Ser Ser Asp Ser Ser Asp Ser Ser Asp Ser Ser
            355                 360                 365

Asp Ser Ser Asp Ser Ser Asp Ser Ser Asp Ser Ser Asp Ser Ser Asp
        370                 375                 380

Ser Ser Asp Ser Ser Asp Ser Ser Asp Ser Ser Asp Ser Ser Asp Ser
385                 390                 395                 400

Ser Asp Ser Ser Asp Ser Ser Asp Ser Ser Asp Ser Ser Asp Ser Ser
            405                 410                 415

Asp Ser Ser Asp Ser Ser Asp Ser Ser Asp Ser Ser Asp Ser Ser Asp
        420                 425                 430

Ser Ser Asp Ser Ser Asp Ser Ser Asp Ser Ser Asp Ser Ser Asp Ser
        435                 440                 445

Ser Asp Ser Ser Asp Ser Ser Asp Ser Ser Asp Ser Ser Asp Ser Ser
        450                 455                 460

Asp Ser Ser Asp Ser Ser Asp Ser Ser Asp Ser Ser Asp Ser Ser Asp
465                 470                 475                 480

Ser Ser Asp Ser Ser Asp Ser Ser Asp Ser Ser Asp Ser Ser Asp Ser
            485                 490                 495

Ser Asp Ser Ser Asp Ser Ser Asp Ser Ser Asp Ser Ser Asp Ser Ser
            500                 505                 510

Asp Ser Ser Asp Ser Ser Asp Ser Ser Asp Ser Ser Asp Ser Ser Asp
            515                 520                 525

```
Ser Ser Asp Ser Ser Asp Ser Ser Asp Ser Ser Asp Ser
    530                 535                 540

Ser Asp Ser Ser Asp Ser Ser Asp Ser Ser Asp Ser
545                 550                 555                 560

Asp Ser Ser Asp Ser Ser Asp Ser Ser Asp Ser Ser Asp
                565                 570                 575

Ser Ser Asp Ser Ser Asp Ser Ser Asp Ser Ser Asp Ser
            580                 585                 590

Ser Asp Ser Ser Asp Ser Ser Asp
        595                 600

<210> SEQ ID NO 90
<211> LENGTH: 1200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 4 to 200
      "Ser-Ser-Asp-Ser-Ser-Asn" repeating units

<400> SEQUENCE: 90

Ser Ser Asp Ser Ser Asn Ser Ser Asp Ser Ser Asn Ser Ser Asp Ser
1               5                   10                  15

Ser Asn Ser Ser Asp Ser Ser Asn Ser Ser Asp Ser Ser Asn Ser Ser
            20                  25                  30

Asp Ser Ser Asn Ser Ser Asp Ser Ser Asn Ser Ser Asp Ser Ser Asn
        35                  40                  45

Ser Ser Asp Ser Ser Asn Ser Ser Asp Ser Ser Asn Ser Ser Asp Ser
50                  55                  60

Ser Asn Ser Ser Asp Ser Ser Asn Ser Ser Asp Ser Ser Asn Ser Ser
65                  70                  75                  80

Asp Ser Ser Asn Ser Ser Asp Ser Ser Asn Ser Ser Asp Ser Ser Asn
            85                  90                  95

Ser Ser Asp Ser Ser Asn Ser Ser Asp Ser Ser Asn Ser Ser Asp Ser
        100                 105                 110

Ser Asn Ser Ser Asp Ser Ser Asn Ser Ser Asp Ser Ser Asn Ser Ser
        115                 120                 125

Asp Ser Ser Asn Ser Ser Asp Ser Ser Asn Ser Ser Asp Ser Ser Asn
    130                 135                 140

Ser Ser Asp Ser Ser Asn Ser Ser Asp Ser Ser Asn Ser Ser Asp Ser
145                 150                 155                 160

Ser Asn Ser Ser Asp Ser Ser Asn Ser Ser Asp Ser Ser Asn Ser Ser
                165                 170                 175

Asp Ser Ser Asn Ser Ser Asp Ser Ser Asn Ser Ser Asp Ser Ser Asn
            180                 185                 190

Ser Ser Asp Ser Ser Asn Ser Ser Asp Ser Ser Asn Ser Ser Asp Ser
        195                 200                 205

Ser Asn Ser Ser Asp Ser Ser Asn Ser Ser Asp Ser Ser Asn Ser Ser
    210                 215                 220

Asp Ser Ser Asn Ser Ser Asp Ser Ser Asn Ser Ser Asp Ser Ser Asn
225                 230                 235                 240

Ser Ser Asp Ser Ser Asn Ser Ser Asp Ser Ser Asn Ser Ser Asp Ser
                245                 250                 255

Ser Asn Ser Ser Asp Ser Ser Asn Ser Ser Asp Ser Ser Asn Ser Ser
            260                 265                 270
```

Asp Ser Ser Asn Ser Ser Asp Ser Ser Asn Ser Ser Asp Ser Ser Asn
            275                 280                 285

Ser Ser Asp Ser Ser Asn Ser Ser Asp Ser Ser Asn Ser Ser Asp Ser
290                 295                 300

Ser Asn Ser Ser Asp Ser Ser Asn Ser Ser Asp Ser Ser Asn Ser Ser
305                 310                 315                 320

Asp Ser Ser Asn Ser Ser Asp Ser Ser Asn Ser Ser Asp Ser Ser Asn
            325                 330                 335

Ser Ser Asp Ser Ser Asn Ser Ser Asp Ser Ser Asn Ser Ser Asp Ser
        340                 345                 350

Ser Asn Ser Ser Asp Ser Ser Asn Ser Ser Asp Ser Ser Asn Ser Ser
            355                 360                 365

Asp Ser Ser Asn Ser Ser Asp Ser Ser Asn Ser Ser Asp Ser Ser Asn
        370                 375                 380

Ser Ser Asp Ser Ser Asn Ser Ser Asp Ser Ser Asn Ser Ser Asp Ser
385                 390                 395                 400

Ser Asn Ser Ser Asp Ser Ser Asn Ser Ser Asp Ser Ser Asn Ser Ser
                405                 410                 415

Asp Ser Ser Asn Ser Ser Asp Ser Ser Asn Ser Ser Asp Ser Ser Asn
            420                 425                 430

Ser Ser Asp Ser Ser Asn Ser Ser Asp Ser Ser Asn Ser Ser Asp Ser
        435                 440                 445

Ser Asn Ser Ser Asp Ser Ser Asn Ser Ser Asp Ser Ser Asn Ser Ser
        450                 455                 460

Asp Ser Ser Asn Ser Ser Asp Ser Ser Asn Ser Ser Asp Ser Ser Asn
465                 470                 475                 480

Ser Ser Asp Ser Ser Asn Ser Ser Asp Ser Ser Asn Ser Ser Asp Ser
                485                 490                 495

Ser Asn Ser Ser Asp Ser Ser Asn Ser Ser Asp Ser Ser Asn Ser Ser
            500                 505                 510

Asp Ser Ser Asn Ser Ser Asp Ser Ser Asn Ser Ser Asp Ser Ser Asn
        515                 520                 525

Ser Ser Asp Ser Ser Asn Ser Ser Asp Ser Ser Asn Ser Ser Asp Ser
530                 535                 540

Ser Asn Ser Ser Asp Ser Ser Asn Ser Ser Asp Ser Ser Asn Ser Ser
545                 550                 555                 560

Asp Ser Ser Asn Ser Ser Asp Ser Ser Asn Ser Ser Asp Ser Ser Asn
                565                 570                 575

Ser Ser Asp Ser Ser Asn Ser Ser Asp Ser Ser Asn Ser Ser Asp Ser
            580                 585                 590

Ser Asn Ser Ser Asp Ser Ser Asn Ser Ser Asp Ser Ser Asn Ser Ser
        595                 600                 605

Asp Ser Ser Asn Ser Ser Asp Ser Ser Asn Ser Ser Asp Ser Ser Asn
        610                 615                 620

Ser Ser Asp Ser Ser Asn Ser Ser Asp Ser Ser Asn Ser Ser Asp Ser
625                 630                 635                 640

Ser Asn Ser Ser Asp Ser Ser Asn Ser Ser Asp Ser Ser Asn Ser Ser
                645                 650                 655

Asp Ser Ser Asn Ser Ser Asp Ser Ser Asn Ser Ser Asp Ser Ser Asn
            660                 665                 670

Ser Ser Asp Ser Ser Asn Ser Ser Asp Ser Ser Asn Ser Ser Asp Ser
        675                 680                 685

```
Ser Asn Ser Ser Asp Ser Ser Asn Ser Ser Asp Ser Ser Asn Ser Ser
    690                 695                 700

Asp Ser Ser Asn Ser Ser Asp Ser Ser Asn Ser Ser Asp Ser Ser Asn
705                 710                 715                 720

Ser Ser Asp Ser Ser Asn Ser Ser Asp Ser Ser Asn Ser Ser Asp Ser
            725                 730                 735

Ser Asn Ser Ser Asp Ser Ser Asn Ser Ser Asp Ser Ser Asn Ser Ser
        740                 745                 750

Asp Ser Ser Asn Ser Ser Asp Ser Ser Asn Ser Ser Asp Ser Ser Asn
            755                 760                 765

Ser Ser Asp Ser Ser Asn Ser Ser Asp Ser Ser Asn Ser Ser Asp Ser
770                 775                 780

Ser Asn Ser Ser Asp Ser Ser Asn Ser Ser Asp Ser Ser Asn Ser Ser
785                 790                 795                 800

Asp Ser Ser Asn Ser Ser Asp Ser Ser Asn Ser Ser Asp Ser Ser Asn
                805                 810                 815

Ser Ser Asp Ser Ser Asn Ser Ser Asp Ser Ser Asn Ser Ser Asp Ser
        820                 825                 830

Ser Asn Ser Ser Asp Ser Ser Asn Ser Ser Asp Ser Ser Asn Ser Ser
    835                 840                 845

Asp Ser Ser Asn Ser Ser Asp Ser Ser Asn Ser Ser Asp Ser Ser Asn
850                 855                 860

Ser Ser Asp Ser Ser Asn Ser Ser Asp Ser Ser Asn Ser Ser Asp Ser
865                 870                 875                 880

Ser Asn Ser Ser Asp Ser Ser Asn Ser Ser Asp Ser Ser Asn Ser Ser
                885                 890                 895

Asp Ser Ser Asn Ser Ser Asp Ser Ser Asn Ser Ser Asp Ser Ser Asn
            900                 905                 910

Ser Ser Asp Ser Ser Asn Ser Ser Asp Ser Ser Asn Ser Ser Asp Ser
        915                 920                 925

Ser Asn Ser Ser Asp Ser Ser Asn Ser Ser Asp Ser Ser Asn Ser Ser
    930                 935                 940

Asp Ser Ser Asn Ser Ser Asp Ser Ser Asn Ser Ser Asp Ser Ser Asn
945                 950                 955                 960

Ser Ser Asp Ser Ser Asn Ser Ser Asp Ser Ser Asn Ser Ser Asp Ser
            965                 970                 975

Ser Asn Ser Ser Asp Ser Ser Asn Ser Ser Asp Ser Ser Asn Ser Ser
        980                 985                 990

Asp Ser Ser Asn Ser Ser Asp Ser  Ser Asn Ser Ser Asp  Ser Ser Asn
            995                 1000                1005

Ser Ser  Asp Ser Ser Asn Ser  Ser Asp Ser Ser Asn  Ser Ser Asp
    1010                1015                1020

Ser Ser  Asn Ser Ser Asp Ser  Ser Asn Ser Ser Asp  Ser Ser Asn
    1025                1030                1035

Ser Ser  Asp Ser Ser Asn Ser  Ser Asp Ser Ser Asn  Ser Ser Asp
    1040                1045                1050

Ser Ser  Asn Ser Ser Asp Ser  Ser Asn Ser Ser Asp  Ser Ser Asn
    1055                1060                1065

Ser Ser  Asp Ser Ser Asn Ser  Ser Asp Ser Ser Asn  Ser Ser Asp
    1070                1075                1080

Ser Ser  Asn Ser Ser Asp Ser  Ser Asn Ser Ser Asp  Ser Ser Asn
    1085                1090                1095

Ser Ser  Asp Ser Ser Asn Ser  Ser Asp Ser Ser Asn  Ser Ser Asp
```

```
                    1100                1105                 1110

Ser  Ser   Asn  Ser  Ser  Asp  Ser   Ser  Asn  Ser  Ser  Asp   Ser  Ser  Asn
     1115                1120                 1125

Ser  Ser   Asp  Ser  Ser  Asn  Ser   Ser  Asp  Ser  Ser  Asn   Ser  Ser  Asp
     1130                1135                 1140

Ser  Ser   Asn  Ser  Ser  Asp  Ser   Ser  Asn  Ser  Ser  Asp   Ser  Ser  Asn
     1145                1150                 1155

Ser  Ser   Asp  Ser  Ser  Asn  Ser   Ser  Asp  Ser  Ser  Asn   Ser  Ser  Asp
     1160                1165                 1170

Ser  Ser   Asn  Ser  Ser  Asp  Ser   Ser  Asn  Ser  Ser  Asp   Ser  Ser  Asn
     1175                1180                 1185

Ser  Ser   Asp  Ser  Ser  Asn  Ser   Ser  Asp  Ser  Ser  Asn
     1190                1195                 1200

<210> SEQ ID NO 91
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 4 to 200
      "Ser-Ser-Glu" repeating units

<400> SEQUENCE: 91

Ser  Ser  Glu  Ser  Ser  Glu  Ser  Ser  Glu  Ser  Ser  Glu  Ser  Ser  Glu  Ser
1                   5                   10                  15

Ser  Glu  Ser  Ser  Glu  Ser  Ser  Glu  Ser  Ser  Glu  Ser  Ser  Glu  Ser  Ser
              20                  25                  30

Glu  Ser  Ser  Glu  Ser  Ser  Glu  Ser  Ser  Glu  Ser  Ser  Glu  Ser  Ser  Glu
         35                  40                  45

Ser  Ser  Glu  Ser  Ser  Glu  Ser  Ser  Glu  Ser  Ser  Glu  Ser  Ser  Glu  Ser
     50                  55                  60

Ser  Glu  Ser  Ser  Glu  Ser  Ser  Glu  Ser  Ser  Glu  Ser  Ser  Glu  Ser  Ser
65                  70                  75                  80

Glu  Ser  Ser  Glu  Ser  Ser  Glu  Ser  Ser  Glu  Ser  Ser  Glu  Ser  Ser  Glu
              85                  90                  95

Ser  Ser  Glu  Ser  Ser  Glu  Ser  Ser  Glu  Ser  Ser  Glu  Ser  Ser  Glu  Ser
         100                 105                 110

Ser  Glu  Ser  Ser  Glu  Ser  Ser  Glu  Ser  Ser  Glu  Ser  Ser  Glu  Ser  Ser
     115                 120                 125

Glu  Ser  Ser  Glu  Ser  Ser  Glu  Ser  Ser  Glu  Ser  Ser  Glu  Ser  Ser  Glu
130                 135                 140

Ser  Ser  Glu  Ser  Ser  Glu  Ser  Ser  Glu  Ser  Ser  Glu  Ser  Ser  Glu  Ser
145                 150                 155                 160

Ser  Glu  Ser  Ser  Glu  Ser  Ser  Glu  Ser  Ser  Glu  Ser  Ser  Glu  Ser  Ser
              165                 170                 175

Glu  Ser  Ser  Glu  Ser  Ser  Glu  Ser  Ser  Glu  Ser  Ser  Glu  Ser  Ser  Glu
         180                 185                 190

Ser  Ser  Glu  Ser  Ser  Glu  Ser  Ser  Glu  Ser  Ser  Glu  Ser  Ser  Glu  Ser
     195                 200                 205

Ser  Glu  Ser  Ser  Glu  Ser  Ser  Glu  Ser  Ser  Glu  Ser  Ser  Glu  Ser  Ser
         210                 215                 220

Glu  Ser  Ser  Glu  Ser  Ser  Glu  Ser  Ser  Glu  Ser  Ser  Glu  Ser  Ser  Glu
225                 230                 235                 240
```

Ser Ser Glu Ser Ser Glu Ser Ser Glu Ser Ser Glu Ser
            245                 250                 255

Ser Glu Ser Ser Glu Ser Ser Glu Ser Ser Glu Ser Ser
        260                 265                 270

Glu Ser Ser Glu Ser Ser Glu Ser Ser Glu Ser Ser Glu
    275                 280                 285

Ser Ser Glu Ser Ser Glu Ser Ser Glu Ser Ser Glu Ser
    290                 295                 300

Ser Glu Ser Ser Glu Ser Ser Glu Ser Ser Glu Ser Ser
305                 310                 315                 320

Glu Ser Ser Glu Ser Ser Glu Ser Ser Glu Ser Ser Glu
            325                 330                 335

Ser Ser Glu Ser Ser Glu Ser Ser Glu Ser Ser Glu Ser
        340                 345                 350

Ser Glu Ser Ser Glu Ser Ser Glu Ser Ser Glu Ser Ser
    355                 360                 365

Glu Ser Ser Glu Ser Ser Glu Ser Ser Glu Ser Ser Glu
    370                 375                 380

Ser Ser Glu Ser Ser Glu Ser Ser Glu Ser Ser Glu Ser
385                 390                 395                 400

Ser Glu Ser Ser Glu Ser Ser Glu Ser Ser Glu Ser Ser
            405                 410                 415

Glu Ser Ser Glu Ser Ser Glu Ser Ser Glu Ser Ser Glu
        420                 425                 430

Ser Ser Glu Ser Ser Glu Ser Ser Glu Ser Ser Glu Ser
    435                 440                 445

Ser Glu Ser Ser Glu Ser Ser Glu Ser Ser Glu Ser Ser
    450                 455                 460

Glu Ser Ser Glu Ser Ser Glu Ser Ser Glu Ser Ser Glu
465                 470                 475                 480

Ser Ser Glu Ser Ser Glu Ser Ser Glu Ser Ser Glu Ser
            485                 490                 495

Ser Glu Ser Ser Glu Ser Ser Glu Ser Ser Glu Ser Ser
        500                 505                 510

Glu Ser Ser Glu Ser Ser Glu Ser Ser Glu Ser Ser Glu
    515                 520                 525

Ser Ser Glu Ser Ser Glu Ser Ser Glu Ser Ser Glu Ser
    530                 535                 540

Ser Glu Ser Ser Glu Ser Ser Glu Ser Ser Glu Ser Ser
545                 550                 555                 560

Glu Ser Ser Glu Ser Ser Glu Ser Ser Glu Ser Ser Glu
            565                 570                 575

Ser Ser Glu Ser Ser Glu Ser Ser Glu Ser Ser Glu Ser
        580                 585                 590

Ser Glu Ser Ser Glu Ser Ser Glu
    595                 600

<210> SEQ ID NO 92
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (2)..(2)
<223> OTHER INFORMATION: Ser, Asp, Glu, Thr or Pro
<220> FEATURE:
<221> NAME/KEY: MOD_RES
<222> LOCATION: (4)..(4)
<223> OTHER INFORMATION: Ser, Asp, Glu, Thr or Pro
<220> FEATURE:
<221> NAME/KEY: MOD_RES
<222> LOCATION: (6)..(6)
<223> OTHER INFORMATION: Ser, Asp, Glu, Thr or Pro
<220> FEATURE:
<221> NAME/KEY: MOD_RES
<222> LOCATION: (8)..(8)
<223> OTHER INFORMATION: Ser, Asp, Glu, Thr or Pro
<220> FEATURE:
<221> NAME/KEY: MOD_RES
<222> LOCATION: (10)..(10)
<223> OTHER INFORMATION: Ser, Asp, Glu, Thr or Pro
<220> FEATURE:
<221> NAME/KEY: MOD_RES
<222> LOCATION: (12)..(12)
<223> OTHER INFORMATION: Ser, Asp, Glu, Thr or Pro
<220> FEATURE:
<221> NAME/KEY: MOD_RES
<222> LOCATION: (14)..(14)
<223> OTHER INFORMATION: Ser, Asp, Glu, Thr or Pro
<220> FEATURE:
<221> NAME/KEY: MOD_RES
<222> LOCATION: (16)..(16)
<223> OTHER INFORMATION: Ser, Asp, Glu, Thr or Pro
<220> FEATURE:
<221> NAME/KEY: MOD_RES
<222> LOCATION: (18)..(18)
<223> OTHER INFORMATION: Ser, Asp, Glu, Thr or Pro
<220> FEATURE:
<221> NAME/KEY: MOD_RES
<222> LOCATION: (20)..(20)
<223> OTHER INFORMATION: Ser, Asp, Glu, Thr or Pro
<220> FEATURE:
<221> NAME/KEY: MOD_RES
<222> LOCATION: (22)..(22)
<223> OTHER INFORMATION: Ser, Asp, Glu, Thr or Pro
<220> FEATURE:
<221> NAME/KEY: MOD_RES
<222> LOCATION: (24)..(24)
<223> OTHER INFORMATION: Ser, Asp, Glu, Thr or Pro
<220> FEATURE:
<221> NAME/KEY: MOD_RES
<222> LOCATION: (26)..(26)
<223> OTHER INFORMATION: Ser, Asp, Glu, Thr or Pro
<220> FEATURE:
<221> NAME/KEY: MOD_RES
<222> LOCATION: (28)..(28)
<223> OTHER INFORMATION: Ser, Asp, Glu, Thr or Pro
<220> FEATURE:
<221> NAME/KEY: MOD_RES
<222> LOCATION: (30)..(30)
<223> OTHER INFORMATION: Ser, Asp, Glu, Thr or Pro
<220> FEATURE:
<221> NAME/KEY: MOD_RES
<222> LOCATION: (32)..(32)
<223> OTHER INFORMATION: Ser, Asp, Glu, Thr or Pro
<220> FEATURE:
<221> NAME/KEY: MOD_RES
<222> LOCATION: (34)..(34)
<223> OTHER INFORMATION: Ser, Asp, Glu, Thr or Pro
<220> FEATURE:
<221> NAME/KEY: MOD_RES
<222> LOCATION: (36)..(36)
<223> OTHER INFORMATION: Ser, Asp, Glu, Thr or Pro
<220> FEATURE:
<221> NAME/KEY: MOD_RES
<222> LOCATION: (38)..(38)
<223> OTHER INFORMATION: Ser, Asp, Glu, Thr or Pro
<220> FEATURE:
<221> NAME/KEY: MOD_RES
<222> LOCATION: (40)..(40)
<223> OTHER INFORMATION: Ser, Asp, Glu, Thr or Pro
```

```
<400> SEQUENCE: 92

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa Gly Xaa
            20                  25                  30

Gly Xaa Gly Xaa Gly Xaa Gly Xaa
        35                  40

<210> SEQ ID NO 93
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser, Asp, Glu, Thr or Pro
<220> FEATURE:
<221> NAME/KEY: MOD_RES
<222> LOCATION: (6)..(6)
<223> OTHER INFORMATION: Ser, Asp, Glu, Thr or Pro
<220> FEATURE:
<221> NAME/KEY: MOD_RES
<222> LOCATION: (9)..(9)
<223> OTHER INFORMATION: Ser, Asp, Glu, Thr or Pro
<220> FEATURE:
<221> NAME/KEY: MOD_RES
<222> LOCATION: (12)..(12)
<223> OTHER INFORMATION: Ser, Asp, Glu, Thr or Pro
<220> FEATURE:
<221> NAME/KEY: MOD_RES
<222> LOCATION: (15)..(15)
<223> OTHER INFORMATION: Ser, Asp, Glu, Thr or Pro
<220> FEATURE:
<221> NAME/KEY: MOD_RES
<222> LOCATION: (18)..(18)
<223> OTHER INFORMATION: Ser, Asp, Glu, Thr or Pro
<220> FEATURE:
<221> NAME/KEY: MOD_RES
<222> LOCATION: (21)..(21)
<223> OTHER INFORMATION: Ser, Asp, Glu, Thr or Pro
<220> FEATURE:
<221> NAME/KEY: MOD_RES
<222> LOCATION: (24)..(24)
<223> OTHER INFORMATION: Ser, Asp, Glu, Thr or Pro
<220> FEATURE:
<221> NAME/KEY: MOD_RES
<222> LOCATION: (27)..(27)
<223> OTHER INFORMATION: Ser, Asp, Glu, Thr or Pro
<220> FEATURE:
<221> NAME/KEY: MOD_RES
<222> LOCATION: (30)..(30)
<223> OTHER INFORMATION: Ser, Asp, Glu, Thr or Pro
<220> FEATURE:
<221> NAME/KEY: MOD_RES
<222> LOCATION: (33)..(33)
<223> OTHER INFORMATION: Ser, Asp, Glu, Thr or Pro
<220> FEATURE:
<221> NAME/KEY: MOD_RES
<222> LOCATION: (36)..(36)
<223> OTHER INFORMATION: Ser, Asp, Glu, Thr or Pro
<220> FEATURE:
<221> NAME/KEY: MOD_RES
<222> LOCATION: (39)..(39)
<223> OTHER INFORMATION: Ser, Asp, Glu, Thr or Pro

<400> SEQUENCE: 93

Gly Gly Xaa Gly Gly Xaa Gly Gly Xaa Gly Gly Xaa Gly Gly Xaa Gly
1               5                   10                  15

Gly Xaa Gly Gly Xaa Gly Gly Xaa Gly Gly Xaa Gly Gly Xaa Gly Gly
            20                  25                  30
```

```
Xaa Gly Gly Xaa Gly Gly Xaa
        35

<210> SEQ ID NO 94
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser, Asp, Glu, Thr or Pro
<220> FEATURE:
<221> NAME/KEY: MOD_RES
<222> LOCATION: (8)..(8)
<223> OTHER INFORMATION: Ser, Asp, Glu, Thr or Pro
<220> FEATURE:
<221> NAME/KEY: MOD_RES
<222> LOCATION: (12)..(12)
<223> OTHER INFORMATION: Ser, Asp, Glu, Thr or Pro
<220> FEATURE:
<221> NAME/KEY: MOD_RES
<222> LOCATION: (16)..(16)
<223> OTHER INFORMATION: Ser, Asp, Glu, Thr or Pro
<220> FEATURE:
<221> NAME/KEY: MOD_RES
<222> LOCATION: (20)..(20)
<223> OTHER INFORMATION: Ser, Asp, Glu, Thr or Pro
<220> FEATURE:
<221> NAME/KEY: MOD_RES
<222> LOCATION: (24)..(24)
<223> OTHER INFORMATION: Ser, Asp, Glu, Thr or Pro
<220> FEATURE:
<221> NAME/KEY: MOD_RES
<222> LOCATION: (28)..(28)
<223> OTHER INFORMATION: Ser, Asp, Glu, Thr or Pro
<220> FEATURE:
<221> NAME/KEY: MOD_RES
<222> LOCATION: (32)..(32)
<223> OTHER INFORMATION: Ser, Asp, Glu, Thr or Pro
<220> FEATURE:
<221> NAME/KEY: MOD_RES
<222> LOCATION: (36)..(36)
<223> OTHER INFORMATION: Ser, Asp, Glu, Thr or Pro
<220> FEATURE:
<221> NAME/KEY: MOD_RES
<222> LOCATION: (40)..(40)
<223> OTHER INFORMATION: Ser, Asp, Glu, Thr or Pro

<400> SEQUENCE: 94

Gly Gly Gly Xaa Gly Gly Gly Xaa Gly Gly Gly Xaa Gly Gly Gly Xaa
1               5                   10                  15

Gly Gly Gly Xaa Gly Gly Gly Xaa Gly Gly Gly Xaa Gly Gly Gly Xaa
            20                  25                  30

Gly Gly Gly Xaa Gly Gly Gly Xaa
        35                  40

<210> SEQ ID NO 95
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Asp, Glu, Thr or Pro
<220> FEATURE:
<221> NAME/KEY: MOD_RES
<222> LOCATION: (10)..(10)
```

<223> OTHER INFORMATION: Ser, Asp, Glu, Thr or Pro
<220> FEATURE:
<221> NAME/KEY: MOD_RES
<222> LOCATION: (15)..(15)
<223> OTHER INFORMATION: Ser, Asp, Glu, Thr or Pro
<220> FEATURE:
<221> NAME/KEY: MOD_RES
<222> LOCATION: (20)..(20)
<223> OTHER INFORMATION: Ser, Asp, Glu, Thr or Pro
<220> FEATURE:
<221> NAME/KEY: MOD_RES
<222> LOCATION: (25)..(25)
<223> OTHER INFORMATION: Ser, Asp, Glu, Thr or Pro
<220> FEATURE:
<221> NAME/KEY: MOD_RES
<222> LOCATION: (30)..(30)
<223> OTHER INFORMATION: Ser, Asp, Glu, Thr or Pro
<220> FEATURE:
<221> NAME/KEY: MOD_RES
<222> LOCATION: (35)..(35)
<223> OTHER INFORMATION: Ser, Asp, Glu, Thr or Pro
<220> FEATURE:
<221> NAME/KEY: MOD_RES
<222> LOCATION: (40)..(40)
<223> OTHER INFORMATION: Ser, Asp, Glu, Thr or Pro

<400> SEQUENCE: 95

Gly Gly Gly Gly Xaa Gly Gly Gly Gly Xaa Gly Gly Gly Gly Xaa Gly
1               5                   10                  15

Gly Gly Gly Xaa Gly Gly Gly Gly Xaa Gly Gly Gly Gly Xaa Gly Gly
            20                  25                  30

Gly Gly Xaa Gly Gly Gly Gly Xaa
        35                  40

<210> SEQ ID NO 96
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 1 to 20 Gly residues
<220> FEATURE:
<221> NAME/KEY: MOD_RES
<222> LOCATION: (21)..(21)
<223> OTHER INFORMATION: Ser, Asp, Glu, Thr or Pro
<220> FEATURE:
<221> NAME/KEY: MOD_RES
<222> LOCATION: (22)..(41)
<223> OTHER INFORMATION: This region may encompass 1 to 20 Gly residues
<220> FEATURE:
<221> NAME/KEY: MOD_RES
<222> LOCATION: (42)..(42)
<223> OTHER INFORMATION: Ser, Asp, Glu, Thr or Pro
<220> FEATURE:
<221> NAME/KEY: MOD_RES
<222> LOCATION: (43)..(62)
<223> OTHER INFORMATION: This region may encompass 1 to 20 Gly residues
<220> FEATURE:
<221> NAME/KEY: MOD_RES
<222> LOCATION: (63)..(63)
<223> OTHER INFORMATION: Ser, Asp, Glu, Thr or Pro
<220> FEATURE:
<221> NAME/KEY: MOD_RES
<222> LOCATION: (64)..(83)
<223> OTHER INFORMATION: This region may encompass 1 to 20 Gly residues
<220> FEATURE:
<221> NAME/KEY: MOD_RES
<222> LOCATION: (84)..(84)
<223> OTHER INFORMATION: Ser, Asp, Glu, Thr or Pro
<220> FEATURE:
<221> NAME/KEY: MOD_RES

```
<222> LOCATION: (85)..(104)
<223> OTHER INFORMATION: This region may encompass 1 to 20 Gly residues
<220> FEATURE:
<221> NAME/KEY: MOD_RES
<222> LOCATION: (105)..(105)
<223> OTHER INFORMATION: Ser, Asp, Glu, Thr or Pro
<220> FEATURE:
<221> NAME/KEY: MOD_RES
<222> LOCATION: (106)..(125)
<223> OTHER INFORMATION: This region may encompass 1 to 20 Gly residues
<220> FEATURE:
<221> NAME/KEY: MOD_RES
<222> LOCATION: (126)..(126)
<223> OTHER INFORMATION: Ser, Asp, Glu, Thr or Pro
<220> FEATURE:
<221> NAME/KEY: MOD_RES
<222> LOCATION: (127)..(146)
<223> OTHER INFORMATION: This region may encompass 1 to 20 Gly residues
<220> FEATURE:
<221> NAME/KEY: MOD_RES
<222> LOCATION: (147)..(147)
<223> OTHER INFORMATION: Ser, Asp, Glu, Thr or Pro
<220> FEATURE:
<221> NAME/KEY: MOD_RES
<222> LOCATION: (148)..(167)
<223> OTHER INFORMATION: This region may encompass 1 to 20 Gly residues
<220> FEATURE:
<221> NAME/KEY: MOD_RES
<222> LOCATION: (168)..(168)
<223> OTHER INFORMATION: Ser, Asp, Glu, Thr or Pro
<220> FEATURE:
<221> NAME/KEY: MOD_RES
<222> LOCATION: (169)..(188)
<223> OTHER INFORMATION: This region may encompass 1 to 20 Gly residues
<220> FEATURE:
<221> NAME/KEY: MOD_RES
<222> LOCATION: (189)..(189)
<223> OTHER INFORMATION: Ser, Asp, Glu, Thr or Pro
<220> FEATURE:
<221> NAME/KEY: MOD_RES
<222> LOCATION: (190)..(209)
<223> OTHER INFORMATION: This region may encompass 1 to 20 Gly residues
<220> FEATURE:
<221> NAME/KEY: MOD_RES
<222> LOCATION: (210)..(210)
<223> OTHER INFORMATION: Ser, Asp, Glu, Thr or Pro
<220> FEATURE:
<221> NAME/KEY: MOD_RES
<222> LOCATION: (211)..(230)
<223> OTHER INFORMATION: This region may encompass 1 to 20 Gly residues
<220> FEATURE:
<221> NAME/KEY: MOD_RES
<222> LOCATION: (231)..(231)
<223> OTHER INFORMATION: Ser, Asp, Glu, Thr or Pro
<220> FEATURE:
<221> NAME/KEY: MOD_RES
<222> LOCATION: (232)..(251)
<223> OTHER INFORMATION: This region may encompass 1 to 20 Gly residues
<220> FEATURE:
<221> NAME/KEY: MOD_RES
<222> LOCATION: (252)..(252)
<223> OTHER INFORMATION: Ser, Asp, Glu, Thr or Pro
<220> FEATURE:
<221> NAME/KEY: MOD_RES
<222> LOCATION: (253)..(272)
<223> OTHER INFORMATION: This region may encompass 1 to 20 Gly residues
<220> FEATURE:
<221> NAME/KEY: MOD_RES
<222> LOCATION: (273)..(273)
<223> OTHER INFORMATION: Ser, Asp, Glu, Thr or Pro
<220> FEATURE:
<221> NAME/KEY: MOD_RES
<222> LOCATION: (273)..(293)
<223> OTHER INFORMATION: This region may encompass 1 to 20 Gly residues
<220> FEATURE:
<221> NAME/KEY: MOD_RES
<222> LOCATION: (294)..(294)
<223> OTHER INFORMATION: Ser, Asp, Glu, Thr or Pro
<220> FEATURE:
```

<221> NAME/KEY: MOD_RES
<222> LOCATION: (295)..(314)
<223> OTHER INFORMATION: This region may encompass 1 to 20 Gly residues
<220> FEATURE:
<221> NAME/KEY: MOD_RES
<222> LOCATION: (315)..(315)
<223> OTHER INFORMATION: Ser, Asp, Glu, Thr or Pro

<400> SEQUENCE: 96

```
Gly Gly Gly Gly Gly Gly Gly Gly Gly Gly Gly Gly Gly Gly Gly Gly
 1               5                  10                  15
Gly Gly Gly Gly Xaa Gly Gly Gly Gly Gly Gly Gly Gly Gly Gly Gly
                20                  25                  30
Gly Gly Gly Gly Gly Gly Gly Gly Xaa Gly Gly Gly Gly Gly Gly Gly
            35                  40                  45
Gly Gly Gly Gly Gly Gly Gly Gly Gly Gly Gly Gly Xaa Gly
        50                  55                  60
Gly Gly Gly Gly Gly Gly Gly Gly Gly Gly Gly Gly Gly Gly Gly Gly
 65                  70                  75                  80
Gly Gly Gly Xaa Gly Gly Gly Gly Gly Gly Gly Gly Gly Gly Gly Gly
                85                  90                  95
Gly Gly Gly Gly Gly Gly Gly Xaa Gly Gly Gly Gly Gly Gly
           100                 105                 110
Gly Gly Gly Gly Gly Gly Gly Gly Gly Gly Gly Xaa Gly Gly
       115                 120                 125
Gly Gly Gly Gly Gly Gly Gly Gly Gly Gly Gly Gly Gly Gly
   130                 135                 140
Gly Gly Xaa Gly Gly Gly Gly Gly Gly Gly Gly Gly Gly Gly Gly Gly
145                 150                 155                 160
Gly Gly Gly Gly Gly Gly Gly Xaa Gly Gly Gly Gly Gly Gly Gly
                165                 170                 175
Gly Gly Gly Gly Gly Gly Gly Gly Gly Gly Gly Xaa Gly Gly Gly
            180                 185                 190
Gly Gly Gly Gly Gly Gly Gly Gly Gly Gly Gly Gly Gly Gly Gly
        195                 200                 205
Gly Xaa Gly Gly Gly Gly Gly Gly Gly Gly Gly Gly Gly Gly
    210                 215                 220
Gly Gly Gly Gly Gly Gly Xaa Gly Gly Gly Gly Gly Gly Gly Gly
225                 230                 235                 240
Gly Gly Gly Gly Gly Gly Gly Gly Gly Gly Xaa Gly Gly Gly
               245                 250                 255
Gly Gly Gly Gly Gly Gly Gly Gly Gly Gly Gly Gly Gly Gly
            260                 265                 270
Xaa Gly Gly Gly Gly Gly Gly Gly Gly Gly Gly Gly Gly
       275                 280                 285
Gly Gly Gly Gly Gly Xaa Gly Gly Gly Gly Gly Gly Gly Gly
    290                 295                 300
Gly Gly Gly Gly Gly Gly Gly Gly Gly Xaa
305                 310                 315
```

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

```
<400> SEQUENCE: 97

His His His His His His
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Lys Val Ile Leu Phe Glu
1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Arg Ala Arg Ala Arg
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Ala Asp Ala Asp Ala
1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Lys Val Ile Leu Phe
1               5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ala Arg Ala Arg Ala
1               5

<210> SEQ ID NO 103
<211> LENGTH: 14
<212> TYPE: PRT
```

<213> ORGANISM: Homo sapiens

<400> SEQUENCE: 103

```
Gly Gly Gly Ser Gly Gly Gly Ser Gly Ser Gly Gly Gly
1               5                   10
```

<210> SEQ ID NO 104
<211> LENGTH: 11
<212> TYPE: PRT
<213> ORGANISM: Homo sapiens

<400> SEQUENCE: 104

```
Gly Ser Gly Ser Gly Gly Gly Gly Ser Gly Gly
1               5                   10
```

<210> SEQ ID NO 105
<211> LENGTH: 13
<212> TYPE: PRT
<213> ORGANISM: Homo sapiens

<400> SEQUENCE: 105

```
Ser Gly Gly Gly Gly Ser Gly Gly Gly Ser Gly Ser Gly
1               5                   10
```

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Gly Gly Gly Ser Gly Ser Gly Gly Gly Gly Ser
1               5                   10
```

<210> SEQ ID NO 107
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 2 to 40
      "Gly-Gly-Gly-Ser-Gly-Ser-Gly-Gly-Gly-Gly-Ser" repeating units

<400> SEQUENCE: 107

```
Gly Gly Gly Ser Gly Ser Gly Gly Gly Gly Ser Gly Gly Gly Ser Gly
1               5                   10                  15

Ser Gly Gly Gly Gly Ser Gly Gly Gly Ser Gly Ser Gly Gly Gly Gly
            20                  25                  30

Ser Gly Gly Gly Ser Gly Ser Gly Gly Gly Gly Ser Gly Gly Gly Ser
        35                  40                  45

Gly Ser Gly Gly Gly Gly Ser Gly Gly Gly Ser Gly Ser Gly Gly Gly
    50                  55                  60

Gly Ser Gly Gly Gly Ser Gly Ser Gly Gly Gly Gly Ser Gly Gly Gly
65                  70                  75                  80

Ser Gly Ser Gly Gly Gly Gly Ser Gly Gly Gly Ser Gly Ser Gly Gly
                85                  90                  95

Gly Gly Ser Gly Gly Gly Ser Gly Ser Gly Gly Gly Gly Ser Gly Gly
                100                 105                 110

Gly Ser Gly Ser Gly Gly Gly Gly Ser Gly Gly Gly Ser Gly Ser Gly
```

-continued

```
            115                 120                 125
Gly Gly Gly Ser Gly Gly Gly Ser Gly Ser Gly Gly Gly Ser Gly
            130                 135                 140

Gly Gly Ser Gly Ser Gly Gly Gly Ser Gly Gly Gly Ser Gly Ser
145                 150                 155                 160

Gly Gly Gly Gly Ser Gly Gly Gly Ser Gly Ser Gly Gly Gly Ser
                165                 170                 175

Gly Gly Gly Ser Gly Ser Gly Gly Gly Ser Gly Gly Gly Ser Gly
                180                 185                 190

Ser Gly Gly Gly Gly Ser Gly Gly Ser Gly Ser Gly Gly Gly Gly
                195                 200                 205

Ser Gly Gly Gly Ser Gly Ser Gly Gly Gly Ser Gly Gly Gly Ser
                210                 215                 220

Gly Ser Gly Gly Gly Gly Ser Gly Gly Gly Ser Gly Ser Gly Gly
225                 230                 235                 240

Gly Gly Ser Gly Gly Gly Ser Gly Ser Gly Gly Gly Ser Gly Gly
                245                 250                 255

Gly Ser Gly Ser Gly Gly Gly Ser Gly Gly Gly Ser Gly Ser Gly
                260                 265                 270

Gly Gly Ser Gly Gly Gly Ser Gly Ser Gly Gly Gly Ser Gly Gly
                275                 280                 285

Gly Ser Gly Ser Gly Gly Gly Ser Gly Gly Gly Ser Gly Ser Gly
                290                 295                 300

Gly Gly Gly Ser Gly Gly Gly Ser Gly Ser Gly Gly Gly Ser Gly
305                 310                 315                 320

Gly Gly Ser Gly Ser Gly Gly Gly Ser Gly Gly Gly Ser Gly Ser
                325                 330                 335

Gly Gly Gly Gly Ser Gly Gly Gly Ser Gly Ser Gly Gly Gly Ser
                340                 345                 350

Gly Gly Gly Ser Gly Ser Gly Gly Gly Ser Gly Gly Gly Ser Gly
                355                 360                 365

Ser Gly Gly Gly Gly Ser Gly Gly Gly Ser Gly Gly Gly Gly Gly
                370                 375                 380

Ser Gly Gly Gly Ser Gly Ser Gly Gly Gly Ser Gly Gly Gly Ser
385                 390                 395                 400

Gly Ser Gly Gly Gly Gly Ser Gly Gly Gly Ser Gly Ser Gly Gly
                405                 410                 415

Gly Ser Gly Gly Gly Ser Gly Ser Gly Gly Gly Gly Ser Gly Gly
                420                 425                 430

Ser Gly Ser Gly Gly Gly Gly Ser
        435                 440

<210> SEQ ID NO 108
<211> LENGTH: 37
<212> TYPE: PRT
<213> ORGANISM: Homo sapiens

<400> SEQUENCE: 108

Gly Pro Gly Gly Gly Gly Gly Pro Gly Gly Gly Gly Pro Gly Gly
1               5                   10                  15

Gly Gly Pro Gly Gly Gly Gly Gly Gly Pro Gly Gly Gly Gly
                20                  25                  30

Gly Pro Gly Gly Gly
        35
```

```
<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Gly Gly Gly Pro Gly Gly Gly Gly Pro
1               5                   10

<210> SEQ ID NO 110
<211> LENGTH: 16
<212> TYPE: PRT
<213> ORGANISM: Homo sapiens

<400> SEQUENCE: 110

Gly Ala Gly Gly Glu Gly Gly Gly Gly Glu Gly Gly Gly Pro Gly Gly
1               5                   10                  15

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Gly Gly Glu
1               5

<210> SEQ ID NO 112
<211> LENGTH: 62
<212> TYPE: PRT
<213> ORGANISM: Laticauda semifasciata

<400> SEQUENCE: 112

Arg Ile Cys Phe Asn His Gln Ser Ser Gln Pro Gln Thr Thr Lys Thr
1               5                   10                  15

Cys Ser Pro Gly Glu Ser Ser Cys Tyr Asn Lys Gln Trp Ser Asp Phe
                20                  25                  30

Arg Gly Thr Ile Ile Glu Arg Gly Cys Gly Cys Pro Thr Val Lys Pro
            35                  40                  45

Gly Ile Lys Leu Ser Cys Cys Glu Ser Glu Val Cys Asn Asn
        50                  55                  60

<210> SEQ ID NO 113
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gly Ser Gly Gly Glu Gly Gly Ser Gly Gly Glu Gly Gly Ser Gly Gly
1               5                   10                  15

Glu Gly Gly Ser Gly Gly Glu Gly Gly Ser Gly Gly Glu Gly Gly Ser
                20                  25                  30

Gly Gly Glu Gly Gly Ser Gly Gly Glu Gly Gly Ser Gly Gly Glu Gly
            35                  40                  45
```

Gly Ser Gly Gly Glu Gly Gly Ser Gly Gly Glu Gly Gly Ser Gly Gly
        50                  55                  60

Glu Gly Gly Ser Gly Gly Glu Gly Gly Ser Gly Gly Glu Gly Gly Ser
65                  70                  75                  80

Gly Gly Glu Gly Gly Ser Gly Gly Glu Gly Gly Ser Gly Gly Glu Gly
                85                  90                  95

Gly Ser Gly Gly Glu Gly Gly Ser Gly Gly Glu Gly Gly Ser Gly Gly
            100                 105                 110

Glu Gly Gly Ser Gly Gly Glu Gly Gly Ser Gly Gly Glu Gly Gly Ser
            115                 120                 125

Gly Gly Glu Gly Gly Ser Gly Gly Glu Gly Gly Ser Gly Gly Glu Gly
        130                 135                 140

Gly Ser Gly Gly Glu Gly Gly Ser Gly Gly Glu Gly Gly Ser Gly Gly
145                 150                 155                 160

Glu Gly Gly Ser Gly Gly Glu Gly Gly Ser Gly Gly Glu Gly Gly Ser
                165                 170                 175

Gly Gly Glu Gly Gly Ser Gly Gly Glu Gly Gly Ser Gly Gly Glu Gly
                180                 185                 190

Gly Ser Gly Gly Glu Gly Gly Ser Gly Gly Glu Gly Gly Ser Gly Gly
            195                 200                 205

Glu Gly Gly Ser Gly Gly Glu Gly Gly Ser Gly Gly Glu Gly Gly Ser
            210                 215                 220

Gly Gly Glu Gly Gly Ser Gly Gly Glu Gly Gly Ser Gly Gly Glu Gly
225                 230                 235                 240

Gly Ser Gly Gly Glu Gly Gly Ser Gly Gly Glu Gly Gly Ser Gly Gly
                245                 250                 255

Glu Gly Gly Ser Gly Gly Glu Gly Gly Ser Gly Gly Glu Gly Gly Ser
            260                 265                 270

Gly Gly Glu Gly Gly Ser Gly Gly Glu Gly Gly Ser Gly Gly Glu Gly
        275                 280                 285

<210> SEQ ID NO 114
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Ser Gly Gly Glu Gly Gly Ser Gly Gly Glu Gly Gly Ser Gly Gly
1               5                   10                  15

Glu Gly Gly Ser Gly Gly Glu Gly Gly Ser Gly Gly Glu Gly Gly Ser
            20                  25                  30

Gly Gly Glu Gly
        35

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Ser Gly Gly Glu Gly Gly Ser Gly Gly Glu Gly
1               5                   10

<210> SEQ ID NO 116
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
aggtagtggw ggwgarggwg gwtcyggwgg agaagg                          36

<210> SEQ ID NO 117
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
acctccttct ccwccrgawc cwccytcwcc wccact                          36

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aggttcgtct tcactcgagg gtac                                       24

<210> SEQ ID NO 119
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cctcgagtga agacga                                                16

<210> SEQ ID NO 120
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gly Ser Gly Gly Glu Gly Gly Ser Gly Gly Ser Gly Gly Ser Gly Gly
1               5                   10                  15

Glu Gly Gly Ser Gly Gly Ser Gly Gly Ser Gly Gly Glu Gly Gly Ser
            20                  25                  30

Gly Gly Ser Gly Gly Ser Gly Gly Glu Gly Gly Ser Gly Gly Ser Gly
        35                  40                  45

Gly Ser Gly Gly Glu Gly Gly Ser Gly Gly Ser Gly Gly Ser Gly Gly
    50                  55                  60

Glu Gly Gly Ser Gly Gly Ser Gly Gly Ser Gly Gly Glu Gly Gly Ser
65                  70                  75                  80

Gly Gly Ser Gly Gly Ser Gly Gly Glu Gly Gly Ser Gly Gly Ser Gly

```
            85                  90                  95
Gly Ser Gly Gly Glu Gly Gly Ser Gly Ser Gly Gly Ser Gly Gly
        100                 105                 110
Glu Gly Gly Ser Gly Gly Ser Gly Gly Ser Gly Gly Glu Gly Gly Ser
    115                 120                 125
Gly Gly Ser Gly Gly Ser Gly Gly Glu Gly Gly Ser Gly Gly Ser Gly
130                 135                 140
Gly Ser Gly Gly Glu Gly Gly Ser Gly Gly Ser Gly Gly Ser Gly Gly
145                 150                 155                 160
Glu Gly Gly Ser Gly Gly Ser Gly Gly Ser Gly Gly Glu Gly Gly Ser
                165                 170                 175
Gly Gly Ser Gly Gly Ser Gly Gly Glu Gly Gly Ser Gly Gly Ser Gly
            180                 185                 190
Gly Ser Gly Gly Glu Gly Gly Ser Gly Gly Ser Gly Gly Ser Gly Gly
        195                 200                 205
Glu Gly Gly Ser Gly Gly Ser Gly Gly Ser Gly Gly Glu Gly Gly Ser
    210                 215                 220
Gly Gly Ser Gly Gly Ser Gly Gly Glu Gly Gly Ser Gly Gly Ser Gly
225                 230                 235                 240
Gly Ser Gly Gly Glu Gly Gly Ser Gly Gly Ser Gly Gly Ser Gly Gly
                245                 250                 255
Glu Gly Gly Ser Gly Gly Ser Gly Gly Ser Gly Gly Glu Gly Gly Ser
            260                 265                 270
Gly Gly Ser Gly Gly Ser Gly Gly Glu Gly Gly Ser Gly Gly Ser Gly
        275                 280                 285

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Phe Thr Cys Thr Asn His Trp Cys Pro Ser
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Phe Gln Cys Thr Arg His Trp Cys Pro Ile
1               5                   10

<210> SEQ ID NO 123
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Gly Ser Gly Gly Ser Gly Gly Ser Gly Gly Ser Gly Gly Ser Gly
1               5                   10                  15
```

Gly Ser Gly Gly Ser Gly Gly Ser Gly Gly Ser Gly Gly
            20                  25                  30

Ser Gly Gly Ser
        35

<210> SEQ ID NO 124
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other

<400> SEQUENCE: 124
nnsnnsnnst gcnnsnnstg tnnsnnsnns                                         30

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)

<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other

<400> SEQUENCE: 125
nnsnnstgcn nsnnsnnstg tnnsnnsnns                                              30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other

<400> SEQUENCE: 126
nnsnnstgcn nsnnsnnsnn stgtnnsnns                                              30

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other

```
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other

<400> SEQUENCE: 127
nnstgcnnsn nsnnsnnsnn stgtnnsnns                              30

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other

<400> SEQUENCE: 128
nnstgcnnsn nsnnsnnsnn snnstgtnns                              30

<210> SEQ ID NO 129
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other

<400> SEQUENCE: 129
tgcnnsnnsn nsnnsnnsnn snnstgtnns                                           30

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
```

```
<223> OTHER INFORMATION: a, c, g, t, unknown or other

<400> SEQUENCE: 130
tgcnnsnnsn nsnnsnnsnn snnsnnstgt                                           30

<210> SEQ ID NO 131
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other

<400> SEQUENCE: 131
tgcnnsnnsn nsnnsnnsnn snnsnnsnns tgt                                       33

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
```

-continued

```
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other

<400> SEQUENCE: 132
tgcnnsnnsn nsnnsnnsnn snnsnnsnns nnstgt                              36

<210> SEQ ID NO 133
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
```

<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 133
nnsnnsnnsn nsnnsnnstg cnnsnnstgt nnsnnsnnsn nsnnsnns            48

<210> SEQ ID NO 134
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other

```
<220> FEATURE:
<221> NAME/KEY: modified_base
<222> LOCATION: (46)..(47)
<223> OTHER INFORMATION: a, c, g, t, unknown or other

<400> SEQUENCE: 134
nnsnnsnnsn nsnnstgcnn snnsnnstgt nnsnnsnnsn nsnnsnns                         48

<210> SEQ ID NO 135
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 135
nnsnnsnnsn nsnnstgcnn snnsnnsnns tgtnnsnnsn nsnnsnns                         48
```

```
<210> SEQ ID NO 136
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 136
nnsnnsnnsn nstgcnnsnn snnsnnsnns tgtnnsnnsn nsnnsnns            48

<210> SEQ ID NO 137
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
```

```
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 137
nnsnnsnnsn nstgcnnsnn snnsnnsnns nnstgtnnsn nsnnsnns                48

<210> SEQ ID NO 138
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
```

<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 138
nnsnnsnnst gcnnsnnsnn snnsnnsnns nnstgtnnsn nsnnsnns        48

<210> SEQ ID NO 139
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)

<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 139
nnsnnsnnst gcnnsnnsnn snnsnnsnns nnsnnstgtn nsnnsnns         48

<210> SEQ ID NO 140
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:

```
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 140
nnsnnstgcn nsnnsnnsnn snnsnnsnns nnsnnstgtn nsnnsnns        48

<210> SEQ ID NO 141
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<221> NAME/KEY: modified_base
<222> LOCATION: (13)..(14)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (34)..(35)
```

<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 141
nnsnnstgcn nsnnsnnsnn snnsnnsnns nnsnnsnnst gtnnsnns                48

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Tyr Ile Cys His Asn Cys Leu Leu Ser
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Leu Arg Cys Trp Gly Met Leu Cys Tyr Ala
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Leu Arg Cys Ile Gly Gln Ile Cys Trp Arg
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Leu Lys Cys Leu Tyr Asn Ile Cys Trp Val
1               5                   10

<210> SEQ ID NO 146
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 146

Arg Pro Gly Met Ala Cys Ser Gly Gln Leu Cys Trp Leu Asn Ser Pro
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Pro His Ala Leu Gln Cys Tyr Gly Ser Leu Cys Trp Pro Ser His Leu
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ala Gly Ile Thr Cys His Gly His Leu Cys Trp Pro Ile Thr Asp
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Pro Ala Leu Lys Cys Ile Gly Thr Leu Cys Ser Leu Ala Asn Pro
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Pro His Gly Leu Trp Cys His Gly Ser Leu Cys His Tyr Pro Leu Ala
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Pro His Gly Leu Ile Cys Ala Gly Ser Ile Cys Phe Trp Pro Pro Pro
1               5                   10                  15
```

```
<210> SEQ ID NO 152
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Arg Asn Leu Thr Cys Tyr Gly Gln Ile Cys Phe Gln Ser Gln His
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Pro His Asn Leu Ala Cys Gln Asn Ser Ile Cys Val Arg Leu Pro Arg
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Pro His Gly Leu Thr Cys Thr Asn Gln Ile Cys Phe Tyr Gly Asn Thr
1               5                   10                  15

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Leu Phe Cys Trp Gly Asn Val Cys His Phe
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Leu Thr Cys Trp Gly Gln Val Cys Phe Arg
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 157

Arg Cys Pro Ser Arg Val Pro Trp Cys Val
1               5                   10

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Leu Val Cys Gly Phe Ser Asp Ser Ser Arg Leu Cys Tyr Met Arg
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Leu Cys Tyr Ile Thr Ser Pro Gly Asn Arg Leu Cys Ser Pro Tyr
1               5                   10                  15

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Glu Cys Thr Gln His Trp Cys Pro Ser
1               5                   10

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Pro Phe Phe Ser Cys Ser Phe Gly Phe Cys Arg Asp Leu Gln Thr
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Thr Pro Tyr Phe Arg Cys Gln Phe Gly Phe Cys Phe Asp Ser Phe Ser
1               5                   10                  15

<210> SEQ ID NO 163
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 163

Asn Pro Phe Phe Tyr Cys Val Ala Gly Lys Cys Val Asp Ala Pro Leu
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asp Met Arg Phe Leu Cys Arg His Gly Lys Cys His Asp Leu Pro Leu
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Pro Pro Phe Phe Val Cys Ser Leu Gly Lys Cys Arg Asp Ala His Leu
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Pro Gln Phe Gln Cys Val Arg Gly Lys Cys Phe Asp Leu Thr Phe
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ile Ser Thr Phe Phe Cys Ser Asn Gly Ser Cys Val Asp Val Pro Ala
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Pro Pro His Phe Arg Cys Phe Asn Gly Ser Cys Val Asp Leu Ser Arg
1               5                   10                  15
```

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asn Val His Phe Trp Cys His Asn His Lys Cys His Asp Leu Val Ser
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Leu Phe Phe Lys Cys Asp Val Gly His Gly Cys Tyr Asp Ile Lys His
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Leu Tyr Phe Gln Cys Phe Pro Asn Arg Gly Cys Ser Thr Leu Gln Pro
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Pro Ser Phe Phe Cys Ser Pro Leu Leu Gly Cys Arg Asp Ser Leu Ser
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Thr Pro Arg Cys Asn Pro Phe Arg Gln Phe Cys Ala Ile Pro Ser
1               5                   10                  15

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Leu Cys Leu Pro Leu Gly Arg Trp Cys Pro
1               5                   10

<210> SEQ ID NO 175
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Thr Ser Pro Ala Cys Asn Pro Phe Arg His Phe Cys Thr Leu Pro Thr
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gln Pro Pro Ile Cys Asn Pro Phe Arg Gln Leu Cys Gly Ile Pro Leu
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Val His Thr Phe Cys Asn Pro Phe Arg Gln Met Cys Ser Leu Pro Met
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Met Val Asn Cys Asn Pro Phe Asn Ser Trp Cys Ser Leu Pro Ser
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Lys His Met Cys Asn Pro Phe His Ser Trp Cys Gly Val Pro Leu
1               5                   10                  15

<210> SEQ ID NO 180
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Trp Pro Val Cys Asn Pro Phe Leu Gly Tyr Cys Gly Ile Pro Asn
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Lys Pro Thr Cys Asn Val Phe Asn Ser Trp Cys Ser Val Pro Leu
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Pro Pro Ala Cys Asn Leu Phe Leu Ser Trp Cys Ser Tyr Asp Ser
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Arg Ser Val Cys Asn Pro Tyr Lys Ser Trp Cys Pro Val Arg Gln
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Ser Ser Cys Lys Asp Ser Pro His Phe Arg Cys Leu Phe Pro Leu
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Leu Ala Asn Cys Pro Asn Ser Pro Gly Phe Leu Cys Leu His Ala Val
```

```
1               5                   10                  15
```

<210> SEQ ID NO 186
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Pro Phe Ala Cys Pro His Ser Ser Gly Phe Arg Cys Leu Tyr Asn Ile
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Phe Thr Cys Ser Leu Phe Pro Ser Pro His Cys Thr Thr Leu Arg
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Leu Arg Leu Cys Thr Tyr Gly Gly Gly Lys Tyr Asp Cys Ser Ser Thr
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Ser Tyr Cys Gln Tyr Arg Pro Phe Ser Ser Phe Cys Asn Arg Ser
1               5                   10                  15

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Cys Ser Tyr Asn Gln Val Leu Gly Arg Ala Cys
1               5                   10

<210> SEQ ID NO 191
<211> LENGTH: 16
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 191

Pro His Cys Arg Gln His Pro Leu Asp Arg Trp Met Cys Ser Pro Ser
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Leu Cys Ser Met Phe Gly Asp Thr Pro His Trp Asn Cys Val Pro
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Ser Cys Ser Leu Phe Asn Asn Thr Arg His Trp Ser Cys Thr Asp
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Thr Thr Ala Tyr Pro Asp Cys Phe Trp Cys Ser Leu Phe Gly Pro Pro
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Met Leu Asp Thr Thr Ile Cys Pro Trp Cys Ser Leu Phe Gly Pro Val
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 196

Met Leu Xaa Thr Thr Ile Cys Pro Trp Cys Ser Leu Phe Gly Pro Val

-continued

```
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Glu Leu Leu Leu Glu Arg Cys Ser Trp Cys Ser Leu Phe Gly Pro Pro
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Leu Ser Gln Gln Ser Cys Asp Trp Cys Trp Leu Phe Gly Pro Pro
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Lys Arg Leu Leu Glu Cys Gly Ala Leu Cys Ala Leu Phe Gly Pro Pro
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

His Thr Ile Leu Thr Cys Asp Ser Gly Phe Cys Thr Leu Phe Gly Pro
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Asn Leu Trp His Val Cys His Thr Ser Leu Cys His Ser Arg Leu Ala
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 202

Asn Ser Phe Tyr Leu Cys His Ser Ser Val Cys Gly Gln Leu Pro Ser
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Gly Phe Ser Cys Glu Asn Tyr Phe Phe Cys Pro Pro Lys Asn Leu
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Trp Cys Thr Val Phe Gly Asn His Asp Pro Ser Cys Asn Ser Arg
1               5                   10                  15

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Ser Ser Asn Gly Arg Trp Lys Ala His Cys
1               5                   10

<210> SEQ ID NO 206
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Leu Pro Asn Met Trp Arg Val Val Pro Asp Val Tyr Asp Arg Arg
1               5                   10                  15

<210> SEQ ID NO 207
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Lys His Tyr Cys Phe Gly Pro Lys Ser Trp Thr Thr Cys Ala Arg Gly
1               5                   10                  15

<210> SEQ ID NO 208

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Pro Trp Cys His Leu Cys Pro Gly Ser Pro Ser Arg Cys Cys Gln Pro
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Pro Glu Ser Lys Leu Ile Ser Glu Glu Asp Leu Asn Gly Asp Val Ser
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ile Trp Asp Arg Val Cys Arg Met Asn Thr Cys His Gln His Ser His
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Pro Tyr Thr Ile Phe Cys Leu His Ser Ser Cys Arg Ser Ser Ser Ser
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Trp Cys Leu Thr Gly Pro Asn Thr Leu Ser Phe Cys Pro Arg Arg
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213
```

```
Leu Ser Thr Trp Arg Cys Leu His Asp Val Cys Trp Pro Pro Leu Lys
1               5                   10                  15
```

<210> SEQ ID NO 214
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Val Tyr Leu Thr Gln Cys Gly Ala Gln Leu Cys Leu Lys Arg Thr Asn
1               5                   10                  15
```

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Pro Tyr Leu Thr Ser Cys Gly Asp Arg Val Cys Leu Lys Arg Pro Pro
1               5                   10                  15
```

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Pro Tyr Leu Ser Arg Cys Gly Gly Arg Ile Cys Met His Asp Arg Leu
1               5                   10                  15
```

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Leu Lys Leu Thr Pro Cys Ser His Gly Val Cys Met His Arg Leu Arg
1               5                   10                  15
```

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Tyr Tyr Leu Thr Asn Cys Pro Lys Gly His Cys Leu Arg Arg Val Asp
1               5                   10                  15
```

<210> SEQ ID NO 219
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 219

Leu Tyr Leu His Ser Cys Ser Arg Gly Ile Cys Leu Ser Pro Arg Val
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Phe Ser Cys Gln Ser Ser Phe Pro Gly Arg Arg Met Cys Glu Leu Arg
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

His Arg Cys Ser Ala His Gly Ser Ser Ser Phe Cys Pro Gly Ser
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Lys Thr Trp Asp Cys Arg Asn Ser Gly His Cys Val Ile Thr Phe Lys
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Thr Trp Asp Cys Arg Asp His Asn Phe Ser Cys Val Arg Leu Ser
1               5                   10                  15

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Leu Arg Cys Trp Gly Met Leu Cys Tyr Ala
1               5                   10
```

```
<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Leu Arg Cys Ile Gly Gln Ile Cys Trp Arg
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Leu Lys Cys Leu Tyr Asn Ile Cys Trp Val
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Leu Phe Cys Trp Gly Asn Val Cys His Phe
1               5                   10

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Leu Thr Cys Trp Gly Gln Val Cys Phe Arg
1               5                   10

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Arg Pro Gly Met Ala Cys Ser Gly Gln Leu Cys Trp Leu Asn Ser Pro
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230
```

Pro His Ala Leu Gln Cys Tyr Gly Ser Leu Cys Trp Pro Ser His Leu
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Arg Ala Gly Ile Thr Cys His Gly His Leu Cys Trp Pro Ile Thr Asp
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Arg Pro Ala Leu Lys Cys Ile Gly Thr Leu Cys Ser Leu Ala Asn Pro
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Pro His Gly Leu Trp Cys His Gly Ser Leu Cys His Tyr Pro Leu Ala
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Pro His Gly Leu Ile Cys Ala Gly Ser Ile Cys Phe Trp Pro Pro Pro
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Pro Arg Asn Leu Thr Cys Tyr Gly Gln Ile Cys Phe Gln Ser Gln His
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Pro His Asn Leu Ala Cys Gln Asn Ser Ile Cys Val Arg Leu Pro Arg
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Pro His Gly Leu Thr Cys Thr Asn Gln Ile Cys Phe Tyr Gly Asn Thr
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

His Ser Leu Thr Cys Tyr Gly Gln Ile Cys Trp Val Ser Asn Ile
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Pro Thr Leu Thr Cys Tyr Asn Gln Val Cys Trp Val Asn Arg Thr
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Pro Ala Leu Arg Cys Leu Gly Gln Leu Cys Trp Val Thr Pro Thr
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Pro Gly Leu Arg Cys Leu Gly Thr Leu Cys Trp Val Pro Asn Arg
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Arg Asn Leu Thr Cys Trp Asn Thr Val Cys Tyr Ala Tyr Pro Asn
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Arg Gly Leu Lys Cys Leu Gly Gln Leu Cys Trp Val Ser Ser Asn
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Pro Thr Leu Lys Cys Ser Gly Gln Ile Cys Trp Val Pro Pro Pro
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Arg Asn Leu Glu Cys Leu Gly Asn Val Cys Ser Leu Leu Asn Gln
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Pro Thr Leu Thr Cys Leu Asn Asn Leu Cys Trp Val Pro Pro Gln
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 247

Arg Gly Leu Lys Cys Ser Gly His Leu Cys Trp Val Thr Pro Gln
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

His Gly Leu Thr Cys His Asn Thr Val Cys Trp Val His His Pro
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

His Thr Leu Glu Cys Leu Gly Asn Ile Cys Trp Val Ile Asn Gln
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

His Gly Leu Thr Cys Tyr Asn Gln Ile Cys Trp Ala Pro Arg Pro
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

His Gly Leu Ala Cys Tyr Asn Gln Leu Cys Trp Val Asn Pro His
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Arg Gly Leu Ala Cys Gln Gly Asn Ile Cys Trp Arg Leu Asn Pro
1               5                   10                  15

<210> SEQ ID NO 253
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 253

Arg Ala Ile Thr Cys Leu Gly Thr Leu Cys Trp Pro Thr Ser Pro
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Leu Thr Leu Glu Cys Ile Gly Asn Ile Cys Tyr Val Pro His His
1               5                   10                  15

<210> SEQ ID NO 255
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
caggcagcgg gcccgtctgg cccgtgyttt acttgtacga atcattggtg tcct            54

<210> SEQ ID NO 256
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, g, t, unknown or other

<400> SEQUENCE: 256
caggcagcgg gcccgtctgg cccgtgynnk tttacttgta cgaatcattg gtgtcct         57

<210> SEQ ID NO 257
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other

<400> SEQUENCE: 257
caggcagcgg gcccgtctgg cccgtgynnk nnktttactt gtacgaatca ttggtgtcct      60

<210> SEQ ID NO 258
<211> LENGTH: 63
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: a, c, g, t, unknown or other
<220> FEATURE:
<221> NAME/KEY: modified_base
<222> LOCATION: (31)..(31)
<223> OTHER INFORMATION: a, c, g, t, unknown or other
<220> FEATURE:
<221> NAME/KEY: modified_base
<222> LOCATION: (34)..(34)
<223> OTHER INFORMATION: a, c, g, t, unknown or other

<400> SEQUENCE: 258
caggcagcgg gcccgtctgg cccgtgynht nhtnhtttta cttgtacgaa tcattggtgt    60
cct                                                                 63

<210> SEQ ID NO 259
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: a, c, g, t, unknown or other
<220> FEATURE:
<221> NAME/KEY: modified_base
<222> LOCATION: (31)..(31)
<223> OTHER INFORMATION: a, c, g, t, unknown or other
<220> FEATURE:
<221> NAME/KEY: modified_base
<222> LOCATION: (34)..(34)
<223> OTHER INFORMATION: a, c, g, t, unknown or other
<220> FEATURE:
<221> NAME/KEY: modified_base
<222> LOCATION: (37)..(37)
<223> OTHER INFORMATION: a, c, g, t, unknown or other

<400> SEQUENCE: 259
caggcagcgg gcccgtctgg cccgtgynht nhtnhtnhtt ttacttgtac gaatcattgg    60
tgtcct                                                              66

<210> SEQ ID NO 260
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
caggcagcgg gcccgtctgg cccgtgykmt kmtkmtkmtk mttttacttg tacgaatcat    60
tggtgtcc                                                            68

<210> SEQ ID NO 261
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
```
accggaacca ccagactggc crcacgaagg acaccaatga ttcgtacaa    49

<210> SEQ ID NO 262
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: a, c, g, t, unknown or other

<400> SEQUENCE: 262
accggaacca ccagactggc crcamnncga aggacaccaa tgattcgtac aa    52

<210> SEQ ID NO 263
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: a, c, g, t, unknown or other
<220> FEATURE:
<221> NAME/KEY: modified_base
<222> LOCATION: (29)..(30)
<223> OTHER INFORMATION: a, c, g, t, unknown or other

<400> SEQUENCE: 263
accggaacca ccagactggc crcamnnmnn cgaaggacac caatgattcg tacaa    55

<210> SEQ ID NO 264
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (30)..(30)
<223> OTHER INFORMATION: a, c, g, t, unknown or other
<220> FEATURE:
<221> NAME/KEY: modified_base
<222> LOCATION: (33)..(33)
<223> OTHER INFORMATION: a, c, g, t, unknown or other

<400> SEQUENCE: 264
accggaacca ccagactggc crcaadnadn adncgaagga caccaatgat tcgtacaa    58

<210> SEQ ID NO 265
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: a, c, g, t, unknown or other
<220> FEATURE:

```
<221> NAME/KEY: modified_base
<222> LOCATION: (30)..(30)
<223> OTHER INFORMATION: a, c, g, t, unknown or other
<220> FEATURE:
<221> NAME/KEY: modified_base
<222> LOCATION: (33)..(33)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other

<400> SEQUENCE: 265
accggaacca ccagactggc crcaadnadn adnadncgaa ggacaccaat gattcgtaca    60
a                                                                   61

<210> SEQ ID NO 266
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
accggaacca ccagactggc crcaakmakm akmakmakmc gaaggacacc aatgattcgt    60
acaa                                                                64

<210> SEQ ID NO 267
<211> LENGTH: 4
<212> TYPE: PRT
<213> ORGANISM: Homo sapiens

<400> SEQUENCE: 267

Cys Gly Trp Cys
1

<210> SEQ ID NO 268
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Pro Ser Gly Pro Ser Cys His Thr Thr Asn His Trp Pro Ile Ser Ala
1               5                   10                  15

Val Thr Cys Pro Pro
            20

<210> SEQ ID NO 269
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Gly Gly Ser Gly Ser Gly Gly Gly Gly Ser Gly Gly Gly Ser Gly
1               5                   10                  15

Ser Gly Gly Gly Gly Ser Gly Gly Gly Ser Gly Ser Gly Gly Gly Gly
            20                  25                  30
```

```
<210> SEQ ID NO 270
<211> LENGTH: 13
<212> TYPE: PRT
<213> ORGANISM: Homo sapiens

<400> SEQUENCE: 270

Gly Gly Ser Gly Ser Gly Gly Gly Ser Gly Gly Gly
1               5                   10

<210> SEQ ID NO 271
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gly Gly Gly Gly Gly Pro Gly Gly Gly Gly Pro Gly Gly Gly Gly
1               5                   10                  15

Pro Gly Gly Gly Gly Pro Gly Gly Gly Gly Pro Gly Gly Gly Gly
            20                  25                  30

Pro

<210> SEQ ID NO 272
<211> LENGTH: 864
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(864)

<400> SEQUENCE: 272 ggt agt ggt ggt gaa gga ggt tct ggt gga gaa gga ggt agt gga ggt      48
Gly Ser Gly Gly Glu Gly Gly Ser Gly Gly Glu Gly Gly Ser Gly Gly
1               5                   10                  15 gaa ggt gga tcc gga gga gaa gga ggt agt gga ggt gaa ggt gga tcc      96
Glu Gly Gly Ser Gly Gly Glu Gly Gly Ser Gly Gly Glu Gly Gly Ser
            20                  25                  30 gga gga gaa gga ggt agt ggt ggt gaa gga ggt tct ggt gga gaa gga     144
Gly Gly Glu Gly Gly Ser Gly Gly Glu Gly Gly Ser Gly Gly Glu Gly
        35                  40                  45 ggt agt gga ggt gaa ggt gga tcc gga gga gaa gga ggt agt gga ggt     192
Gly Ser Gly Gly Glu Gly Gly Ser Gly Gly Glu Gly Gly Ser Gly Gly
    50                  55                  60 gaa gga gga tcc gga gga gaa gga ggt agt gga ggt gaa ggt gga tcc     240
Glu Gly Gly Ser Gly Gly Glu Gly Gly Ser Gly Gly Glu Gly Gly Ser
65                  70                  75                  80 ggt gga gaa gga ggt agt gga ggt gaa gga ggt tcc ggt gga gaa gga     288
Gly Gly Glu Gly Gly Ser Gly Gly Glu Gly Gly Ser Gly Gly Glu Gly
                85                  90                  95 ggt agt gga gga gag ggt gga tct gga gga gaa gga ggt agt gga gga     336
Gly Ser Gly Gly Glu Gly Gly Ser Gly Gly Glu Gly Gly Ser Gly Gly
            100                 105                 110 gag ggt ggt tct gga gga gaa gga ggt agt gga gga gag ggt gga tct     384
Glu Gly Gly Ser Gly Gly Glu Gly Gly Ser Gly Gly Glu Gly Gly Ser
        115                 120                 125 ggt gga gaa gga ggt agt gga gga gaa ggt ggt tct gga gga gaa gga     432
Gly Gly Glu Gly Gly Ser Gly Gly Glu Gly Gly Ser Gly Gly Glu Gly
    130                 135                 140
```

```
ggt agt ggt ggt gaa gga ggt tct ggt gga gaa gga ggt agt gga ggt        480
Gly Ser Gly Gly Glu Gly Gly Ser Gly Gly Glu Gly Gly Ser Gly Gly
145                 150                 155                 160 gaa ggt gga tcc gga gga gaa gga ggt agt gga ggt gaa gga gga tcc        528
Glu Gly Gly Ser Gly Gly Glu Gly Gly Ser Gly Gly Glu Gly Gly Ser
                165                 170                 175 gga gga gaa gga ggt agt ggt ggt gaa gga ggt tct ggt gga gaa gga        576
Gly Gly Glu Gly Gly Ser Gly Gly Glu Gly Gly Ser Gly Gly Glu Gly
            180                 185                 190 ggt agt gga ggt gaa ggt gga tcc gga gga gaa gga ggt agt gga ggt        624
Gly Ser Gly Gly Glu Gly Gly Ser Gly Gly Glu Gly Gly Ser Gly Gly
195                 200                 205 gaa gga gga tcc gga gga gaa gga ggt agt gga ggt gaa ggt gga tcc        672
Glu Gly Gly Ser Gly Gly Glu Gly Gly Ser Gly Gly Glu Gly Gly Ser
    210                 215                 220 ggt gga gaa gga ggt agt gga ggt gaa gga ggt tcc ggt gga gaa gga        720
Gly Gly Glu Gly Gly Ser Gly Gly Glu Gly Gly Ser Gly Gly Glu Gly
225                 230                 235                 240 ggt agt gga gga gag ggt gga tct gga gga gaa gga ggt agt gga gga        768
Gly Ser Gly Gly Glu Gly Gly Ser Gly Gly Glu Gly Gly Ser Gly Gly
                245                 250                 255 gag ggt ggt tct gga gga gaa gga ggt agt ggt gga gag ggt gga tct        816
Glu Gly Gly Ser Gly Gly Glu Gly Gly Ser Gly Gly Glu Gly Gly Ser
            260                 265                 270 ggt gga gaa gga ggt agt gga gga gaa ggt ggt tct gga gga gaa gga        864
Gly Gly Glu Gly Gly Ser Gly Gly Glu Gly Gly Ser Gly Gly Glu Gly
275                 280                 285
```

<210> SEQ ID NO 273
<211> LENGTH: 288
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 273

```
Gly Ser Gly Gly Glu Gly Gly Ser Gly Gly Glu Gly Gly Ser Gly Gly
1               5                   10                  15

Glu Gly Gly Ser Gly Gly Glu Gly Gly Ser Gly Gly Glu Gly Gly Ser
                20                  25                  30

Gly Gly Glu Gly Gly Ser Gly Gly Glu Gly Gly Ser Gly Gly Glu Gly
            35                  40                  45

Gly Ser Gly Gly Glu Gly Gly Ser Gly Gly Glu Gly Gly Ser Gly Gly
        50                  55                  60

Glu Gly Gly Ser Gly Gly Glu Gly Gly Ser Gly Gly Glu Gly Gly Ser
65                  70                  75                  80

Gly Gly Glu Gly Gly Ser Gly Gly Glu Gly Gly Ser Gly Gly Glu Gly
                85                  90                  95

Gly Ser Gly Gly Glu Gly Gly Ser Gly Gly Glu Gly Gly Ser Gly Gly
            100                 105                 110

Glu Gly Gly Ser Gly Gly Glu Gly Gly Ser Gly Gly Glu Gly Gly Ser
        115                 120                 125

Gly Gly Glu Gly Gly Ser Gly Gly Glu Gly Gly Ser Gly Gly Glu Gly
130                 135                 140

Gly Ser Gly Gly Glu Gly Gly Ser Gly Gly Glu Gly Gly Ser Gly Gly
145                 150                 155                 160

Glu Gly Gly Ser Gly Gly Glu Gly Gly Ser Gly Gly Glu Gly Gly Ser
                165                 170                 175
```

Gly Gly Glu Gly Gly Ser Gly Gly Glu Gly Gly Ser Gly Gly Glu Gly
            180                 185                 190

Gly Ser Gly Gly Glu Gly Gly Ser Gly Gly Glu Gly Gly Ser Gly Gly
        195                 200                 205

Glu Gly Gly Ser Gly Gly Glu Gly Gly Ser Gly Gly Glu Gly Gly Ser
    210                 215                 220

Gly Gly Glu Gly Gly Ser Gly Gly Glu Gly Gly Ser Gly Gly Glu Gly
225                 230                 235                 240

Gly Ser Gly Gly Glu Gly Gly Ser Gly Gly Glu Gly Gly Ser Gly Gly
            245                 250                 255

Glu Gly Gly Ser Gly Gly Glu Gly Gly Ser Gly Gly Glu Gly Gly Ser
        260                 265                 270

Gly Gly Glu Gly Gly Ser Gly Gly Glu Gly Gly Ser Gly Gly Glu Gly
    275                 280                 285

<210> SEQ ID NO 274
<211> LENGTH: 864
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(864)

<400> SEQUENCE: 274

```
ggt agt ggt ggt gag ggt gga tcc gga gga agt gga ggt agt ggt gga      48
Gly Ser Gly Gly Glu Gly Gly Ser Gly Gly Ser Gly Gly Ser Gly Gly
1               5                  10                  15 gaa gga gga tct ggt gga agt gga ggt agt gga ggt gag gga gga tct      96
Glu Gly Gly Ser Gly Gly Ser Gly Gly Ser Gly Gly Glu Gly Gly Ser
                20                  25                  30 ggt gga agt gga ggt agt ggt ggt gag ggt ggt tcc gga gga agt gga     144
Gly Gly Ser Gly Gly Ser Gly Gly Glu Gly Gly Ser Gly Gly Ser Gly
            35                  40                  45 ggt agt gga gga gaa ggt ggt tcc ggt gga agt gga ggt agt ggt gga     192
Gly Ser Gly Gly Glu Gly Gly Ser Gly Gly Ser Gly Gly Ser Gly Gly
        50                  55                  60 gag ggt gga tct gga gga agt gga ggt agt ggt ggt gag ggt ggt tcc     240
Glu Gly Gly Ser Gly Gly Ser Gly Gly Ser Gly Gly Glu Gly Gly Ser
65                  70                  75                  80 gga gga agt gga ggt agt gga gga gaa ggt ggt tcc ggt gga agt gga     288
Gly Gly Ser Gly Gly Ser Gly Gly Glu Gly Gly Ser Gly Gly Ser Gly
                85                  90                  95 ggt agt ggt gga gag ggt gga tct gga gga agt gga ggt agt gga gga     336
Gly Ser Gly Gly Glu Gly Gly Ser Gly Gly Ser Gly Gly Ser Gly Gly
                100                 105                 110 gaa gga gga tct gga gga agt gga ggt agt ggt gga gaa gga ggt tcc     384
Glu Gly Gly Ser Gly Gly Ser Gly Gly Ser Gly Gly Glu Gly Gly Ser
            115                 120                 125 ggt gga agt gga ggt agt ggt gga gaa gga ggt tcc gga gga agt gga     432
Gly Gly Ser Gly Gly Ser Gly Gly Glu Gly Gly Ser Gly Gly Ser Gly
        130                 135                 140 ggt agt ggt ggt gag gga gga tct ggt gga agt gga ggt agt gga gga     480
Gly Ser Gly Gly Glu Gly Gly Ser Gly Gly Ser Gly Gly Ser Gly Gly
145                 150                 155                 160 gag gga ggt tct ggt gga agt gga ggt agt ggt ggt gag ggt ggt tcc     528
Glu Gly Gly Ser Gly Gly Ser Gly Gly Ser Gly Gly Glu Gly Gly Ser
                165                 170                 175
```

```
ggt gga agt gga ggt agt ggt ggt gaa gga ggt tct gga gga agt gga      576
Gly Gly Ser Gly Gly Ser Gly Gly Glu Gly Gly Ser Gly Gly Ser Gly
            180                 185                 190 ggt agt ggt gga gaa ggt ggt tcc ggt gga agt gga ggt agt gga gga      624
Gly Ser Gly Gly Glu Gly Gly Ser Gly Gly Ser Gly Gly Ser Gly Gly
        195                 200                 205 gaa gga gga tct gga gga agt gga ggt agt ggt ggt gag ggt ggt tcc      672
Glu Gly Gly Ser Gly Gly Ser Gly Gly Ser Gly Gly Glu Gly Gly Ser
    210                 215                 220 gga gga agt gga ggt agt gga gga gaa ggt ggt tcc ggt gga agt gga      720
Gly Gly Ser Gly Gly Ser Gly Gly Glu Gly Gly Ser Gly Gly Ser Gly
225                 230                 235                 240 ggt agt ggt gga gag ggt gga tct gga gga agt gga ggt agt ggt ggt      768
Gly Ser Gly Gly Glu Gly Gly Ser Gly Gly Ser Gly Gly Ser Gly Gly
            245                 250                 255 gaa ggt ggt tcc ggt gga agt gga ggt agt gga ggt gaa ggt gga tct      816
Glu Gly Gly Ser Gly Gly Ser Gly Gly Ser Gly Gly Glu Gly Gly Ser
        260                 265                 270 ggt gga agt gga ggt agt gga ggt gag ggt ggt tcc gga gga agt gga      864
Gly Gly Ser Gly Gly Ser Gly Gly Glu Gly Gly Ser Gly Gly Ser Gly
    275                 280                 285
```

<210> SEQ ID NO 275
<211> LENGTH: 288
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 275

```
Gly Ser Gly Gly Glu Gly Gly Ser Gly Gly Ser Gly Gly Ser Gly Gly
1               5                   10                  15

Glu Gly Gly Ser Gly Gly Ser Gly Gly Ser Gly Gly Glu Gly Gly Ser
            20                  25                  30

Gly Gly Ser Gly Gly Ser Gly Gly Glu Gly Gly Ser Gly Gly Ser Gly
        35                  40                  45

Gly Ser Gly Gly Glu Gly Gly Ser Gly Gly Ser Gly Gly Ser Gly Gly
    50                  55                  60

Glu Gly Gly Ser Gly Gly Ser Gly Gly Ser Gly Gly Glu Gly Gly Ser
65                  70                  75                  80

Gly Gly Ser Gly Gly Ser Gly Gly Glu Gly Gly Ser Gly Gly Ser Gly
                85                  90                  95

Gly Ser Gly Gly Glu Gly Gly Ser Gly Gly Ser Gly Gly Ser Gly Gly
            100                 105                 110

Glu Gly Gly Ser Gly Gly Ser Gly Gly Ser Gly Gly Glu Gly Gly Ser
        115                 120                 125

Gly Gly Ser Gly Gly Ser Gly Gly Glu Gly Gly Ser Gly Gly Ser Gly
    130                 135                 140

Gly Ser Gly Gly Glu Gly Gly Ser Gly Gly Ser Gly Gly Ser Gly Gly
145                 150                 155                 160

Glu Gly Gly Ser Gly Gly Ser Gly Gly Ser Gly Gly Glu Gly Gly Ser
                165                 170                 175

Gly Gly Ser Gly Gly Ser Gly Gly Glu Gly Gly Ser Gly Gly Ser Gly
            180                 185                 190

Gly Ser Gly Gly Glu Gly Gly Ser Gly Gly Ser Gly Gly Ser Gly Gly
        195                 200                 205
```

```
Glu Gly Gly Ser Gly Gly Ser Gly Gly Ser Glu Gly Gly Ser
    210                 215                 220
Gly Gly Ser Gly Gly Ser Gly Glu Gly Gly Ser Gly Gly Ser Gly
225                 230                 235                 240
Gly Ser Gly Gly Glu Gly Gly Ser Gly Gly Ser Gly Gly Ser Gly
                245                 250                 255
Glu Gly Gly Ser Gly Gly Ser Gly Gly Ser Gly Glu Gly Gly Ser
                260                 265                 270
Gly Gly Ser Gly Gly Ser Gly Glu Gly Gly Ser Gly Gly Ser Gly
            275                 280                 285

<210> SEQ ID NO 276
<211> LENGTH: 671
<212> TYPE: PRT
<213> ORGANISM: Homo sapiens

<400> SEQUENCE: 276

Ser Asp Ser Ser Asp Ser Asp Ser Ser Asp Ser Ser Asn Ser Ser Asp
1               5                   10                  15
Ser Ser Asp Ser Ser Asp Ser Asp Ser Ser Asp Ser Asn Ser Ser Ser
                20                  25                  30
Asp Ser Asp Ser Ser Asp Ser Asp Ser Ser Asp Ser Ser Asp Ser Asp
            35                  40                  45
Ser Ser Asp Ser Ser Asn Ser Ser Asp Ser Ser Asp Ser Ser Asp Ser
        50                  55                  60
Ser Asp Ser Ser Asp Ser Ser Asp Ser Asp Ser Lys Ser Asp Ser
65                  70                  75                  80
Ser Lys Ser Glu Ser Asp Ser Ser Asp Ser Asp Ser Lys Ser Asp Ser
                85                  90                  95
Ser Asp Ser Asn Ser Ser Asp Ser Asp Asn Ser Asp Ser Ser Asp
            100                 105                 110
Ser Ser Asn Ser Ser Asn Ser Ser Asp Ser Ser Asp Ser Ser Asp Ser
        115                 120                 125
Ser Asp Ser Ser Ser Ser Ser Asp Ser Ser Ser Ser Asp Ser Ser
    130                 135                 140
Asn Ser Ser Asp Ser Ser Asp Ser Ser Asp Ser Ser Asn Ser Ser Glu
145                 150                 155                 160
Ser Ser Asp Ser Ser Asp Ser Ser Asp Ser Ser Asp Ser Ser Asp Ser Ser
                165                 170                 175
Asp Ser Ser Asn Ser Asn Ser Ser Asp Ser Ser Asp Ser Asn Ser Ser
            180                 185                 190
Asp Ser Ser Asp Ser Ser Asp Ser Ser Asp Ser Ser Asn Ser Ser Asp
        195                 200                 205
Ser Ser Asp Ser Ser Asp Ser Ser Asn Ser Ser Asp Ser Ser Asp Ser
    210                 215                 220
Ser Asp Ser Ser Asp Ser Ser Asp Ser Ser Asn Ser Ser Asp Ser Asn
225                 230                 235                 240
Asp Ser Ser Asn Ser Ser Asp Ser Ser Asp Ser Ser Asn Ser Ser Asp
                245                 250                 255
Ser Ser Asn Ser Ser Asp Ser Ser Asp Ser Ser Asp Ser Ser Asp Ser
            260                 265                 270
Asp Ser Ser Asn Ser Ser Asp Ser Ser Asn Ser Ser Asp Ser Ser Asp
        275                 280                 285
Ser Ser Asn Ser Ser Asp Ser Ser Asp Ser Ser Asp Ser Ser Asp Ser
    290                 295                 300
```

Ser Asp Ser Asp Ser Ser Asn Arg Ser Asp Ser Ser Asn Ser Ser Asp
305                 310                 315                 320

Ser Ser Asp Ser Ser Asp Ser Ser Asn Ser Ser Asp Ser Ser Asp Ser
            325                 330                 335

Ser Asp Ser Ser Asp Ser Asn Glu Ser Ser Asn Ser Ser Asp Ser Ser
        340                 345                 350

Asp Ser Ser Asn Ser Ser Asp Ser Ser Ser Asp Ser Ser Asn Ser
            355                 360                 365

Ser Asp Ser Ser Asp Ser Ser Asn Ser Ser Asp Ser Ser Glu Ser Ser
    370                 375                 380

Asn Ser Ser Asp Asn Ser Asn Ser Ser Asp Ser Ser Asn Ser Ser Asp
385                 390                 395                 400

Ser Ser Asp Ser Ser Asp Ser Ser Asn Ser Ser Asp Ser Ser Asn Ser
            405                 410                 415

Gly Asp Ser Ser Asn Ser Ser Asp Ser Ser Asp Ser Asn Ser Ser Asp
            420                 425                 430

Ser Ser Asp Ser Ser Asn Ser Ser Asp Ser Ser Asp Ser Ser Asp Ser
            435                 440                 445

Ser Asp Ser Ser Asp Ser Ser Asp Ser Ser Asn Ser Ser Asp Ser Ser
    450                 455                 460

Asp Ser Ser Asp Ser Ser Asp Ser Ser Asn Ser Ser Asp Ser Ser Asn
465                 470                 475                 480

Ser Ser Asp Ser Ser Asp Ser Ser Asp Ser Ser Asp Ser Ser Asp Ser
            485                 490                 495

Ser Asp Ser Ser Asn Ser Ser Asp Ser Ser Asp Ser Ser Asp Ser Ser
            500                 505                 510

Asp Ser Ser Asp Ser Ser Gly Ser Ser Asp Ser Ser Asp Ser Ser Asp
            515                 520                 525

Ser Ser Asp Ser Ser Asp Ser Ser Asp Ser Ser Asp Ser Ser Asp Ser
            530                 535                 540

Ser Asp Ser Ser Glu Ser Ser Asp Ser Ser Asp Ser Ser Asp Ser Ser
545                 550                 555                 560

Asp Ser Ser Asp Ser Ser Asp Ser Ser Asp Ser Ser Asp Ser Ser Asp
            565                 570                 575

Ser Ser Asp Ser Ser Asp Ser Ser Asn Ser Ser Asp Ser Ser Asp Ser
            580                 585                 590

Ser Asp Ser Ser Asp Ser Ser Asp Ser Ser Asp Ser Ser Asp Ser Ser
            595                 600                 605

Asp Ser Ser Asp Ser Ser Asp Ser Ser Asp Ser Ser Asp Ser Ser Asp
            610                 615                 620

Ser Ser Asp Ser Ser Asp Ser Ser Asp Ser Ser Asp Ser Asn Glu Ser
625                 630                 635                 640

Ser Asp Ser Ser Asp Ser Ser Asp Ser Ser Asp Ser Ser Asn Ser Ser
            645                 650                 655

Asp Ser Ser Asp Ser Ser Asp Ser Ser Asp Ser Thr Ser Asp Ser
            660                 665                 670

<210> SEQ ID NO 277
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 277

Ser Ser Asp Ser Ser Asn
1               5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Arg Ala Asp Ala Arg Ala Asp Ala
1               5

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Arg Ala Arg Ala Arg Ala Arg Ala
1               5

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Asp Ala Asp Ala Asp Ala Asp Ala
1               5

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

His Ala His Ala His Ala His Ala
1               5

<210> SEQ ID NO 282
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(8)
<223> OTHER INFORMATION: Wobble base to accommodate diversity in pool
<220> FEATURE:
<221> NAME/KEY: MOD_RES
<222> LOCATION: (10)..(12)
<223> OTHER INFORMATION: Any amino acid

<400> SEQUENCE: 282
```

```
Cys Cys Xaa Xaa Xaa Xaa Xaa Xaa Cys Xaa Xaa Xaa Cys
1               5                   10
```

<210> SEQ ID NO 283
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(11)
<223> OTHER INFORMATION: Wobble base to accommodate diversity in pool

<400> SEQUENCE: 283

```
Cys Xaa Xaa Xaa Cys Xaa Xaa Xaa Xaa Xaa Xaa Cys Cys
1               5                   10
```

<210> SEQ ID NO 284
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(9)
<223> OTHER INFORMATION: Wobble base to accommodate diversity in pool
<220> FEATURE:
<221> NAME/KEY: MOD_RES
<222> LOCATION: (11)..(11)
<223> OTHER INFORMATION: Any amino acid

<400> SEQUENCE: 284

```
Cys Xaa Cys Xaa Xaa Xaa Xaa Xaa Xaa Cys Xaa Cys
1               5                   10
```

<210> SEQ ID NO 285
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(10)
<223> OTHER INFORMATION: Wobble base to accommodate diversity in pool
<220> FEATURE:
<221> NAME/KEY: MOD_RES
<222> LOCATION: (12)..(13)
<223> OTHER INFORMATION: Any amino acid

<400> SEQUENCE: 285

```
Cys Xaa Xaa Cys Xaa Xaa Xaa Xaa Xaa Xaa Cys Xaa Xaa Cys
1               5                   10
```

```
<210> SEQ ID NO 286
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(11)
<223> OTHER INFORMATION: Wobble base to accommodate diversity in pool
<220> FEATURE:
<221> NAME/KEY: MOD_RES
<222> LOCATION: (13)..(15)
<223> OTHER INFORMATION: Any amino acid

<400> SEQUENCE: 286

Cys Xaa Xaa Xaa Cys Xaa Xaa Xaa Xaa Xaa Xaa Cys Xaa Xaa Xaa Cys
1               5                   10                  15

<210> SEQ ID NO 287
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (7)..(12)
<223> OTHER INFORMATION: Wobble base to accommodate diversity in pool
<220> FEATURE:
<221> NAME/KEY: MOD_RES
<222> LOCATION: (14)..(17)
<223> OTHER INFORMATION: Any amino acid

<400> SEQUENCE: 287

Cys Xaa Xaa Xaa Xaa Cys Xaa Xaa Xaa Xaa Xaa Xaa Cys Xaa Xaa Xaa
1               5                   10                  15

Xaa Cys

<210> SEQ ID NO 288
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (8)..(13)
<223> OTHER INFORMATION: Wobble base to accommodate diversity in pool
<220> FEATURE:
<221> NAME/KEY: MOD_RES
<222> LOCATION: (15)..(19)
<223> OTHER INFORMATION: Any amino acid

<400> SEQUENCE: 288

Cys Xaa Xaa Xaa Xaa Xaa Cys Xaa Xaa Xaa Xaa Xaa Xaa Cys Xaa Xaa
1               5                   10                  15
```

Xaa Xaa Xaa Cys
            20

<210> SEQ ID NO 289
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(14)
<223> OTHER INFORMATION: Wobble base to accommodate diversity in pool
<220> FEATURE:
<221> NAME/KEY: MOD_RES
<222> LOCATION: (16)..(21)
<223> OTHER INFORMATION: Any amino acid

<400> SEQUENCE: 289

Cys Xaa Xaa Xaa Xaa Xaa Xaa Cys Xaa Xaa Xaa Xaa Xaa Xaa Cys Xaa
1               5                   10                  15

Xaa Xaa Xaa Xaa Xaa Cys
            20

<210> SEQ ID NO 290
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(15)
<223> OTHER INFORMATION: Wobble base to accommodate diversity in pool
<220> FEATURE:
<221> NAME/KEY: MOD_RES
<222> LOCATION: (17)..(23)
<223> OTHER INFORMATION: Any amino acid

<400> SEQUENCE: 290

Cys Xaa Xaa Xaa Xaa Xaa Xaa Xaa Cys Xaa Xaa Xaa Xaa Xaa Xaa Cys
1               5                   10                  15

Xaa Xaa Xaa Xaa Xaa Xaa Xaa Cys
            20

<210> SEQ ID NO 291
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid
<220> FEATURE:
<221> NAME/KEY: MOD_RES
<222> LOCATION: (11)..(16)
<223> OTHER INFORMATION: Wobble base to accommodate diversity in pool
<220> FEATURE:
<221> NAME/KEY: MOD_RES -continued

```
<222> LOCATION: (18)..(25)
<223> OTHER INFORMATION: Any amino acid

<400> SEQUENCE: 291

Cys Xaa Xaa Xaa Xaa Xaa Xaa Xaa Cys Xaa Xaa Xaa Xaa Xaa Xaa
1               5                   10                  15

Cys Xaa Xaa Xaa Xaa Xaa Xaa Xaa Cys
            20                  25

<210> SEQ ID NO 292
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gaaagtggcg gcgaaagccg gtctgcccgg cc                                32

<210> SEQ ID NO 293
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (19)..(30)
<223> OTHER INFORMATION: a, c, t, g, unknown or other
<220> FEATURE:
<221> NAME/KEY: modified_base
<222> LOCATION: (34)..(51)
<223> OTHER INFORMATION: a, c, t, g, unknown or other
<220> FEATURE:
<221> NAME/KEY: modified_base
<222> LOCATION: (55)..(66)
<223> OTHER INFORMATION: a, c, t, g, unknown or other

<400> SEQUENCE: 293
gaaagcggcg gtgaaagcnn nnnnnnnnnn tgcnnnnnnn nnnnnnnnnn ntgtnnnnnn    60
nnnnnnagct ccggatctgg tggttccagc ggcggtgaaa gc                     102

<210> SEQ ID NO 294
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
```

```
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid

<400> SEQUENCE: 294

Glu Ser Gly Gly Glu Ser Xaa Xaa Xaa Xaa Cys Xaa Xaa Xaa Xaa Xaa
1               5                   10                  15

Xaa Cys Xaa Xaa Xaa Xaa Ser Ser Gly Ser Gly Gly Ser Ser Gly Gly
            20                  25                  30

Glu Ser

<210> SEQ ID NO 295
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
agaccaccaa ggtcgccgcc tctttcg                                        27

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
gaaagtggcg gcgaccttgg                                                20

<210> SEQ ID NO 297
<211> LENGTH: 92
<212> TYPE: DNA
<213> ORGANISM: Artificial Sequence
<220> FEATURE:
```

```
<223> OTHER INFORMATION: Description of Artificial Sequence: Synthetic
      polynucleotide
<220> FEATURE:
<221> NAME/KEY: modified_base
<222> LOCATION: (16)..(27)
<223> OTHER INFORMATION: a, c, g, t, unknown or other
<220> FEATURE:
<221> NAME/KEY: modified_base
<222> LOCATION: (31)..(48)
<223> OTHER INFORMATION: a, c, g, t, unknown or other
<220> FEATURE:
<221> NAME/KEY: modified_base
<222> LOCATION: (52)..(63)
<223> OTHER INFORMATION: a, c, g, t, unknown or other

<400> SEQUENCE: 297
tgcggcggtg aaagcnnnnn nnnnnnntgc nnnnnnnnnn nnnnnnnntg tnnnnnnnn       60 nnngctccgg atctgggtcc agtctggtgg tg                                    92

<210> SEQ ID NO 298
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(23)
<223> OTHER INFORMATION: Any amino acid

<400> SEQUENCE: 298

Gly Ser Ser Gly Gly Glu Ser Xaa Xaa Xaa Xaa Cys Xaa Xaa Xaa Xaa
1               5                   10                  15

Xaa Xaa Cys Xaa Xaa Xaa Xaa Ser Ser Gly Ser Gly
            20                  25

<210> SEQ ID NO 299
<211> LENGTH: 84
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(27)
<223> OTHER INFORMATION: a, c, g, t, unknown or other
<220> FEATURE:
<221> NAME/KEY: modified_base
<222> LOCATION: (31)..(48)
<223> OTHER INFORMATION: a, c, g, t, unknown or other
<220> FEATURE:
<221> NAME/KEY: modified_base
<222> LOCATION: (52)..(63)
<223> OTHER INFORMATION: a, c, g, t, unknown or other

<400> SEQUENCE: 299
acccagatcc ggagcnnnnn nnnnnnnaca nnnnnnnnnn nnnnnnnngc annnnnnnnn       60
nnngctttca ccgccgctgg aacc                                             84

<210> SEQ ID NO 300
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
cgaggcctag acccaggtca gaccacctg                                          29

<210> SEQ ID NO 301
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(34)
<223> OTHER INFORMATION: a, c, t, g, unknown or other
<220> FEATURE:
<221> NAME/KEY: modified_base
<222> LOCATION: (38)..(40)
<223> OTHER INFORMATION: a, c, t, g, unknown or other
<220> FEATURE:
<221> NAME/KEY: modified_base
<222> LOCATION: (44)..(46)
<223> OTHER INFORMATION: a, c, t, g, unknown or other
<220> FEATURE:
<221> NAME/KEY: modified_base
<222> LOCATION: (83)..(85)
<223> OTHER INFORMATION: a, c, t, g, unknown or other
<220> FEATURE:
<221> NAME/KEY: modified_base
<222> LOCATION: (89)..(91)
<223> OTHER INFORMATION: a, c, t, g, unknown or other
<220> FEATURE:
<221> NAME/KEY: modified_base
<222> LOCATION: (95)..(97)
<223> OTHER INFORMATION: a, c, t, g, unknown or other

<400> SEQUENCE: 301
ggcccgtctg gccgaaagcg gcggtgaaag cnnntgcnnn tgtnnnagct ccggatctgg        60
tggttccggt agcggcggta gcnnntgcnn ntgtnnngct ccggatctgg gt              112

<210> SEQ ID NO 302
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
```

<221> NAME/KEY: MOD_RES
<222> LOCATION: (28)..(28)
<223> OTHER INFORMATION: Any amino acid

<400> SEQUENCE: 302

Glu Ser Gly Gly Glu Ser Xaa Cys Xaa Cys Xaa Ser Ser Gly Ser Gly
1               5                   10                  15

Gly Ser Ser Gly Gly Glu Ser Xaa Cys Xaa Cys Xaa Ser Ser Gly Ser
            20                  25                  30

Gly

<210> SEQ ID NO 303
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (28)..(30)
<223> OTHER INFORMATION: a, c, g, t, unknown or other
<220> FEATURE:
<221> NAME/KEY: modified_base
<222> LOCATION: (34)..(36)
<223> OTHER INFORMATION: a, c, g, t, unknown or other
<220> FEATURE:
<221> NAME/KEY: modified_base
<222> LOCATION: (40)..(42)
<223> OTHER INFORMATION: a, c, g, t, unknown or other
<220> FEATURE:
<221> NAME/KEY: modified_base
<222> LOCATION: (79)..(81)
<223> OTHER INFORMATION: a, c, g, t, unknown or other
<220> FEATURE:
<221> NAME/KEY: modified_base
<222> LOCATION: (85)..(87)
<223> OTHER INFORMATION: a, c, g, t, unknown or other
<220> FEATURE:
<221> NAME/KEY: modified_base
<222> LOCATION: (91)..(93)
<223> OTHER INFORMATION: a, c, g, t, unknown or other

<400> SEQUENCE: 303
ccaccagact ggacccagat ccggagcnnn acannngcan nngctaccgc cgctaccgga      60
accaccagat ccggagctnn nacannngca nnngctttca ccgccgcttt cggccagacg     120
ggcc                                                                 124

<210> SEQ ID NO 304
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Met Asp Tyr Lys Asp Asp Asp Lys Gly Ser Pro Gly Ser Gly Gly
1               5                   10                  15

Glu Gly Gly Ser Gly Gly Glu Gly Gly Ser Gly Gly Glu Gly Gly Ser
            20                  25                  30

Gly Gly Glu Gly Gly Ser Gly Gly Glu Gly Gly Ser Gly Gly Glu Gly
            35                  40                  45

Gly Ser His Thr Leu Glu Cys Leu Gly Asn Ile Cys Trp Val Ile Asn
            50                  55                  60

Gln Gly Gly Glu Gly Gly Ser Gly Gly Glu Gly Gly Ser Gly Gly Glu

```
                65                  70                  75                  80
Gly Gly Ser Gly Gly Glu Gly Ser Gly Gly Glu Gly Gly Ser Gly
                    85                  90                  95
Gly Glu Gly Gly Ser His Thr Leu Glu Cys Leu Gly Asn Ile Cys Trp
                    100                 105                 110
Val Ile Asn Gln Gly Gly Glu Gly Gly Ser Gly Gly Glu Gly Gly Ser
                115                 120                 125
Gly Gly Glu Gly Gly Ser Gly Gly Glu Gly Gly Ser Gly Gly Glu Gly
            130                 135                 140
Gly Ser Gly Gly Glu Gly Gly Ser His Thr Leu Glu Cys Leu Gly Asn
        145                 150                 155                 160
Ile Cys Trp Val Ile Asn Gln Gly Gly Glu Gly Gly Ser Gly Gly Glu
                    165                 170                 175
Gly Gly Ser Gly Gly Glu Gly Gly Ser Gly Gly Glu Gly Gly Ser Gly
                180                 185                 190
Gly Glu Gly Gly Ser Gly Gly Glu Gly Gly Ser His Thr Leu Glu Cys
            195                 200                 205
Leu Gly Asn Ile Cys Trp Val Ile Asn Gln Ser Ser Leu Glu Gly Thr
        210                 215                 220
His His His His His His
225                 230

<210> SEQ ID NO 305
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Gly Glu Ser Gly Gly Glu Ser His Thr Leu Glu Cys Leu Gly Asn
1               5                   10                  15
Ile Cys Trp Val Ile Asn Gln Ser Ser Gly Ser Gly Gly Ser Gly
            20                  25                  30

<210> SEQ ID NO 306
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid

<400> SEQUENCE: 306

Ser Xaa Xaa Xaa Cys Xaa Xaa Xaa Xaa Xaa Xaa Cys Xaa Xaa Xaa Gly
1               5                   10                  15
Ser Gly Gly Glu Ser Gly Gly Glu Ser His Thr Leu Glu Cys Leu Gly
            20                  25                  30
Asn Ile Cys Trp Val Ile Asn Gln Ser Ser Gly Ser Gly Gly Ser Gly
```

```
                    35                  40                  45

<210> SEQ ID NO 307
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(36)
<223> OTHER INFORMATION: Any amino acid
<220> FEATURE:
<221> NAME/KEY: MOD_RES
<222> LOCATION: (38)..(43)
<223> OTHER INFORMATION: Any amino acid
<220> FEATURE:
<221> NAME/KEY: MOD_RES
<222> LOCATION: (45)..(47)
<223> OTHER INFORMATION: Any amino acid

<400> SEQUENCE: 307

Gly Gly Glu Ser Gly Gly Glu Ser His Thr Leu Glu Cys Leu Gly Asn
1               5                   10                  15

Ile Cys Trp Val Ile Asn Gln Ser Ser Gly Ser Gly Ser Gly Gly
            20                  25                  30

Ser Xaa Xaa Xaa Cys Xaa Xaa Xaa Xaa Xaa Xaa Cys Xaa Xaa Xaa Gly
        35                  40                  45

Ser Gly Ser
    50

<210> SEQ ID NO 308
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid

<400> SEQUENCE: 308

Ser Xaa Xaa Xaa Cys Xaa Xaa Xaa Xaa Xaa Xaa Cys Xaa Xaa Xaa Gly
1               5                   10                  15

Ser Gly Gly Glu Ser Gly Gly Glu Ser His Thr Leu Glu Cys Leu Gly
            20                  25                  30

Asn Ile Cys Trp Val Ile Asn Gln Ser Ser Gly Ser
        35                  40

<210> SEQ ID NO 309
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (7)..(9)
<223> OTHER INFORMATION: Any amino acid
<220> FEATURE:
<221> NAME/KEY: MOD_RES
<222> LOCATION: (11)..(16)
<223> OTHER INFORMATION: Any amino acid
<220> FEATURE:
<221> NAME/KEY: MOD_RES
<222> LOCATION: (18)..(20)
<223> OTHER INFORMATION: Any amino acid

<400> SEQUENCE: 309

Gly Gly Ser Gly Gly Ser Xaa Xaa Xaa Cys Xaa Xaa Xaa Xaa Xaa Xaa
1               5                   10                  15

Cys Xaa Xaa Xaa Gly Ser Gly Ser
            20

<210> SEQ ID NO 310
<211> LENGTH: 57
<212> TYPE: PRT
<213> ORGANISM: Laticauda semifasciata

<400> SEQUENCE: 310

Cys Phe Asn His Gln Ser Gln Pro Gln Thr Thr Lys Thr Cys Ser Pro
1               5                   10                  15

Gly Glu Ser Ser Cys Tyr Asn Lys Gln Trp Ser Asp Phe Arg Gly Thr
            20                  25                  30

Ile Ile Glu Arg Gly Cys Gly Cys Pro Thr Val Lys Pro Gly Ile Lys
        35                  40                  45

Leu Ser Cys Cys Glu Ser Glu Val Cys
    50                  55

<210> SEQ ID NO 311
<211> LENGTH: 55
<212> TYPE: PRT
<213> ORGANISM: Micrurus nigrocinctus

<400> SEQUENCE: 311

Cys His Asn Gln Gln Ser Gln Pro Pro Thr Ile Lys Thr Cys Ser Glu
1               5                   10                  15

Gly Gln Cys Tyr Lys Lys Thr Trp Arg Asp His Arg Gly Thr Ile Ser
            20                  25                  30

Glu Arg Gly Cys Gly Cys Pro Thr Val Lys Pro Gly Ile His Ile Ser
        35                  40                  45

Cys Cys Ala Ser Asp Lys Cys
    50                  55

<210> SEQ ID NO 312
<211> LENGTH: 56
<212> TYPE: PRT
<213> ORGANISM: Naja haje

<400> SEQUENCE: 312

Cys Tyr Lys Gln Arg Ser Gln Phe Pro Ile Thr Thr Val Cys Pro Gly
1               5                   10                  15

Glu Lys Asn Cys Tyr Lys Lys Gln Trp Ser Gly His Arg Gly Thr Ile
            20                  25                  30

Ile Glu Arg Gly Cys Gly Cys Pro Ser Val Lys Lys Gly Ile Glu Ile
        35                  40                  45

Asn Cys Cys Thr Thr Asp Lys Cys
    50                  55

<210> SEQ ID NO 313
<211> LENGTH: 56
<212> TYPE: PRT
<213> ORGANISM: Hemachatus haemachatus

<400> SEQUENCE: 313

Cys His Asn Gln Gln Ser Gln Pro Pro Thr Thr Lys Ser Cys Pro Gly
1               5                   10                  15

Asp Thr Asn Cys Tyr Asn Lys Arg Trp Arg Asp His Arg Gly Thr Ile
            20                  25                  30

Ile Glu Arg Gly Cys Gly Cys Pro Thr Val Lys Pro Gly Ile Asn Leu
        35                  40                  45

Lys Cys Cys Thr Thr Asp Arg Cys
    50                  55

<210> SEQ ID NO 314
<211> LENGTH: 56
<212> TYPE: PRT
<213> ORGANISM: Boulengerina annulata

<400> SEQUENCE: 314

Cys Tyr Asn Gln Pro Ser Gln His Pro Thr Thr Lys Ala Cys Pro Gly
1               5                   10                  15

Glu Lys Asn Cys Tyr Arg Lys Gln Trp Ser Asp His Arg Gly Thr Ile
            20                  25                  30

Ile Glu Arg Gly Cys Gly Cys Pro Thr Val Lys Pro Gly Val Lys Leu
        35                  40                  45

His Cys Cys Thr Thr Glu Lys Cys
    50                  55

<210> SEQ ID NO 315
<211> LENGTH: 57
<212> TYPE: PRT
<213> ORGANISM: Naja atra

<400> SEQUENCE: 315

Cys His Asn Gln Gln Ser Gln Thr Pro Thr Thr Thr Gly Cys Ser Gly
1               5                   10                  15

Gly Glu Thr Asn Cys Tyr Lys Lys Arg Trp Arg Asp His Arg Gly Tyr
            20                  25                  30

Arg Thr Glu Arg Gly Cys Gly Cys Pro Ile Val Lys Asn Gly Ile Glu
        35                  40                  45

Ser Asn Cys Cys Thr Thr Asp Arg Cys
    50                  55

<210> SEQ ID NO 316
<211> LENGTH: 57
<212> TYPE: PRT
<213> ORGANISM: Naja mossambica

<400> SEQUENCE: 316

Cys His Asn Gln Met Ser Gln Pro Pro Thr Thr Thr Arg Cys Ser Arg
1               5                   10                  15

Trp Glu Thr Asn Cys Tyr Lys Lys Arg Trp Arg Asp His Arg Gly Tyr
            20                  25                  30

Lys Thr Glu Arg Gly Cys Gly Cys Pro Thr Val Lys Lys Gly Ile Gln
        35                  40                  45

Leu His Cys Cys Thr Ser Asp Asn Cys
    50                  55

<210> SEQ ID NO 317
<211> LENGTH: 57
<212> TYPE: PRT
<213> ORGANISM: Laticauda colubrina

<400> SEQUENCE: 317

Cys Phe Asn Gln Gln Ser Gln Pro Lys Thr Thr Lys Ser Cys Pro Pro
1               5                   10                  15

Gly Glu Asn Ser Cys Tyr Asn Lys Gln Trp Arg Asp His Arg Gly Ser
            20                  25                  30

Ile Thr Glu Arg Gly Cys Gly Cys Pro Lys Val Lys Pro Gly Ile Lys
        35                  40                  45

Leu Arg Cys Cys Glu Ser Glu Asp Cys
    50                  55

<210> SEQ ID NO 318
<211> LENGTH: 55
<212> TYPE: PRT
<213> ORGANISM: Dendroaspis polylepis

<400> SEQUENCE: 318

Cys Tyr Asn His Gln Ser Thr Arg Ala Thr Thr Lys Ser Cys Glu Glu
1               5                   10                  15

Asn Ser Cys Tyr Lys Lys Tyr Trp Arg Asp His Arg Gly Thr Ile Ile
            20                  25                  30

Glu Arg Gly Cys Gly Cys Pro Lys Val Lys Pro Gly Val Gly Ile His
        35                  40                  45

Cys Cys Gln Ser Asp Lys Cys
    50                  55

<210> SEQ ID NO 319
<211> LENGTH: 53
<212> TYPE: PRT
<213> ORGANISM: Dendroaspis jamesoni

<400> SEQUENCE: 319

Cys Tyr Asn His Gln Ser Thr Pro Ala Thr Thr Lys Ser Cys Val Glu
1               5                   10                  15

Asn Ser Cys Tyr Lys Ser Ile Trp Ala Asp His Arg Gly Thr Ile Ile
            20                  25                  30

Lys Arg Gly Cys Gly Cys Pro Arg Val Lys Ser Lys Ile Lys Cys Cys
        35                  40                  45

Lys Ser Asp Asn Cys
    50

<210> SEQ ID NO 320
<211> LENGTH: 57
<212> TYPE: PRT
<213> ORGANISM: Oxyuranus scutellatus

<400> SEQUENCE: 320

Cys Tyr Asn Gln Gln Ser Glu Ala Lys Thr Thr Thr Cys Ser Gly Gly
1               5                   10                  15

Gly Val Ser Ser Cys Tyr Lys Lys Thr Trp Ser Asp Gly Arg Gly Thr
            20                  25                  30

Ile Ile Glu Arg Gly Cys Gly Cys Pro Ser Val Lys Lys Gly Ile Glu
        35                  40                  45

Arg Ile Cys Cys Arg Thr Asp Lys Cys 50              55

<210> SEQ ID NO 321
<211> LENGTH: 57
<212> TYPE: PRT
<213> ORGANISM: Ophiophagus hannah

<400> SEQUENCE: 321

Cys Leu Lys Gln Glu Pro Gln Pro Glu Thr Thr Thr Thr Cys Pro Glu
1               5                   10                  15

Gly Glu Asp Ala Cys Tyr Asn Leu Phe Trp Ser Asp His Ser Glu Ile
                20                  25                  30

Lys Ile Glu Met Gly Cys Gly Cys Pro Lys Thr Glu Pro Tyr Thr Asn
            35                  40                  45

Leu Tyr Cys Cys Lys Ile Asp Ser Cys
    50                  55

<210> SEQ ID NO 322
<211> LENGTH: 55
<212> TYPE: PRT
<213> ORGANISM: Dendroaspis angusticeps

<400> SEQUENCE: 322

Cys Tyr Ser His Lys Leu Gln Ala Lys Thr Thr Lys Thr Cys Glu Glu
1               5                   10                  15

Asn Ser Cys Tyr Lys Arg Ser Leu Pro Lys Ile Pro Leu Ile Ile Ile
                20                  25                  30

Gly Arg Gly Cys Gly Cys Pro Leu Thr Leu Pro Phe Leu Arg Ile Lys
            35                  40                  45

Cys Cys Thr Ser Asp Lys Cys
    50                  55

<210> SEQ ID NO 323
<211> LENGTH: 55
<212> TYPE: PRT
<213> ORGANISM: Dendroaspis angusticeps

<400> SEQUENCE: 323

Cys Tyr Ser His Lys Thr Gln Pro Ser Ala Thr Ile Thr Cys Glu Glu
1               5                   10                  15

Lys Thr Cys Tyr Lys Lys Ser Val Arg Lys Leu Pro Ala Ile Val Ala
                20                  25                  30

Gly Arg Gly Cys Gly Cys Pro Ser Lys Glu Met Leu Val Ala Ile His
            35                  40                  45

Cys Cys Arg Ser Asp Lys Cys
    50                  55

<210> SEQ ID NO 324
<211> LENGTH: 55
<212> TYPE: PRT
<213> ORGANISM: Dendroaspis polylepis

<400> SEQUENCE: 324

Cys Tyr Ile His Lys Ala Leu Pro Arg Ala Thr Lys Thr Cys Val Glu
1               5                   10                  15

Asn Thr Cys Tyr Lys Met Phe Ile Arg Thr Gln Arg Glu Tyr Ile Ser
                20                  25                  30

Glu Arg Gly Cys Gly Cys Pro Thr Ala Met Trp Pro Tyr Gln Thr Glu
            35                  40                  45

```
Cys Cys Lys Gly Asp Arg Cys
    50                  55
```

<210> SEQ ID NO 325
<211> LENGTH: 55
<212> TYPE: PRT
<213> ORGANISM: Dendroaspis jamesoni

<400> SEQUENCE: 325

```
Cys Tyr Thr His Lys Ser Gln Ala Lys Thr Thr Lys Ser Cys Glu Gly
1               5                   10                  15

Asn Thr Cys Tyr Lys Met Phe Ile Arg Thr Ser Arg Glu Tyr Ile Ser
            20                  25                  30

Glu Arg Gly Cys Gly Cys Pro Thr Ala Met Trp Pro Tyr Gln Thr Glu
        35                  40                  45

Cys Cys Lys Gly Asp Arg Cys
    50                  55
```

<210> SEQ ID NO 326
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: His, Ile, Lys, Leu, Asn, Pro, Gln, Arg, Ser or
      Thr
<220> FEATURE:
<221> NAME/KEY: MOD_RES
<222> LOCATION: (5)..(5)
<223> OTHER INFORMATION: Ala, Asp, Glu, Gly, His, Lys, Asn, Pro, Gln,
      Arg, Ser or Thr
<220> FEATURE:
<221> NAME/KEY: MOD_RES
<222> LOCATION: (6)..(6)
<223> OTHER INFORMATION: Lys, Pro, Gln, Arg, Thr, Ala, Asp, Ser or Tyr
<220> FEATURE:
<221> NAME/KEY: MOD_RES
<222> LOCATION: (7)..(7)
<223> OTHER INFORMATION: Ala, Asp, Gly, Asn, Ser or Thr
<220> FEATURE:
<221> NAME/KEY: MOD_RES
<222> LOCATION: (8)..(8)
<223> OTHER INFORMATION: His, Lys, Asn, Pro, Gln, Arg, Ser or Thr
<220> FEATURE:
<221> NAME/KEY: MOD_RES
<222> LOCATION: (9)..(9)
<223> OTHER INFORMATION: Ala or Pro
<220> FEATURE:
<221> NAME/KEY: MOD_RES
<222> LOCATION: (10)..(10)
<223> OTHER INFORMATION: Ile, Lys, Leu, Pro, Gln, Arg or Thr
<220> FEATURE:
<221> NAME/KEY: MOD_RES
<222> LOCATION: (11)..(11)
<223> OTHER INFORMATION: Ala, Asp, Glu, Gly, Ile, Lys, Asn, Arg, Ser,
      Thr or Val
<220> FEATURE:
<221> NAME/KEY: MOD_RES
<222> LOCATION: (28)..(28)
<223> OTHER INFORMATION: Gly, Ile, Leu, Arg, Ser or Val
<220> FEATURE:
<221> NAME/KEY: MOD_RES
<222> LOCATION: (29)..(29)
<223> OTHER INFORMATION: Ala, Asp, Gly, His, Pro or Arg
<220> FEATURE:
<221> NAME/KEY: MOD_RES
<222> LOCATION: (30)..(30)
<223> OTHER INFORMATION: Ala, Gly, Ser or Thr
<220> FEATURE:

```
<221> NAME/KEY: MOD_RES
<222> LOCATION: (31)..(31)
<223> OTHER INFORMATION: Ile, Leu, Ser or Thr
<220> FEATURE:
<221> NAME/KEY: MOD_RES
<222> LOCATION: (32)..(32)
<223> OTHER INFORMATION: Pro or Arg
<220> FEATURE:
<221> NAME/KEY: MOD_RES
<222> LOCATION: (33)..(33)
<223> OTHER INFORMATION: Ala, Glu or Gly
<220> FEATURE:
<221> NAME/KEY: MOD_RES
<222> LOCATION: (34)..(34)
<223> OTHER INFORMATION: Glu, Gly, Lys, Arg, Phe, Ile, Asn, Ser, Thr or
      Tyr
<220> FEATURE:
<221> NAME/KEY: MOD_RES
<222> LOCATION: (35)..(35)
<223> OTHER INFORMATION: Glu, Gly, Ile, Lys, Arg or Val
<220> FEATURE:
<221> NAME/KEY: MOD_RES
<222> LOCATION: (36)..(36)
<223> OTHER INFORMATION: Ala, Ile, Leu, Ser, Thr or Val
<220> FEATURE:
<221> NAME/KEY: MOD_RES
<222> LOCATION: (37)..(37)
<223> OTHER INFORMATION: Asp, Glu, Gly, Ile, Lys, Asn, Arg, Ser or Val
<220> FEATURE:
<221> NAME/KEY: MOD_RES
<222> LOCATION: (38)..(38)
<223> OTHER INFORMATION: Leu, Met or Arg

<400> SEQUENCE: 326

Ser Cys His Xaa Xaa Xaa Xaa Xaa Xaa Xaa Ala Val Thr Cys Pro
1               5                   10                  15

Pro Gly Glu Asn Leu Cys Tyr Arg Lys Met Trp Xaa Xaa Xaa Xaa
                20                  25                  30

Xaa Xaa Xaa Xaa Xaa Xaa Gly Cys Ala Ala Thr Cys Pro Ser Val Lys
            35                  40                  45

Pro Tyr Glu Glu Val Thr Cys Cys Ser Thr Asp Lys Cys Gly
    50                  55                  60

<210> SEQ ID NO 327
<211> LENGTH: 42
<212> TYPE: PRT
<213> ORGANISM: Homo sapiens

<400> SEQUENCE: 327

Cys Arg His Phe Gln Ser Cys Ser Gln Cys Leu Ser Ala Pro Pro Phe
1               5                   10                  15

Val Gln Cys Gly Trp Cys His Asp Lys Cys Val Arg Ser Glu Glu Cys
                20                  25                  30

Leu Ser Gly Thr Trp Thr Gln Gln Ile Cys
            35                  40

<210> SEQ ID NO 328
<211> LENGTH: 42
<212> TYPE: PRT
<213> ORGANISM: Rhinolophus ferrumequinum

<400> SEQUENCE: 328

Cys Glu His Phe Gln Ser Cys Ser Gln Cys Leu Ser Ala Pro Pro Phe
1               5                   10                  15

Val Gln Cys Gly Trp Cys His Asn Lys Cys Val Arg Ser Glu Glu Cys
                20                  25                  30

Pro Ser Gly Val Trp Thr Gln Asp Val Cys
```

```
            35                  40

<210> SEQ ID NO 329
<211> LENGTH: 42
<212> TYPE: PRT
<213> ORGANISM: Carollia perspicillata

<400> SEQUENCE: 329

Cys Glu His Phe Gln Ser Cys Ser Gln Cys Leu Ser Ala Pro Pro Phe
1               5                   10                  15

Val Gln Cys Gly Trp Cys His Asp Lys Cys Val Arg Leu Glu Thr Cys
            20                  25                  30

Pro Ser Gly Ala Trp Thr Gln Glu Ile Cys
            35                  40

<210> SEQ ID NO 330
<211> LENGTH: 42
<212> TYPE: PRT
<213> ORGANISM: Otolemur garnettii

<400> SEQUENCE: 330

Cys Glu His Phe Gln Ser Cys Ser Gln Cys Leu Ser Ala Pro Pro Phe
1               5                   10                  15

Val Gln Cys Gly Trp Cys His Asp Lys Cys Val Arg Ser Glu Glu Cys
            20                  25                  30

Pro Ser Gly Ser Trp Thr Gln Glu Thr Cys
            35                  40

<210> SEQ ID NO 331
<211> LENGTH: 42
<212> TYPE: PRT
<213> ORGANISM: Sus scrofa

<400> SEQUENCE: 331

Cys Glu His Phe Gln Ser Cys Ser Gln Cys Leu Ser Ala Pro Pro Phe
1               5                   10                  15

Val Gln Cys Gly Trp Cys Gln Asp Lys Cys Val Gln Leu Glu Glu Cys
            20                  25                  30

Pro Ser Gly Thr Trp Thr Gln Glu Ile Cys
            35                  40

<210> SEQ ID NO 332
<211> LENGTH: 42
<212> TYPE: PRT
<213> ORGANISM: Canis familiaris

<400> SEQUENCE: 332

Cys Glu His Phe Gln Ser Cys Ser Gln Cys Leu Ser Ala Pro Pro Phe
1               5                   10                  15

Val Gln Cys Gly Trp Cys His Asp Arg Cys Val His Leu Glu Glu Cys
            20                  25                  30

Pro Thr Gly Ala Trp Thr Gln Glu Val Cys
            35                  40

<210> SEQ ID NO 333
<211> LENGTH: 42
<212> TYPE: PRT
<213> ORGANISM: Rattus norvegicus

<400> SEQUENCE: 333

Cys Gly His Phe Gln Ser Cys Ser Gln Cys Leu Ser Pro Pro Tyr Phe
```

```
                1               5                   10                  15
Ile Gln Cys Gly Trp Cys His Asn Arg Cys Val His Ser Asn Glu Cys
                20                  25                  30

Pro Ser Gly Thr Trp Thr Gln Glu Ile Cys
        35                  40

<210> SEQ ID NO 334
<211> LENGTH: 42
<212> TYPE: PRT
<213> ORGANISM: Gallus gallus

<400> SEQUENCE: 334

Cys His His Phe Gln Ser Cys Ser Gln Cys Leu Leu Ala Pro Ala Phe
1               5                   10                  15

Met Arg Cys Gly Trp Cys Gly Gln Gln Cys Leu Arg Ala Pro Glu Cys
                20                  25                  30

Asn Gly Gly Thr Trp Thr Gln Glu Thr Cys
        35                  40

<210> SEQ ID NO 335
<211> LENGTH: 42
<212> TYPE: PRT
<213> ORGANISM: Takifugu rubripes

<400> SEQUENCE: 335

Cys Asp His Leu Thr Thr Cys Thr Ser Cys Leu Val Ser Ser Arg Val
1               5                   10                  15

Thr Glu Cys Gly Trp Cys Glu Gly Arg Cys Thr Arg Ala Asn Gln Cys
                20                  25                  30

Pro Pro Ser Val Trp Thr Gln Glu Tyr Cys
        35                  40

<210> SEQ ID NO 336
<211> LENGTH: 41
<212> TYPE: PRT
<213> ORGANISM: Takifugu rubripes

<400> SEQUENCE: 336

Cys Gln His Phe Leu Thr Cys Ala Val Cys Leu Thr Ala Pro Lys Phe
1               5                   10                  15

Val Gly Cys Gly Trp Cys Ser Gly Val Cys Ser Trp Glu Ser Asp Cys
                20                  25                  30

Asp His His Trp Arg Asn Asp Ser Cys
        35                  40

<210> SEQ ID NO 337
<211> LENGTH: 41
<212> TYPE: PRT
<213> ORGANISM: Tetraodon nigroviridis

<400> SEQUENCE: 337

Cys Gln His Phe Leu Thr Cys Ala Met Cys Leu Met Ala Pro Gln Phe
1               5                   10                  15

Met Gly Cys Gly Trp Cys Ser Gly Val Cys Ser Trp Glu Asn Gln Cys
                20                  25                  30

Asp Asp Arg Trp Arg Asn Glu Ser Cys
        35                  40

<210> SEQ ID NO 338
<211> LENGTH: 41
```

```
<212> TYPE: PRT
<213> ORGANISM: Tetraodon nigroviridis

<400> SEQUENCE: 338

Cys Ala His Phe Arg Thr Cys Ser Met Cys Leu Met Ala Pro Arg Phe
1               5                   10                  15

Met Asn Cys Gly Trp Cys Ser Gly Val Cys Ser Arg Gln His Glu Cys
            20                  25                  30

Thr Ser Trp Gln Thr Ser Ala Ser Cys
        35                  40

<210> SEQ ID NO 339
<211> LENGTH: 41
<212> TYPE: PRT
<213> ORGANISM: Takifugu rubripes

<400> SEQUENCE: 339

Cys Ala His Phe Arg Thr Cys Ser Met Cys Leu Met Ala Pro Arg Phe
1               5                   10                  15

Met Asn Cys Gly Trp Cys Ser Gly Val Cys Ser Arg Gln His Gln Cys
            20                  25                  30

Asp Met Gln Trp Glu Lys Asp Ser Cys
        35                  40

<210> SEQ ID NO 340
<211> LENGTH: 41
<212> TYPE: PRT
<213> ORGANISM: Homo sapiens

<400> SEQUENCE: 340

Cys Arg His Phe Leu Thr Cys Gly Arg Cys Leu Arg Ala Trp His Phe
1               5                   10                  15

Met Gly Cys Gly Trp Cys Gly Asn Met Cys Gly Gln Gln Lys Glu Cys
            20                  25                  30

Pro Gly Ser Trp Gln Gln Asp His Cys
        35                  40

<210> SEQ ID NO 341
<211> LENGTH: 41
<212> TYPE: PRT
<213> ORGANISM: Canis familiaris

<400> SEQUENCE: 341

Cys His His Phe Leu Thr Cys Gly Ser Cys Leu Arg Ala Gln Arg Phe
1               5                   10                  15

Met Gly Cys Gly Trp Cys Gly Gly Met Cys Gly Arg Gln Lys Glu Cys
            20                  25                  30

Pro Gly Ser Trp Gln Gln Asp His Cys
        35                  40

<210> SEQ ID NO 342
<211> LENGTH: 41
<212> TYPE: PRT
<213> ORGANISM: Mus musculus

<400> SEQUENCE: 342

Cys Arg His Phe Leu Thr Cys Trp Arg Cys Leu Arg Ala Gln Arg Phe
1               5                   10                  15

Met Gly Cys Gly Trp Cys Gly Asp Arg Cys Asp Arg Gln Lys Glu Cys
            20                  25                  30
```

```
Pro Gly Ser Trp Gln Gln Asp His Cys
        35                  40
```

<210> SEQ ID NO 343
<211> LENGTH: 41
<212> TYPE: PRT
<213> ORGANISM: Gallus gallus

<400> SEQUENCE: 343

```
Cys Arg His Phe Ser Thr Cys Asp Arg Cys Leu Arg Ala Glu Arg Phe
1               5                   10                  15

Met Gly Cys Gly Trp Cys Gly Asn Gly Cys Thr Arg His His Glu Cys
                20                  25                  30

Ala Gly Pro Trp Val Gln Asp Ser Cys
        35                  40
```

<210> SEQ ID NO 344
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Glu, Gly, His, Gln or Arg
<220> FEATURE:
<221> NAME/KEY: MOD_RES
<222> LOCATION: (5)..(5)
<223> OTHER INFORMATION: Phe or Leu
<220> FEATURE:
<221> NAME/KEY: MOD_RES
<222> LOCATION: (6)..(6)
<223> OTHER INFORMATION: His, Ile, Lys, Leu, Asn, Pro, Gln, Arg, Ser or
      Thr
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (9)..(9)
<223> OTHER INFORMATION: Ala, Gly, Arg, Ser, Thr or Trp
<220> FEATURE:
<221> NAME/KEY: MOD_RES
<222> LOCATION: (10)..(10)
<223> OTHER INFORMATION: Lys, Leu, Met, Gln or Arg
<220> FEATURE:
<221> NAME/KEY: MOD_RES
<222> LOCATION: (13)..(13)
<223> OTHER INFORMATION: Gly, Ile, Leu, Met, Arg, Ser or Val
<220> FEATURE:
<221> NAME/KEY: MOD_RES
<222> LOCATION: (14)..(14)
<223> OTHER INFORMATION: Ala or Ser
<220> FEATURE:
<221> NAME/KEY: MOD_RES
<222> LOCATION: (15)..(15)
<223> OTHER INFORMATION: Ala, Glu, Pro, Gln, Ser or Trp
<220> FEATURE:
<221> NAME/KEY: MOD_RES
<222> LOCATION: (16)..(16)
<223> OTHER INFORMATION: Ala, Asp, Glu, Gly, His, Pro, Gln or Arg
<220> FEATURE:
<221> NAME/KEY: MOD_RES
<222> LOCATION: (17)..(17)
<223> OTHER INFORMATION: Phe or Val
<220> FEATURE:
<221> NAME/KEY: MOD_RES
<222> LOCATION: (18)..(18)
<223> OTHER INFORMATION: Ala, Ile, Met, Thr or Val
<220> FEATURE:
<221> NAME/KEY: MOD_RES
<222> LOCATION: (19)..(19)
<223> OTHER INFORMATION: Asp, Glu, Gly, His, Lys, Asn, Gln, Arg or Ser

<400> SEQUENCE: 344

Ser Cys Xaa His Xaa Xaa Xaa Cys Xaa Xaa Cys Leu Xaa Xaa Xaa Xaa
1               5                   10                  15

Xaa Xaa Xaa Cys Gly Trp Cys His Asp Lys Cys Val Arg Ser Glu Glu
            20                  25                  30

Cys Leu Ser Gly Thr Trp Thr Gln Gln Ile Cys Gly
        35                  40

<210> SEQ ID NO 345
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(26)
<223> OTHER INFORMATION: Asp, Gly, His, Asn, Arg or Ser
<220> FEATURE:
<221> NAME/KEY: MOD_RES
<222> LOCATION: (25)..(25)
<223> OTHER INFORMATION: Asp, Gly, Asn or Ser
<220> FEATURE:
<221> NAME/KEY: MOD_RES
<222> LOCATION: (26)..(26)
<223> OTHER INFORMATION: Glu, Gly, Lys, Met, Arg or Val
<220> FEATURE:
<221> NAME/KEY: MOD_RES
<222> LOCATION: (28)..(28)
<223> OTHER INFORMATION: Ala, Gly, Ile, Ser, Thr or Val
<220> FEATURE:
<221> NAME/KEY: MOD_RES
<222> LOCATION: (29)..(29)
<223> OTHER INFORMATION: His, Gln, Arg or Trp
<220> FEATURE:
<221> NAME/KEY: MOD_RES
<222> LOCATION: (30)..(30)
<223> OTHER INFORMATION: Ser, Leu, Ala, Asp, Glu, His or Gln
<220> FEATURE:
<221> NAME/KEY: MOD_RES
<222> LOCATION: (31)..(31)
<223> OTHER INFORMATION: Asp, Glu, His, Lys, Asn or Gln
<220> FEATURE:
<221> NAME/KEY: MOD_RES
<222> LOCATION: (32)..(32)
<223> OTHER INFORMATION: Asp, Glu, His or Gln
<220> FEATURE:
<221> NAME/KEY: MOD_RES
<222> LOCATION: (34)..(34)
<223> OTHER INFORMATION: Ala, Asp, His, Asn, Pro or Thr
<220> FEATURE:
<221> NAME/KEY: MOD_RES
<222> LOCATION: (35)..(35)
<223> OTHER INFORMATION: Ala, Asp, Gly, Asn, Ser or Thr
<220> FEATURE:
<221> NAME/KEY: MOD_RES
<222> LOCATION: (36)..(36)
<223> OTHER INFORMATION: Asp, Glu, Gly, His, Lys, Asn, Gln, Arg or Ser
<220> FEATURE:
<221> NAME/KEY: MOD_RES
<222> LOCATION: (37)..(37)
<223> OTHER INFORMATION: Ala, Phe, Ile, Ser, Thr, Val or not present
<220> FEATURE:
<221> NAME/KEY: MOD_RES
<222> LOCATION: (39)..(39)
<223> OTHER INFORMATION: Gln, Arg or Thr
<220> FEATURE:
<221> NAME/KEY: MOD_RES
<222> LOCATION: (40)..(40)
<223> OTHER INFORMATION: His, Lys, Asn or Gln
<220> FEATURE:

```
<221> NAME/KEY: MOD_RES
<222> LOCATION: (41)..(41)
<223> OTHER INFORMATION: Asp, Glu, His or Gln
<220> FEATURE:
<221> NAME/KEY: MOD_RES
<222> LOCATION: (42)..(42)
<223> OTHER INFORMATION: Ala, Asp, Phe, His, Ile, Leu, Asn, Pro, Ser,
      Thr, Val or Tyr

<400> SEQUENCE: 345

Ser Cys Arg His Phe Gln Ser Cys Ser Gln Cys Leu Ser Ala Pro Pro
1               5                   10                  15

Phe Val Gln Cys Gly Trp Cys Xaa Xaa Xaa Cys Xaa Xaa Xaa Xaa Xaa
                20                  25                  30

Cys Xaa Xaa Xaa Xaa Trp Xaa Xaa Xaa Xaa Cys Gly
            35                  40

<210> SEQ ID NO 346
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (13)..(19)
<223> OTHER INFORMATION: Any amino acid

<400> SEQUENCE: 346

Ser Cys Xaa His Xaa Xaa Xaa Cys Xaa Xaa Cys Leu Xaa Xaa Xaa Xaa
1               5                   10                  15

Xaa Xaa Xaa Cys Gly Trp Cys His Asp Lys Cys Val Arg Ser Glu Glu
                20                  25                  30

Cys Leu Ser Gly Thr Trp Thr Gln Gln Ile Cys Gly
            35                  40

<210> SEQ ID NO 347
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(26)
<223> OTHER INFORMATION: Any amino acid
<220> FEATURE:
<221> NAME/KEY: MOD_RES
<222> LOCATION: (28)..(32)
<223> OTHER INFORMATION: Any amino acid
<220> FEATURE:
<221> NAME/KEY: MOD_RES
<222> LOCATION: (34)..(37)
<223> OTHER INFORMATION: Any amino acid
<220> FEATURE:
<221> NAME/KEY: MOD_RES
<222> LOCATION: (39)..(42)
```

<223> OTHER INFORMATION: Any amino acid

<400> SEQUENCE: 347

Ser Cys Arg His Phe Gln Ser Cys Ser Gln Cys Leu Ser Ala Pro Pro
1               5                   10                  15

Phe Val Gln Cys Gly Trp Cys Xaa Xaa Xaa Cys Xaa Xaa Xaa Xaa
            20                  25                  30

Cys Xaa Xaa Xaa Xaa Trp Xaa Xaa Xaa Xaa Cys Gly
        35                  40

<210> SEQ ID NO 348
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ser Cys His His Phe Ile Ser Cys Gly Arg Cys Leu Arg Ser Trp His
1               5                   10                  15

Val Val Asp Cys Gly Trp Cys His Asp Lys Cys Val Arg Ser Glu Glu
            20                  25                  30

Cys Leu Ser Gly Thr Trp Thr Gln Gln Ile Cys Gly
        35                  40

<210> SEQ ID NO 349
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ser Cys Arg His Phe Gln Ser Cys Ser Gln Cys Leu Ser Ala Pro Pro
1               5                   10                  15

Phe Val Gln Cys Gly Trp Cys Gly Asp Met Cys Ala Arg Val Gln Gln
            20                  25                  30

Cys His Asp Arg Trp Thr His His Ala Cys Gly
        35                  40

<210> SEQ ID NO 350
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ser Cys Arg His Phe Gln Ser Cys Ser Gln Cys Leu Ser Ala Pro Pro
1               5                   10                  15

Phe Val Gln Cys Gly Trp Cys His Asp Lys Cys Gly His Gln Asp Glu
            20                  25                  30

Cys Thr Ala Ser Trp Arg Lys Glu Ala Cys Gly
        35                  40

<210> SEQ ID NO 351
<211> LENGTH: 44
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 351

Ser Cys Arg His Phe Gln Ser Cys Ser Gln Cys Leu Ser Ala Pro Pro
1               5                   10                  15

Phe Val Gln Cys Gly Trp Cys Arg Asn Met Cys Val Gln Glu Lys Gln
            20                  25                  30

Cys Asp Asp Ser Ile Trp Lys Asn Gln His Cys Gly
        35                  40

<210> SEQ ID NO 352
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ser Cys Arg His Phe Gln Ser Cys Ser Gln Cys Leu Ser Ala Pro Pro
1               5                   10                  15

Phe Val Gln Cys Gly Trp Cys Asp Arg Cys Ser Arg Glu Asp His
            20                  25                  30

Cys Pro Thr Lys Thr Trp Arg Asn His Pro Cys Gly
        35                  40

<210> SEQ ID NO 353
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ser Cys Arg His Phe Gln Ser Cys Ser Gln Cys Leu Ser Ala Pro Pro
1               5                   10                  15

Phe Val Gln Cys Gly Trp Cys Asn Asn Val Cys Ser Arg His Asn Asp
            20                  25                  30

Cys Asp Asn Asn Trp Gln His Gln Asn Cys Gly
        35                  40

<210> SEQ ID NO 354
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ser Cys Arg His Phe Gln Ser Cys Ser Gln Cys Leu Ser Ala Pro Pro
1               5                   10                  15

Phe Val Gln Cys Gly Trp Cys Asn Ser Met Cys Gly Arg Ala His Asp
            20                  25                  30

Cys Thr Asp His Trp Gln Lys Gln His Cys Gly
        35                  40

<210> SEQ ID NO 355
<211> LENGTH: 43
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 355

Ser Cys Arg His Phe Gln Ser Cys Ser Gln Cys Leu Ser Ala Pro Pro
1               5                   10                  15

Phe Val Gln Cys Gly Trp Cys Gly Asn Met Cys Val Arg Ser Glu Glu
            20                  25                  30

Cys His Thr Asp Trp Arg His Asp Thr Cys Gly
        35                  40

<210> SEQ ID NO 356
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ser Cys Arg His Phe Gln Ser Cys Ser Gln Cys Leu Ser Ala Pro Pro
1               5                   10                  15

Phe Val Gln Cys Gly Trp Cys Asn Ser Met Cys Gly Arg Ala Gln Asp
            20                  25                  30

Cys Asn Asp Arg Thr Trp Lys Gln His Thr Cys Gly
        35                  40

<210> SEQ ID NO 357
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gln Ala Ala Gly Pro Ser Gly Pro Cys Ser Tyr Tyr Ala Tyr Phe Thr
1               5                   10                  15

Cys Thr Asn His Trp Cys Pro Ser Pro Pro Phe Ala Phe Thr Cys Thr
            20                  25                  30

Asn His Trp Cys Pro Ser Tyr Tyr Asp Ser Ala Tyr Cys Gly Gln Ser
        35                  40                  45

Gly Gly Ser
    50

<210> SEQ ID NO 358
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gln Ala Ala Gly Pro Ser Gly Pro Cys Ala Ala Tyr Ala Tyr Phe Thr
1               5                   10                  15

Cys Thr Asn His Trp Cys Pro Ser Tyr Tyr Ser Ala Ala Cys Gly Gln
            20                  25                  30

Ser Gly Gly Ser Gly
        35
```

```
<210> SEQ ID NO 359
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Gln Ala Ala Gly Pro Ser Gly Pro Cys Ala Tyr Ala Tyr Tyr Phe Thr
1               5                   10                  15

Cys Thr Asn His Trp Cys Pro Ser Tyr Tyr Ala Tyr Tyr Cys Gly Gln
            20                  25                  30

Ser Gly Gly Ser Gly
        35

<210> SEQ ID NO 360
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gln Ala Ala Gly Pro Ser Gly Pro Cys Ala Tyr Tyr Ser Tyr Phe Thr
1               5                   10                  15

Cys Thr Asn His Trp Cys Pro Ser Tyr Tyr Ser Ser Tyr Cys Gly Gln
            20                  25                  30

Ser Gly Gly Ser Gly
        35

<210> SEQ ID NO 361
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(39)
<220> FEATURE:
<221> NAME/KEY: CDS
<222> LOCATION: (58)..(126)

<400> SEQUENCE: 361 atg gat tat aaa gac gat gac gat aaa ggg tct cca ggt tagtaaccta      49
Met Asp Tyr Lys Asp Asp Asp Asp Lys Gly Ser Pro Gly
1               5                   10 ggtgatag gga ggt tcg tct tca ctc gag ggt acc cat cac cat cac cat    99
         Gly Gly Ser Ser Ser Leu Glu Gly Thr His His His His His
             15                  20                  25 cac gag ctc gta ccg gta gaa aaa atg                                126
His Glu Leu Val Pro Val Glu Lys Met
        30                  35

<210> SEQ ID NO 362
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362
```

Met Asp Tyr Lys Asp Asp Asp Lys Gly Ser Pro Gly
1               5                   10

<210> SEQ ID NO 363
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gly Gly Ser Ser Ser Leu Glu Gly Thr His His His His His Glu
1               5                   10                  15

Leu Val Pro Val Glu Lys Met
            20

<210> SEQ ID NO 364
<211> LENGTH: 463
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 364

Met Gly His His His His His His Gly Gly Ser Gly Gly Glu Gly Gly
1               5                   10                  15

Ser Gly Gly Glu Gly Gly Ser Gly Gly Glu Gly Gly Ser Gly Gly Glu
                20                  25                  30

Gly Gly Ser Gly Gly Glu Gly Gly Ser Gly Gly Glu Gly Gly Ser Gly
            35                  40                  45

Gly Glu Gly Gly Ser Gly Gly Glu Gly Gly Ser Gly Gly Glu Gly Gly
        50                  55                  60

Ser Gly Gly Glu Gly Gly Ser Gly Gly Glu Gly Gly Ser Gly Gly Glu
65                  70                  75                  80

Gly Gly Ser Gly Gly Glu Gly Gly Ser Gly Gly Glu Gly Gly Ser Gly
                85                  90                  95

Gly Glu Gly Gly Ser Gly Gly Glu Gly Gly Ser Gly Gly Glu Gly Gly
            100                 105                 110

Ser Gly Gly Glu Gly Gly Ser Gly Gly Glu Gly Gly Ser Gly Gly Glu
        115                 120                 125

Gly Gly Ser Gly Gly Glu Gly Gly Ser Gly Gly Glu Gly Gly Ser Gly
    130                 135                 140

Gly Glu Gly Gly Ser Gly Gly Glu Gly Gly Ser Gly Gly Glu Gly Gly
145                 150                 155                 160

Ser Gly Gly Glu Gly Gly Ser Gly Gly Glu Gly Gly Ser Gly Gly Glu
                165                 170                 175

Gly Gly Ser Gly Gly Glu Gly Gly Ser Gly Gly Glu Gly Gly Ser Gly
            180                 185                 190

Gly Glu Gly Gly Ser Gly Gly Glu Gly Gly Ser Gly Gly Glu Gly Gly
        195                 200                 205

Ser Gly Gly Glu Gly Gly Ser Gly Gly Glu Gly Gly Ser Gly Gly Glu
    210                 215                 220

Gly Gly Ser Gly Gly Glu Gly Gly Ser Gly Gly Glu Gly Gly Ser Gly
225                 230                 235                 240

Gly Glu Gly Gly Ser Gly Gly Glu Gly Gly Ser Gly Gly Glu Gly Gly
                245                 250                 255

```
Ser Gly Gly Glu Gly Gly Ser Gly Gly Glu Gly Gly Glu
            260                 265                 270

Gly Gly Ser Gly Gly Glu Gly Gly Ser Gly Gly Glu Gly Gly Ser Gly
            275                 280                 285

Gly Glu Gly Gly Ser Gly Gly Glu Gly Gly Cys Asp Leu Pro Gln Thr
            290                 295                 300

His Ser Leu Gly Ser Arg Arg Thr Leu Met Leu Leu Ala Gln Met Arg
305                 310                 315                 320

Lys Ile Ser Leu Phe Ser Cys Leu Lys Asp Arg His Asp Phe Gly Phe
                325                 330                 335

Pro Gln Glu Glu Phe Gly Asn Gln Phe Gln Lys Ala Glu Thr Ile Pro
            340                 345                 350

Val Leu His Glu Met Ile Gln Gln Ile Phe Asn Leu Phe Ser Thr Lys
            355                 360                 365

Asp Ser Ser Ala Ala Trp Asp Glu Thr Leu Leu Asp Lys Phe Tyr Thr
370                 375                 380

Glu Leu Tyr Gln Gln Leu Asn Asp Leu Glu Ala Cys Val Ile Gln Gly
385                 390                 395                 400

Val Gly Val Thr Glu Thr Pro Leu Met Lys Glu Asp Ser Ile Leu Ala
                405                 410                 415

Val Arg Lys Tyr Phe Gln Arg Ile Thr Leu Tyr Leu Lys Glu Lys Lys
                420                 425                 430

Tyr Ser Pro Cys Ala Trp Glu Val Val Arg Ala Glu Ile Met Arg Ser
                435                 440                 445

Phe Ser Leu Ser Thr Asn Leu Gln Glu Ser Leu Arg Ser Lys Glu
            450                 455                 460

<210> SEQ ID NO 365
<211> LENGTH: 472
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 365

Met Gly His His His His His His Gly Gly Ser Gly Gly Glu Gly Gly
1               5                   10                  15

Ser Gly Gly Glu Gly Gly Ser Gly Gly Glu Gly Gly Ser Gly Gly Glu
            20                  25                  30

Gly Gly Ser Gly Gly Glu Gly Gly Ser Gly Gly Glu Gly Gly Ser Gly
            35                  40                  45

Gly Glu Gly Gly Ser Gly Gly Glu Gly Gly Ser Gly Gly Glu Gly Gly
        50                  55                  60

Ser Gly Gly Glu Gly Gly Ser Gly Gly Glu Gly Gly Ser Gly Gly Glu
65                  70                  75                  80

Gly Gly Ser Gly Gly Glu Gly Gly Ser Gly Gly Glu Gly Gly Ser Gly
                85                  90                  95

Gly Glu Gly Gly Ser Gly Gly Glu Gly Gly Ser Gly Gly Glu Gly Gly
            100                 105                 110

Ser Gly Gly Glu Gly Gly Ser Gly Gly Glu Gly Gly Ser Gly Gly Glu
            115                 120                 125

Gly Gly Ser Gly Gly Glu Gly Gly Ser Gly Gly Glu Gly Gly Ser Gly
        130                 135                 140

Gly Glu Gly Gly Ser Gly Gly Glu Gly Gly Ser Gly Gly Glu Gly Gly
145                 150                 155                 160
```

Ser Gly Gly Glu Gly Gly Ser Gly Gly Glu Gly Gly Ser Gly Gly Glu
            165                 170                 175

Gly Gly Ser Gly Gly Glu Gly Gly Ser Gly Gly Glu Gly Gly Ser Gly
            180                 185                 190

Gly Glu Gly Gly Ser Gly Gly Glu Gly Gly Ser Gly Gly Glu Gly Gly
            195                 200                 205

Ser Gly Gly Glu Gly Gly Ser Gly Gly Glu Gly Gly Ser Gly Gly Glu
            210                 215                 220

Gly Gly Ser Gly Gly Glu Gly Gly Ser Gly Gly Glu Gly Gly Ser Gly
225                 230                 235                 240

Gly Glu Gly Gly Ser Gly Gly Glu Gly Gly Ser Gly Gly Glu Gly Gly
            245                 250                 255

Ser Gly Gly Glu Gly Gly Ser Gly Gly Glu Gly Gly Ser Gly Gly Glu
            260                 265                 270

Gly Gly Ser Gly Gly Glu Gly Gly Ser Gly Gly Glu Gly Gly Ser Gly
            275                 280                 285

Gly Glu Gly Gly Ser Gly Gly Glu Gly Gly Thr Pro Leu Gly Pro Ala
            290                 295                 300

Ser Ser Leu Pro Gln Ser Phe Leu Leu Lys Cys Leu Glu Gln Val Arg
305                 310                 315                 320

Lys Ile Gln Gly Asp Gly Ala Ala Leu Gln Glu Lys Leu Cys Ala Thr
            325                 330                 335

Tyr Lys Leu Cys His Pro Glu Glu Leu Val Leu Leu Gly His Ser Leu
            340                 345                 350

Gly Ile Pro Trp Ala Pro Leu Ser Ser Cys Pro Ser Gln Ala Leu Gln
            355                 360                 365

Leu Ala Gly Cys Leu Ser Gln Leu His Ser Gly Leu Phe Leu Tyr Gln
370                 375                 380

Gly Leu Leu Gln Ala Leu Glu Gly Ile Ser Pro Glu Leu Gly Pro Thr
385                 390                 395                 400

Leu Asp Thr Leu Gln Leu Asp Val Ala Asp Phe Ala Thr Thr Ile Trp
            405                 410                 415

Gln Gln Met Glu Glu Leu Gly Met Ala Pro Ala Leu Gln Pro Thr Gln
            420                 425                 430

Gly Ala Met Pro Ala Phe Ala Ser Ala Phe Gln Arg Arg Ala Gly Gly
            435                 440                 445

Val Leu Val Ala Ser His Leu Gln Ser Phe Leu Glu Val Ser Tyr Arg
450                 455                 460

Val Leu Arg His Leu Ala Gln Pro
465                 470

<210> SEQ ID NO 366
<211> LENGTH: 489
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 366

Met Gly His His His His His His Gly Gly Ser Gly Gly Glu Gly Gly
1               5                   10                  15

Ser Gly Gly Glu Gly Gly Ser Gly Gly Glu Gly Gly Ser Gly Gly Glu
            20                  25                  30

Gly Gly Ser Gly Gly Glu Gly Gly Ser Gly Gly Glu Gly Gly Ser Gly

```
            35                  40                  45
Gly Glu Gly Gly Ser Gly Gly Glu Gly Gly Ser Gly Gly Glu Gly Gly
         50                  55                  60
Ser Gly Gly Glu Gly Gly Ser Gly Gly Glu Gly Gly Ser Gly Gly Glu
 65                  70                  75                  80
Gly Gly Ser Gly Gly Glu Gly Gly Ser Gly Gly Glu Gly Gly Ser Gly
             85                  90                  95
Gly Glu Gly Gly Ser Gly Gly Glu Gly Gly Ser Gly Gly Glu Gly Gly
            100                 105                 110
Ser Gly Gly Glu Gly Gly Ser Gly Gly Glu Gly Gly Ser Gly Gly Glu
        115                 120                 125
Gly Gly Ser Gly Gly Glu Gly Gly Ser Gly Gly Glu Gly Gly Ser Gly
        130                 135                 140
Gly Glu Gly Gly Ser Gly Gly Glu Gly Gly Ser Gly Gly Glu Gly Gly
145                 150                 155                 160
Ser Gly Gly Glu Gly Gly Ser Gly Gly Glu Gly Gly Ser Gly Gly Glu
            165                 170                 175
Gly Gly Ser Gly Gly Glu Gly Gly Ser Gly Gly Glu Gly Gly Ser Gly
        180                 185                 190
Gly Glu Gly Gly Ser Gly Gly Glu Gly Gly Ser Gly Gly Glu Gly Gly
        195                 200                 205
Ser Gly Gly Glu Gly Gly Ser Gly Gly Glu Gly Gly Ser Gly Gly Glu
210                 215                 220
Gly Gly Ser Gly Gly Glu Gly Gly Ser Gly Gly Glu Gly Gly Ser Gly
225                 230                 235                 240
Gly Glu Gly Gly Ser Gly Gly Glu Gly Gly Ser Gly Gly Glu Gly Gly
            245                 250                 255
Ser Gly Gly Glu Gly Gly Ser Gly Gly Glu Gly Gly Ser Gly Gly Glu
            260                 265                 270
Gly Gly Ser Gly Gly Glu Gly Gly Ser Gly Gly Glu Gly Gly Ser Gly
        275                 280                 285
Gly Glu Gly Gly Ser Gly Gly Glu Gly Gly Phe Pro Thr Ile Pro Leu
290                 295                 300
Ser Arg Leu Phe Asp Asn Ala Met Leu Arg Ala His Arg Leu His Gln
305                 310                 315                 320
Leu Ala Phe Asp Thr Tyr Gln Glu Phe Glu Glu Ala Tyr Ile Pro Lys
            325                 330                 335
Glu Gln Lys Tyr Ser Phe Leu Gln Asn Pro Gln Thr Ser Leu Cys Phe
        340                 345                 350
Ser Glu Ser Ile Pro Thr Pro Ser Asn Arg Glu Glu Thr Gln Gln Lys
        355                 360                 365
Ser Asn Leu Glu Leu Leu Arg Ile Ser Leu Leu Ile Gln Ser Trp
    370                 375                 380
Leu Glu Pro Val Gln Phe Leu Arg Ser Val Phe Ala Asn Ser Leu Val
385                 390                 395                 400
Tyr Gly Ala Ser Asp Ser Asn Val Tyr Asp Leu Leu Lys Asp Leu Glu
            405                 410                 415
Glu Gly Ile Gln Thr Leu Met Gly Arg Leu Glu Asp Gly Ser Pro Arg
        420                 425                 430
Thr Gly Gln Ile Phe Lys Gln Thr Tyr Ser Lys Phe Asp Thr Asn Ser
        435                 440                 445
His Asn Asp Asp Ala Leu Leu Lys Asn Tyr Gly Leu Leu Tyr Cys Phe
450                 455                 460
```

```
Arg Lys Asp Met Asp Lys Val Glu Thr Phe Leu Arg Ile Val Gln Cys
465                 470                 475                 480
Arg Ser Val Glu Gly Ser Cys Gly Phe
                485
```

BIOLOGICALLY ACTIVE PROTEINS HAVING INCREASED IN VIVO AND/OR IN VITRO STABILITY

CROSS-REFERENCE

This application is a Continuation application which claims the benefit of U.S. application Ser. No. 14/102,297 filed Dec. 10, 2013, which is a Continuation application which claims the benefit of U.S. application Ser. No. 13/439,738 filed Apr. 4, 2012, which is a Continuation application which claims the benefit of Ser. No. 13/396,403 filed Feb. 14, 2012, which is a Continuation application which claims the benefit of U.S. application Ser. No. 12/634,556, filed Dec. 9, 2009, now abandoned; which is a Continuation application of Ser. No. 11/715,276, filed Mar. 6, 2007, now U.S. Pat. No. 7,855,279, which claims benefit of 60/743,410, filed Mar. 6, 2006 and is a continuation-in-part application of Ser. No. 11/528,927, filed Sep. 27, 2006, now abandoned, and Ser. No. 11/528,950, now abandoned, both of which were filed on Sep. 27, 2006, which in turn claim priority to provisional applications Ser. No. 60/721,270, filed on Sep. 27, 2005 and 60/721,188, filed on Sep. 27, 2005 and 60/743,622, filed on Mar. 21, 2006, all of which are herein incorporated by reference in their entirety.

REGARDING FEDERALLY SPONSORED RESEARCH

This invention was made with government support under SBIR grant 1R43GM079873-01 and 2R44GM079873-02 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 10, 2016, is named 32808-704-306-Seqlist.txt and is 209 Kilobytes in size.

BACKGROUND OF THE INVENTION

It has been well documented that properties of proteins, in particular plasma clearance and immunogenicity, can be improved by attaching hydrophilic polymers to these proteins (Kochendoerfer, G. (2003) *Expert Opin Biol Ther*, 3: 1253-61), (Greenwald, R. B., et al. (2003) *Adv Drug Deliv Rev*, 55: 217-50), (Harris, J. M., et al. (2003) *Nat Rev Drug Discov*, 2: 214-21). Examples of polymer-modified proteins that have been approved by the FDA for treatment of patients are Adagen, Oncaspar, PEG-Intron, Pegasys, Somavert, and Neulasta. Many more polymer-modified proteins are in clinical trials. These polymers exert their effect by increasing the hydrodynamic radius (also called Stokes' radius) of the modified protein relative to the unmodified protein, which reduces the rate of clearance by kidney filtration (Yang, K., et al. (2003) *Protein Eng*, 16: 761-70). In addition, polymer attachment can reduce interaction of the modified protein with other proteins, cells, or surfaces. In particular, polymer attachment can reduce interactions between the modified protein and antibodies and other components of the immune system thus reducing the formation of a host immune response to the modified protein. Of particular interest is protein modification by PEGylation, i.e. by attaching linear or branched polymers of polyethylene glycol. Reduced immunogenicity upon PEGylation was shown for example for phenylalanine ammonia lyase (Gamez, A., et al. (2005) *Mol Ther*, 11: 986-9), antibodies (Deckert, P. M., et al. (2000) *Int J Cancer*, 87: 382-90.), Staphylokinase (Collen, D., et al. (2000) *Circulation*, 102: 1766-72), and hemoglobin (Jin, C., et al. (2004) *Protein Pept Lett*, 11: 353-60). Typically, such polymers are conjugated with the protein of interest via a chemical modification step after the unmodified protein has been purified.

Various polymers can be attached to proteins. Of particular interest are hydrophilic polymers that have flexible conformations and are well hydrated in aqueous solutions. A frequently used polymer is polyethylene glycol (PEG). These polymers tend to have large hydrodynamic radi relative to their molecular weight (Kubetzko, S., et al. (2005) *Mol Pharmacol*, 68: 1439-54). The attached polymers tend to have limited interactions with the protein they have been attached to and thus the polymer-modified protein retains its relevant functions.

The chemical conjugation of polymers to proteins requires complex multi-step processes. Typically, the protein component needs to be produced and purified prior to the chemical conjugation step. The conjugation step can result in the formation of product mixtures that need to be separated leading to significant product loss. Alternatively, such mixtures can be used as the final pharmaceutical product. Some examples are currently marketed PEGylated Interferon-alpha products that are used as mixtures (Wang, B. L., et al. (1998) *J Submicrosc Cytol Pathol*, 30: 503-9; Dhalluin, C., et al. (2005) *Bioconjug Chem*, 16: 504-17). Such mixtures are difficult to manufacture and characterize and they contain isomers with reduced or no therapeutic activity.

Methods have been described that allow the site-specific addition of polymers like PEG. Examples are the selective PEGylation at a unique glycosylation site of the target protein or the selective PEGylation of a non-natural amino acid that has been engineered into the target proteins. In some cases it has been possible to selectively PEGylate the N-terminus of a protein while avoiding PEGylation of lysine side chains in the target protein by carefully controlling the reaction conditions. Yet another approach for the site-specific PEGylation of target proteins is the introduction of cysteine residues that allow selective conjugation. All these methods have significant limitations. The selective PEGylation of the N-terminus requires careful process control and side reactions are difficult to eliminate. The introduction of cysteines for PEGylation can interfere with protein production and/or purification. The specific introduction of non-natural amino acids requires specific host organisms for protein production. A further limitation of PEGylation is that PEG is typically manufactured as a mixture of polymers with similar but not uniform length. The same limitations are inherent in many other chemical polymers.

Chemical conjugation using multifunctional polymers which would allow the synthesis of products with multiple protein modules is even more complex then the polymer conjugation of a single protein domain.

Recently, it has been observed that some proteins of pathogenic organisms contain repetitive peptide sequences that seem to lead to a relatively long serum halflife of the proteins containing these sequences (Alvarez, P., et al. (2004) *J Biol Chem*, 279: 3375-81). It has also been demonstrated that oligomeric sequences that are based on such pathogen-derived repetitive sequences can be fused to other proteins resulting in increased serum halflife. However, these pathogen-derived oligomers have a number of deficiencies. The pathogen-derived sequences tend to be immunogenic. It has been described that the sequences can be modified to reduce their immunogenicity. However, no attempts have been reported to remove T cell epitopes from the sequences contributing to the formation of immune reactions. Furthermore, the pathogen-derived sequences have not been optimized for pharmacological applications which require sequences with good solubility and a very low affinity for other target proteins.

Thus there is a significant need for compositions and methods that would allow one to combine multiple polymer modules and multiple protein modules into defined multi-domain products.

SUMMARY OF THE INVENTION

The present invention provides an unstructured recombinant polymer (URP) comprising at least 40 contiguous amino acids, wherein said URP is substantially incapable of non-specific binding to a serum protein, and wherein (a) the sum of glycine (G), aspartate (D), alanine (A), serine (S), threonine (T), glutamate (E) and proline (P) residues contained in the URP, constitutes more than about 80% of the total amino acids of the URP; and/or (b) at least 50% of the amino acids are devoid of secondary structure as determined by Chou-Fasman algorithm. In a related embodiment, the present invention provides an unstructured recombinant polymer (URP) comprising at least 40 contiguous amino acids, wherein said URP has an in vitro serum degradation half-life greater than about 24 hours, and wherein (a) the sum of glycine (G), aspartate (D), alanine (A), serine (S), threonine (T), glutamate (E) and proline (P) residues contained in the URP, constitutes more than about 80% of the total amino acids of the URP; and/or (b) at least 50% of the amino acids are devoid of secondary structure as determined by Chou-Fasman algorithm. The subject URP can comprises a non-natural amino acid sequence. Where desired, the URP is selected for incorporation into a heterologous protein, and wherein upon incorporation the URP into a heterologous protein, said heterologous protein exhibits a longer serum secretion half-life and/or higher solubility as compared to the corresponding protein that is deficient in said URP. The half-life can be extended by two folds, three folds, five folds, ten folds or more. In some aspects, incorporation of the URP into a heterologous protein results in at least a 2-fold, 3-fold, 4-fold, 5-fold or more increase in apparent molecular weight of the protein as approximated by size exclusion chromatography. In some aspects, the URPs has a Tepitope score less than −3.5 (e.g., −4 or less, −5 or less). In some aspects, the URPs can contain predominantly hydrophilic residues. Where desired, at least 50% of the amino acids of the URP are devoid of secondary structure as determined by Chou-Fasman algorithm. The glycine residues contained in the URP may constitute at least about 50% of the total amino acids of the URP. In some aspect, any one type of the amino acids alone selected from the group consisting of glycine (G), aspartate (D), alanine (A), serine (S), threonine (T), glutamate (E) and proline (P) contained in the URP constitutes more than about 20%, 30%, 40%, 50%, 60% or more of the total amino acids of the URP. In some aspects, the URP comprises more than about 100, 150, 200 or more contiguous amino acids.

The present invention also provides a protein comprising one or more of the subject URPs, wherein the subject URPs are heterologous with respect to the protein. The total length of URPs in aggregation can exceed about 40, 50, 60, 100, 150, 200, or more amino acids. The protein can comprise one or more functional modules selected from the group consisting of effector module, binding module, N-terminal module, C-terminal module, and any combinations thereof. Where desired, the subject protein comprises a plurality of binding modules, wherein the individual binding modules exhibit binding specificities to the same or different targets. The binding module may comprise a disulfide-containing scaffold formed by intra-scaffold pairing of cysteines. The binding module may bind to a target molecule target is selected from the group consisting of cell surface protein, secreted protein, cytosolic protein, and nuclear protein. The target can be an ion channel and/or GPCR. Where desired, the effector module can be a toxin. The subject URP-containing protein typically an extended serum secretion half-life by at least 2, 3, 4, 5, 10 or more folds as compared to a corresponding protein that is deficient in said URP.

In a separate embodiment, the present invention provides a non-naturally occurring protein comprising at least 3 repeating units of amino acid sequences, each of the repeating unit comprising at least 6 amino acids, wherein the majority of segments comprising about 6 to about 15 contiguous amino acids of the at least 3 repeating units are present in one or more native human proteins. In one aspect, the majority of the segments, or each segment comprising about 9 to about 15 contiguous amino acids within the repeating units are present in one or more native human proteins. The segments can comprise about 9 to about 15 amino acids. The three repeating units may share substantial sequence homology, e.g., share sequence identify of greater than about 50%, 60%, 70%, 80%, 90% or 100% when aligned. Such non-natural protein may also comprise one or more modules selected from the group consisting of binding modules, effector modules, multimerization modules, C-terminal modules, and N-terminal modules. Where desired, the non-natural protein may comprise individual repeating unit having the subject unstructured recombinant polymer (URP).

The present invention also provides recombinant polynucleotides comprising coding sequences that encode the subject URPs, URP-containing proteins, microproteins and toxins. Also provided in the present invention are vectors containing the subject polynucleotides, host cells harboring the vectors, genetic packages displaying the subject URPs, URP-containing proteins, toxins and any other proteinaceous entities disclosed herein. Further provided are selectable library of expression vectors of the present invention.

The present invention also provides method of producing a protein comprising an unstructured recombinant polymer (URP). The method involves (i) providing a host cell comprising a recombinant polynucleotide encoding the protein, said protein comprising one or more URP, said URP comprising at least 40 contiguous amino acids, wherein said URP is substantially incapable of non-specific binding to a serum protein, and wherein (a) the sum of glycine (G), aspartate (D), alanine (A), serine (S), threonine (T), glutamate (E) and proline (P) residues contained in the URP, constitutes more than about 80% of the total amino acids of the URP; and/or (b) at least 50% of the amino acids are devoid of secondary structure as determined by Chou-Fasman algorithm; and (ii) culturing said host cell in a suitable culture medium under conditions to effect expression of said protein from said polynucleotide. Suitable host cells are eukaryotic (e.g., CHO cells) and prokaryotic cells.

The present invention also provides a method of increasing serum secretion half-life of a protein, comprising: fusing said protein with one or more unstructured recombinant polymers (URPs), wherein the URP comprises at least about 40 contiguous amino acids, and wherein (a) the sum of glycine (G), aspartate (D), alanine (A), serine (S), threonine (T), glutamate (E) and proline (P) residues contained in the URP, constitutes more than about 80% of the total amino acids of the URP; and/or (b) at least 50% of the amino acids are devoid of secondary structure as determined by Chou-Fasman algorithm; and wherein said URP is substantially incapable of non-specific binding to a serum protein.

Also provided in the present invention is a method of detecting the presence or absence of a specific interaction between a target and an exogenous protein that is displayed on a genetic package, wherein said protein comprises one or more unstructured recombinant polymer (URP), the method comprising: (a) providing a genetic package displaying a protein that comprises one or more unstructured recombinant polymers (URPs); (b) contacting the genetic package with the target under conditions suitable to produce a stable protein-target complex; and (c) detecting the formation of the stable protein-target complex on the genetic package, thereby detecting the presence of a specific interaction. The method may further comprises obtaining a nucleotide sequence from the genetic package that encodes the exogenous protein. In some aspects, the presence or absence of a specific interaction is between the URP and a target comprising a serum protein. In some aspects, the presence or absence of a specific interaction is between the URP and a target comprising a serum protease.

Further included in the present invention is a genetic package displaying a microprotein, wherein said microprotein retains binding capability to its native target. In some aspects, the microprotein exhibits binding capability towards at least one family of ion channel selected from the group consisting of a sodium, a potassium, a calcium, an acetylcholine, and a chlorine channel. Where desired, the microprotein is an ion-channel-binding microprotein, and is modified such that (a) the microprotein binds to a different family of channel as compared to the corresponding unmodified microprotein; (b) the microprotein binds to a different subfamily of the same channel family as compared to the corresponding unmodified microprotein; (c) the microprotein binds to a different species of the same subfamily of channel as compared to the corresponding unmodified microprotein; (d) the microprotein binds to a different site on the same channel as compared to the corresponding unmodified microprotein; and/or (e) the microprotein binds to the same site of the same channel but yield a different biological effect as compared to the corresponding unmodified microprotein. In some aspect, the microprotein is a toxin. The present invention also provides a library of genetic packages displaying the subject microproteins and/or toxins. Where desired, the genetic package displays a proteinaceous toxin that retains in part or in whole its toxicity spectrum. The toxin cna be derived from a single toxin protein, or derived from a family of toxins. The present invention also provides a library of genetic packages wherein the library displays a family of toxins, wherein the family retains in part or in whole its native toxicity spectrum.

The present invention further provides a protein comprising a plurality of ion-channel binding domains, wherein individual domains are microprotein domains that have been modified such that (a) the microprotein domains bind to a different family of channel as compared to the corresponding unmodified microprotein domains; (b) the microprotein domains bind to a different subfamily of the same channel family as compared to the corresponding unmodified microprotein domains; (c) the microprotein domains bind to a different species of the same subfamily as compared to the corresponding unmodified microprotein domains; (d) the microprotein domains bind to a different site on the same channel as compared to the corresponding unmodified microprotein domains; (e) the microprotein domains bind to the same site of the same channel but yield a different biological effect as compared to the corresponding unmodified microprotein domains; and/or (f) the microprotein domains bind to the same site of the same channel and yield the same biological effect as compared to the corresponding unmodified microprotein domains.

Also embodied in the invention is a method of obtaining a microprotein with desired property, comprising: (a) providing a subject library; and (b) screening the selectable library to obtain at least one phage displaying a microprotein with the desired property. Polynucleotides, vectors, genetic packages, host cells for use in any one of the disclosed methods are also provided.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows the modular components of an MURP. Binding modules, effector modules, and multimerization modules are depicted as circles. URP modules, N-terminal, and C-terminal modules are shown as rectangles.

FIG. 2 shows examples of modular architectures of MURPs. Binding modules (BM) in one MURP can have identical or differing target specificities.

FIG. 3 shows that a repeat protein that is based on a human sequence can contain novel amino acid sequences, which can contain T cell epitopes. These novel sequences are formed at the junction between neighboring repeat units.

FIG. 4 illustrates the design of a URP sequence that is a repeat protein based on three human donor sequences D1, D2, and D3. The repeating unit of this URP was chosen such that even 9-mer sequences that span the junction between neighboring units can be found in at least one of the human donor sequences.

FIG. 5 Example of a URP sequence (SEQ ID NO: 269) that is a repeat protein based on the sequences of three human proteins. The lower portion of the figure illustrates that all 9-mer subsequences in the URP occur in at least one of the human donor proteins. CAG38801, NP 009060 and Q9Y2X9 sequences disclosed as SEQ ID NOS 105, 103 and 270, respectively.

FIG. 6 Example URP sequence (SEQ ID NO: 271) based on the human POU domain residues 146-182 (SEQ ID NO: 6).

FIG. 7 shows the advantage of separating modules with information rich sequences by inserting URP modules between such sequences. The left side of the figure shows that the direct fusion of modules A and B leads to novel sequences in the junction region. These junction sequences can be epitopes. The right half of the figure shows that the insertion of a URP module between module A and B prevents the formation of such junction sequences that contain partial sequences from modules A and B. Instead, the termini of modules A and B yield junction sequences that contain URP sequences and thus are predicted to have low immunogenicity.

FIG. 8 shows drug delivery constructs that are based on URPs. The drug molecules depicted as hexagons are chemically conjugated to the MURP.

FIG. 9 shows and MURP containing a protease-sensitive site. The URP module is designed such that it blocks the effector module from its function. Protease cleavage removes a portion of the URP module and results in increased activity of the effector function.

FIG. 10 shows how an URP module can act as a linker between a binding module and an effector module. The binding module can bind to a target and as a consequence it increases the local concentration of the effector module in the proximity of the target.

FIG. 11 Shows a process to construct genes encoding URP sequences from libraries of short URP modules. The URP module library can be inserted into a stuffer vector that contains green fluorescent protein (GFP) as a reporter to facilitate the identification of URP sequences with high expression. The figure illustrates that genes encoding long URP sequences can be build by iterative dimerization.

FIG. 12 shows MURPs that contain multiple binding modules for death receptors. Death receptors are triggered by trimerization and thus MURPs containing at least three binding elements for one death receptor particularly potent in inducing cell death. The lower portion of the figure illustrates that one can increase the specificity of the MURP for diseased tissue by adding one or more binding modules with specificity for tumor tissue.

FIG. 13 shows a MURP that comprises four binding modules (rectangles) with specificity for a tumor antigen with an effector module like interleukin 2.

FIG. 14 shows the flow chart for the construction of URP modules with 288 residues. The URP modules were constructed as fusion proteins with GFP. Libraries of URP modules with 36 amino acids were constructed first followed by iterative dimerization to yield URP modules with 288 amino acids (rPEG_H288 and rPEG_J288).

FIG. 15 Amino acid (SEQ ID NO: 273) and nucleotide (SEQ ID NO: 272) sequence of a URP module with 288 amino acids (rPEG_J288).

FIG. 16 Amino acid (SEQ ID NO: 275) and nucleotide (SEQ ID NO: 274) sequence of a URP module with 288 amino acids (rPEG_H288).

FIG. 17 Amino acid sequence of a serine-rich sequence region of the human protein dentin sialophosphoprotein (SEQ ID NO: 276). SSDSSN peptide disclosed as SEQ ID NO: 277.

FIG. 18 shows a depot derivative of a MURP. The protein contains two cysteine residues that can form a weak SS bridge. The protein can be manufactured with the SS bridge intact. It can be formulated and injected into patients in reduced form. After injection it will be oxidized in proximity to the injection site and as a result in can form a high molecular weight polymer with very limited diffusivity. The active MURP can slowly leach from the injection site by limited proteolysis or limited reduction of the cross linking SS bond.

FIG. 19 shows a depot form of a MURP. The MURP has very limited diffusivity at the injection site and can be liberated from the injection site by limited proteolysis.

FIG. 20 shows a depot form of a MURP that contains a histidine-rich sequence. The MURP can be formulated and injected in combination with insoluble beads that contain immobilized nickel. The MURP binds to the nickel beads at the injection site and is released slowly into the circulation. 6xHis tag disclosed as SEQ ID NO: 97.

FIG. 21 shows MURPs that contain multimerization modules. The upper part of the figure shows an MURP that contains one dimerization sequence. As a result it forms a dimer which effectively doubles its molecular weight. The center of the figure shows three MURP designs that comprise two multimerization sequences. Such MURPs can form multimers with very high effective molecular weight. The lower part of the figure illustrated an MURP that contains multiple RGD sequences that are known to bind to cell surface receptors and thus confer half-life. RADARADA, RARARARA, DADADADA and HAHAHAHA sequences disclosed as SEQ ID NOS 278-281, respectively.

FIG. 22 Shows a variety of MURPs that are designed to block or modulate ion channel function. Circles indicate binding modules with specificity for ion channels. These binding modules can be derived or identical to natural toxins with affinity for ion channel receptors. The figure illustrates that other binding domains can be added on either side of the ion channel-specific binding modules thus conferring the MURPs increased efficacy or specificity for a particular cell type.

FIG. 23 shows several MURP designs for increased half-life. Increased effective molecular weight can be achieved by increasing chain length (A), chemical multimerization (B), adding multiple copies of binding modules into a molecule separated by non-binding sites (C), construction of chemical multimers similar to C (D, E), including multimerization sequences (F).

FIG. 24 shows MURPs that can be formed by chemical conjugation of binding modules to a recombinant URP sequence. The URP sequence is designed to contain multiple lysine residues (K) as conjugation sites.

FIG. 25 shows the design of a library of 2SS binding modules. The sequences contain a constant 1SS sequence in the center which is flanked by random sequences that contain cysteine residues in varying distance from the 1 SS core.

FIG. 26 shows the design of a library of 2SS binding modules. The sequences contain a constant 1SS sequence in the center which is flanked by random sequences that contain cysteine residues in varying distance from the 1SS core. FIG. 26A discloses SEQ ID NO: 282. FIG. 26B discloses SEQ ID NO: 283. FIG. 26C discloses SEQ ID NOS 284-291, respectively, in order or appearance.

FIG. 27 shows the design of a library of dimers of 1SS binding modules. Initially, a collection of 1SS binding modules is amplified by two PCR reactions. The resulting PCR products are combined and dimers are generated in a subsequent PCR step. Figure discloses SEQ ID NOS 292-303, respectively, in order or appearance.

FIG. 28 show the Western analysis of a fusion protein containing the 288 amino acid URP sequence rPEG_J288 after incubation of up to 3 days in 50% mouse serum.

FIG. 29 shows results of a binding assay testing for pre-existing antibodies against a URP sequence of 288 amino acids.

FIG. 30 shows the binding of MURPs containing one (Monomer), two (Dimer), four (Tetramer), or zero (rPEG36) binding modules with specificity for VEGF which was coated to microtiter plates.

FIG. 31 shows the amino acid sequence of an MURP with specificity for EpCAM (SEQ ID NO: 304). The sequence contains four binding modules with affinity for EpCAM (underlined). The sequence contains an N-terminal Flag sequence which contains the only two lysine residues of the entire sequence.

FIG. 32 shows the design of 1SS addition libraries. Random 1SS modules can be added to the N-or C-terminus of a pre-selected binding module or simultaneously to both sides. Figure discloses SEQ ID NOS 305-309, respectively, in order or appearance.

FIG. 33 shows the alignment of three finger toxin-related sequences (SEQ ID NOS 310-325, respectively, in order or appearance). The figure also shows a 3D structure that was solved by NMR. Short 3FT scaffold sequence disclosed as SEQ ID NO: 112.

FIG. 34 shows the design of a three-finger toxin-based library (SEQ ID NO: 326). Residues designated X were randomized. The codon choice for each random position is indicated.

FIG. 35 shows the alignment of plexin-related sequences (SEQ ID NOS 327-343, respectively, in order or appearance).

FIG. 36 shows the design of a plexin-based library (SEQ ID NOS 344-345, respectively, in order or appearance). Residues designated X were randomized. The codon choice for each random position is indicated.

FIG. 37 Sequences of plexin-related binding modules with specificity for DR4, ErbB2, and HGFR (SEQ ID NOS 346-356, respectively, in order or appearance).

FIG. 38 shows a binding assay for microprotein-based binding domains with specificity for VEGF.

FIG. 39 shows sequences of 2SS and 3SS binding modules that were isolated from buildup libraries with specificity for VEGF (SEQ ID NOS 357-360, respectively, in order or appearance). The upper part of the figure shows PAGE gel analysis of the proteins purified by heat-lysis.

FIG. 40 shows cloning steps to construct the URP sequence rPEG_J72.

FIG. 41 shows the construction of a library of URP modules with 36 amino acids called rPEG_J36. The region encoding rPEG_J36 was assembled by ligating three shorter segments encoding rPEG_J12 and a stopper module.

FIG. 42 shows the nucleotide sequence (SEQ ID NO: 361) and translation (SEQ ID NOS 362-363 ) of the stuffer vector pCW0051. The stuffer region is flanked by BsaI and BbsI sites and contains multiple stop codons. 6xHis tag disclosed as SEQ ID NO: 97.

FIG. 43 shows a PAGE gel of the purification of the URP rPEG_J288 fused to GFP. Lane 2 shows the cell lysate; lane 3: product purified by IMAC; lane 4: product purified by anti-Flag.

FIG. 44 Amino acid sequence of fusion proteins between rPEG__J288 and human effector domains interferon alpha (SEQ ID NO: 364), G-CSF (SEQ ID NO: 365), and human growth hormone (SEQ ID NO: 366).

FIG. 45 shows the Western analysis of expression of fusion proteins between rPEG_J288 and human growth hormone (lanes 1 and 2), interferon alpha (lanes 3 and 4), and GFP (lanes 5 and 6). Both soluble and insoluble material was analyzed for each protein.

FIG. 46 shows the design of MURPs based on the toxin OSK1. The figure shows that URP sequences and/or binding modules can be added to either side of OSK1

FIG. 47 depicts exemplary product formats comprising the subject URPs.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

General Techniques:

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions:

As used in the specification and claims, the singular form "a", "an" and "the" include plural references unless the context clearly dictates otherwise. For example, the term "a cell" includes a plurality of cells, including mixtures thereof.

The terms "polypeptide", "peptide", "amino acid sequence" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including but not limited to glycine and both the D or L optical isomers, and amino acid analogs and peptidomimetics Standard single or three letter codes are used to designate amino acids.

A "repetitive sequence" refers to an amino acid sequence that can be described as an oligomer of repeating peptide sequences, forming direct repeats, or inverted repeats or alternating repeats of multiple sequence motifs. These repeating oligomer sequences can be identical or homologous to each other, but there can also be multiple repeated motifs. Repetitive sequences are characterized by a very low information content. A repetitive sequence is not a required feature of a URP and in some cases a non-repetitive sequence will in fact be preferred.

Amino acids can be characterized based on their hydrophobicity. A number of scales have been developed. An example is a scale developed by Levitt, M et al. (see Levitt, M (1976) J Mol Biol 104, 59, #3233, which is listed in Hopp, T P, et al. (1981) Proc Natl Acad Sci USA 78, 3824, #3232). Examples of "hydrophilic amino acids" are arginine, lysine, threonine, alanine, asparagine, and glutamine Of particular interest are the hydrophilic amino acids aspartate, glutamate, and serine, and glycine. Examples of "hydrophobic amino acids" are tryptophan, tyrosine, phenylalanine, methionine, leucine, isoleucine, and valine.

The term "denatured conformation" describes the state of a peptide in solution that is characterized by a large conformational freedom of the peptide backbone. Most peptides and proteins adopt a denatured conformation in the presence of high concentrations of denaturants or at elevated temperatures. Peptides in denatured conformation have characteristic CD spectra and they are generally characterized by a lack of long range interactions as determined by e.g., NMR. Denatured conformation and unfolded conformation will be used synonymously.

The terms "unstructured protein (UNP) sequences" and "unstructured recombinant polymer" (URP) are used herein interchangeably. The terms refer to amino acid sequences that share commonality with denatured peptide sequences, e.g., exhibiting a typical behavior like denatured peptide sequences, under physiological conditions, as detailed herein. URP sequences lack a defined tertiary structure and they have limited or no secondary structure as detected by, e.g., Chou-Fasman algorithm.

As used herein, the term "cell surface proteins" refers to the plasma membrane components of a cell. It encompasses integral and peripheral membrane proteins, glycoproteins, polysaccharides and lipids that constitute the plasma membrane. An integral membrane protein is a transmembrane protein that extends across the lipid bilayer of the plasma membrane of a cell. A typical integral membrane protein consists of at least one membrane spanning segment that generally comprises hydrophobic amino acid residues. Peripheral membrane proteins do not extend into the hydrophobic interior of the lipid bilayer and they are bound to the membrane surface via covalent or noncovalent interaction directly or indirectly with other membrane components.

The terms "membrane", "cytosolic", "nuclear" and "secreted" as applied to cellular proteins specify the extracellular and/or subcellular location in which the cellular protein is mostly, predominantly, or preferentially localized.

"Cell surface receptors" represent a subset of membrane proteins, capable of binding to their respective ligands. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions.

The term "module" refers to a portion of a protein that is physically or functionally distinguished from other portions of the protein or peptide. A module can comprise one or more domains. In general, a module or domain can be a single, stable three-dimensional structure, regardless of size. The tertiary structure of a typical domain is stable in solution and remains the same whether such a member is isolated or covalently fused to other domains. A domain generally has a particular tertiary structure formed by the spatial relationships of secondary structure elements, such as beta-sheets, alpha helices, and unstructured loops. In domains of the microprotein family, disulfide bridges are generally the primary elements that determine tertiary structure. In some instances, domains are modules that can confer a specific functional activity, such as avidity (multiple binding sites to the same target), multi-specificity (binding sites for different targets), halflife (using a domain, cyclic peptide or linear peptide) which binds to a serum protein like human serum albumin (HSA) or to IgG (hIgG1, 2, 3 or 4) or to red blood cells. Functionally-defined domains have a distinct biological function(s). The ligand-binding domain of a receptor, for example, is that domain that binds ligand. An antigen-binding domain refers to the part of an antigen-binding unit or an antibody that binds to the antigen. Functionally-defined domains need not be encoded by contiguous amino acid sequences. Functionally-defined domains may contain one or more physically-defined domain Receptors, for example, are generally divided into the extracellular ligand-binding domain, a transmembrane domain, and an intracellular effector domain. A "membrane anchorage domain" refers to the portion of a protein that mediates membrane association. Generally, the membrane anchorage domain is composed of hydrophobic amino acid residues. Alternatively, the membrane anchorage domain may contain modified amino acids, e.g. amino acids that are attached to a fatty acid chain, which in turn anchors the protein to a membrane.

"Non-naturally occurring" as applied to a protein means that the protein contains at least one amino acid that is different from the corresponding wildtype or native protein. Non-natural sequences can be determined by performing BLAST search using, e.g., the lowest smallest sum probability where the comparison window is the length of the sequence of interest (the queried) and when compared to the non-redundant ("nr") database of Genbank using BLAST 2.0. The BLAST 2.0 algorithm, which is described in Altschul et al. (1990) J. Mol. Biol. 215:403-410, respectively. Software for performing BLAST analyses is publicly available through the National Center for Biotechnology Information.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

As used herein, the term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring the polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart.

"Linked" and "fused" or "fusion" are used interchangeably herein. These terms refer to the joining together of two more chemical elements or components, by whatever means including chemical conjugation or recombinant means. An "in-frame fusion" refers to the joining of two or more open reading frames (OFRs) to form a continuous longer OFR, in a manner that maintains the correct reading frame of the original OFRs. Thus, the resulting recombinant fusion protein is a single protein containing two ore more segments that correspond to polypeptides encoded by the original OFRs (which segments are not normally so joined in nature.)

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide which is known to comprise additional residues in one or both directions.

"Heterologous" means derived from a genotypically distinct entity from the rest of the entity to which it is being compared. For example, a glycine rich sequence removed from its native coding sequence and operatively linked to a coding sequence other than the native sequence is a heterologous glycine rich sequence. The term "heterologous" as applied to a polynucleotide, a polypeptide, means that the polynucleotide or polypeptide is derived from a genotypically distinct entity from that of the rest of the entity to which it is being compared.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Recombinant" as applied to a polynucleotide means that the polynucleotide is the product of various combinations of cloning, restriction and/or ligation steps, and other procedures that result in a construct that is distinct from a polynucleotide found in nature.

The terms "gene" or "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

A "vector" is a nucleic acid molecule, preferably self-replicating, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

The "target" as used in the context of MURPs is a biochemical molecule or structure to which the Binding Module or the URP-linked Binding Module can bind and where the binding event results in a desired biological activity. The target can be a protein ligand or receptor that is inhibited, activated or otherwise acted upon by the t protein. Examples of targets are hormones, cytokines, antibodies or antibody fragments, cell surface receptors, kinases, growth factors and other biochemical structures with biological activity.

A "functional module" can be any non-URP in a protein product. Thus a functional module can be a binding module (BM), an effector module (EM), a multimerization module (MM), a C-terminal module (CM), or an N-terminal module (NM). In general, functional modules are characterized by a high information content of their amino acid sequence, i.e they contain many different amino acids and many of these amino acids are important for the function of a functional module. A functional module typically has secondary and tertiary structure, may be a folded protein domain and may contain 1, 2, 3, 4, 5 or more disulfide bonds.

The term 'microproteins' refers to a classification in the SCOP database. Microproteins are usually the smallest proteins with a fixed structure and typically but not exclusively have as few as 15 amino acids with two disulfides or up to 200 amino acids with more than ten disulfides. A microprotein may contain one or more microprotein domains Some microprotein domains or domain families can have multiple more-or-less stable and multiple more or less similar structures which are conferred by different disulfide bonding patterns, so the term stable is used in a relative way to differentiate microproteins from peptides and non-microprotein domains Most microprotein toxins are composed of a single domain, but the cell-surface receptor microproteins often have multiple domains Microproteins can be so small because their folding is stabilized either by disulfide bonds and/or by ions such as Calcium, Magnesium, Manganese, Copper, Zinc, Iron or a variety of other multivalent ions, instead of being stabilized by the typical hydrophobic core.

The term "scaffold" refers to the minimal polypeptide 'framework' or 'sequence motif' that is used as the conserved, common sequence in the construction of protein libraries. In between the fixed or conserved residues/positions of the scaffold lie variable and hypervariable positions. A large diversity of amino acids is provided in the variable regions between the fixed scaffold residues to provide specific binding to a target molecule. A scaffold is typically defined by the conserved residues that are observed in an alignment of a family of sequence-related proteins. Fixed residues may be required for folding or structure, especially if the functions of the aligned proteins are different. A full description of a microprotein scaffold may include the number, position or spacing and bonding pattern of the cysteines, as well as position and identity of any fixed residues in the loops, including binding sites for ions such as Calcium.

The "fold" of a microprotein is largely defined by the linkage pattern of the disulfide bonds (i.e., 1-4, 2-6, 3-5). This pattern is a topological constant and is generally not amenable to conversion into another pattern without unlinking and relinking the disulfides such as by reduction and oxidation (redox agents). In general, natural proteins with related sequences adopt the same disulfide bonding patterns. The major determinants are the cysteine distance pattern (CDP) and some fixed non-cys residues, as well as a metal-binding site, if present. In few cases the folding of proteins is also influenced by the surrounding sequences (ie pro-peptides) and in some cases by chemical derivatization (ie gamma-carboxylation) of residues that allow the protein to bind divalent metal ions (ie Ca++) which assists their folding. For the vast majority of microproteins such folding help is not required.

However, proteins with the same bonding pattern may still comprise multiple folds, based on differences in the length and composition of the loops that are large enough to give the protein a rather different structure. An example are the conotoxin, cyclotoxin and anato domain families, which have the same DBP but a very different CDP and are considered to be different folds. Determinants of a protein fold are any attributes that greatly alter structure relative to a different fold, such as the number and bonding pattern of the cysteines, the spacing of the cysteines, differences in the sequence motifs of the inter-cysteine loops (especially fixed loop residues which are likely to be needed for folding, or in the location or composition of the calcium (or other metal or co-factor) binding site.

The term "disulfide bonding pattern" or "DBP" refers to the linking pattern of the cysteines, which are numbered 1-n from the N-terminus to the C-terminus of the protein. Disulfide bonding patterns are topologically constant, meaning they can only be changed by unlinking one or more disulfides such as using redox conditions. The possible 2-, 3-, and 4-disulfide bonding patterns are listed below in paragraphs 0048-0075.

The term "cysteine distance pattern" or "CDP" refers to the number of non-cysteine amino acids that separate the cysteines on a linear protein chain. Several notations are used: C5C0C3C (SEQ ID NO: 1) equals C5CC3C (SEQ ID NO: 1) equals CxxxxxCCxxxC (SEQ ID NO: 1).

The term 'Position n6' or 'n7=4' refers to the intercysteine loops and 'n6' is defined as the loop between C6 and C7; 'n7=4' means the loop between C7 and C8 is 4 amino acids long, not counting the cysteines.

Serum degradation resistance—Proteins can be eliminated by degradation in the blood, which typically involves proteases in the serum or plasma. The serum degradation resistance is measured by combining the protein with human (or mouse, rat, monkey, as appropriate) serum or plasma, typically for a range of days (ie 0.25, 0.5, 1, 2, 4, 8, 16 days) at 37 C. The samples for these timepoints are then run on a western assay and the protein is detected with an antibody. The antibody can be to a tag in the protein. If the protein shows a single band on the western, where the protein's size is identical to that of the injected protein, then no degradation has occurred. The timepoint where 50% of the protein is degraded, as judged by western, is the serum degradation halflife of the protein.

Serum protein binding—While the MURP typically has a number of modules that bind to cell-surface targets and/or serum proteins, it is desirable that the URP substantially lack unintended activities. The URP should be designed to minimize avoid interaction with (binding to) serum proteins, including antibodies. Different URP designs can be screened for serum protein binding by ELISA, immobilizing the serum proteins and then adding the URP, incubating, washing and then detecting the amount of bound URP. One approach is to detect the URP using an antibody that recognizes a tag that has been added to the URP. A different approach is to immobilize the URP (such as via a fusion to GFP) and come in with human serum, incubating, washing, and then detecting the amount of human antibodies that remain bound to the URP using secondary antibodies like goat anti-human IgG. Using these approaches we have designed our URPs to show very low levels of binding to serum proteins. However, in some applications binding to serum proteins or serum-exposed proteins is desired, for example because it can further extend the secretion half life. In such cases one can use these same assays to design URPs that bind to serum proteins or serum-exposed proteins such as HSA or IgG. In other cases the MURP can be given binding modules that contain peptides that have been designed to bind to serum proteins or serum-exposed proteins such as HAS or IgG.

Unstructured Recombinant Polymers (URPs):

One aspect of the present invention is the design of unstructured recombinant polymers (URPs). The subject URPs are particularly useful for generating recombinant proteins of therapeutic and/or diagnostic value. The subject URPs exhibit one or more following features.

The subject URPs comprise amino acid sequences that typically share commonality with denatured peptide sequences under physiological conditions. URP sequences typically behave like denatured peptide sequences under physiological conditions. URP sequences lack well defined secondary and tertiary structures under physiological conditions. A variety of methods have been established in the art to ascertain the second and tertiary structures of a given polypeptide. For example, the secondary structure of a polypeptide can be determined by CD spectroscopy in the "far-UV" spectral region (190-250 nm). Alpha-helix, beta-sheet, and random coil structures each give rise to a characteristic shape and magnitude of CD spectra. Secondary structure can also be ascertained via certain computer programs or algorithms such as the Chou-Fasman algorithm (Chou, P. Y., et al. (1974) *Biochemistry*, 13: 222-45). For a given URP sequence, the algorithm can predict whether there exists some or no secondary structure at all. In general, URP sequences will have spectra that resemble denatured sequences due to their low degree of secondary and tertiary structure. Where desired, URP sequences can be designed to have predominantly denatured conformations under physiological conditions. URP sequences typically have a high degree of conformational flexibility under physiological conditions and they tend to have large hydrodynamic radii (Stokes' radius) compared to globularproteins of similar molecular weight. As used herein, physiological conditions refer to a set of conditions including temperature, salt concentration, pH that mimic those conditions of a living subject. A host of physioloigcally relevant conditions for use in in vitro assays have been established. Generally, a physiological buffer contains a physiological concentration of salt and at adjusted to a neutral pH ranging from about 6.5 to about 7.8, and preferably from about 7.0 to about 7.5. A variety of physiological buffers is listed in Sambrook et al. (1989) supra and hence is not detailed herein. Physiologically relevant temperature ranges from about 25° C. to about 38° C., and preferably from about 30° C. to about 37° C.

The subject URPs can be sequences with low immunogenicity. Low immunogenicity can be a direct result of the conformational flexibility of URP sequences. Many antibodies recognize so-called conformational epitopes in protein antigens. Conformational epitopes are formed by regions of the protein surface that are composed of multiple discontinuous amino acid sequences of the protein antigen. The precise folding of the protein brings these sequences into a well-defined special configuration that can be recognized by antibodies. Preferred URPs are designed to avoid formation of conformational epitopes. For example, of particular interest are URP sequences having a low tendency to adapt compactly folded conformations in aqueous solution. In particular, low immunogenicity can be achieved by choosing sequences that resist antigen processing in antigen presenting cells, choosing sequences that do not bind MHC well and/or by choosing sequences that are derived from human sequences.

The subject URPs can be sequences with a high degree of protease resistance. Protease resistance can also be a result of the conformational flexibility of URP sequences. Protease resistance can be designed by avoiding known protease recognition sites. Alternatively, protease resistant sequences can be selected by phage display or related techniques from random or semi-random sequence libraries. Where desired for special applications, such as slow release from a depot protein, serum protease cleavage sites can be built into an URP. Of particular interest are URP sequences with high stability (e.g., long serum half-life, less prone to cleavage by proteases present in bodily fluid) in blood.

The subject URP can also be characterized by the effect in that wherein upon incorporation of it into a protein, the protein exhibits a longer serum half-life and/or higher solubility as compared to the corresponding protein that is deficient in the URP. Methods of ascertaining serum half-life are known in the art (see e.g., Alvarez, P., et al. (2004) *J Biol Chem*, 279: 3375-81). One can readily determine whether the resulting protein has a longer serum half-life as compared to the unmodified protein by practicing any methods available in the art or exemplified herein.

The subject URP can be of any length necessary to effect (a) extension of serum half-life of a protein comprising the URP; (b) an increase in solubility of the resulting protein; (c) an increased resistance to protease; and/or (d) a reduced immunogenicity of the resulting protein that comprises the URP. Typically, the subject URP has about 30, 40, 50, 60, 70, 80, 90, 100, 150, 200, 300, 400 or more contiguous amino acids. When incorporated into a protein, the URP can be fragmented such that the resulting protein contains multiple URPs, or multiple fragments of URPs. Some or all of these individual URP sequences may be shorter that 40 amino acids as long as the combined length of all URP sequences in the resulting protein is at least 40 amino acids. Preferably, the resulting protein has a combined length of URP sequences exceeding 40, 50, 60, 70, 80, 90, 100, 150, 200 or more amino acids.

URPs may have an isoelectric point (pI) of 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5 or even 13.0.

In general, URP sequences are rich in hydrophilic amino acids and contain a low percentage of hydrophobic or aromatic amino acids. Suitable hydrophilic residues include but are not limited to glycine, serine, aspartate, glutamate, lysine, arginine, and threonine. Hydrophobic residues that are less favored in construction of URPs include tryptophan, phenylalanine, tyrosine, leucine, isoleucine, valine, and methionine. URP sequences can be rich in glycine but URP sequences can also be rich in the amino acids glutamate, aspartate, serine, threonine, alanine or proline. Thus the predominant amino acid may be G, E, D, S, T, A or P. The inclusion of proline residues tends to reduce sensitivity to proteolytic degradation.

The inclusion of hydrophilic residues typically increases URPs' solubility in water and aqueous media under physiological conditions. As a result of their amino acid composition, URP sequences have a low tendency to form aggregates in aqueous formulations and the fusion of URP sequences to other proteins or peptides tends to enhance their solubility and reduce their tendency to form aggregates, which is a separate mechanism to reduce immunogenicity.

URP sequences can be designed to avoid certain amino acids that confer undesirable properties to the protein. For instance, one can design URP sequences to contain few or none of the following amino acids: cysteine (to avoid disulfide formation and oxidation), methionine (to avoid oxidation), asparagine and glutamine (to avoid desamidation).

Glycine-rich URPs:

In one embodiment, the subject URP comprises a glycine rich sequence (GRS). For example, glycine can be present predominantly such that it is the most prevalent residues present in the sequence of interest. In another example, URP sequences can be designed such that glycine residues constitute at least about 30%, 35%, 40%, 45%, 50%, 55%, 60%, 65%, 70%, 75%, 80%, 85%, 90%, 95%, 100% of the total amino acids. URPs can also contain 100% glycines. In yet another example, the URPs contain at least 30% glycine and the total concentration of tryptophan, phenylalanine, tyrosine, valine, leucine, and isoleucine is less then 20%. In still another example, the URPs contain at least 40% glycine and the total concentration of tryptophan, phenylalanine, tyrosine, valine, leucine, and isoleucine is less then 10%. In still yet another example, the URPs contain at least about 50% glycine and the total concentration of tryptophan, phenylalanine, tyrosine, valine, leucine, and isoleucine is less then 5%.

The length of GRS can vary between about 5 amino acids and 200 amino acids or more. For example, the length of a single, contiguous GRS can contain 5, 10, 15, 20, 25, 30, 35, 40, 45, 50, 55, 60, 70, 80, 90, 100, 120, 140, 160, 180, 200, 240, 280, 320 or 400 or more amino acids. GRS may comprise glycine residues at both ends.

GRS can also have a significant content of other amino acids, for example Ser, Thr, Ala, or Pro. GRS can contain a significant fraction of negatively charged amino acids including but not limited to Asp and Glu. GRS can contain a significant fraction of positively charged amino acids including but not limited to Arg or Lys. Where desired, URPs can be designed to contain only a single type of amino acid (i.e., Gly or Glu), sometimes only a few types of amino acid, e.g., two to five types of amino acids (e.g., selected from G, E, D, S, T, A and P), in contrast to typical proteins and typical linkers which generally are composed of most of the twenty types of amino acids. URPs may contain negatively charged residues (Asp, Glu) in 30, 25, 20, 15, 12, 10, 9, 8, 7, 6, 5, 4, 3, 2, or 1 percent of the amino acids positions.

Typically, the subject GRS-containing URP has about 30, 40, 50, 60, 70, 80, 90, 100, or more contiguous amino acids. When incorporated into a protein, the URP can be fragmented such that the resulting protein contains multiple URPs, or multiple fragments of URPs. Some or all of these individual URP sequences may be shorter that 40 amino acids as long as the combined length of all URP sequences in the resulting protein is at least 30 amino acids. Preferably, the resulting protein has a combined length of URP sequences exceeding 40, 50, 60, 70, 80, 90, 100, or more amino acids.

The GRS-containing URPs are of particular interest due to, in part, the increased conformational freedom of glycine-containing peptides. Denatured peptides in solution have a high degree of conformational freedom. Most of that conformational freedom is lost upon binding of said peptides to a target like a receptor, an antibody, or a protease. This loss of entropy needs to be offset by the energy of interaction between the peptide and its target. The degree of conformational freedom of a denatured peptide is dependent on its amino acid sequences. Peptides containing many amino acids with small side chains tend to have more conformational freedom than peptides that are composed of amino acids with larger side chains Peptides containing the amino acid glycine have particularly large degrees of freedom. It has been estimated that glycine-containing peptide bonds have about 3.4 times more entropy in solution as compared to corresponding alanine-containing sequences (D'Aquino, J. A., et al. (1996) *Proteins,* 25: 143-56). This factor increases with the number of glycine residues in a sequence. As a result, such peptides tend to lose more entropy upon binding to targets, which reduces their overall ability to interact with other proteins as well as their ability to adopt defined three-dimensional structures. The large conformational flexibility of glycine-peptide bonds is also evident when analyzing Ramachandran plots of protein structures where glycine peptide bonds occupy areas that are rarely occupied by other peptide bonds (Venkatachalam, C M., et al. (1969) *Annu Rev Biochem,* 38: 45-82). Stites et al. studied a database of 12,320 residues from 61 nonhomologous, high resolution crystal structures to determine the phi, psi conformational preferences of each of the 20 amino acids. The observed distributions in the native state of proteins are assumed to also reflect the distributions found in the denatured state. The distributions were used to approximate the energy surface for each residue, allowing the calculation of relative conformational entropies for each residue relative to glycine. In the most extreme case, replacement of glycine by proline, conformational entropy changes will stabilize the native state relative to the denatured state by −0.82+/−0.08 kcal/mol at 20° C. (Stites, W. E., et al. (1995) *Proteins,* 22: 132). These observations confirm the special role of glycine among the 20 natural amino acids.

In designing the subject URPs, natural or non-natural sequences can be used. For example, a host of natural sequences containing high glycine content is provided in Table 1, Table 2, Table 3, and Table 4. One skilled in the art may adopt any one of the sequences as an URP, or modify the sequences to achieve the intended properties. Where immunogenicity to the host subject is of concern, it is preferable to design GRS-containing URRs based on glycine rich sequences derived from the host. Preferred GRS-containing URPs are sequences from human proteins or sequences that share substantial homology to the corresponding glycine rich sequences in the reference human proteins.

TABLE 1

Structural analysis of proteins that contain glycine rich sequences

| PDB file | Protein function | Glycine rich sequences | SEQ ID NO: |
|---|---|---|---|
| 1K3V | Porcine Parvovirus capsid | sggggggggggrgagg | 2 |
| 1FPV | Feline Panleukopenia Virus | tgsgngsggggggggsgg | 3 |
| 1IJS | CpV strain D, mutant A300d | tgsgngsggggggsgg | 4 |
| 1MVM | Mvm (strain I) virus | ggsgggsgggg | 5 |

TABLE 2

Open reading frames encoding GRS with 300 or more glycine residues

| Accession | Organism | Gly (%) | GRS length | Gene length | Predicted Function |
|---|---|---|---|---|---|
| NP_974499 | *Arabidopsis thaliana* | 64 | 509 | 579 | unknown |
| ZP_00458077 | *Burkholderia cenocopacia* | 66 | 373 | 518 | putative lipoprotein |
| XP_477841 | *Oryza sativa* | 74 | 371 | 422 | unknown |
| NP_910409 | *Oryza sativa* | 75 | 368 | 400 | putative cell-wall precursor |
| NP_610660 | *Drosophila melanogaster* | 66 | 322 | 610 | transposable element |

TABLE 3

Examples of human GRS

| Accession | Gly (%) | GRS length | Gene length | Hydro- phobics | Predicted Function |
|---|---|---|---|---|---|
| NP_000217 | 62 | 135 | 622 | yes | keratin 9 |
| NP_631961 | 61 | 73 | 592 | yes | TBP-associated factor 15 isoform 1 |
| NP_476429 | 65 | 70 | 629 | yes | keratin 3 |
| NP_000418 | 70 | 66 | 316 | yes | loricrin, cell envelope |
| NP_056932 | 60 | 66 | 638 | yes | cytokeratin 2 |

TABLE 4

Additional examples of human GRS

| Accession | Sequences | SEQ ID NO: | Number of amino acids |
|---|---|---|---|
| NP_006228 | GPGGGGGPGGGGGPGGGGPGGGGGGPGGGGGPGGG | 6 | 37 |
| NP_787059 | GAGGGGGGGGGGGGSGGGGGGGAGAGGAGAG | 7 | 33 |
| NP_009060 | GGGSGSGGAGGGSGGGSGSGGGGGAGGGGGG | 8 | 32 |
| NP_031393 | GDGGGAGGGGGGGSGGGSGGGGGGG | 9 | 27 |
| NP_005850 | GSGSGSGGGGGGGGGGGSGGGGG | 10 | 25 |

TABLE 4-continued

| | | | |
|---|---|---|---|
| NP_061856 | GGGRGGRGGGRGGGGRGGGRGGG | 11 | 22 |
| NP_787059 | GAGGGGGGGGGGGGGSGGGGGGGGGAGAGGAGAG | 12 | 33 |
| NP_009060 | GGGSGSGGAGGGSGGGSGSGGGGGGAGGGGGG | 13 | 32 |
| NP_031393 | GDGGGAGGGGGGGGSGGGGSGGGGGGG | 14 | 27 |
| NP_115818 | GSGGSGGSGGGPGPGPGGGGG | 15 | 21 |
| XP_376532 | GEGGGGGGEGGGAGGGSG | 16 | 18 |
| NP_065104 | GGGGGGGGDGGG | 17 | 12 |

GGGSGSGGAGGGSGGGSGSGGGGGGAGGGGGSSGGGSGTAGGHSG (SEQ ID NO: 18)

POU domain, class 4, transcription factor 1 [*Homo sapiens*]
GPGGGGGPGGGGPGGGGPGGGGGGPGGGGGPGGG (SEQ ID NO: 19)

YEATS domain containing 2 [*Homo sapiens*]
GGSGAGGGGGGGGGGSGSGGGGSTGGGGGTAGGG (SEQ ID NO: 20)

AT rich interactive domain 1B (SWI1-like) isoform 3;
BRG1-binding protein ELD/OSA1; Eld (eyelid)/Osa protein
[*Homo sapiens*]
GAGGGGGGGGGGGGGSGGGGGGGGAGAGGAGAG (SEQ ID NO: 21)

AT rich interactive domain 1B (SWI1-like) isoform 2;
BRG1-binding protein ELD/OSA1; Eld (eyelid)/Osa protein
[*Homo sapiens*]
GAGGGGGGGGGGGGGSGGGGGGGGAGAGGAGAG (SEQ ID NO: 22)

AT rich interactive domain 1B (SWI1-like) isoform 1;
BRG1-binding protein ELD/OSA1; Eld (eyelid)/Osa protein
[*Homo sapiens*]
GAGGGGGGGGGGGGGSGGGGGGGGAGAGGAGAG (SEQ ID NO: 23)

purine-rich element binding protein A; purine-rich single-
stranded DNA-binding protein alpha; transcriptional
activator protein PUR-alpha [*Homo sapiens*]
GHPGSGSGSGGGGGGGGGGGGGSGGGGGGAPGG (SEQ ID NO: 24)

regulatory factor X1; trans-acting regulatory factor 1;
enhancer factor C; MHC class II regulatory factor RFX
[*Homo sapiens*]
GGGGSGGGGGGGGGGGGGSGSTGGGGSGAG (SEQ ID NO: 25)

bromo domain-containing protein disrupted in leukemia
[*Homo sapiens*
GGRGRGGRGRGSRGRGGGGTRGRGRGRGGRG (SEQ ID NO: 26)

unknown protein [*Homo sapiens*]
GSGGSGGSGGGPGPGPGGGGGPSGSGSGPG (SEQ ID NO: 27)

PREDICTED: hypothetical protein XP_059256 [*Homo sapiens*]
GGGGGGGGGGGRGGGRGGGRGGGEGGG (SEQ ID NO: 28)

zinc finger protein 281; ZNP-99 transcription factor
[*Homo sapiens*]
GGGGTGSSGGSGSGGGGSGGGGGGGSSG (SEQ ID NO: 29)

RNA binding protein (autoantigenic, hnRNP-associated
with lethal yellow) short isoform; RNA-binding protein
(autoantigenic); RNA-binding protein (autoantigenic,
hnRNP-associated with lethal yellow) [*Homo sapiens*]
GDGGGAGGGGGGGSGGGGSGGGGGGG (SEQ ID NO: 30)

signal recognition particle 68 kDa [*Homo sapiens*]
GGGGGGGSGGGGGSGGGGSGGGRGAGG (SEQ ID NO: 31)

KIAA0265 protein [*Homo sapiens*]
GGGAAGAGGGGSGAGGGSGGSGGRGTG (SEQ ID NO: 32)

engrailed homolog 2; Engrailed-2 [*Homo sapiens*
GAGGGRGGGAGGEGGASGAEGGGGAGG (SEQ ID NO: 33)

TABLE 4-continued

RNA binding protein (autoantigenic, hnRNP-associated with lethal yellow) long isoform; RNA binding protein (autoantigenic); RNA-binding protein (autoantigenic, hnRNP-associated with lethal yellow) [Homo sapiens]
GDGGGAGGGGGGGSGGGGSGGGGGG (SEQ ID NO: 34)

androgen receptor; dihydrotestosterone receptor [Homo sapiens]
GGGGGGGGGGGGGGGGGGGGGGEAG (SEQ ID NO: 35)

homeo box D11; homeo box 4F; Hox-4.6, mouse, homolog of; homeobox protein Hox-D11 [Homo sapiens]
GGGGGGSAGGGSSGGGPGGGGGGAGG (SEQ ID NO: 36)

frizzled 8; frizzled (Drosophila) homolog 8 [Homo sapiens]
GGGGGPGGGGGGPGGGGPGGGG (SEQ ID NO: 37)

ocular development-associated gene [Homo sapiens]
GRGGAGSGGAGSGAAGGTGSSGGGG (SEQ ID NO: 38)

homeo box B3; homeo box 2G; homeobox protein Hox-B3 [Homo sapiens]
GGGGGGGGGGSGGSGGGGGGGGG (SEQ ID NO: 39)

chromosome 2 open reading frame 29 [Homo sapiens]
GGSGGGRGGASGPGSGSGGPGGPAG (SEQ ID NO: 40)

DKFZP564F0522 protein [Homo sapiens]
GGHHGDRGGGRGGRGGRGGRGGRAG (SEQ ID NO: 41)

PREDICTED: similar to Homeobox even-skipped homolog protein 2 (EVX-2) [Homo sapiens
GSRGGGGGGGGGGGGGGGAGAGGG (SEQ ID NO: 42)

ras homolog gene family, member U; Ryu GTPase; Wnt-1 responsive Cdc42 homolog; 2310026M05Rik; GTP-binding protein like 1; CDC42-like GTPase [Homo sapiens]
GGRGGRGPGEPGGRGRAGGAEGRG (SEQ ID NO: 43)

scratch 2 protein; transcriptional repressor scratch 2; scratch (drosophila homolog) 2, zinc finger protein [Homo sapiens]
GGGGGDAGGSGDAGGAGGRAGRAG (SEQ ID NO: 44)

nucleolar protein family A, member 1; GAR1 protein [Homo sapiens]
GGGRGGRGGGRGGGGRGGGRGGG (SEQ ID NO: 45)

keratin 1; Keratin-1; cytokeratin 1; hair alpha protein [Homo sapiens]
GGSGGGGGGSSGGRGSGGGSSGG (SEQ ID NO: 46)

hypothetical protein FLJ31413 [Homo sapiens]
GSGPGTGGGSGSGGGGGSGGG (SEQ ID NO: 47)

one cut domain, family member 2; onecut 2 [Homo sapiens]
GARGGGSGGGGGGGGGGGGPG (SEQ ID NO: 48)

POU domain, class 3, transcription factor 2 [Homo sapiens]
GGGGGGGGGGGGGGGGGGGGDG (SEQ ID NO: 49)

PREDICTED: similar to THO complex subunit 4 (Tho4) (RNA and export factor binding protein 1) (REF1-I) (Ally of AML-1 and LEF-1) (Aly/REF) [Homo sapiens]
GGTRGGTRGGTRGGDRGRGRGAG (SEQ ID NO: 50)

PREDICTED: similar to THO complex subunit 4 (Tho4) (RNA and export factor binding protein 1) (REF1-I) (Ally of AML-1 and LEF-1) (Aly/REF) [Homo sapiens]
GGTRGGTRGGTRGGDRGRGRGAG (SEQ ID NO: 51)

TABLE 4-continued

POU domain, class 3, transcription factor 3
[Homo sapiens]
GAGGGGGGGGGGGGGAGGGGGG (SEQ ID NO: 52)

nucleolar protein family A, member 1; GAR1 protein
[Homo sapiens]
GGGRGGRGGGRGGGRGGGRGGGRGGG (SEQ ID NO: 53)

fibrillarin; 34-kD nucleolar scleroderma antigen;
RNA, U3 small nucleolar interacting protein 1
[Homo sapiens]
GRGRGGGGGGGGGGGGRGGGG (SEQ ID NO: 54)

zinc finger protein 579 [Homo sapiens]
GRGRGRGRGRGRGRGRGRGGAG (SEQ ID NO: 55)

calpain, small subunit 1; calcium-activated neutral
proteinase; calpain, small polypeptide; calpain 4,
small subunit (30K);
calcium-dependent protease, small subunit
[Homo sapiens]
GAGGGGGGGGGGGGGGGGGGG (SEQ ID NO: 56)

keratin 9 [Homo sapiens]
GGGSGGGHSGGSGGGHSGGSGG (SEQ ID NO: 57)

forkhead box D1; forkhead-related activator 4;
Forkhead, drosophila, homolog-like 8; forkhead
(Drosophila)-like 8 [Homo sapiens]
GAGAGGGGGGGAGGGGSAGSG (SEQ ID NO: 58)

PREDICTED: similar to RIKEN cDNA C230094B15
[Homo sapiens]
GGPGTGSGGGGAGTGGGAGGPG (SEQ ID NO: 59)

GGGGGGGGGAGGAGGAGSAGGG (SEQ ID NO: 60)

cadherin 22 precursor; ortholog of rat PB-cadherin
[Homo sapiens]
GGDGGGSAGGGAGGGSGGGAG (SEQ ID NO: 61)

AT-binding transcription factor 1; AT motif-binding
factor 1 [Homo sapiens]
GGGGGGSGGGGGGGGGGGGG (SEQ ID NO: 62)

eomesodermin; t box, brain, 2; eomesodermin
(Xenopus laevis) homolog [Homo sapiens]
GPGAGAGSGAGGSSGGGGGPG (SEQ ID NO: 63)

phosphatidylinositol transfer protein, membrane-
associated 2; PYK2 N-terminal domain-interacting
receptor 3; retinal degeneration B alpha 2
(Drosophila) [Homo sapiens]
GGGGGGGGGGSSGGGGSSGG (SEQ ID NO: 64)

sperm associated antigen 8 isoform 2; sperm
membrane protein 1 [Homo sapiens]
GSGSGPGPGSGPGSGPGHGSG (SEQ ID NO: 65)

PREDICTED: RNA binding motif protein 27
[Homo sapiens]
GPGPGPGPGPGPGPGPGPGPG (SEQ ID NO: 66)

AP1 gamma subunit binding protein 1 isoform 1;
gamma-synergin; adaptor-related protein
complex 1 gamma subunit-binding protein 1
[Homo sapiens]
GAGSGGGGAAGAGAGSAGGGG (SEQ ID NO: 67)

AP1 gamma subunit binding protein 1 isoform 2;
gamma-synergin; adaptor-related protein
complex 1 gamma subunit-binding protein 1
[Homo sapiens]
GAGSGGGGAAGAGAGSAGGGG (SEQ ID NO: 68)

TABLE 4-continued ankyrin repeat and sterile alpha motif domain
containing 1; ankyrin repeat and SAM domain
containing 1 [Homo sapiens]
GGGGGGGSGGGGGGSGGGGGG (SEQ ID NO: 69)

methyl-CpG binding domain protein 2 isoform 1
[Homo sapiens]
GRGRGRGRGRGRGRGRGRGRG (SEQ ID NO: 70)

triple functional domain (PTPRF interacting)
[Homo sapiens]
GGGGGGGSGGSGGGGGSGGGG (SEQ ID NO: 71)

forkhead box D3 [Homo sapiens]
GGEEGGASGGGPGAGSGSAGG (SEQ ID NO: 72)

sperm associated antigen 8 isoform 1; sperm
membrane protein 1 [Homo sapiens]
GSGSGPGPGSGPGSGPGHGSG (SEQ ID NO: 73)

methyl-CpG binding domain protein 2 testis-
specific isoform [Homo sapiens]
GRGRGRGRGRGRGRGRGRGRG (SEQ ID NO: 74)

cell death regulator aven; programmed cell
death 12 [Homo sapiens]
GGGGGGGGDGGGRRGRGRGRG (SEQ ID NO: 75)

regulator of nonsense transcripts 1; delta
helicase; up-frameshift mutation 1 homolog
(S. cerevisiae); nonsense mRNA reducing
factor 1; yeast Upf1p homolog [Homo sapiens]
GGPGGPGGGGAGGPGGAGAG (SEQ ID NO: 76)

small conductance calcium-activated potassium
channel protein 2 isoform a; apamin-sensitive
small-conductance Ca2+-activated potassium
channel [Homo sapiens]
GTGGGGSTGGGGGGGSGHG (SEQ ID NO: 77)

SRY (sex determining region Y)-box 1; SRY-related
HMG-box gene 1 [Homo sapiens]
GPAGAGGGGGGGGGGGGGG (SEQ ID NO: 78)

transcription factor 20 isoform 2; stromelysin-1
platelet-derived growth factor-responsive element
binding protein; stromelysin 1 PDGF-responsive
element-binding protein; SPRE-binding protein;
nuclear factor SPBP [Homo sapiens]
GGTGGSSGSSGSGSGGGRRG (SEQ ID NO: 79)

transcription factor 20 isoform 1; stromelysin-1
platelet-derived growth factor-responsive element
binding protein; stromelysin 1 PDGF-responsive
element-binding protein; SPRE-binding protein;
nuclear factor SPBP [Homo sapiens]
GGTGGSSGSSGSGSGGGRRG (SEQ ID NO: 80)

Ras-interacting protein 1 [Homo sapiens]
GSGTGTTGSSGAGGPGTPGG (SEQ ID NO: 81)

BMP-2 inducible kinase isoform b [Homo sapiens]
GGSGGGAAGGGAGGAGAGAG (SEQ ID NO: 82)

BMP-2 inducible kinase isoform a [Homo sapiens]
GGSGGGAAGGGAGGAGAGAG (SEQ ID NO: 83)

forkhead box C1; forkhead-related activator 3;
Forkhead, drosophila, homolog-like 7; forkhead
(Drosophila)-like 7; iridogoniodysgenesis type
1 [Homo sapiens]
GSSGGGGGAGAAGGAGGAG (SEQ ID NO: 84)

splicing factor p54; arginine-rich 54 kDa nuclear
protein [Homo sapiens]
GPGPSGGPGGGGGGGGGGG (SEQ ID NO: 85)

TABLE 4-continued

```
v-maf musculoaponeurotic fibrosarcoma oncogene
homolog; Avian musculoaponeurotic fibrosarcoma
(MAF) protooncogene; v-maf musculoaponeurotic
fibrosarcoma (avian) oncogene homolog
[Homo sapiens]
GGGGGGGGGGGGGGAAGAGG (SEQ ID NO: 86)

small nuclear ribonucleoprotein D1 polypeptide
16 kDa; snRNP core protein D1; Sm-D autoantigen;
small nuclear ribonucleoprotein D1 polypeptide
(16 kD) [Homo sapiens]
GRGRGRGRGRGRGRGRGRGG (SEQ ID NO: 87)

hypothetical protein H41 [Homo sapiens]
GSAGGSSGAAGAAGGGAGAG (SEQ ID NO: 88)
```

URPs Containing Non-glycine Residues (NGR):

The sequences of non-glycine residues in these GRS can be selected to optimize the properties of URPs and hence the proteins that contain the desired URPs. For instance, one can optimize the sequences of URPs to enhance the selectivity of the resulting protein for a particular tissue, specific cell type or cell lineage. For example, one can incorporate protein sequences that are not ubiquitously expressed, but rather are differentially expressed in one or more of the body tissues including heart, liver, prostate, lung, kidney, bone marrow, blood, skin, bladder, brain, muscles, nerves, and selected tissues that are affected by diseases such as infectious diseases, autoimmune disease, renal, neronal, cardiac disorders and cancers. One can employ sequences representative of a specific developmental origin, such as those expressed in an embryo or an adult, during ectoderm, endoderm or mesoderm formation in a multi-cellular organism. One can also utilize sequence involved in a specific biological process, including but not limited to cell cycle regulation, cell differentiation, apoptosis, chemotaxis, cell motility and cytoskeletal rearrangement. One can also utilize other non-ubiquitously expressed protein sequences to direct the resulting protein to a specific subcellular locations: extracellular matrix, nucleus, cytoplasm, cytoskeleton, plasma and/or intracellular membranous structures which include but are not limited to coated pits, Golgi apparatus, endoplasmic reticulum, endosome, lysosome, and mitochondria.

A variety of these tissue-specific, cell-type specific, subcellular location specific sequences are known and available from numerous protein databases. Such selective URP sequences can be obtained by generating libraries of random or semi-random URP sequences, injecting them into animals or patients, and determining sequences with the desired tissue selectivity in tissue samples. Sequence determination can be performed by mass spectrometry. Using similar methods one can select URP sequences that facilitate oral, buccal, intestinal, nasal, thecal, peritoneal, pulmonary, rectal, or dermal uptake.

Of particular interest are URP sequences that contain regions that are relatively rich in the positively charged amino acids arginine or lysine which favor cellular uptake or transport through membranes. URP sequences can be designed to contain one or several protease-sensitive sequences. Such URP sequences can be cleaved once the product of the invention has reached its target location. This cleavage may trigger an increase in potency of the pharmaceutically active domain (pro-drug activation) or it may enhance binding of the cleavage product to a receptor. URP sequences can be designed to carry excess negative charges by introducing aspartic acid or glutamic acid residues. Of particular interest are URP that contain great than 5%, greater than 6%, 7%, 8%, 9%, 10%, 15%, 30% or more glutamic acid and less than 2% lysine or arginine. Such URPs carry an excess negative charge and as a result they have a tendency to adopt open conformations due to electrostatic repulsion between individual negative charges of the peptide. Such an excess negative charge leads to an effective increase in their hydrodynamic radius and as a result it can lead to reduced kidney clearance of such molecules. Thus, one can modulate the effective net charge and hydrodynamic radius of a URP sequence by controlling the frequency and distribution of negatively charged amino acids in the URP sequences. Most tissues and surfaces in a human or animal carry excess negative charges. By designing URP sequences to carry excess negative charges one can minimize non-specific interactions between the resulting protein comprising the URP and various surfaces such as blood vessels, healthy tissues, or various receptors.

URPs may have a repetitive amino acid sequence of the format (Motif)$_x$ in which a sequence motif forms a direct repeat (ie ABCABCABCABC) or an inverted repeat (ABC-CBAABCCBA) and the number of these repeats can be 2, 3, 4, 5, 6, 7, 8, 9, 10, 12, 14, 16, 18, 20, 22, 24, 26, 28, 30, 35, 40, 50 or more. URPs or the repeats inside URPs often contain only 1, 2, 3, 4, 5 or 6 different types of amino acids. URPs typically consist of repeats of human amino acid sequences that are 4, 5, 6, 7, 8, 9, 10, 11, 12, 13, 14, 15, 16, 17, 18, 19, 20, 22, 24, 26, 28, 30, 32, 34, 36 or more amino acids long, but URPs may also consist of non-human amino acid sequences that are 20, 22, 24, 26, 28, 30, 32, 34 36, 38 40, 42, 44, 46, 48, 50 amino acids long.

URPs Derived from Human Sequences:

URPs can be derived from human sequences. The human genome contains many subsequences that are rich in one particular amino acid. Of particular interest are such amino acid sequences that are rich in a hydrophilic amino acid like serine, threonine, glutamate, aspartate, or glycine. Of particular interest are such subsequences that contain few hydrophobic amino acids. Such subsequences are predicted to be unstructured and highly soluable in aqeuous solution. Such human subsequences can be modified to further improve their utility. FIG. 17 shows an exemplary human sequence that is rich in serine and that can be isolated as the subject URP. The exemplified dentin sialophosphoprotein contains a 670-amino acid subsequence in which 64% of the residues are serine and most other positions are hydrophilic amino acids such as aspartate, asparagines, and glutamate. The sequence is extremely repetitive and as a result it has a low information content. One can directly use subsequences of such a human protein. Where desired, one can modify the sequence in a way that preserves its overall character but which makes it more suitable for pharmaceutical applications. Examples of sequences that are related to dentin sialophosphoprotein are $(SSD)_n$ (SEQ ID NO: 89), $(SSDSSN)_n$ (SEQ ID NO: 90), $(SSE)_n$ (SEQ ID NO: 91), where n is between about 4 and 200.

The use of sequences from human proteins is particularly desirable in design of URPs with reduced immunogenicity in a human subject. A key step for eliciting an immune response to a foreign protein is the presentation of peptide fragments of said protein by MHC class II receptors. These MHCII-bound fragments can then be detected by T cell receptors, which triggers the proliferation of T helper cells and initiates an immune response. The elimination of T cell epitopes from pharmaceutical proteins has been recognized as a means to reduce the risk of eliciting an immune reaction (Stickler, M., et al. (2003) *J Immunol Methods*, 281: 95-108). MHCII receptors typically interact with an epitope having e.g., a 9-amino acid long region of the displayed peptides. Thus, one can reduce the risk of eliciting an immune response to a protein in patients if all or most of the possible 9mer subsequences of the protein can be found in human proteins and if so, these sequences and repeats of these sequences will not be recognized by the patient as foreign sequences. One can incorporate human sequences into the design of URP sequences by oligomerizing or concatenating human sequences that have suitable amino acid compositions. These can be direct repeats or inverted repeats or mixtures of different repeats. For instance one can oligomerize the sequences shown in table 2. Such oligomers have reduced risk of being immunogenic. However, the junction sequences between the monomer units can still contain T cell epitopes that can trigger an immune reaction, which is illustrated in FIG. 3. One can further reduce the risk of eliciting an immune response by designing URP sequences based on multiple overlapping human sequences. This approach is illustrated in FIG. 4. The URP sequence in FIG. 2 designed as an oligomer based on multiple human sequences such that each 9mer subsequences of the oligomer can be found in a human protein. In these designs, every 9-mer subsequence is a human sequence. An example of a URP sequence based on three human sequences is shown in FIG. 5. It is also possible to design URP sequences based on a single human sequences such that all possible 9mer subsequences in the oligomeric URP sequences occur in the same human protein. An example is shown in FIG. 6 based on the POU domain that is rich in glycine and proline. The repeating monomer in the URP sequence is only a fragment of the human protein and its flanking sequences is identical to the repeating unit as illustrated in FIG. 6. Non-oligomeric URP sequences can be designed based on human proteins as well. The primary conditions are that all 9mer sub-sequences can be found in human sequences. The amino acid composition of the sequences preferably contains few hydrophobic residues. Of particular interest are URP sequences that are designed based on human sequences and that contain a large fraction of glycine residues.

Utilizing this or similar scheme, one can design a class of URPs that comprise repeat sequences with low immunogenicity to the host of interest. Host of interest can be any animals, including vertebrates and invertebrates. Preferred hosts are mammals such as primates (e.g. chimpanzees and humans), cetaceans (e.g. whales and dolphins), chiropterans (e.g. bats), perrisodactyls (e.g. horses and rhinoceroses), rodents (e.g. rats), and certain kinds of insectivores such as shrews, moles and hedgehogs. Where human is selected as the host, the URPs typically contain multiple copies of the repeat sequences or units, wherein the majority of segments comprising about 6 to about 15 contiguous amino acids are present in one or more native human proteins. One can also design URPs in which the majority of segments comprising between about 9 to about 15 contiguous amino acids are found in one or more native human proteins. As used herein, majority of the segments refers to more than about 50%, preferably 60%, preferably 70%, preferably 80%, preferably 90%, preferably 100%. Where desired, each of the possible segments between about 6 to 15 amino acids, preferably between about 9 to 15 amino acids within the repeating units are present in one or more native human proteins. The URPs can comprise multiple repeating units or sequences, for example having 2, 3, 4, 5, 6, 7, 8, 9, 10, or more repeating units.

Design of URPs that are Substantially Free of Human T-cell Epitopes:

URP sequences can be designed to be substantially free of epitopes recognized by human T cells. For instance, one can synthesize a series of semi-random sequences with amino acid compositions that favor denatured, unstructured conformations and evaluate these sequences for the presence of human T cell epitopes and whether they are human sequences. Assays for human T cell epitopes have been described (Stickler, M., et al. (2003) *J Immunol Methods*, 281: 95-108). Of particular interest are peptide sequences that can be oligomerized without generating T cell epitopes or non-human sequences. This can be achieved by testing direct repeats of these sequences for the presence of T-cell epitopes and for the occurrence of 6 to 15-mer and in particular 9-mer subsequences that are not human. An alternative is to evaluate multiple peptide sequences that can be assembled into repeating units as described in the previous section for the assembly of human sequences. Another alternative is to design URP sequences that result in low scores using epitope prediction algorithms like TEPITOPE (Sturniolo, T., et al. (1999) *Nat Biotechnol*, 17: 555-61). Another approach to avoiding T-cell epitopes is to avoid amino acids that can serve as anchor residues during peptide display on MHC, such as M, I, L, V, F. Hydrophobic amino acids and positively charged amino acids can frequently serve as such anchor residues and minimizing their frequency in a URP sequences reduces the chance of generating T-cell epitopes and thus eliciting an immune reaction. The selected URPs generally contain subsequences that are found in at least one human protein, and have a lower content of hydrophobic amino acids.

URP sequences can be designed to optimize protein production. This can be achieved by avoiding or minimizing repetitiveness of the encoding DNA. URP sequences such as poly-glycine may have very desirable pharmaceutical properties but their manufacturing can be difficult due to the high GC-content of DNA sequences encoding for GRS and due to the presence of repeating DNA sequences that can lead to recombination.

As noted above, URP sequences can be designed to be highly repetitive at the amino acid level. As a result the URP sequences have very low information content and the risk of eliciting an immune reaction can be reduced.

Non-limiting examples of URPs containing repeating amino acids are: poly-glycine, poly-glutamic acid, poly-aspartic acid, poly-serine, poly-threonine, $(GX)_n$ (SEQ ID NO: 92) where G is glycine and X is serine, aspartic acid, glutamic acid, threonine, or proline and n is at least 20, $(GGX)_n$ (SEQ ID NO: 93) where X is serine, aspartic acid, glutamic acid, threonine, or proline and n is at least 13, $(GGGX)_n$ (SEQ ID NO: 94) where X is serine, aspartic acid, glutamic acid, threonine, or proline and n is at least 10, (GGGGX)$_n$ (SEQ ID NO: 95) where X is serine, aspartic acid, glutamic acid, threonine, or proline and n is at least 8, (G$_z$X)$_n$ (SEQ ID NO: 96) where X is serine, aspartic acid, glutamic acid, threonine, or proline, n is at least 15, and z is between 1 and 20.

The number of these repeats can be any number between 10 and 100. Products of the invention may contain URP sequences that are semi-random sequences. Examples are semi-random sequences containing at least 30, 40, 50, 60 or 70% glycine in which the glycines are well dispersed and in which the total concentration of tryptophan, phenylalanine, tyrosine, valine, leucine, and isoleucine is less then 70, 60, 50, 40, 30, 20, or 10% when combined. A preferred semi-random URP sequence contains at least 40% glycine and the total concentration of tryptophan, phenylalanine, tyrosine, valine, leucine, and isoleucine is less then 10%. A more preferred random URP sequence contains at least 50% glycine and the total concentration of tryptophan, phenylalanine, tyrosine, valine, leucine, and isoleucine is less then 5%. URP sequences can be designed by combining the sequences of two or more shorter URP sequences or fragments of URP sequences. Such a combination allows one to better modulate the pharmaceutical properties of the product containing the URP sequences and it allows one to reduce the repetitiveness of the DNA sequences encoding the URP sequences, which can improve expression and reduce recombination of the URP encoding sequences.

URP sequences can be designed and selected to possess several of the following desired properties: a) high genetic stability of the coding sequences in the production host, b) high level of expression, c) low (predicted/calculated) immunogenicity, d) high stability in presence of serum proteases and/or other tissue proteases, e) large hydrodynamic radius under physiological conditions. One exemplary approach to obtain URP sequences that meet multiple criteria is to construct a library of candidate sequences and to identify from the library the suitable subsequences. Libraries can comprise random and/or semi-random sequences. Of particular utility are codon libraries, which is a library of DNA molecules that contains multiple codons for the identical amino acid residue. Codon randomization can be applied to selected amino acid positions of a certain type or to most or all positions. True codon libraries encode only a single amino acid sequence, but they can easily be combined with amino acid libraries, which is a population of DNA molecules encoding a mixture of (related or unrelated) amino acids at the same residue position. Codon libraries allow the identification of genes that have relatively low repetitiveness at the DNA level but that encode highly repetitive amino acid sequences. This is useful because repetitive DNA sequences tend to recombine, leading to instability. One can also construct codon libraries that encode limited amino acid diversity. Such libraries allow introduction of a limited number of amino acids in some positions of the sequence while other positions allow for codon variation but all codons encode the same amino acid. One can synthesize partially random oligonucleotides by incorporating mixtures of nucleotides at the same position during oligonucleotide synthesis. Such partially random oligonucleotides can be fused by overlap PCR or ligation-based approaches. In particular, one can multimerize semi-random oligonucleotides that encode glycine-rich sequences. These oligonucleotides can differ in length and sequences and codon usage. As a result, one obtains a library of candidate URP sequences. Another method to generate libraries is to synthesize a starting sequence and subsequently subject said sequence to partial randomization. This can be done by cultivation of the gene encoding the URP sequences in a mutator strain or by amplification of the encoding gene under mutagenic conditions (Leung, D., et al. (1989) Technique, 1: 11-15). URP sequences with desirable properties can be identified from libraries using a variety of methods. Sequences that have a high degree of genetic stability can be enriched by cultivating the library in a production host. Sequences that are unstable will accumulate mutations, which can be identified by DNA sequencing. Variants of URP sequences that can be expressed at high level can be identified by screening or selection using multiple protocols known to someone skilled in the art. For instance one can cultivate multiple isolates from a library and compare expression levels. Expression levels can be measured by gel analysis, analytical chromatography, or various ELISA-based methods. The determination of expression levels of individual sequence variants can be facilitated by fusing the library of candidate URP sequences to sequence tags like myc-tag, His-tag, HA-tag. Another approach is to fuse the library to an enzyme or other reporter protein like green fluorescent protein. Of particular interest is the fusion of the library to a selectable marker like beta-lactamase or kanamycin-acyl transferase. One can use antibiotic selection to enrich for variants with high level of expression and good genetic stability. Variants with good protease resistance can be identified by screening for intact sequences after incubation with proteases. An effective way to identify protease-resistant URP sequences is bacterial phage display or related display methods. Multiple systems have been described where sequences that undergo rapid proteolysis can be enriched by phage display. These methods can be easily adopted to enrich for protease resistant sequences. For example, one can clone a library of candidate URP sequences between an affinity tag and the pIII protein of M13 phage. The library can then be exposed to proteases or protease-containing biological samples like blood or lysosomal preparations. Phage that contain protease-resistant sequences can be captured after protease treatment by binding to the affinity tag. Sequences that resist degradation by lysosomal preparations are of particular interest because lysosomal degradation is a key step during antigen presentation in dendritic and other antigen presenting cells. Phage display can be utilized to identify candidate URP sequences that do not bind to a particular immune serum in order to identify URP sequences with low immunogenicity. One can immunize animals with a candidate URP sequence or with a library of URP sequences to raise antibodies against the URP sequences in the library. The resulting serum can then be used for phage panning to remove or identify sequences that are recognized by antibodies in the resulting immune serum. Other methods like bacterial display, yeast display, ribosomal display can be utilized to identify variants of URP sequences with desirable properties. Another approach is the identification of URP sequences of interest by mass spectrometry. For instance, one can incubate a library of candidate URP sequences with a protease or biological sample of interest and identify sequences that resist degradation by mass spectrometry. In a similar approach one can identify URP sequences that facilitate oral uptake. One can feed a mixture of candidate URP sequences to animals or humans and identify variants with the highest transfer or uptake efficiency across some tissue barrier (ie dermal, etc) by mass spectrometry. In a similar way, one can identify URP sequences that favor other uptake mechanisms like pulmonary, intranasal, rectal, transdermal delivery. One can also identify URP sequences that favor cellular uptake or URP sequences that resist cellular uptake.

URP sequences can be designed by combining URP sequences or fragments of URP sequences that were designed by any of the methods described above. In addition, one can apply semi-random approaches to optimize sequences that were designed based on the rules described above. Of particular interest is codon optimization with the goal of improving expression of the enhanced proteins and to improve the genetic stability of the encoding gene in the production hosts. Codon optimization is of particular importance for URP sequences that are rich in glycine or that have very repetitive amino acid sequences. Codon optimization can be performed using computer programs (Gustafsson, C., et al. (2004) *Trends Biotechnol*, 22: 346-53), some of which minimize ribosomal pausing (Coda Genomics Inc.). When designing URP sequences one can consider a number of properties. One can minimize the repetitiveness in the encoding DNA sequences. In addition, one can avoid or minimize the use of codons that are rarely used by the production host (ie the AGG and AGA arginine codons and one Leucine codon in *E. coli*) DNA sequences that have a high level of glycine tend to have a high GC content that can lead to instability or low expression levels. Thus, when possible it is preferred to choose codons such that the GC-content of URP-encoding sequence is suitable for the production organism that will be used to manufacture the URP.

URP encoding genes can be made in one or more steps, either fully synthetically or by synthesis combined with enzymatic processes, such as restriction enzyme-mediated cloning, PCR and overlap extension. URP modules can be constructed such that the URP module-encoding gene has low repetitiveness while the encoded amino acid sequence has a high degree of repetitiveness. The approach is illustrated in FIG. 11. As a first step, one constructs a library of relatively short URP sequences. This can be a pure codon library such that each library member has the same amino acid sequence but many different coding sequences are possible. To facilitate the identification of well-expressing library members one can construct the library as fusion to a reporter protein. Examples of suitable reporter genes are green fluorescent protein, luciferace, alkaline phosphatase, beta-galactosidase. By screening one can identify short URP sequences that can be expressed in high concentration in the host organism of choice. Subsequently, one can generate a library of random URP dimers and repeat the screen for high level of expression. Dimerization can be performed by ligation, overlap extension or similar cloning techniques. This process of dimerization and subsequent screening can be repeated multiple times until the resulting URP sequence has reached the desired length. Optionally, one can sequence clones in the library to eliminate isolates that contain undesirable sequences. The initial library of short URP sequences can allow some variation in amino acid sequence. For instance one can randomize some codons such that a number of hydrophilic amino acids can occur in said position. During the process of iterative multimerization one can screen library members for other characteristics like solubility or protease resistance in addition to a screen for high-level expression. Instead of dimerizing URP sequences one can also generate longer multimers. This allows one to faster increase the length of URP modules.

Many URP sequences contain particular amino acids at high fraction. Such sequences can be difficult to produce by recombinant techniques as their coding genes can contain repetitive sequences that are subject to recombination. Furthermore, genes that contain particular codons at very high frequencies can limit expression as the respective loaded tRNAs in the production host become limiting. An example is the recombinant production of GRS. Glycine residues are encoded by 4 triplets, GGG, GGC, GGA, and GGT. As a result, genes encoding GRS tend to have high GC-content and tend to be particularly repetitive. An additional challenge can result from codon bias of the production host. In the case of *E. coli*, two glycine codons, GGA and GGG, are rarely used in highly expressed proteins. Thus codon optimization of the gene encoding URP sequences can be very desirable. One can optimize codon usage by employing computer programs that consider codon bias of the production host (Gustafsson, C., et al. (2004) *Trends Biotechnol*, 22: 346-53). As an alternative, one can construct codon libraries where all members of the library encode the same amino acid sequence but where codon usage is varied. Such libraries can be screened for highly expressing and genetically stable members which are particularly suitable for the large-scale production of URP-containing products.

Multivalent Unstructured Recombinant Proteins (MURPs):

As noted above, the subject URPs are particularly useful as modules for design of proteins of therapeutic value. Accordingly, the present invention provides proteins comprising one or more subject URPs. Such proteins are termed herein Multivalent Unstructured Recombinant Proteins (MURPs).

To construct MURPs, one or more URP sequences can be fused to the N-terminus or C-terminus of a protein or inserted in the middle of the protein, e.g., into loops of a protein or in between modules of the protein of interest, to give the resulting modified protein improved properties relative to the unmodified protein. The combined length of URP sequences that are attached to a protein can be 40, 50, 60, 70, 80, 90, 100, 150, 200 or more amino acids.

The subject MURPs exhibit one or more improved properties as detailed below.

Improved Half-life:

Adding a URP sequences to a pharmaceutically active protein can improve many properties of that protein. In particular, adding a long URP sequence can significantly increase the serum half-life of the protein. Such URPs typically contain amino acid sequences of at least about 40, 50, 60, 70, 80, 90, 100, 150, 200 or more amino acids.

The URPs can be fragmented such that the resulting protein contains multiple URPs, or multiple fragments of URPs. Some or all of these individual URP sequences may be shorter that 40 amino acids as long as the combined length of all URP sequences in the resulting protein is at least 30 amino acids. Preferably, the resulting protein has a combined length of URP sequences exceeding 40, 50, 60, 70, 80, 90, 100, 150, 200 or more amino acids. In one aspect, the fused URPS can increase the hydrodynamic radius of a protein and thus reduces its clearance from the blood by the kidney. The increase in the hydrodynamic radius of the resulting fusion protein relative to the unmodified protein can be detected by ultracentrifugation, size exclusion chromatography, or light scattering.

Improved Tissue Selectivity:

Increasing the hydrodynamic radius can also lead to reduced penetration into tissues, which can be exploited to minimize side effects of a pharmaceutically active protein. It is well documented that hydrophilic polymers have a tendency to accumulate selectively in tumor tissue which is caused by the enhanced permeability and retention (EPR) effect. The underlying cause of the EPR effect is the leaky nature of tumor vasculature (McDonald, D. M., et al. (2002)

Cancer Res, 62: 5381-5) and the lack of lymphatic drainage in tumor tissues. Therefore, the selectivity of pharmaceutically active proteins for tumor tissues can be enhanced by adding hydrophilic polymers. As such, the therapeutic index of a given pharmaceutically active protein can be increased via incorporating the subject URPS.

Protection from Degradation and Reduced Immunogenicity:

Adding URP sequences can significantly improve the protease resistance of a protein. URP sequences themselves can be designed to be protease resistant and by attaching them to a protein one can shield that protein from the access of degrading enzymes. URP sequences can be added to pharmaceutically active proteins with the goal of reducing undesirable interactions of the protein with other receptors or surfaces. To achieve this, it can be beneficial to add the URP sequences to the pharmaceutically active protein in proximity to the site of the protein that makes such undesirable contacts. In particular, one can add URP sequences to pharmaceutically active proteins with the goal of reducing their interactions with any component of the immune system to prevent an immune response against the product of the invention. Adding a URP sequence to a pharmaceutically active protein can reduce interaction with pre-existing antibodies or B-cell receptors. Furthermore, the addition of URP sequences can reduce the uptake and processing of the product of the invention by antigen presenting cells. Adding one or more URP sequence to a protein is a preferred way of reducing its immunogenicity as it will suppress an immune response in many species allowing one to predict the expected immunogenicity of a product in patients based on animal data. Such species independent testing of immunogenicity is not possible for approaches that are based on the identification and removal of human T cell epitopes or sequences comparison with human sequences.

Interruption of T Cell Epitopes:

URP sequences can be introduced into proteins in order to interrupt T cell epitopes. This is particularly useful for proteins that combine multiple separate functional modules. The formation of T cell epitopes requires that peptide fragments of a protein antigen bind to MHC. MHC molecules interact with a short segment of amino acids typically 9 contiguous residues of the presented peptides. The direct fusion of different binding modules in a protein molecule can lead to T cell epitopes that span two neighboring domains By separating the functional modules by URP modules prevents the generation of such module-spanning T cell epitopes as illustrated in FIG. 7. The insertion of URP sequences between functional modules can also interfere with proteolytic processing in antigen presenting cells, which will lead to an additional reduction of immunogenicity. Another approach to reduce the risk of immunogenicity is to disrupt T cell epitopes within functional modules of a product. In the case of microproteins, one approach is to have some of the intercysteine loops (those that are not involved in target binding) be glycine-rich. In microproteins, whose structure is due to a small number of cysteines, one could in fact replace most or all of the residues that are not involved in target binding with glycine, serine, glutamate, threonine, thus reducing the potential for immunogenicity while not affecting the affinity for the target. For instance, this can be carried out by performing a 'glycine-scan' of all residues, in which each residue is replaced by a glycine, then selecting the clones which retain target binding using phage display or screening, and then combining all of the glycine substitutions that are permitted. In general, functional modules have a much higher probability to contain T cell epitopes than URP modules. One can reduce the frequency of T cell epitopes in functional modules by replacing all or many non-critical amino acid residues with small hydrophilic residues like gly, ser, ala, glu, asp, asn, gln, thr. Positions in a functional module that allow replacement can be identified using a variety of random or structure based protein engineering approaches.

Improved Solubility:

Functional modules of a protein can have limited solubility. In particular, binding modules tend to carry hydrophobic residues on their surface, which can limit their solubility and can lead to aggregation. By spacing or flanking such functional modules with URP modules one can improve the overall solubility of the resulting product. This is in particular true for URP modules that carry a significant percentage of hydrophilic or charged residues. By separating functional modules with soluble URP modules one can reduce intramolecular interactions between these functional modules Improved pH Profile and Homogeneity of Product Charge:

URP sequences can be designed to carry an excess of negative or positive charges. As a result they confer an electrostatic field to any fusion partner which can be utilized to shift the pH profile of an enzyme or a binding interaction. Furthermore, the electrostatic field of a charged URP sequence can increase the homogeneity of pKa values of surface charges of a protein product, which leads to sharpened pH profiles of ligand interactions and to sharpened separations by isoelectric focusing or chromatofocusing.

Improved Purification Properties Due to Sharper Product pKa:

Each amino acid in solution by itself has a single, fixed pKa, which is the pH at which its functional groups are half protonated. In a typical protein you have many types of residues and due to proximity and protein breathing effects, they also change each other's effective pKa in variable ways. Because of this, at a wide range of pH conditions, typical proteins can adopt hundreds of differently ionized species, each with a different molecular weight and net charge, due to large numbers of combinations of charged and neutral amino acid residues. This is referred to as a broad ionization spectrum and makes the analysis (ie Mass Spec) and purification of such proteins more difficult.

PEG is uncharged and does not affect the ionization spectrum of the protein it is attached to, leaving it with a broad ionization spectrum. However, a URP with a high content of Gly and Glu in principle exist in only two states: neutral (—COOH) when the pH is below the pKa of Glutamate and negatively charged ($—COO^-$) when the pH is above the pKa of Glutamate URP modules can form a single, homogeneously ionizated type of molecule and can yield a single mass in mass spectrometry.

Where desired, MURPs can be expressed as a fusion with an URP having a single type of charge (Glu) distributed at constant spacing through the URP module. One may choose to incorporate 25-50 Glu residues per 20 kD of URP and all of these 25-50 residues would have very similar pKa.

In addition, adding 25-50 negative charges to a small protein like IFN, hGH or GCSF (with only 20 charged residues) will increase the charge homogeneity of the product and sharpen its isoelectric point, which will be very close to the pKa of free glutamate.

The increase in the homogeneity of the charge of the protein population has favorable processing properties, such as in ion exchange, isoelectric focusing, massspec, etc. compared to traditional PEGylation.

Improved Formulation and/or Delivery:

Addition of URP sequences to pharmaceutically active proteins can significantly simplify the formulation and/or the delivery of the resulting products. URP sequences can be designed to be very hydrophilic and as a result they improve the solubility of (for example) human proteins, which often contain hydrophobic patches that they use to bind to other human proteins. The formulation of such human proteins, like antibodies, can be quite challenging and often limits their concentration and delivery options. URPs can reduce product precipitation and aggregation and it allows one to use simpler formulations containing fewer ingredients, that are typically needed to stabilize a product in solution. The improved solubility of URP sequences-containing products allows to formulate these products at higher concentration and as a result one can reduce the injection volume for injectable products, which may enable home injection, which is limited to a very low injected volume. Addition of a URP sequence can also simplify the storage of the resulting formulated products. URP sequences can be added to pharmaceutically active proteins to facilitate their oral, pulmonary, rectal, or intranasal uptake. URP sequences can facilitate various modes of delivery because they allow higher product concentrations and improved product stability. Additional improvements can be achieved by designing URP sequences that facilitate membrane penetration.

Improved Production:

Adding URP sequences can have significant benefits for the production of the resulting product. Many recombinant products, especially native human proteins, have a tendency to form aggregates during production that can be difficult or impossible to dissolve and even when removed from the final product they may re-occur. These are usually due to hydrophobic patches by which these (native human) proteins contacted other (native human) proteins and mutating these residues is considered risky because of immunogenicity. However, URPs can increase the hydrophilicity of such proteins and enable their formulation without mutating the sequence of the human protein. URP sequences can facilitate the folding of a protein to reach its native state. Many pharmaceutically active proteins are produced by recombinant methods in a non-native aggregated state. These products need to be denatured and subsequently they are incubated under conditions that allow the proteins to fold into their native active state. A frequent side reaction during renaturation is the formation of aggregates. The fusion of URP sequences to a protein significantly reduces its tendency to form aggregates and thus it facilitates the folding of the pharmaceutically active component of the product. URP-containing products are much easier to prepare as compared to polymer-modified proteins. Chemical polymer-modification requires extra modification and purification steps after the active protein has been purified. In contrast, URP sequences can be manufactured using recombinant DNA methods together with the pharmaceutically active protein. The products of the invention are also significantly easier to characterize compared to polymer-modified products. Due to the recombinant production process one can obtain more homogeneous products with defined molecular characteristics. URP sequences can also facilitate the purification of a product. For instance URP sequences can include subsequences that can be captured by affinity chromatography. An example are sequences rich in histidine, which can be captured on resins with immobilized metals like nickel. URP sequences can also be designed to have an excess of negatively or positively charged amino acids. As a result they can significantly impact the net charge of a product, which can facilitate product purification by ion-exchange chromatography or preparative electrophoresis.

The subject MURPs can contain a variety of modules, including but not limited to binding modules, effector modules, multimerization modules, C-terminal modules, and N-terminal modules. FIG. 1 depicts an exemplary MURP having multiple modules. However, MURPs can also have relatively simple architectures that are illustrated in FIG. 2. MURPs can also contain fragmentation sites. These can be protease-sensitive sequences or chemically sensitive sequences that can be preferentially cleaved when the MURPs reach their target site.

Binding Module (BM):

The MURPs of the present invention may comprise one or more binding modules. Binding module (BM) refers to a peptide or protein sequence that can bind specifically to one or several targets, which may be one or more therapeutic targets or accessory targets, such as for cell-, tissue- or organ targeting. BMs can be linear or cyclic peptides, cysteine-constrained peptides, microproteins, scaffold proteins (e.g., fibronectin, ankyrins, crystalline, streptavidin, antibody fragments, domain antibodies), peptidic hormones, growth factors, cytokines, or any type of protein domain, human or non-human, natural or non-natural, and they may be based on a natural scaffold or not based on a natural scaffold, or based on combinations or they may be fragments of any of the above. Optionally, these BMs can be engineered by adding, removing or replacing one or multiple amino acids in order to enhance their binding properties, their stability, or other properties. Binding modules can be obtained from natural proteins, by design or by genetic package display, including phage display, cellular display, ribosomal display or other display methods. Binding modules may bind to the same copy of the same target, which results in avidity, or they may bind to different copies of the same target (which can result in avidity if these copies are somehow connected or linked, such as by a cell membrane), or they may bind to two unrelated targets (which yields avidity if these targets are somehow linked, such as by a membrane). Binding modules can be identified by screening or otherwise analyzing random libraries of peptides or proteins.

Particularly desirable binding modules are those that upon incorporation into a MURP, the MURP yield a desirable Tepitope score. The Tepitope score of a protein is the log of the Kd (dissociation constant, affinity, off-rate) of the binding of that protein to multiple of the most common human MHC alleles, as disclosed in Sturniolo, T. et al. (1999) Nature Biotechnology 17:555). The score ranges over at least 15 logs, from about 10, 9, 8, 7, 6, 5, 4, 3, 2, 1, 0, −1, −2, −3, −4, −5 ($10e^{10}$ Kd) to about −5. Preferred MURPs yield a score less than about −3.5.

Of particular interest are also binding modules comprising disulfide bonds formed by pairing two cysteine residues. In certain embodiments, the binding modules comprise polypeptides having high cysteine content or high disulfide density (HDD). Binding modules of the HDD family typically have 5-50% (5, 6, 7, 8, 9, 10, 12, 14, 16, 18, 20, 25, 30, 35, 40, 45 or 50%) cysteine residues and each domain typically contains at least two disulfides and optionally a co-factor such as calcium or another ion.

The presence of HDD scaffold allows these modules to be small but still adopt a relatively rigid structure. Rigidity is important to obtain high binding affinities, resistance to proteases and heat, including the proteases involved in antigen processing, and thus contributes to the low or non-immunogenicity of these modules. The disulfide framework folds the modules without the need for a large number of hydrophobic side chain interactions in the interior of most modules. The small size is also advantageous for fast tissue penetration and for alternative delivery such as oral, nasal, intestinal, pulmonary, blood-brain-barrier, etc. In addition, the small size also helps to reduce immunogenicity. A higher disulfide density is obtainable, either by increasing the number of disulfides or by using domains with the same number of disulfides but fewer amino acids. It is also desirable to decrease the number of non-cysteine fixed residues, so that a higher percentage of amino acids is available for target binding.

The cysteine-containing binding modules can adopt a wide range of disulfide bonding patterns (DBPs). For example, two-disulfide modules can have three different disulfide bonding patterns (DBPs), three-disulfide modules can have 15 different DBPs and four-disulfide modules have up to 105 different DBPs. Natural examples exist for all of the 2SS DBPs, the majority of the 3SS DBPs and less than half of the 4SS DBPs. In one aspect, the total number of disulfide bonding patterns can be calculated according to the formula: Error! Objects cannot be created from editing field codes, wherein n=the predicted number of disulfide bonds formed by the cysteine residues, and wherein Error! Objects cannot be created from editing field codes. represents the product of $(2i-1)$, where i is a positive integer ranging from 1 up to n.

Accordingly, in one embodiment, the modules used in MURPs are natural or non-naturally occurring cysteine (C)-containing scaffold exhibiting a binding specificity towards a target molecule, wherein the non-naturally occurring cysteine (C)-containing scaffold comprise intra-scaffold cysteines according to a pattern selected from the group of permutations represented by the formula Error! Objects cannot be created from editing field codes, wherein n equals to the predicted number of disulfide bonds formed by the cysteine residues, and wherein Error! Objects cannot be created from editing field codes.represents the product of $(2i-1)$, where i is a positive integer ranging from 1 up to n. In one aspect, the natural or non-naturally occurring cysteine (C)-containing module comprises a polypeptide having two disulfide bonds formed by pairing cysteines contained in the polypeptide according to a pattern selected from the group consisting of $C^{1-2, 3-4}$, $C^{1-3, 2-4}$, and $C^{1-4, 2-3}$, wherein the two numerical numbers linked by a hyphen indicate which two cysteines counting from N-terminus of the polypeptide are paired to form a disulfide bond. In another aspect, the natural or non-naturally occurring cysteine (C)-containing module comprises a polypeptide having three disulfide bonds formed by pairing intra-scaffold cysteines according to a pattern selected from the group consisting of $C^{1-2, 3-4, 5-6}$, $C^{1-2, 3-5, 4-6}$, $C^{1-2, 3-6, 4-5}$, $C^{1-3, 2-4, 5-6}$, $C^{1-3, 2-5, 4-6}$, $C^{1-3, 2-6, 4-5}$, $C^{1-4, 2-3, 5-6}$, $C^{1-4, 2-6, 3-5}$, $C^{1-5, 2-3, 4-6}$, $C^{1-5, 2-4, 3-6}$, $C^{1-5, 2-6, 3-4}$, $C^{1-6, 2-3, 4-5}$, and $C^{1-6, 2-5, 3-4}$, wherein the two numerical numbers linked by a hyphen indicate which two cysteines counting from N-terminus of the polypeptide are paired to form a disulfide bond. In yet another aspect, the natural or non-naturally occurring cysteine (C)-containing module comprises a polypeptide having at least four disulfide bonds formed by pairing cysteines contained in the polypeptide according to a pattern selected from the group of permutations defined by the formula above. In yet another aspect, the natural or non-naturally occurring cysteine (C)-containing module comprises a polypeptide having at least five, six, or more disulfide bonds formed by pairing intra-protein cysteines according to a pattern selected from the group of permutations represented by the formula above. Any of the cysteine-containing proteins or scaffolds disclosed in the co-pending application Ser. Nos. 11/528,927 and 11/528,950, which are incorporated herein by reference in their entiety] are candidate binding modules.

Figure 26:
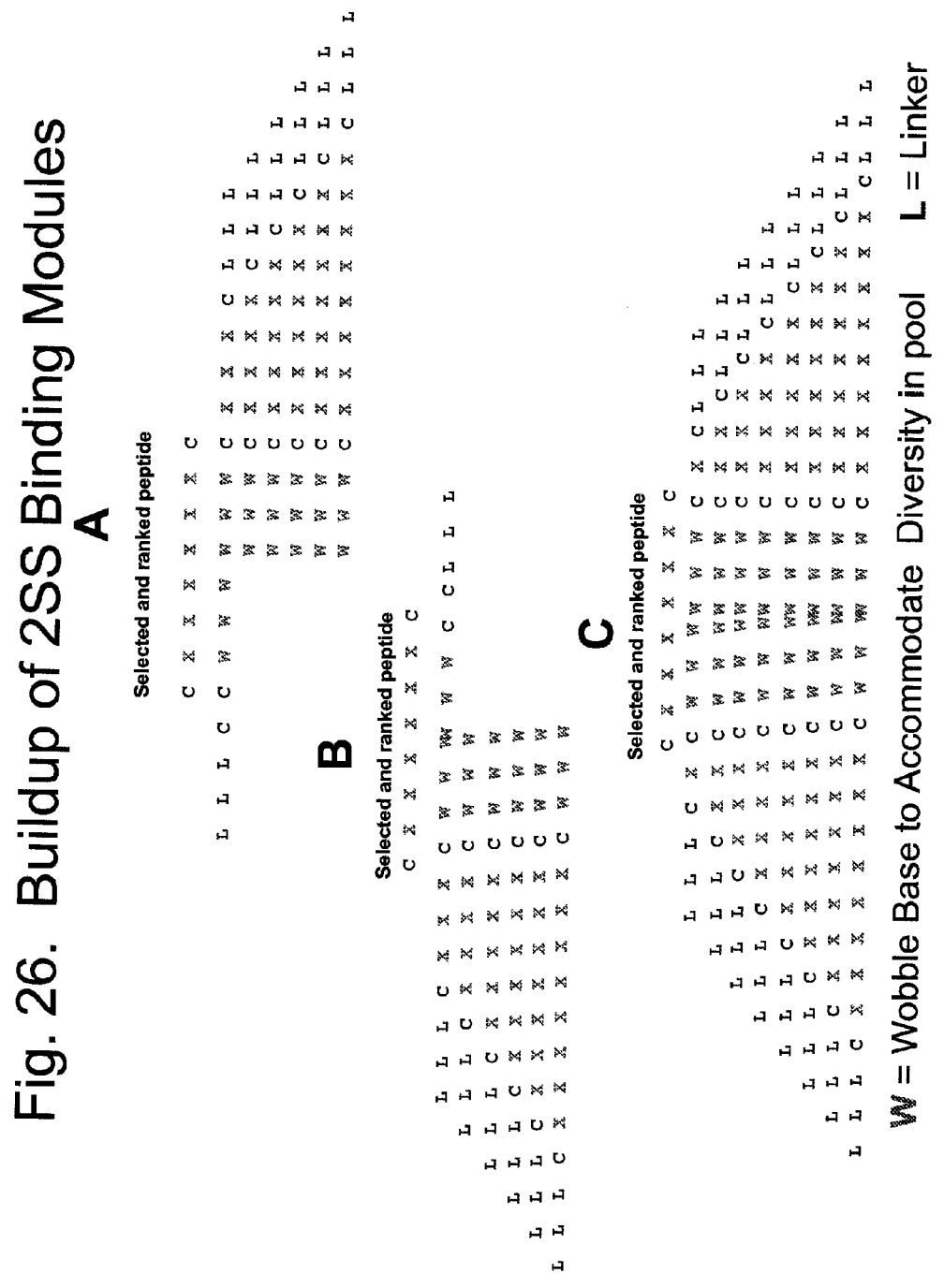

Binding modules can also be selected from libraries of cysteine-constrained cyclic peptides with 4, 5, 6, 7, 8, 9, 10, 11 and 12 randomized or partially randomized amino acids between the disulfide-bonded cystines (e.g., in a build-up manner), and in some cases additional randomized amino acids on the outside of the cystine pair can be constructed using a variety of methods. Library members with specificity for a target of interest can be identified using various methods including phage display, ribosomal display, yeast display and other methods known in the art. Such cyclic peptides can be utilized as binding modules in MURPs. In a preferred embodiment one can further engineer cysteine-constrained peptides to increase there binding affinity, proteolytic stability, and/or specificity using buildup approaches that lead to binding modules containing more than one disulfide bond. One particular buildup approach is illustrated in FIG. 25. It is based on the addition of a single cysteine plus multiple randomized residues on the N-terminal side of the previously selected cyclic peptide, as well as on the C-terminal side. One can generate libraries that have been designed as illustrated in FIG. 25. Binding modules with improved properties can be identified by phage display or similar methods. Such buildup libraries can contain between 1 and 12 random positions on the N-terminal as well as on the C-terminal side of a cyclic peptide. The distance between the cysteine residues in the newly added random flanks and the cysteine residues in the cyclic peptide can be varied between 1 and 12 residues. Such libraries will contain four cysteine residues per library member, with two cysteines resulting from the original cyclic peptide and two cysteine residues in the newly added flanks. This approach favors a 1-4 2-3 DBP or a change in DBP, breaking up the preexisting 1-2 disulfide (=2-3 in the 4-cysteine construct) to form a 1-2 3-4 or a 1-3 2-4 DBP. Such buildup approaches can be performed with clone-specific primers so that it leaves no fixed sequence between the library areas as shown in FIG. 25, or it can be performed with primers that use (and thus leave) a fixed sequence on both sides of the previously selected peptide and therefore these same primers can be used for any previously selected clone as illustrated in FIG. 26. The method illustrated in FIG. 26 can be applied to a collection of cyclic peptides with specificity for a target of interest. Both buildup approaches were shown to work for anti-VEGF affinity maturation by build-up. This approach can be repeated to generate binding modules with six or more cysteine residues.

Another buildup of a one-disulfide into a 2-disulfide sequence is illustrated in FIG. 27. It involves the dimerization of a previously selected pool of 1-disulfide peptides with itself so that the preselected peptide pool ends up in the N-terminal as well as in the C-terminal position. This approach favors the build up of 2-disulfide sequences that recognize two separate epitopes on a target.

Another buildup approach involves the addition of a (partially) randomized sequence of 6-15 residues containing two cysteines that are spaced 4, 5, 6, 7, 8, 9, or 10 amino acids apart, with optionally additional randomized positions outside the linked cysteines. This 2-cysteine random sequence is added on the N-terminal side of the previously selected peptide, or on the C-terminal side. This approach favors a 1-2 3-4 DBP, although other DBPs may be formed. This approach can be repeated to generate binding modules with six or more cysteine residues.

Binding modules can be constructed based on natural protein scaffolds. Such scaffolds can be identified by data base searching. Libraries that are based on natural scaffolds can be subjected to phage display panning followed by screening to identify sequences that specifically bind to a target of interest.

A wide selection of natural scaffolds is available for constructing the binding modules. The choice of a particular scaffold will depend on the intended target. Non-limiting examples of natural scaffolds include snake-toxin-like proteins such as snake venom toxins and extracellular domain of human cell surface receptors. Non-limiting examples of snake venom toxins are Erabutoxin B, gamma-Cardiotoxin, Faciculin, Muscarininc toxin, Erabutoxin A, Neurotoxin I, Cardiotoxin V4II (Toxin III), Cardiotoxin V, alpha-Cobratoxin, long Neurotoxin 1, FS2 toxin, Bungarotoxin, Bucandin, Cardiotoxin CTXI, Cardiotoxin CTX IIB, Cardiotoxin II, Cardiotoxin III, Cardiotoxin IV, Cobrotoxin 2, alpha-toxins, Neurotoxin II (cobrotoxin B), Toxin B (long neurotoxin), Candotoxin, Bucain. Non-limiting examples of extracellular domain of (human) cell surface receptors include CD59, Type II activin receptor, BMP receptor Ia ectodomain, TGF-beta type II receptor extracellular domain Other natural scaffolds include but are not limited to A-domains, EGF, Ca-EGF, TNF-R, Notch, DSL, Trefoil, PD, TSP1, TSP2, TSP3, Anato, Integrin Beta, Thyroglobulin, Defensin 1, Defensin 2, Cyclotide, SHKT, Disintegrins, Myotoxins, Gamma-Thioneins, Conotoxin, Mu-Conotoxin, Omega-Atracotoxins, Delta-Atracotoxins, as well as additional families disclosed in co-pending application Ser. Nos. 11/528,927 and 11/528,950, which are incorporated herein in their entirety.

A large variety of methods has been described that allow one to identify binding molecules in a large library of variants. One method is chemical synthesis. Library members can be synthesized on beads such that each bead carries a different peptide sequence. Beads that carry ligands with a desirable specificity can be identified using labeled binding partners. Another approach is the generation of sub-libraries of peptides which allows one to identify specific binding sequences in an iterative procedure (Pinilla, C., et al. (1992) *BioTechniques,* 13: 901-905). More commonly used are display methods where a library of variants is expressed on the surface of a phage, protein, or cell. These methods have in common, that that DNA or RNA coding for each variant in the library is physically linked to the ligand. This enables one to detect or retrieve the ligand of interest and then determine its peptide sequence by sequencing the attached DNA or RNA. Display methods allow one skilled in the art to enrich library members with desirable binding properties from large libraries of random variants. Frequently, variants with desirable binding properties can be identified from enriched libraries by screening individual isolates from an enriched library for desirable properties. Examples of display methods are fusion to lac repressor (Cull, M., et al. (1992) *Proc. Natl. Acad. Sci. USA,* 89: 1865-1869), cell surface display (Wittrup, K. D. (2001) *Curr Opin Biotechnol,* 12: 395-9). Of particular interest are methods were random peptides or proteins are linked to phage particles. Commonly used are M13 phage (Smith, G. P., et al. (1997) *Chem Rev,* 97: 391-410) and T7 phage (Danner, S., et al. (2001) *Proc Natl Acad Sci USA,* 98: 12954-9). There are multiple methods available to display peptides or proteins on M13 phage. In many cases, the library sequence is fused to the N-terminus of peptide pIII of the M13 phage. Phage typically carry 3-5 copies of this protein and thus phage in such a library will in most cases carry between 3-5 copies of a library member. This approach is referred to as multivalent display. An alternative is phagemid display where the library is encoded on a phagemid. Phage particles can be formed by infection of cells carrying a phagemid with a helper phage. (Lowman, H. B., et al. (1991) *Biochemistry,* 30: 10832-10838). This process typically leads to monovalent display. In some cases, monovalent display is preferred to obtain high affinity binders. In other cases multivalent display is preferred (O'Connell, D., et al. (2002) *J Mol Biol,* 321: 49-56).

A variety of methods have been described to enrich sequences with desirable characteristics by phage display. One can immobilize a target of interest by binding to immunotubes, microtiter plates, magnetic beads, or other surfaces. Subsequently, a phage library is contacted with the immobilized target, phage that lack a binding ligand are washed away, and phage carrying a target specific ligand can be eluted by a variety of conditions. Elution can be performed by low pH, high pH, urea or other conditions that tend to break protein-protein contacts. Bound phage can also be eluted by adding *E. coli* cells such that eluting phage can directly infect the added *E. coli* host. An interesting protocol is the elution with protease which can degrade the phage-bound ligand or the immobilized target. Proteases can also be utilized as tools to enrich protease resistant phage-bound ligands. For instance, one can incubate a library of phage-bound ligands with one or more (human or mouse) proteases prior to panning on the target of interest. This process degrades and removes protease-labile ligands from the library (Kristensen, P., et al. (1998) *Fold Des,* 3: 321-8). Phage display libraries of ligands can also be enriched for binding to complex biological samples. Examples are the panning on immobilized cell membrane fractions (Tur, M. K., et al. (2003) *Int J Mol Med,* 11: 523-7), or entire cells (Rasmussen, U. B., et al. (2002) *Cancer Gene Ther,* 9: 606-12; Kelly, K. A., et al. (2003) *Neoplasia,* 5: 437-44). In some cases one has to optimize the panning conditions to improve the enrichment of cell specific binders from phage libraries (Watters, J. M., et al. (1997) *Immunotechnology,* 3: 21-9). Phage panning can also be performed in live patients or animals. This approach is of particular interest for the identification of ligands that bind to vascular targets (Arap, W., et al. (2002) *Nat Med,* 8: 121-7).

A variety of cloning methods are available that allow one skilled in the art to generate libraries of DNA sequences that encode libraries of peptides. Random mixtures of nucleotides can be utilized to synthesize oligonucleotides that contain one or multiple random positions. This process allows one to control the number of random positions as well as the degree of randomization. In addition, one can obtain random or semi-random DNA sequences by partial digestion of DNA from biological samples. Random oligonucleotides can be used to construct libraries of plasmids or phage that are randomized in pre-defined locations. This can be done by PCR fusion as described in (de Kruif, J., et al. (1995) *J Mol Biol,* 248: 97-105). Other protocols are based on DNA ligation (Felici, F., et al. (1991) *J Mol Biol,* 222: 301-10; Kay, B. K., et al. (1993) *Gene,* 128: 59-65). Another commonly used approach is Kunkel mutagenesis where a mutagenized strand of a plasmid or phagemid is synthesized using single stranded cyclic DNA as template. See, Sidhu, S. S., et al. (2000) *Methods Enzymol,* 328: 333-63; Kunkel, T. A., et al. (1987) *Methods Enzymol,* 154: 367-82.

Kunkel mutagenesis uses templates containing randomly incorporated uracil bases which can be obtained from *E. coli* strains like CJ236. The uracil-containing template strand is preferentially degraded upon transformation into *E. coli* while the in vitro synthesized mutagenized strand is retained. As a result most transformed cells carry the mutagenized version of the phagemid or phage. A valuable approach to increase diversity in a library is to combine multiple sub-libraries. These sub-libraries can be generated by any of the methods described above and they can be based on the same or on different scaffolds.

A useful method to generate large phage libraries of short peptides has been recently described (Scholle, M. D., et al. (2005) Comb Chem High Throughput Screen, 8: 545-51). This method is related to the Kunkel approach but it does not require the generation of single stranded template DNA that contains random uracil bases. Instead, the method starts with a template phage that carries one or more mutations close to the area to be mutagenized and said mutation renders the phage non-infective. The method uses a mutagenic oligonucleotide that carries randomized codons in some positions and that correct the phage-inactivating mutation in the template. As a result, only mutagenized phage particles are infective after transformation and very few parent phage are contained in such libraries. This method can be further modified in several ways. For instance, one can utilize multiple mutagenic oligonucleotides to simultaneously mutagenize multiple discontiguous regions of a phage. We have taken this approach one step further by applying it to whole microproteins of >25, 30, 35, 40, 45, 50, 55 and 60 amino acids, instead of short peptides of <10, 15 or 20 amino acids, which poses an additional challenge. This approach now yields libraries of more than 10e10 transformants (up to 10e11) with a single transformation, so that a single library with a diversity of 10e12 is expected from 10 transformations.

Another variation of the Scholle method is to design the mutagenic oligonucleotide such that an amber stop codon in the template is converted into an ochre stop codon, and an ochre into an amber in the next cycle of mutagenesis. In this case the template phage and the mutagenized library members must be cultured in different suppressor strains of E. coli, alternating an ochre suppressor with amber suppressor strains. This allows one to perform successive rounds of mutagenesis of a phage by alternating between these two types of stop codons and two suppressor strains.

Yet another variation of the Scholle approach involves the use of megaprimers with a single stranded phage DNA template. The megaprimer is a long ssDNA that was generated from the library inserts of the selected pool of phage from the previous round of panning. The goal is to capture the full diversity of library inserts from the previous pool, which was mutagenized in one or more areas, and transfer it to a new library in such a way that an additional area can be mutagenized. The megaprimer process can be repeated for multiple cycles using the same template which contains a stop-codon in the gene of interest. The megaprimer is a ssDNA (optionally generated by PCR) which contains 1) 5' and 3' overlap areas of at least 15 bases for complementarity to the ssDNA template, and 2) one or more previously selected library areas (1, 2, 3, 4 or more) which were copied (optionally by PCR) from the pool of previously selected clones, and 3) a newly mutagenized library area that is to be selected in the next round of panning. The megaprimer is optionally prepared by 1) synthesizing one or more oligonucleotides encoding the newly synthesized library area and 2) by fusing this, optionally using overlap PCR, to a DNA fragment (optionally obtained by PCR) which contains any other library areas which were previously optimized Run-off or single stranded PCR of the combined (overlap) PCR product is used to generate the single stranded megaprimer that contains all of the previously optimized areas as well as the new library for an additional area that is to be optimized in the next panning experiment. This approach is expected to allow affinity maturation of proteins using multiple rapid cycles of library creation generating 10e11 to 10e12 diversity per cycle, each followed by panning.

A variety of methods can be applied to introduce sequence diversity into (previously selected or naïve) libraries of microproteins or to mutate individual microprotein clones with the goal of enhancing their binding or other properties like manufacturing, stability or immunogenicity. In principle, all the methods that can be used to generate libraries can also be used to introduce diversity into enriched (previously selected) libraries of microproteins. In particular, one can synthesize variants with desirable binding or other properties and design partially randomized oligonucleotides based on these sequences. This process allows one to control the positions and degree of randomization. One can deduce the utility of individual mutations in a protein from sequence data of multiple variants using a variety of computer algorithms (Jonsson, J., et al. (1993) Nucleic Acids Res, 21: 733-9; Amin, N., et al. (2004) Protein Eng Des Sel, 17: 787-93). Of particular interest for the re-mutagenesis of enriched libraries is DNA shuffling (Stemmer, W. P. C. (1994) Nature, 370: 389-391), which generates recombinants of individual sequences in an enriched library. Shuffling can be performed using a variety modified PCR conditions and templates may be partially degraded to enhance recombination. An alternative is the recombination at pre-defined positions using restriction enzyme-based cloning. Of particular interest are methods utilizing type IIS restriction enzymes that cleave DNA outside of their sequence recognition site (Collins, J., et al. (2001) J Biotechnol, 74: 317-38. Restriction enzymes that generate non-palindromic overhangs can be utilized to cleave plasmids or other DNA encoding variant mixtures in multiple locations and complete plasmids can be re-assembled by ligation (Berger, S. L., et al. (1993) Anal Biochem, 214: 571-9). Another method to introduce diversity is PCR-mutagenesis where DNA sequences encoding library members are subjected to PCR under mutagenic conditions. PCR conditions have been described that lead to mutations at relatively high mutation frequencies (Leung, D., et al. (1989) Technique, 1: 11-15). In addition, a polymerase with reduced fidelity can be employed (Vanhercke, T., et al. (2005) Anal Biochem, 339: 9-14). A method of particular interest is based on mutator strains (Irving, R. A., et al. (1996) Immunotechnology, 2: 127-43; Coia, G., et al. (1997) Gene, 201: 203-9). These are strains that carry defects in one or more DNA repair genes. Plasmids or phage or other DNA in these strains accumulate mutations during normal replication. One can propagate individual clones or enriched populations in mutator strains to introduce genetic diversity. Many of the methods described above can be utilized in an iterative process. One can apply multiple rounds of mutagenesis and screening or panning to entire genes, or to portions of a gene, or one can mutagenize different portions of a protein during each subsequent round (Yang, W. P., et al. (1995) J Mol Biol, 254: 392-403).

The libraries can be further treated to reduce artifacts. Known artifacts of phage panning include 1) no-specific binding based on hydrophobicity, and 2) multivalent binding to the target, either due to a) the pentavalency of the pIII phage protein, or b) due to the formation of disulfides between different microproteins, resulting in multimers, or c) due to high density coating of the target on a solid support and 3) context-dependent target binding, in which the context of the target or the context of the microproteins becomes critical to the binding or inhibition activity. Different treatment steps can be taken to minimize the magnitude of these problems. For example, such treatments are applied to the whole library, but some useful treatments that remove bad clones can only be applied to pools of soluble proteins or only to individual soluble proteins.

Libraries of cysteine-containing scaffolds are likely to contain free thiols, which can complicate directed evolution by cross-linking to other proteins. One approach is to remove the worst clones from the library by passing it over a free-thiol column, thus removing all clones that have one or more free sulfhydryls. Clones with free SH groups can also be reacted with biotin-SH reagents, enabling efficient removal of clones with reactive SH groups using Streptavidin columns Another approach is to not remove the free thiols, but to inactivate them by capping them with sulfhydryl-reactive chemicals such as iodoacetic acid. Of particular interest are bulky or hydrophilic sulfhydryl reagents that reduce the non-specific target binding or modified variants.

Examples of context dependence are all of the constant sequences, including pIII protein, linkers, peptide tags, biotin-streptavidin, Fc and other fusion proteins that contribute to the interaction. The typical approach for avoiding context-dependence involves switching the context as frequently as practical in order to avoid buildup. This may involve alternating between different display systems (ie M13 versus T7, or M13 versus Yeast), alternating the tags and linkers that are used, alternating the (solid) support used for immobilization (ie immobilization chemistry) and alternating the target proteins itself (different vendors, different fusion versions).

Library treatments can also be used to select for proteins with preferred qualities. One option is the treatment of libraries with proteases in order to remove unstable variants from the library. The proteases used are typically those that would be encountered in the application. For pulmonary delivery, one would use lung proteases, for example obtained by a pulmonary lavage. Similarly, one would obtain mixtures of proteases from serum, saliva, stomach, intestine, skin, nose, etc. However, it is also possible to use mixtures of single purified proteases. An extensive list of proteases is shown in [Appendix E]. The phage themselves are exceptionally resistant to most proteases and other harsh treatments.

For example, it is possible to select the library for the most stable structures, ie those with the strongest disulfide bonds, by exposing it to increasing concentrations of reducing agents (ie DTT or betamercaptoethanol), thus eliminating the least stable structures first. One would typically use reducing agent (ie DTT, BME, other) concentrations from 2.5 mM, to 5 mM, 10 mM, 20 mM, 30 mM, 40 mM, 50 mM, 60 mM, 70 mM, 80 mM, 90 mM or even 100 mM, depending on the desired stability.

It is also possible to select for clones that can be efficiently refolded in vitro, by reducing the entire display library with a high level of reducing agent, followed by gradually re-oxidizing the protein library to reform the disulfides, followed by the removal of clones with free SH groups, as described above. This process can be applied once or multiple times to eliminate clones that have low refolding efficiency in vitro.

One approach is to apply a genetic selection for protein expression level, folding and solubility as described by A. C. Fisher et al. (2006) Genetic selection for protein solubility enabled by the folding quality control feature of the twin-arginine translocation pathway. Protein Science (online).

After panning of display libraries (optional), one would like to avoid screening thousands of clones at the protein level for target binding, expression level and folding. An alternative is to clone the whole pool of selected inserts into a betalactamase fusion vector, which, when plated on betalactam, the authors demonstrated to be selective for well-expressed, fully disulfide bonded and soluble proteins.

Following M13 Phage display of protein libraries and panning on targets for one or more cycles, there are a variety of ways to proceed, including (1) screening of individual phage clones by phage ELISA, which measures the number of phage particles (using anti-M13 antibodies) that bind to an immobilized target; (2) transferring from M13 into T7 phage display libraries. The second approach is particularly useful in reducing the occurrence of false positives based on valency. Any single library format tends to favor clones that can form high-avidity contacts with the target. This is the reason that screening of soluble proteins is important, although this is a tedious solution. The multivalency achieved in T7 phage display is likely very different from that achieved in M13 display, and cycling between T7 and M13 can be an excellent approach to reducing the occurrence of false positives based on valency.

Filter lift is another methodology that can be with bacterial colonies grown at high density on large agar plates (10e2-10e5) Small amounts of some proteins are secreted into the media and end up bound to the filter membrane (nitrocellulose or nylon). The filters are then blocked in non-fat milk, 1% Casein hydrolysate or a 1% BSA solution and incubated with the target protein that has been labeled with a fluorescent dye or an indicator enzyme (directly or indirectly via antibodies or via biotin-streptavidin). The location of the colony is determined by overlaying the filter on the back of the plate and all of the positive colonies are selected and used for additional characterization. The advantage of filter lifts is that it can be made to be affinity-selective by reading the signal after washing for different periods of time. The signal of high affinity clones 'fades' slowly, whereas the signal of low affinity clones fades rapidly. Such affinity characterization typically requires a 3-point assay with a well-based assay and may provide better clone-to-clone comparability than well-based assays. Gridding of colonies into an array is useful since it minimizes differences due to colony size or location.

N-terminal Modules:

The subject MURPs can contain N-terminal modules (NM), which are particularly useful e.g., in facilitating production of the MURPs. The NM can be a single methionine residue when the products is expressed in the *E. coli* cytoplasm. A typical product format is an URP fused to a therapeutic protein, which is expressed in the bacterial cytoplasm so that the N-terminus is formyl-methionine. The formyl-methionine can either be permanent or temporary, if it is removed by biological or chemical processing.

The NM can also be a peptide sequence that has been engineered for proteolytic processing, which can be used to remove tags or to remove fusion proteins. The N-terminal module can be engineered to facilitate the purification of the MURP by including an affinity tag such as the Flag-, Myc-, HA- or His-tag. The N-terminal module can also include an affinity tag that can be used for the detection of the MURP. An NM can be engineered or selected for high-level expression of the MURP. It can also be engineered or selected to enhance the protease resistance of the resulting MURP. MURPs can be produced with an N-terminal module that facilitates expression and/or purification. This N-terminal module can be cleaved off during the production process with a protease, such that the final product does not contain an N-terminal module.

By optimizing the amino acid and codon choice of the N-terminal module one can increase recombinant production. The N-terminal module can also contain a processing site that can be cleaved by a specific protease like factor Xa, thrombin, or enterokinase, Tomato Etch Virus (TEV) protease. Processing sites can also be designed to be cleavable by chemical hydrolysis. An example is the amino acid sequence asp-pro that can be cleaved under acidic conditions. An N-terminal module can also be designed to facilitate the purification of a MURP. For example, N-terminal modules can be designed to contain multiple his residues which allow product capture by immobilized metal chromatography. N-terminal modules can contain peptide sequences that can be specifically captured or detected by antibodies. Examples are FLAG, HA, c-myc.

C-terminal Modules:

MURPs can contain a C-terminal module, which are particularly useful e.g., in facilitating production of the MURPs. For example, C-terminal module can comprise a cleavage site to effect proteolytic processing to remove sequences that are fused and hence increasing protein expression or facilitating purification. In particular, the C-terminal module can also contain a processing site that can be cleaved by a specific protease like factor Xa, thrombin, TEV protease or enterokinase Processing sites can also be designed to be cleavable by chemical hydrolysis. An example is the amino acid sequence asp-pro that can be cleaved under acidic conditions. The C-terminal module can be an affinity tag aimed at facilitating the purification of the MURP. For example, C-terminal modules can be designed to contain multiple his residues which allow product capture by immobilized metal chromatography. C-terminal modules can contain peptide sequences that can be specifically captured or detected by antibodies. Non-limiting examples of the tags include FLAG-, HA-, c-myc, or His-tag. C-terminal module can also be engineered or selected to enhance the protease resistance of the resulting MURP.

Where desired, the N-terminus of the protein can be linked to its own C-terminus. For example, linking these two modules can be carried out by creating an amino acid-like natural linkage (peptide bond) or by using an exogenous linking entity. Of particular interest are cyclotides, a family of small proteins in which this occurs naturally. Adopting a structural format like cyclotides is expected to provide additional stability against exo-proteases. Such intramolecular linkage typically works better at lower protein concentrations.

Effector Modules:

MURPs can comprise one or multiple effector modules (EMs), or none at all. Effector modules typically do not provide the targeting, but they provide an activity required for therapeutic effect, like cell-killing. EMs can be pharmaceutically active small molecules (ie toxic drugs), peptides or proteins. Non-limiting examples are cytokines, antibodies enzymes, growth factors, hormones, receptors, receptor agonists or antagonists, whether whole or a fragment or domain thereof. Effector modules can also comprise peptide sequences that carry chemically linked small molecule drugs, whether synthetic or natural. Optionally, these effector molecules can be linked to the effector module via chemical linkers, which may or may not be cleaved under selected conditions leading to a release of the toxic activity. EMs can also include radioisotopes and their chelates, as well as various labels for PET and MRI. Effector modules can also be toxic to a cell or a tissue. Of particular interest are MURPs that contain toxic effector modules and binding modules with specificity for a diseased tissue or disease cell type. Such MURPs can specifically accumulate in a diseased tissue or in diseased cells and the can exert their toxic action preferentially in the diseased cells or tissues. Listed below are exemplary effector modules.

Enzymes—Effector modules can be enzymes. Of particular interest are enzymes that degrade metabolites that are critical for cellular growth like carbohydrates or amino acids or lipids or co-factors. Other examples for effector modules with enzymatic activity are RNase, DNase, and phosphatase, asparaginase, histidinase, arginase, betalactamase Effector modules with enzymatic activity can be toxic when delivered to a tissue or cell. Of particular interest are MURPs that combine effector modules that are toxic and binding modules that bind specifically to a diseased tissue. Enzymes that convert an inactive prodrug into an active drug at the tumor site are also potential effector modules.

Drug—The subject MURP can contain an effector that is a drug. Where desired, sequences can be designed for the organ-selective delivery of drug molecules. An example is illustrated in FIG. 8. An URP sequence can be fused to a protein that preferentially binds to diseased tissue. The same URP sequence can contain one or more amino acid residues that can be modified for the attachment of drug molecules. Such a conjugate can bind to diseased tissue with high specificity and the attached drug molecules can result in local action while minimizing systemic drug exposure. The MURP can be designed to facilitate the release of drug molecules at the target size by introducing protease-sensitive sites that can be cleaved by native proteases at the site of desired action. A significant advantage of using URP sequences for the design of drug delivery constructs is that one can avoid undesirable interactions between the drug molecule and the targeting domain of the construct. Many drug molecules that can be conjugated to targeting domains have significant hydrophobicity and the resulting conjugates tend to aggregate. By adding hydrophilic URP sequences to such constructs one can improve the solubility of the resulting delivery constructs and as a consequence reduce the aggregation tendency. Furthermore, one can increase the number of drug molecules that can be fused to a targeting domain by adding long URP sequences. In addition, the use of URP sequences allows one to optimize the distance between the drug conjugation sites to facilitate complete conjugation. The list of suitable drugs includes but are not limited to chemotherapeutic agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; duocarmycin, maytansin, auristatin, elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, goserelin, doxorubicin, daunomycin, duocarmycin, vincristin, and vinblastin.

Other drugs that can be used as the effector modules include those that are useful for treating inflammatory conditions, cardiac diseases, infectious diseases, respiratory diseases, autoimmune diseases, neronal and muscular disorders, metabolic disorders, and cancers.

Additional drugs that can be used as the effectors in MURPs include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Other drugs that can be used as effector include agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease.

Radionuclides—MURPs can be designed for the tissue-targeted delivery of radionuclides as well as for imaging with radionuclides. URPs are ideal for imaging because the halflife can be optimized by changing the length of the URP. For most imaging applications a moderately long URP is likely to be preferred, providing a halflife of 5 minutes to a few hours, not days or weeks MURPs can be designed such that they only contain a single or a small defined number of amino groups that can be modified with chelating agents (such as DOTA) for radio isotopes such as technetium, indium, yttrium, (EXPAND). Alternative methods of conjugation are through reserved cysteine side chains. Such radionuclide-carrying MURPs can be employed for the treatment of tumors or other diseased tissues, as well as for imaging.

Many pharmaceutically active proteins or protein domains can used as effector models in MURPs. Examples are the following proteins as well as fragments of these proteins: cytokines, growth factors, enzymes,-receptors, microproteins, hormones, erythopoetin, adenosine deiminase, asparaginase, arginase, interferon, growth hormone, growth hormone releasing hormone, G-CSF, GM-CSM, insulin, hirudin, TNF-receptor, uricase, rasburicase, axokine, RNAse, DNAse, phosphatase, *pseudomonas* exotoxin, ricin, gelonin, desmoteplase, laronidase, thrombin, blood clotting enzyme, VEGF, protropin, somatropin, alteplase, interleukin, factor IIV, factor VIII, factor X, factor IX, dornase, glucocerebrosidase, follitropin, glucagon, thyrotropin, nesiritide, alteplase, teriparatide, agalsidase, laronidase, methioninase Protease-activated MURPs: To enhance the therapeutic index of an effector module, one can insert protease-labile sequences into URP sequences that are sensitive to proteases that are preferentially found in serum or in the target tissue to be treated by the MURP. This approach is illustrated in FIG. 9. Some designs allows one to construct proteins that are selectively activated when reaching a target tissue. Of particular interest are MURPs that are activated at a disease site. To facilitate such target-specific activation one can attach URP sequences in close proximity to the active site or receptor binding site of the effector module such that the resulting fusion protein has limited biological activity. Of particular interest is the activation of an effector module at a tumor site. Many tumor tissues express proteases in relatively high concentrations and sequences that are specifically cleaved by these tumor proteases can be inserted into URP sequences. For example, most prostate tumor tissues contain high concentrations of prostate specific antigen (PSA) which is a serine protease. Prodrugs consisting of a PSA-labile peptide conjugated to the cancer drug doxorubicin have shown selective activation in prostate tissue [DeFeo-Jones, D., et al. (2000) Nat Med, 6: 1248]. Of particular interest for disease-specific activation are proteins with cytostatic or cytotoxic activity like TNFalpha, and many cytokines and interleukins Another application is the selective activation of proteins at the site of inflammation or at site of virus or bacterial infection.

Methods of production—MURPs containing URP sequences can be produced using molecular biology approaches that are well know in the art. A variety of cloning vectors are available for various expression systems like mammalian cells, yeast, and microbes. Of particular interest as expression hosts are E. coli, S. cerevisiae, P. pastoris, and Chinese hamster ovary cells. Of particular interest are hosts that have been optimized to widen their codon usage. Of particular interest is a host that has been modified to enhance expression of GRS. That can be done by providing DNA that encodes glycine-specific tRNAs. In addition, one can engineer the host such that loading of glycine-specific tRNAs is enhanced. The DNA encoding the enhanced protein can be operationally linked to a promoter sequences. The DNA encoding the enhanced protein as well as the operationally linked promoter can be part of a plasmid vector, viral vector or it can be inserted into the chromosome of the host.

For production on can culture the host under conditions that facilitate the production of the enhanced protein. Of particular interest are conditions that improve the production of GRS.

The subject MURPs can adopt a variety of formats. For instance, the MURPs can contain URPs that are fused to pharmaceutically active proteins to produce slow-release products. Such products can be injected or implanted locally for instance into or under the skin of a patient. Due to its large hydrodynamic radius the URP sequences-containing product is slowly released from the injection or implantation site which leads to a reduction of the frequency of injection or implantation. The URP sequences can be designed to contain regions that bind to cell surfaces or tissue in order to prolong the local retention of the drug at the injection site. Of particular interest are URP-containing products that can be formulated as soluble compounds but form aggregates or precipitates upon injection. This aggregation or precipitation can be triggered by a change in pH between the formulated product and the pH at the injection site. Alternatives are URP-containing products that precipitate or form aggregates as a result of a change in redox conditions. Yet another approach is a URP-containing product that is stabilized in solution by addition of non-active solutes, but that precipitates or aggregates upon injection as a result of diffusion of the solubilizing solutes. Another approach is to design URP-containing products that contain one or multiple Lysine or Cysteine residues in their URP sequence and that can be cross-linked prior to injection.

Where desired, the MURP is monomeric (here meaning not-crosslinked) when manufactured and formulated and when injected, but after subcutaneous injection the protein starts to crosslink with itself or with native human proteins, forming a polymer under the skin from which active drug molecules are freed only very gradually. Such release can be by disulfide bond reduction or disulfide shuffling as illustrated in FIG. 18, or it can be mediated by proteolysis as shown in FIG. 19, releasing active fragments into the circulation. It is important that these active fragments are large enough to have a long halflife, because the longer their secretion halflife, the lower the dose of the released protein can be, allowing the use of a lower dose of product to be injected or a longer time between injections.

One approach that offers these advantages is disulfide-mediated crosslinking of proteins. For example, a protein drug would be manufactured with a cyclic peptide in it (one or more). This cyclic peptide may or may not be involved in binding to the target. This protein is manufactured with the cyclic peptide formed, ie in oxidized form, to simplify purification. However, the product is then reduced and formulated to keep the protein in reduced form. It is important that the cyclic peptide reduces at a low concentration of reducing agent, such as 0.25, 0.5, 1.0, 2.0, 4.0 or 8.0 mM Dithiothreitol or Betamercaptoethanol or cysteine or equivalent reducing agent, so that the cyclic peptide can be reduced without reducing other disulfide containing protein modules in the product. The use of FDA approved reducing agents is preferred, such as cysteine or glutathione. After subcutaneous injection, the low molecular weight reducing agent diffuses away rapidly or is neutralized by human proteins, exposing the drug to an oxidizing environment while it is still at a high molar concentration, which causes crosslinking of cysteines located on different protein chains, which leads to polymerization of the drug at the injection site. The longer the distance between the cysteines in the cyclic peptide, and the higher the concentration of the drug, the higher the degree of polymerization of the drug will be, since polymerization competes with cyclic peptide reformation. Over time, disulfide reduction and oxidation will cause disulfide reshuffling, which will lead to cyclic peptide reformation and monomerization and resolubilization of the drug. The release of the drug from the polymer can also occur via proteolysis which could be targeted and controlled or increased by building in cleavage sites for serum proteases. The crosslinking of the proteins could also be performed with a chemical protein-protein crosslinking agent, such as the ones listed herein. Ideally, this is an already FDA-approved agent, such as those used for vaccine conjugation or conjugation of chemicals to proteins.

Instead of using disulfides, one can also stabilize proteins against proteolytic degradation using a wide variety of crosslinking agents. Most of the agents below are sold by Pierce Chemicals under that same name and instructions for their use are available online (www.piercenet.com). The agents that result in the same chain-to-chain distance as obtained with disulfides are the most likely to be useful for this application. The short-linker agents such as DFDNB are the most promising. The interchain distance can be readily determined from the structures of the chemicals as shown in www.piercenet.com.

There are a large number of specific chemical products that work based on the following small number of basic reaction schemes, all of which are described in detail at www.piercenet.com. Examples of useful crosslinking agents are Imidoesters, active halogens, maleimide, pyridyl disulfide, NHS-ester. Homobifunctional crosslinking agents have two identical reactive groups and are often used in a one step chemical crosslinking procedure. Examples are BS3 (a non-cleavable water-soluble DSS analog), BSOCOES (base-reversible), DMA (Dimethyl adipimidate-2HCl), DMP (Dimethyl pimelimidate-2HCl), DMS (Dimethyl suberimidate-2HCl), DSG (5-carbon analog of DSS), DSP (Lomant's reagent), DSS (non-cleavable), DST (cleavable by oxidizing agents), DTBP (Dimethyl 3,3'-dithiobispropionimidate-2HCl), DTSSP, EGS, Sulfo-EGS, THPP, TSAT, DFDNB (1,5-Difluoro-2,4-dinitrobenzene) is especially useful for crosslinking between small spacial distances (Kornblatt, J. A. and Lake, D. F. (1980). Cross-linking of cytochrome oxidase subunits with difluorodinitrobenzene. Can J. Biochem. 58, 219-224).

Sulfhydryl-reactive homobifunctional crosslinking agents are homobifunctional protein crosslinkers that react with sulfhydryls are often based on maleimides, which react with —SH groups at pH 6.5-7.5, forming stable thioether linkages. BM[PEO]3 is an 8-atom polyether spacer that reduces potential for conjugate precipitation in sulfhydryl-to-sulfhydryl cross-linking applications. BM[PEO]4 is similar but with an 11-atom spacer. BMB is a non-cleavable crosslinker with a four-carbon spacer. BMDB makes a linkage that can be cleaved with periodate. BMH is a widely used homobifunctional sulfhydryl-reactive crosslinker. BMOE has an especially short linker DPDPB and DTME are cleavable crosslinkers. HVBS does not have the hydrolysis potential of meleimides. TMEA is another option. Hetero-bifunctional crosslinking agents have two different reactive groups. Examples are NHS-esters and amines/hydrazines via EDC activation, AEDP, ASBA (photoreactive, iodinatable), EDC (water-soluble carbodiimide). Amine-Sulfhydryl reactive bifunctional crosslinkers are AMAS, APDP, BMPS, EMCA, EMCS, GMBS, KMUA, LC-SMCC, LC-SPDP, MBS, SBAP, SIA (extra short), SIAB, SMCC, SMPB, SMPH, SMPT, SPDP, Sulfo-EMCS, Sulfo-GMBS, Sulfo-KMUS, Sulfo-LC-SMPT, Sulfo-LC-SPDP, Sulfo-MBS, Sulfo-SIAB, Sulfo-SMCC, Sulfo-SMPB. Amino-group reactive heterobifunctional crosslinking agents are ANB-NOS, MSA, NHS-ASA, SADP, SAED, SAND, SANPAH, SASD, SFAD, Sulfo-HSAB, Sulfo-NHS-LC-ASA, Sulfo-SADP, Sulfo-SANPAH, TFCS.

A different slow release format has the drug labeled with a His6 tag (SEQ ID NO: 97), which is mixed and co-injected with Nickel-Nitrilotriacetic acid-conjugated beads (Ni-NTA beads), a GMO version of the ones that are available from Qiagen. The drug would slowly teach off the beads, providing depot and slow release as illustrated in FIG. 20. The beads are optional and can be replaced by a crosslinked, polymeric Nickel-nitrilotriacetic acid that leads to assembly of an even larger polymer.

URP sequences can contain sequences that are known to form multimers like alpha2D [Hill, R., et al. (1998) J Am Chem Soc, 120: 1138-1145] that was utilized to dimerize an antibody fragment [Kubetzko, S., et al. (2005) Mol Pharmacol, 68: 1439-54]. Examples of a useful homo dimerization peptide is the sequence SKVILFE (SEQ ID NO: 98). An example of useful heterodimerization sequences are the peptide ARARAR (SEQ ID NO: 99) that can form dimers with the sequence DADADA (SEQ ID NO: 100) and related sequences. Multimerization can improve the biological function of a molecule by increasing its avidity and it can influence pharmacokinetic properties and tissue distribution of the resulting MURPs.

"Multimerization modules" are amino acid sequences that facilitate dimer or multimer formation of MURPs. Multimerization modules may bind to themselves to form dimers or multimers. Alternatively, multimerization modules can bind to other modules of the MURP. These can be leucine zippers or small peptides like Hydra head activator derivatives (SKVILF (SEQ ID NO: 101)-like) which forms antiparallel homopolymers, or peptides like RARARA (SEQ ID NO: 102) and DADADA (SEQ ID NO: 100), which form high affinity antiparallel heteropolymers. Using one, two or more copies of these peptides one can force the formation of protein dimers, linear multimers or branched multimers.

The affinity of the association can be tailored by changing the type, length and composition of the peptides. Some applications require peptides that form homodimers as illustrated in FIG. 21. Other applications require heterodimers. In some cases, once associated, the peptides can be locked into place by forming disulfide bonds between the two protein chains, typically on either side of the peptides. Multimerization modules are useful for linking two MURP molecules together (head to tail, head to head, or tail to tail) as illustrated in FIG. 21. The multimerization modules can be located on either the N- or C-terminus in order to form dimers. If the multimerization modules are present at both termini, long, linear multimers will be formed. If more than two multimerization modules are present per protein, branched polymeric networks can be formed. The concepts of multimerization and chemical conjugation can be combined leading to useful for halflife extension and depot formation, leading to slow release of active drug from the depot or injection site as illustrated in FIG. 23.

The subject MURPs can incorporate a genetic or universal URP. One approach is to express a URP containing a long URP module, which provides halflife and contains multiple (typically 4-10) lysines (or other sites) that allows site-specific conjugation of peptides (ie linear, cyclic, 2SS, 3 SS, etc) that bind to a specific target. The advantage of this approach is that the URP module is generic and can be conjugated with any target-specific peptide. Ideally the linkage of the target-specific peptide to the URP is a directed linkage, so that residues on the URP can only react with a residue on the target-specific peptide and exhaustive coupling can only produce a single species, which is a URP that is linked to a peptide at every lysine, for example. This complex behaves like a high-avidity multimer in it's binding properties but is simple to manufacture. This approach is illustrated in FIG. 24.

The subject MURPs can also incorporate URPs to effect delivery across tissue barriers. URPs can be engineered to enhance delivery across the dermal, oral, buccal, intestinal, nasal, blood-brain, pulmonary, thecal, peritoneal, rectal, vaginal or many other tissue barriers.

One of the key obstacles to oral protein delivery is the sensitivity of most proteins to proteases in the digestive system. Conjugation to URP sequences can improve protease resistance of pharmaceutically active proteins and thus facilitate their uptake. It has been shown that protein uptake in the digestive system can be improved by adding molecular carriers. The main role of these carriers is an improvement of membrane permeability [Stoll, B. R., et al. (2000) J Control Release, 64: 217-28]. Thus one can include sequences into URP sequences that improve membrane permeability. Many sequences that improve membrane permeability are know and examples are sequences rich in arginine [Takenobu, T., et al. (2002) Mol Cancer Ther, 1: 1043-9]. Thus one can design URP sequences that improve cellular or oral uptake of proteins by combining two functions, a reduction in proteolytic degradation of the protein of interest as well as an increase in membrane permeability of the fusion product. Optional, on can add a sequence to the URP sequence that is sensitive to a protease that is preferentially located at in the target tissue for the drug of interest but is stable to proteases in the digestive tract. Examples of such URP sequences are sequences that contain long regions of GRS as well as sequences that are rich in basic amino acids in particular arginine and facilitate membrane transfer. URP can be utilized in a similar way to improve protein uptake via intranasal, intrapulmonary, or other routes of delivery.

Specific Product Examples:

DR4/DR5 agonist—DR4 and DR5 are death receptors that are expressed on many tumor cells. These receptors can be triggered by trimerization which leads to cell death and tumor regression. Binding domains with specificity for DR4 or DR5 can be obtained by phage panning or other display methods. These DR4 or DR5-specific binding domains can be multimerized using URP modules as linkers as illustrated in FIG. 12. Of particular interest are MURPs that contain three or more binding modules with specificity for DR4 or DR5 or both. As illustrated in FIG. 12, MURPs can contain additional binding modules with specificity for tumor antigens that are overexpressed in tumor tissues. This allows one to construct MURPs that specifically accumulate in tumor tissue and trigger cell death. MURPs can contain modules that bind either DR4 or DR5. Of particular interest are MURPs that contain binding modules that bind both DR4 and DR5.

Tumor-targeted Interleukin 2—Interleukin 2 (IL2) is a cytokine that can enhance the immune response to tumor tissue. However, systemic IL2 therapy is characterized by significant side effects. MURPs can be constructed that combine binding domains with specificity for tumor antigens and IL2 as effector module as illustrated in FIG. 13. Such MURP can selectively accumulate in tumor tissue and thus elicit a tumor-selective immune response while minimizing the systemic side effects of cytokine therapy. Such MURPs can target a variety of tumor antigens like EpCAM, Her2, CEA, EGFR, Thomsen Friedenreich antigen. Of particular utility are MURPs that bind to tumor antigens that show slow internalization Similar MURPs can be designed using other cytokines or tumor necrosis factor-alfa as effector modules.

Tumor-selective asparaginase—Asparaginase is used to treat patients with acute leukemia Both asparaginase from *E. coli* and asparaginase from *Erwinia* are used for treatment. Both enzymes can lead to immunogenicity and hypersensitive reactions. Oncaspar is PEGylated version of asparaginase that has reduced immunogenicity. However, the protein is difficult to manufacture and administered as a mixture of isomers. Adding URP sequences to termini and/or to internal loops allows the direct recombinant manufacture of an asparaginase variant that is homogeneous and has low immunogenicity. Various URP sequences and attachment sites can be compared to determine the optimum position for URP sequence attachment. Several other enzymes can degrade amino acids have reported antitumor activity. Examples are arginase, methioninase, phenylalanine ammonia lyase, and tryptophanase Of particular interest is the phenylalanine ammonia lyase of *streptomyces maritimus*, which has a high specific activity and does not require a co-factor [Calabrese, J. C., et al. (2004) *Biochemistry,* 43: 11403-16]. Most of these enzymes are of bacterial or other non-human origin and are likely to elicit immune reactions. The immunogenicity of these enzymes can be reduced by adding one or more URP sequences. In addition, the therapeutic index and PK properties of these enzymes can be improved by increasing their hydrodynamic radius as a result of URP sequences attachment.

The subject MURPs can be designed to target any cellular proteins. A non-limiting list is provided below.

VEGF, VEGF-R1, VEGF-R2, VEGF-R3, Her-1, Her-2, Her-3, EGF-1, EGF-2, EGF-3, Alpha3, cMet, ICOS, CD40L, LFA-1, c-Met, ICOS, LFA-1, IL-6, B7.1, B7.2, OX40, IL-1b, TACI, IgE, BAFF or BLys, TPO-R, CD19, CD20, CD22, CD33, CD28, IL-1-R1, TNFα, TRAIL-R1, Complement Receptor 1, FGFa, Osteopontin, Vitronectin, Ephrin A1-A5, Ephrin B1-B3, alpha-2-macroglobulin, CCL1, CCL2, CCL3, CCL4, CCL5, CCL6, CCL7, CXCL8, CXCL9, CXCL10, CXCL11, CXCL12, CCL13, CCL14, CCL15, CXCL16, CCL16, CCL17, CCL18, CCL19, CCL20, CCL21, CCL22, PDGF, TGFb, GMCSF, SCF, p40 (IL12/IL23), IL1b, IL1a, IL1ra, IL2, IL3, IL4, IL5, IL6, IL8, IL10, IL12, IL15, IL23, Fas, FasL, Flt3 ligand, 41BB, ACE, ACE-2, KGF, FGF-7, SCF, Netrin1,2, IFNa,b,g, Caspase2, 3,7,8,10, ADAM S1,S5,8,9,15, TS1,TS5; Adiponectin, ALCAM, ALK-1, APRIL, Annexin V, Angiogenin, Amphiregulin, Angiopoietin1,2,4, B7-1/CD80, B7-2/CD86, B7-H1, B7-H2, B7-H3, Bcl-2, BACE-1, BAK, BCAM, BDNF, bNGF, bECGF, BMP2,3,4,5,6,7,8; CRP, Cadherin6, 8,11; Cathepsin A,B,C,D,E,L,S,V,X; CD11a/LFA-1, LFA-3, GP2b3a, GH receptor, RSV F protein, IL-23 (p40, p19), IL-12, CD80, CD86, CD28, CTLA-4, α4β1, α4β7, TNF/Lymphotoxin, IgE, CD3, CD20, IL-6, IL-6R, BLYS/BAFF, IL-2R, HER2, EGFR, CD33, CD52, Digoxin, Rho (D), Varicella, Hepatitis, CMV, Tetanus, Vaccinia, Antivenom, Botulinum, Trail-R1, Trail-R2, cMet, TNF-R family, such as LA NGF-R, CD27, CD30, CD40, CD95, Lymphotoxin a/b receptor, Ws1-1, TL1A/TNFSF15, BAFF, BAFF-R/TNFRSF13C, TRAIL R2/TNFRSF10B, TRAIL R2/TNFRSF10B, Fas/TNFRSF6 CD27/TNFRSF7, DR3/TNFRSF25, HVEM/TNFRSF14, TROY/TNFRSF19, CD40 Ligand/TNFSF5, BCMA/TNFRSF17, CD30/TNFRSF8, LIGHT/TNFSF14, 4-1BB/TNFRSF9, CD40/TNFRSF5, GITR/TNFRSF18, Osteoprotegerin/TNFRSF11B, RANK/TNFRSF11A, TRAIL R3/TNFRSF10C, TRAIL/TNFSF10, TRANCE/RANK L/TNFSF11, 4-1BB Ligand/TNFSF9, TWEAK/TNFSF12, CD40 Ligand/TNFSF5, Fas Ligand/TNFSF6, RELT/TNFRSF19L, APRIL/TNFSF13, DcR3/TNFRSF6B, TNF RI/TNFRSF1A, TRAIL R1/TNFRSF10A, TRAIL R4/TNFRSF10D, CD30 Ligand/TNFSF8, GITR Ligand/TNFSF18, TNFSF18, TACI/TNFRSF13B, NGF R/TNFRSF16, OX40 Ligand/TNFSF4, TRAIL R2/TNFRSF10B, TRAIL R3/TNFRSF10C, TWEAK R/TNFRSF12, BAFF/BLyS/TNFSF13, DR6/TNFRSF21, TNF-alpha/TNFSF1A, Pro-TNF-alpha/TNFSF1A, Lymphotoxin beta R/TNFRSF3, Lymphotoxin beta R (LTbR)/Fc Chimera, TNF RI/TNFRSF1A, TNF-beta/TNFSF1B, PGRP-S, TNF RI/TNFRSF1A, TNF RII/TNFRSF1B, EDA-A2, TNF-alpha/TNFSF1A, EDAR, XEDAR, TNF RI/TNFRSF1A.

Of particular interest are human target proteins that are commercially available in purified form. Examples are: 4EBP1, 14-3-3 zeta, 53BP1, 2B4/SLAMF4, CCL21/6Ckine, 4-1BB/TNFRSF9, 8D6A, 4-1BB Ligand/TNFSF9, 8-oxo-dG, 4-Amino-1,8-naphthalimide, A2B5, Aminopeptidase LRAP/ERAP2, A33, Aminopeptidase N/ANPEP, Aag, Aminopeptidase P2/XPNPEP2, ABCG2, Aminopeptidase P1/XPNPEP1, ACE, Aminopeptidase PILS/ARTS1, ACE-2, Amnionless, Actin, Amphiregulin, beta-Actin, AMPK alpha 1/2, Activin A, AMPK alpha 1, Activin AB, AMPK alpha 2, Activin B, AMPK beta 1, Activin C, AMPK beta 2, Activin RIA/ALK-2, Androgen R/NR3C4, Activin RIB/ALK-4, Angiogenin, Activin RIIA, Angiopoietin-1, Activin RIIB, Angiopoietin-2, ADAMS, Angiopoietin-3, ADAM9, Angiopoietin-4, ADAM10, Angiopoietin-like 1, ADAM12, Angiopoietin-like 2, ADAM15, Angiopoietin-like 3, TACE/ADAM17, Angiopoietin-like 4, ADAM19, Angiopoietin-like 7/CDT6, ADAM33, Angiostatin, ADAMTS4, Annexin A1/Annexin I, ADAMTS5, Annexin A7, ADAMTS1, Annexin A10, ADAMTSL-1/Punctin, Annexin V, Adiponectin/Acrp30, ANP, AEBSF, AP Site, Aggrecan, APAF-1, Agrin, APC, AgRP, APE, AGTR-2, APJ, AIF, APLP-1, Akt, APLP-2, Akt1, Apolipoprotein AI, Akt2, Apolipoprotein B, Akt3, APP, Serum Albumin, APRIL/TNFSF13, ALCAM, ARC, ALK-1, Artemin, ALK-7, Arylsulfatase A/ARSA, Alkaline Phosphatase, ASAH2/N-acylsphingosine Amidohydrolase-2, alpha 2u-Globulin, ASC, alpha-1-Acid Glycoprotein, ASGR1, alpha-Fetoprotein, ASK1, ALS, ATM, Ameloblastin, ATRIP, AMICA/JAML, Aurora A, AMIGO, Aurora B, AMIGO2, Axin-1, AMIGO3, Ax1, Aminoacylase/ACY1, Azurocidin/CAP37/HBP, Aminopeptidase A/ENPEP, B4GALT1, BIM, B7-1/CD80, 6-Biotin-17-NAD, B7-2/CD86, BLAME/SLAMF8, B7-H1/PD-L1, CXCL13/BLC/BCA-1, B7-H2, BLIMP1, B7-H3, Blk, B7-H4, BMI-1, BACE-1, BMP-1/PCP, BACE-2, BMP-2, Bad, BMP-3, BAFF/TNFSF13B, BMP-3b/GDF-10, BAFF R/TNFRSF13C, BMP-4, Bag-1, BMP-5, BAK, BMP-6, BAMBI/NMA, BMP-7, BARD1, BMP-8, Bax, BMP-9, BCAM, BMP-10, Bcl-10, BMP-15/GDF-9B, Bcl-2, BMPR-IA/ALK-3, Bcl-2 related protein A1, BMPR-IB/ALK-6, Bcl-w, BMPR-II, Bcl-x, BNIP3L, Bcl-xL, BOC, BCMA/TNFRSF17, BOK, BDNF, BPDE, Benzamide, Brachyury, Common beta Chain, B-Raf, beta IG-H3, CXCL14/BRAK, Betacellulin, BRCA1, beta-Defensin 2, BRCA2, BID, BTLA, Biglycan, Bub-1, Bik-like Killer Protein, c-jun, CD90/Thy1, c-Rel, CD94, CCL6/C10, CD97, C1q R1/CD93, CD151, C1qTNF1, CD160, C1qTNF4, CD163, C1qTNF5, CD164, Complement Component C1r, CD200, Complement Component C1s, CD200 R1, Complement Component C2, CD229/SLAMF3, Complement Component C3a, CD23/Fc epsilon RII, Complement Component C3d, CD2F-10/SLAMF9, Complement Component C5a, CD5L, Cadherin-4/R-Cadherin, CD69, Cadherin-6, CDC2, Cadherin-8, CDC25A, Cadherin-11, CDC25B, Cadherin-12, CDCP1, Cadherin-13, CDO, Cadherin-17, CDX4, E-Cadherin, CEACAM-1/CD66a, N-Cadherin, CEACAM-6, P-Cadherin, Cerberus 1, VE-Cadherin, CFTR, Calbindin D, cGMP, Calcineurin A, Chem R23, Calcineurin B, Chemerin, Calreticulin-2, Chemokine Sampler Packs, CaM Kinase II, Chitinase 3-like 1, cAMP, Chitotriosidase/CHIT1, Cannabinoid R1, Chk1, Cannabinoid R2/CB2/CNR2, Chk2, CAR/NR1I3, CHL-1/L1CAM-2, Carbonic Anhydrase I, Choline Acetyltransferase/ChAT, Carbonic Anhydrase II, Chondrolectin, Carbonic Anhydrase III, Chordin, Carbonic Anhydrase IV, Chordin-Like 1, Carbonic Anhydrase VA, Chordin-Like 2, Carbonic Anhydrase VB, CINC-1, Carbonic Anhydrase VI, CINC-2, Carbonic Anhydrase VII, CINC-3, Carbonic Anhydrase VIII, Claspin, Carbonic Anhydrase IX, Claudin-6, Carbonic Anhydrase X, CLC, Carbonic Anhydrase XII, CLEC-1, Carbonic Anhydrase XIII, CLEC-2, Carbonic Anhydrase XIV, CLECSF13/CLEC4F, Carboxymethyl Lysine, CLECSF8, Carboxypeptidase A1/CPA1, CLF-1, Carboxypeptidase A2, CL-P1/COLEC12, Carboxypeptidase A4, Clusterin, Carboxypeptidase B1, Clusterin-like 1, Carboxypeptidase E/CPE, CMG-2, Carboxypeptidase X1, CMV UL146, Cardiotrophin-1, CMV UL147, Carnosine Dipeptidase 1, CNP, Caronte, CNTF, CART, CNTF R alpha, Caspase, Coagulation Factor II/Thrombin, Caspase-1, Coagulation Factor III/Tissue Factor, Caspase-2, Coagulation Factor VII, Caspase-3, Coagulation Factor X, Caspase-4, Coagulation Factor XI, Caspase-6, Coagulation Factor XIV/Protein C, Caspase-7, COCO, Caspase-8, Cohesin, Caspase-9, Collagen I, Caspase-10, Collagen II, Caspase-12, Collagen IV, Caspase-13, Common gamma Chain/IL-2 R gamma, Caspase Peptide Inhibitors, COMP/Thrombospondin-5, Catalase, Complement Component C1rLP, beta-Catenin, Complement Component C1qA, Cathepsin 1, Complement Component C1qC, Cathepsin 3, Complement Factor D, Cathepsin 6, Complement Factor I, Cathepsin A, Complement MASP3, Cathepsin B, Connexin 43, Cathepsin C/DPPI, Contactin-1, Cathepsin D, Contactin-2/TAG1, Cathepsin E, Contactin-4, Cathepsin F, Contactin-5, Cathepsin H, Corin, Cathepsin L, Cornulin, Cathepsin O, CORS26/C1qTNF, 3, Cathepsin S, Rat Cortical Stem Cells, Cathepsin V, Cortisol, Cathepsin X/Z/P, COUP-TF I/NR2F1, CBP, COUP-TF II/NR2F2, CCI, COX-1, CCK-A R, COX-2, CCL28, CRACC/SLAMF7, CCR1, C-Reactive Protein, CCR2, Creatine Kinase, Muscle/CKMM, CCR3, Creatinine, CCR4, CREB, CCR5, CREG, CCR6, CRELD1, CCR7, CRELD2, CCR8, CRHBP, CCR9, CRHR-1, CCR10, CRIM1, CD155/PVR, Cripto, CD2, CRISP-2, CD3, CRISP-3, CD4, Crossveinless-2, CD4+/45RA−, CRTAM, CD4+/45O−, CRTH-2, CD4+/CD62L−/CD44, CRY1, CD4+/CD62L+/CD44, Cryptic, CD5, CSB/ERCC6, CD6, CCL27/CTACK, CD8, CTGF/CCN2, CD8+/45RA−, CTLA-4, CD8+/45RO−, Cubilin, CD9, CX3CR1, CD14, CXADR, CD27/TNFRSF7, CXCL16, CD27 Ligand/TNFSF7, CXCR3, CD28, CXCR4, CD30/TNFRSF8, CXCR5, CD30 Ligand/TNFSF8, CXCR6, CD31/PECAM-1, Cyclophilin A, CD34, Cyr61/CCN1, CD36/SR-B3, Cystatin A, CD38, Cystatin B, CD40/TNFRSF5, Cystatin C, CD40 Ligand/TNFSF5, Cystatin D, CD43, Cystatin E/M, CD44, Cystatin F, CD45, Cystatin H, CD46, Cystatin H2, CD47, Cystatin S, CD48/SLAMF2, Cystatin SA, CD55/DAF, Cystatin SN, CD58/LFA-3, Cytochrome c, CD59, Apocytochrome c, CD68, Holocytochrome c, CD72, Cytokeratin 8, CD74, Cytokeratin 14, CD83, Cytokeratin 19, CD84/SLAMF5, Cytonin, D6, DISP1, DAN, Dkk-1, DANCE, Dkk-2, DARPP-32, Dkk-3, DAX1/NR0B1, Dkk-4, DCC, DLEC, DCIR/CLEC4A, DLL1, DCAR, DLL4, DcR3/TNFRSF6B, d-Luciferin, DC-SIGN, DNA Ligase IV, DC-SIGNR/CD299, DNA Polymerase beta, DcTRAIL R1/TNFRSF23, DNAM-1, DcTRAIL R2/TNFRSF22, DNA-PKcs, DDR1, DNER, DDR2, Dopa Decarboxylase/DDC, DEC-205, DPCR-1, Decapentaplegic, DPP6, Decorin, DPPA4, Dectin-1/CLEC7A, DPPA5/ESG1, Dectin-2/CLEC6A, DPPII/QPP/DPP7, DEP-1/CD148, DPPIV/CD26, Desert Hedgehog, DR3/TNFRSF25, Desmin, DR6/TNFRSF21, Desmoglein-1, DSCAM, Desmoglein-2, DSCAM-L1, Desmoglein-3, DSPG3, Dishevelled-1, Dtk, Dishevelled-3, Dynamin, EAR2/NR2F6, EphA5, ECE-1, EphA6, ECE-2, EphA7, ECF-L/CHI3L3, EphA8, ECM-1, EphB1, Ecotin, EphB2, EDA, EphB3, EDA-A2, EphB4, EDAR, EphB6, EDG-1, Ephrin, EDG-5, Ephrin-A1, EDG-8, Ephrin-A2, eEF-2, Ephrin-A3, EGF, Ephrin-A4, EGF R, Ephrin-A5, EGR1, Ephrin-B, EG-VEGF/PK1, Ephrin-B1, eIF2 alpha, Ephrin-B2, eIF4E, Ephrin-B3, Elk-1, Epigen, EMAP-II, Epimorphin/Syntaxin 2, EMMPRIN/CD147, Epiregulin, CXCL5/ENA, EPR-1/Xa Receptor, Endocan, ErbB2, Endoglin/CD105, ErbB3, Endoglycan, ErbB4, Endonuclease III, ERCC1, Endonuclease IV, ERCC3, Endonuclease V, ERK1/ERK2, Endonuclease VIII, ERK1, Endorepellin/Perlecan, ERK2, Endostatin, ERK3, Endothelin-1, ERK5/BMK1, Engrailed-2, ERR alpha/NR3B1, EN-RAGE, ERR beta/NR3B2, Enteropeptidase/Enterokinase, ERR gamma/NR3B3, CCL11/Eotaxin, Erythropoietin, CCL24/Eotaxin-2, Erythropoietin R, CCL26/Eotaxin-3, ESAM, EpCAM/TROP-1, ER alpha/NR3A1, EPCR, ER beta/NR3A2, Eph, Exonuclease III, EphA1, Exostosin-like 2/EXTL2, EphA2, Exostosin-like 3/EXTL3, EphA3, FABP1, FGF-BP, FABP2, FGF R1-4, FABP3, FGF R1, FABP4, FGF R2, FABP5, FGF R3, FABP7, FGF R4, FABP9, FGF R5, Complement Factor B, Fgr, FADD, FHR5, FAM3A, Fibronectin, FAM3B, Ficolin-2, FAM3C, Ficolin-3, FAM3D, FITC, Fibroblast Activation Protein alpha/FAP, FKBP38, Fas/TNFRSF6, Flap, Fas Ligand/TNFSF6, FLIP, FATP1, FLRG, FATP4, FLRT1, FATP5, FLRT2, Fc gamma RI/CD64, FLRT3, Fc gamma RIIB/CD32b, Flt-3, Fc gamma RIIC/CD32c, Flt-3 Ligand, Fc gamma RIIA/CD32a, Follistatin, Fc gamma RIII/CD16, Follistatin-like 1, FcRH1/IRTA5, FosB/G0S3, FcRH2/IRTA4, FoxD3, FcRH4/IRTA1, FoxJ1, FcRH5/IRTA2, FoxP3, Fc Receptor-like 3/CD16-2, Fpg, FEN-1, FPR1, Fetuin A, FPRL1, Fetuin B, FPRL2, FGF acidic, CX3CL1/Fractalkine, FGF basic, Frizzled-1, FGF-3, Frizzled-2, FGF-4, Frizzled-3, FGF-5, Frizzled-4, FGF-6, Frizzled-5, FGF-8, Frizzled-6, FGF-9, Frizzled-7, FGF-10, Frizzled-8, FGF-11, Frizzled-9, FGF-12, Frk, FGF-13, sFRP-1, FGF-16, sFRP-2, FGF-17, sFRP-3, FGF-19, sFRP-4, FGF-20, Furin, FGF-21, FXR/NR1H4, FGF-22, Fyn, FGF-23, G9a/EHMT2, GFR alpha-3/GDNF R alpha-3, GABA-A-R alpha 1, GFR alpha-4/GDNF R alpha-4, GABA-A-R alpha 2, GITR/TNFRSF18, GABA-A-R alpha 4, GITR Ligand/TNFSF18, GABA-A-R alpha 5, GLI-1, GABA-A-R alpha 6, GLI-2, GABA-A-R beta 1, GLP/EHMT1, GABA-A-R beta 2, GLP-1 R, GABA-A-R beta 3, Glucagon, GABA-A-R gamma 2, Glucosamine (N-acetyl)-6-Sulfatase/GNS, GABA-B-R2, GluR1, GAD1/GAD67, GluR2/3, GAD2/GAD65, GluR2, GADD45 alpha, GluR3, GADD45 beta, Glut1, GADD45 gamma, Glut2, Galectin-1, Glut3, Galectin-2, Glut4, Galectin-3, Glut5, Galectin-3 BP, Glutaredoxin 1, Galectin-4, Glycine R, Galectin-7, Glycophorin A, Galectin-8, Glypican 2, Galectin-9, Glypican 3, GalNAc4S-6ST, Glypican 5, GAP-43, Glypican 6, GAPDH, GM-CSF, Gas1, GM-CSF R alpha, Gas6, GMF-beta, GASP-1/WFIKKNRP, gp130, GASP-2/WFIKKN, Glycogen Phosphorylase BB/GPBB, GATA-1, GPR15, GATA-2, GPR39, GATA-3, GPVI, GATA-4, GR/NR3C1, GATA-5, Gr-1/Ly-6G, GATA-6, Granulysin, GBL, Granzyme A, GCNF/NR6A1, Granzyme B, CXCL6/GCP-2, Granzyme D, G-CSF, Granzyme G, G-CSF R, Granzyme H, GDF-1, GRASP, GDF-3 GRB2, GDF-5, Gremlin, GDF-6, GRO, GDF-7, CXCL1/GRO alpha, GDF-8, CXCL2/GRO beta, GDF-9, CXCL3/GRO gamma, GDF-11, Growth Hormone, GDF-15, Growth Hormone R, GDNF, GRP75/HSPA9B, GFAP, GSK-3 alpha/beta, GFI-1, GSK-3 alpha, GFR alpha-1/GDNF R alpha-1, GSK-3 beta, GFR alpha-2/GDNF R alpha-2, EZFIT, H2AX, Histidine, H60, HM74A, HAI-1, HMGA2, HAI-2, HMGB1, HAI-2A, TCF-2/HNF-1 beta, HAI-2B, HNF-3 beta/FoxA2, HAND1, HNF-4 alpha/NR2A1, HAPLN1, HNF-4 gamma/NR2A2, Airway Trypsin-like Protease/HAT, HO-1/HMOX1/HSP32, HB-EGF, HO-2/HMOX2, CCL14a/HCC-1, HPRG, CCL14b/HCC-3, Hrk, CCL16/HCC-4, HRP-1, alpha HCG, HS6ST2, Hck, HSD-1, HCR/CRAM-A/B, HSD-2, HDGF, HSP10/EPF, Hemoglobin, HSP27, Hepassocin, HSP60, HES-1, HSP70, HES-4, HSP90, HGF, HTRA/Protease Do, HGF Activator, HTRA1/PRSS11, HGF R, HTRA2/Omi, HIF-1 alpha, HVEM/TNFRSF14, HIF-2 alpha, Hyaluronan, HIN-1/Secretoglobulin 3A1, 4-Hydroxynonenal, Hip, CCL1/I-309/TCA-3, IL-10, cIAP (pan), IL-10 R alpha, cIAP-1/HIAP-2, IL-10 R beta, cIAP-2/HIAP-1, IL-11, IBSP/Sialoprotein II, IL-11 R alpha, ICAM-1/CD54, IL-12, ICAM-2/CD102, IL-12/IL-23 p40, ICAM-3/CD50, IL-12 R beta 1, ICAM-5, IL-12 R beta 2, ICAT, IL-13, ICOS, IL-13 R alpha 1, Iduronate 2-Sulfatase/IDS, IL-13 R alpha 2, IFN, IL-15, IFN-alpha, IL-15 R alpha, IFN-alpha 1, IL-16, IFN-alpha 2, IL-17, IFN-alpha 4b, IL-17 R, IFN-alpha A, IL-17 RC, IFN-alpha B2, IL-17 RD, IFN-alpha C, IL-17B, IFN-alpha D, IL-17B R, IFN-alpha F, IL-17C, IFN-alpha G, IL-17D, IFN-alpha H2, IL-17E, IFN-alpha I, IL-17F, IFN-alpha J1, IL-18/IL-1F4, IFN-alpha K, IL-18 BPa, IFN-alpha WA, IL-18 BPc, IFN-alpha/beta R1, IL-18 BPd, IFN-alpha/beta R2, IL-18 R alpha/IL-1 R5, IFN-beta, IL-18 R beta/IL-1 R7, IFN-gamma, IL-19, IFN-gamma R1, IL-20, IFN-gamma R2, IL-20 R alpha, IFN-omega, IL-20 R beta, IgE, IL-21, IGFBP-1, IL-21 R, IGFBP-2, IL-22, IGFBP-3, IL-22 R, IGFBP-4, IL-22BP, IGFBP-5, IL-23, IGFBP-6, IL-23 R, IGFBP-L1, IL-24, IGFBP-rp1/IGFBP-7, IL-26/AK155, IGFBP-rP10, IL-27, IGF-I, IL-28A, IGF-I R, IL-28B, IGF-II, IL-29/IFN-lambda 1, IGF-II R, IL-31, IgG, IL-31 RA, IgM, IL-32 alpha, IGSF2, IL-33, IGSF4A/SynCAM, ILT2/CD85j, IGSF4B, ILT3/CD85k, IGSF8, ILT4/CD85d, IgY, ILT5/CD85a, IkB-beta, ILT6/CD85e, IKK alpha, Indian Hedgehog, IKK epsilon, INSRR, IKK gamma, Insulin, IL-1 alpha/IL-1F1, Insulin R/CD220, IL-1 beta/IL-1F2, Proinsulin, IL-1ra/IL-1F3, Insulysin/IDE, IL-1F5/FIL1 delta, Integrin alpha 2/CD49b, IL-1F6/FIL1 epsilon, Integrin alpha 3/CD49c, IL-1F7/FIL1 zeta, Integrin alpha 3 beta 1/VLA-3, IL-1F8/FIL1 eta, Integrin alpha 4/CD49d, IL-1F9/IL-1H1, Integrin alpha 5/CD49e, IL-1F10/IL-1HY2, Integrin alpha 5 beta 1, IL-1 RI, Integrin alpha 6/CD49f, IL-1 RII, Integrin alpha 7, IL-1 R3/IL-1 R AcP, Integrin alpha 9, IL-1 R4/ST2, Integrin alpha E/CD103, IL-1 R6/IL-1 R rp2, Integrin alpha L/CD11a, IL-1 R8, Integrin alpha L beta 2, IL-1 R9, Integrin alpha M/CD11b, IL-2, Integrin alpha M beta 2, IL-2 R alpha, Integrin alpha V/CD51, IL-2 R beta, Integrin alpha V beta 5, IL-3, Integrin alpha V beta 3, IL-3 R alpha, Integrin alpha V beta 6, IL-3 R beta, Integrin alpha X/CD11c, IL-4, Integrin beta 1/CD29, IL-4 R, Integrin beta 2/CD18, IL-5, Integrin beta 3/CD61, IL-5 R alpha, Integrin beta 5, IL-6, Integrin beta 6, IL-6 R, Integrin beta 7, IL-7, CXCL10/IP-10/CRG-2, IL-7 R alpha1CD127, IRAK1, CXCR1/IL-8 RA, IRAK4, CXCR2/IL-8 RB, IRS-1, CXCL8/IL-8, Islet-1, IL-9, CXCL11/I-TAC, IL-9 R, Jagged 1, JAM-4/IGSF5, Jagged 2, JNK, JAM-A, JNK1/JNK2, JAM-B/VE-JAM, JNK1, JAM-C, JNK2, Kininogen, Kallikrein 3/PSA, Kininostatin, Kallikrein 4, KIR/CD158, Kallikrein 5, KIR2DL1, Kallikrein 6/Neurosin, KIR2DL3, Kallikrein 7, KIR2DL4/CD158d, Kallikrein 8/Neuropsin, KIR2DS4, Kallikrein 9, KIR3DL1, Plasma Kallikrein/KLKB1, KIR3DL2, Kallikrein 10, Kirre12, Kallikrein 11, KLF4, Kallikrein 12, KLF5, Kallikrein 13, KLF6, Kallikrein 14, Klotho, Kallikrein 15, Klotho beta, KC, KOR, Keap1, Kremen-1, Kell, Kremen-2, KGF/FGF-7, LAG-3, LINGO-2, LAIRL Lipin 2, LAIR2, Lipocalin-1, Laminin alpha 4, Lipocalin-2/NGAL, Laminin gamma 1, 5-Lipoxygenase, Laminin I, LXR alpha/NR1H3, Laminin S, LXR beta/NR1H2, Laminin-1, Livin, Laminin-5, LIX, LAMP, LMIR1/CD300A, Langerin, LMIR2/CD300c, LAR, LMIR3/CD300LF, Latexin, LMIR5/CD300LB, Layilin, LMIR6/CD300LE, LBP, LMO2, LDL R, LOX-1/SR-E1, LECT2, LRH-1/NR5A2, LEDGF, LRIG1, Lefty, LRIG3, Lefty-1, LRP-1, Lefty-A, LRP-6, Legumain, LSECtin/CLEC4G, Leptin, Lumican, Leptin R, CXCL15/Lungkine, Leukotriene B4, XCL1/Lymphotactin, Leukotriene B4 R1, Lymphotoxin, LIF, Lymphotoxin betaITNFSF3, LIF R alpha, Lymphotoxin beta R/TNFRSF3, LIGHT/TNFSF14, Lyn, Limitin, Lyp, LIMPII/SR-B2, Lysyl Oxidase Homolog 2, LIN-28, LYVE-1, LINGO-1, alpha 2-Macroglobulin, CXCL9/MIG, MAD2L1, Mimecan, MAdCAM-1, Mindin, MafB, Mineralocorticoid R/NR3C2, MafF, CCL3L1/MIP-1 alpha Isoform LD78 beta, MafG, CCL3/MIP-1 alpha, MafK, CCL4L1/LAG-1, MAG/Siglec-4a, CCL4/MIP-1 beta, MANF, CCL15/MIP-1 delta, MAP2, CCL9/10/MIP-1 gamma, MAPK, MIP-2, Marapsin/Pancreasin, CCL19/MIP-3 beta, MARCKS, CCL20/MIP-3 alpha, MARCO, MIP-I, Mash1, MIP-II, Matrilin-2, MIP-III, Matrilin-3, MIS/AMH, Matrilin-4, MIS RII, Matriptase/ST14, MIXL1, MBL, MKK3/MKK6, MBL-2, MKK3, Melanocortin 3R/MC3R, MKK4, MCAM/CD146, MKK6, MCK-2, MKK7, Mc1-1, MKP-3, MCP-6, MLH-1, CCL2/MCP-1, MLK4 alpha, MCP-11, MMP, CCL8/MCP-2, MMP-1, CCL7/MCP-3/MARC, MMP-2, CCL13/MCP-4, MMP-3, CCL12/MCP-5, MMP-7, M-CSF, MMP-8, M-CSF R, MMP-9, MCV-type II, MMP-10, MD-1, MMP-11, MD-2, MMP-12, CCL22/MDC, MMP-13, MDL-1/CLEC5A, MMP-14, MDM2, MMP-15, MEA-1, MMP-16/MT3-MMP, MEK1/MEK2, MMP-24/MT5-MMP, MEK1, MMP-25/MT6-MMP, MEK2, MMP-26, Melusin, MMR, MEPE, MOG, Meprin alpha, CCL23/MPIF-1, Meprin beta, M-Ras/R-Ras3, Mer, Mre11, Mesothelin, MRP1 Meteorin, MSK1/MSK2, Methionine Aminopeptidase 1, MSK1, Methionine Aminopeptidase, MSK2, Methionine Aminopeptidase 2, MSP, MFG-E8, MSP R/Ron, MFRP, Mug, MgcRacGAP, MULT-1, MGL2, Musashi-1, MGMT, Musashi-2, MIA, MuSK, MICA, MutY DNA Glycosylase, MICB, MyD88, MICL/CLEC12A, Myeloperoxidase, beta 2 Microglobulin, Myocardin, Midkine, Myocilin, MIF, Myoglobin, NAIP NGFI-B gamma/NR4A3, Nanog, NgR2/NgRH1, CXCL7/NAP-2, NgR3/NgRH2, Nbs1, Nidogen-1/Entactin, NCAM-1/CD56, Nidogen-2, NCAM-L1, Nitric Oxide, Nectin-1, Nitrotyrosine, Nectin-2/CD112, NKG2A, Nectin-3, NKG2C, Nectin-4, NKG2D, Neogenin, NKp30, Neprilysin/CD10, NKp44, Neprilysin-2/MMEL1/MMEL2, NKp46/NCR1, Nestin, NKp80/KLRF1, NETO2, NKX2.5, Netrin-1, NMDA R, NR1 Subunit, Netrin-2, NMDA R, NR2A Subunit, Netrin-4, NMDA R, NR2B Subunit, Netrin-G1a, NMDA R, NR2C Subunit, Netrin-G2a, N-Me-6,7-diOH-TIQ, Neuregulin-1/NRG1, Nodal, Neuregulin-3/NRG3, Noggin, Neuritin, Nogo Receptor, NeuroD1, Nogo-A, Neurofascin, NOMO, Neurogenin-1, Nope, Neurogenin-2, Norrin, Neurogenin-3, eNOS, Neurolysin, iNOS, Neurophysin II, nNOS, Neuropilin-1, Notch-1, Neuropilin-2, Notch-2, Neuropoietin, Notch-3, Neurotrimin, Notch-4, Neurturin, NOV/CCN3, NFAM1, NRAGE, NF-H, NrCAM, NFkB1, NRL, NFkB2, NT-3, NF-L, NT-4, NF-M, NTB-A/SLAMF6, NG2/MCSP, NTH1, NGF R/TNFRSF16, Nucleostemin, beta-NGF, Nurr-1/NR4A2, NGFI-B alpha/NR4A1, OAS2, Orexin B, OBCAM, OSCAR, OCAM, OSF-2/Periostin, OCIL/CLEC2d, Oncostatin M/OSM, OCILRP2/CLEC2i, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF11B, Oligodendrocyte Marker O1, Otx2, Oligodendrocyte Marker O4, OV-6, OMgp, OX40/TNFRSF4, Opticin, OX40 Ligand/TNFSF4, Orexin A, OAS2, Orexin B, OBCAM, OSCAR, OCAM, OSF-2/Periostin, OCIL/CLEC2d, Oncostatin M/OSM, OCILRP2/CLEC2i, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF11B, Oligodendrocyte Marker O1, Otx2, Oligodendrocyte Marker O4, OV-6, OMgp, OX40/TNFRSF4, Opticin, OX40 Ligand/TNFSF4, Orexin A, RACK1, Ret, Rad1, REV-ERB alpha/NR1D1, Rad17, REV-ERB beta/NR1D2, Rad51, Rex-1, Rae-1, RGM-A, Rae-1 alpha, RGM-B, Rae-1 beta, RGM-C, Rae-1 delta, Rheb, Rae-1 epsilon, Ribosomal Protein S6, Rae-1 gamma, RIP1, Raf-1, ROBO1, RAGE, ROBO2, Ra1A/Ra1B, ROBO3, Ra1A, ROBO4, Ra1B, ROR/NR1F1-3 (pan), RANK/TNFRSF11A, ROR alpha/NR1F1, CCL5/RANTES, ROR gamma/NR1F3, Rap1A/B, RTK-like Orphan Receptor 1/ROR1, RAR alpha/NR1B1, RTK-like Orphan Receptor 2/ROR2, RAR beta/NR1B2, RP105, RAR gamma/NR1B3, RPA2, Ras, RSK (pan), RBP4, RSK1/RSK2, RECK, RSK1, Reg 2/PAP, RSK2, Reg I, RSK3, Reg II, RSK4, Reg III, R-Spondin 1, Reg IIIa, R-Spondin 2, Reg IV, R-Spondin 3, Relaxin-1, RUNX1/CBFA2, Relaxin-2, RUNX2/CBFA1, Relaxin-3, RUNX3/CBFA3, RELM alpha, RXR alpha/NR2B1, RELM beta, RXR beta/NR2B2, RELT/TNFRSF19L, RXR gamma/NR2B3, Resistin, S100A10, SLITRK5, S100A8, SLPI, S100A9, SMAC/Diablo, S100B, Smad1, S100P, Smad2, SALL1, Smad3, delta-Sarcoglycan, Smad4, Sca-1/Ly6, Smad5, SCD-1, Smad7, SCF, Smad8, SCF R/c-kit, SMC1, SCGF, alpha-Smooth Muscle Actin, SCL/Tal1, SMUG1, SCP3/SYCP3, Snail, CXCL12/SDF-1, Sodium Calcium Exchanger 1, SDNSF/MCFD2, Soggy-1, alpha-Secretase, Sonic Hedgehog, gamma-Secretase, SorCS1, beta-Secretase, SorCS3, E-Selectin, Sortilin, L-Selectin, SOST, P-Selectin, SOX1, Semaphorin 3A, SOX2, Semaphorin 3C, SOX3, Semaphorin 3E, SOX7, Semaphorin 3F, SOX9, Semaphorin 6A, SOX10, Semaphorin 6B, SOX17, Semaphorin 6C, SOX21 Semaphorin 6D, SPARC, Semaphorin 7A, SPARC-like 1, Separase, SP-D, Serine/Threonine Phosphatase Substrate I, Spinesin, Serpin A1, F-Spondin, Serpin A3, SR-AI/MSR, Serpin A4/Kallistatin, Src, Serpin A5/Protein C Inhibitor, SREC-I/SR-F1, Serpin A8/Angiotensinogen, SREC-II, Serpin B5, SSEA-1, Serpin C1/Antithrombin-III, SSEA-3, Serpin D1/Heparin Cofactor II, SSEA-4, Serpin E1/PAI-1, ST7/LRP12, Serpin E2, Stabilin-1, Serpin F1, Stabilin-2, Serpin F2, Stanniocalcin 1, Serpin G1/C1 Inhibitor, Stanniocalcin 2, Serpin 12, STAT1, Serum Amyloid A1, STAT2, SF-1/NR5A1, STAT3, SGK, STAT4, SHBG, STAT5a/b, SHIP, STAT5a, SHP/NR0B2, STAT5b, SHP-1, STAT6, SHP-2, VE-Statin, SIGIRR, Stella/Dppa3, Siglec-2/CD22, STRO-1, Siglec-3/CD33, Substance P, Siglec-5, Sulfamidase/SGSH, Siglec-6, Sulfatase Modifying Factor 1/SUMF1, Siglec-7, Sulfatase Modifying Factor 2/SUMF2, Siglec-9, SUMO1, Siglec-10, SUMO2/3/4, Siglec-11, SUMO3, Siglec-F, Superoxide Dismutase, SIGNR1/CD209, Superoxide Dismutase-1/Cu—Zn SOD, SIGNR4, Superoxide Dismutase-2/Mn-SOD, SIRP beta 1, Superoxide Dismutase-3/EC-SOD, SKI, Survivin, SLAM/CD150, Synapsin I, Sleeping Beauty Transposase, Syndecan-1/CD138, Slit3, Syndecan-2, SLITRK1, Syndecan-3, SLITRK2, Syndecan-4, SLITRK4, TAC1/TNFRSF13B, TMEFF1/Tomoregulin-1, TAO2, TMEFF2, TAPP1, TNF-alpha/TNFSF1A, CCL17/TARC, TNF-beta/TNFSF1B, Tau, TNF RI/TNFRSF1A, TC21/R-Ras2, TNF RII/TNFRSF1B, TCAM-1, TOR, TCCR/WSX-1, TP-1, TC-PTP, TP63/TP73L, TDG, TR, CCL25/TECK, TR alpha/NR1A1, Tenascin C, TR beta 1/NR1A2, Tenascin R, TR2/NR2C1, TER-119, TR4/NR2C2, TERT, TRA-1-85, Testican 1/SPOCK1, TRADD, Testican 2/SPOCK2, TRAF-1, Testican 3/SPOCK3, TRAF-2, TFPI, TRAF-3, TFPI-2, TRAF-4, TGF-alpha, TRAF-6, TGF-beta, TRAIL/TNFSF10, TGF-beta 1, TRAIL R1/TNFRSF10A, LAP (TGF-beta 1), TRAIL R2/TNFRSF10B, Latent TGF-beta 1, TRAIL R3/TNFRSF10C, TGF-beta 1.2, TRAIL R4/TNFRSF10D, TGF-beta 2, TRANCE/TNFSF11, TGF-beta 3, TfR (Transferrin R), TGF-beta 5, Apo-Transferrin, Latent TGF-beta bp1, Holo-Transferrin, Latent TGF-beta bp2, Trappin-2/Elafin, Latent TGF-beta bp4, TREM-1, TGF-beta RI/ALK-5, TREM-2, TGF-beta RII, TREM-3, TGF-beta RIIb), TREML1/TLT-1, TGF-beta RIII, TRF-1, Thermolysin, TRF-2, Thioredoxin-1, TRH-degrading Ectoenzyme/TRHDE, Thioredoxin-2, TRIM5, Thioredoxin-80, Tripeptidyl-Peptidase I, Thioredoxin-like 5/TRP14, TrkA, THOP1, TrkB, Thrombomodulin/CD141, TrkC, Thrombopoietin, TROP-2, Thrombopoietin R, Troponin I Peptide 3, Thrombospondin-1, Troponin T, Thrombospondin-2, TROY/TNFRSF19, Thrombospondin-4, Trypsin 1, Thymopoietin, Trypsin 2/PRSS2, Thymus Chemokine-1, Trypsin 3/PRSS3, Tie-1, Tryptase-5/Prss32, Tie-2, Tryptase alpha/TPS1, TIM-1/KIM-1/HAVCR, Tryptase beta-1/MCPT-7, TIM-2, Tryptase beta-2/TPSB2, TIM-3, Tryptase epsilon/BSSP-4, TIM-4, Tryptase gamma-1/TPSG1, TIM-5, Tryptophan Hydroxylase, TIM-6, TSC22, TIMP-1, TSG, TIMP-2, TSG-6, TIMP-3, TSK, TIMP-4, TSLP, TL1A/TNFSF15, TSLP R, TLR1, TSP50, TLR2, beta-III Tubulin, TLR3, TWEAK/TNFSF12, TLR4, TWEAK R/TNFRSF12, TLR5, Tyk2, TLR6, Phospho-Tyrosine, TLR9, Tyrosine Hydroxylase, TLX/NR2E1, Tyrosine Phosphatase Substrate I, Ubiquitin, UNC5H3, Ugi, UNC5H4, UGRP1, UNG, ULBP-1, uPA, ULBP-2, uPAR, ULBP-3, URB, UNC5H1, UVDE, UNC5H2, Vanilloid R1, VEGF R, VASA, VEGF R1/Flt-1, Vasohibin, VEGF R2/KDR/Flk-1, Vasorin, VEGF R3/Flt-4, Vasostatin, Versican, Vav-1, VGSQ, VCAM-1, VHR, VDR/NR1I1, Vimentin, VEGF, Vitronectin, VEGF-B, VLDLR, VEGF-C, vWF-A2, VEGF-D, Synuclein-alpha, Ku70, WASP, Wnt-7b, WIF-1, Wnt-8a WISP-1/CCN4, Wnt-8b, WNK1, Wnt-9a, Wnt-1, Wnt-9b, Wnt-3a, Wnt-10a, Wnt-4, Wnt-10b, Wnt-5a, Wnt-11, Wnt-5b, wnvNS3, Wnt7a, XCR1, XPE/DDB1, XEDAR, XPE/DDB2, Xg, XPF, XIAP, XPG, XPA, XPV, XPD, XRCC1, Yes, YY1, EphA4.

Numerous human ion channels are targets of particular interest. Non-limiting examples include 5-hydroxytryptamine 3 receptor B subunit, 5-hydroxytryptamine 3 receptor precursor, 5-hydroxytryptamine receptor 3 subunit C, AAD 14 protein, Acetylcholine receptor protein, alpha subunit precursor, Acetylcholine receptor protein, beta subunit precursor, Acetylcholine receptor protein, delta subunit precursor, Acetylcholine receptor protein, epsilon subunit precursor, Acetylcholine receptor protein, gamma subunit precursor, Acid sensing ion channel 3 splice variant b, Acid sensing ion channel 3 splice variant c, Acid sensing ion channel 4, ADP-ribose pyrophosphatase, mitochondrial precursor, Alpha1A-voltage-dependent calcium channel, Amiloride-sensitive cation channel 1, neuronal, Amiloride-sensitive cation channel 2, neuronal Amiloride-sensitive cation channel 4, isoform 2, Amiloride-sensitive sodium channel, Amiloride-sensitive sodium channel alpha-subunit, Amiloride-sensitive sodium channel beta-subunit, Amiloride-sensitive sodium channel delta-subunit, Amiloride-sensitive sodium channel gamma-subunit, Annexin A7, Apical-like protein, ATP-sensitive inward rectifier potassium channel 1, ATP-sensitive inward rectifier potassium channel 10, ATP-sensitive inward rectifier potassium channel 11, ATP-sensitive inward rectifier potassium channel 14, ATP-sensitive inward rectifier potassium channel 15, ATP-sensitive inward rectifier potassium channel 8, Calcium channel alpha12.2 subunit, Calcium channel alpha12.2 subunit, Calcium channel alpha1E subunit, delta19 delta40 delta46 splice variant, Calcium-activated potassium channel alpha subunit 1, Calcium-activated potassium channel beta subunit 1, Calcium-activated potassium channel beta subunit 2, Calcium-activated potassium channel beta subunit 3, Calcium-dependent chloride channel-1, Cation channel TRPM4B, CDNA FLJ90453 fis, clone NT2RP3001542, highly similar to Potassium channel tetramerisation domain containing 6, CDNA FLJ90663 fis, clone PLACE1005031, highly similar to Chloride intracellular channel protein 5, CGMP-gated cation channel beta subunit, Chloride channel protein, Chloride channel protein 2, Chloride channel protein 3, Chloride channel protein 4, Chloride channel protein 5, Chloride channel protein 6, Chloride channel protein C1C-Ka, Chloride channel protein C1C-Kb, Chloride channel protein, skeletal muscle, Chloride intracellular channel 6, Chloride intracellular channel protein 3, Chloride intracellular channel protein 4, Chloride intracellular channel protein 5, CHRNA3 protein, Clcn3e protein, CLCNKB protein, CNGA4 protein, Cullin-5, Cyclic GMP gated potassium channel, Cyclic-nucleotide-gated cation channel 4, Cyclic-nucleotide-gated cation channel alpha 3, Cyclic-nucleotide-gated cation channel beta 3, Cyclic-nucleotide-gated olfactory channel, Cystic fibrosis transmembrane conductance regulator, Cytochrome B-245 heavy chain, Dihydropyridine-sensitive L-type, calcium channel alpha-2/delta subunits precursor, FXYD domain-containing ion transport regulator 3 precursor, FXYD domain-containing ion transport regulator 5 precursor, FXYD domain-containing ion transport regulator 6 precursor, FXYD domain-containing ion transport regulator 7, FXYD domain-containing ion transport regulator 8 precursor, G protein-activated inward rectifier potassium channel 1, G protein-activated inward rectifier potassium channel 2, G protein-activated inward rectifier potassium channel 3, G protein-activated inward rectifier potassium channel 4, Gamma-aminobutyric-acid receptor alpha-1 subunit precursor, Gamma-aminobutyric-acid receptor alpha-2 subunit precursor, Gamma-aminobutyric-acid receptor alpha-3 subunit precursor, Gamma-aminobutyric-acid receptor alpha-4 subunit precursor, Gamma-aminobutyric-acid receptor alpha-5 subunit precursor, Gamma-aminobutyric-acid receptor alpha-6 subunit precursor, Gamma-aminobutyric-acid receptor beta-1 subunit precursor, Gamma-aminobutyric-acid receptor beta-2 subunit precursor, Gamma-aminobutyric-acid receptor beta-3 subunit precursor, Gamma-aminobutyric-acid receptor delta subunit precursor, Gamma-aminobutyric-acid receptor epsilon subunit precursor, Gamma-aminobutyric-acid receptor gamma-1 subunit precursor, Gamma-aminobutyric-acid receptor gamma-3 subunit precursor, Gamma-aminobutyric-acid receptor pi subunit precursor, Gamma-aminobutyric-acid receptor rho-1 subunit precursor, Gamma-aminobutyric-acid receptor rho-2 subunit precursor, Gamma-aminobutyric-acid receptor theta subunit precursor, GluR6 kainate receptor, Glutamate receptor 1 precursor, Glutamate receptor 2 precursor, Glutamate receptor 3 precursor, Glutamate receptor 4 precursor, Glutamate receptor 7, Glutamate receptor B, Glutamate receptor delta-1 subunit precursor, Glutamate receptor, ionotropic kainate 1 precursor, Glutamate receptor, ionotropic kainate 2 precursor, Glutamate receptor, ionotropic kainate 3 precursor, Glutamate receptor, ionotropic kainate 4 precursor, Glutamate receptor, ionotropic kainate 5 precursor, Glutamate [NMDA] receptor subunit 3A precursor, Glutamate [NMDA] receptor subunit 3B precursor, Glutamate [NMDA] receptor subunit epsilon 1 precursor, Glutamate [NMDA] receptor subunit epsilon 2 precursor, Glutamate [NMDA] receptor subunit epsilon 4 precursor, Glutamate [NMDA] receptor subunit zeta 1 precursor, Glycine receptor alpha-1 chain precursor, Glycine receptor alpha-2 chain precursor, Glycine receptor alpha-3 chain precursor, Glycine receptor beta chain precursor, H/ACA ribonucleoprotein complex subunit 1, High affinity immunoglobulin epsilon receptor beta-subunit, Hypothetical protein DKFZp31310334, Hypothetical protein DKFZp761M1724, Hypothetical protein FLJ12242, Hypothetical protein FLJ14389, Hypothetical protein FLJ14798, Hypothetical protein FLJ14995, Hypothetical protein FLJ16180, Hypothetical protein FLJ16802, Hypothetical protein FLJ32069, Hypothetical protein FLJ37401, Hypothetical protein FLJ38750, Hypothetical protein FLJ40162, Hypothetical protein FLJ41415, Hypothetical protein FLJ90576, Hypothetical protein FLJ90590, Hypothetical protein FLJ90622, Hypothetical protein KCTD15, Hypothetical protein MGC15619, Inositol 1,4,5-trisphosphate receptor type 1, Inositol 1,4,5-trisphosphate receptor type 2, Inositol 1,4,5-trisphosphate receptor type 3, Intermediate conductance calcium-activated potassium channel protein 4, Inward rectifier potassium channel 13, Inward rectifier potassium channel 16, Inward rectifier potassium channel 4, Inward rectifying K(+) channel negative regulator Kir2.2v, Kainate receptor subunit KA2a, KCNH5 protein, KCTD17 protein, KCTD2 protein, Keratinocytes associated transmembrane protein 1, Kv channel-interacting protein 4, Melastatin 1, Membrane protein MLC1, MGC15619 protein, Mucolipin-1, Mucolipin-2, Mucolipin-3, Multidrug resistance-associated protein 4, N-methyl-D-aspartate receptor 2C subunit precursor, NADPH oxidase homolog 1, Nav1.5, Neuronal acetylcholine receptor protein, alpha-10 subunit precursor, Neuronal acetylcholine receptor protein, alpha-2 subunit precursor, Neuronal acetylcholine receptor protein, alpha-3 subunit precursor, Neuronal acetylcholine receptor protein, alpha-4 subunit precursor, Neuronal acetylcholine receptor protein, alpha-5 subunit precursor, Neuronal acetylcholine receptor protein, alpha-6 subunit precursor, Neuronal acetylcholine receptor protein, alpha-7 subunit precursor, Neuronal acetylcholine receptor protein, alpha-9 subunit precursor, Neuronal acetylcholine receptor protein, beta-2 subunit precursor, Neuronal acetylcholine receptor protein, beta-3 subunit precursor, Neuronal acetylcholine receptor protein, beta-4 subunit precursor, Neuronal voltage-dependent calcium channel alpha 2D subunit, P2X purinoceptor 1, P2X purinoceptor 2, P2X purinoceptor 3, P2X purinoceptor 4, P2X purinoceptor 5, P2X purinoceptor 6, P2X purinoceptor 7, Pancreatic potassium channel TALK-1b, Pancreatic potassium channel TALK-1c, Pancreatic potassium channel TALK-1d, Phospholemman precursor, Plasmolipin, Polycystic kidney disease 2 related protein, Polycystic kidney disease 2-like 1 protein, Polycystic kidney disease 2-like 2 protein, Polycystic kidney disease and receptor for egg jelly related protein precursor, Polycystin-2, Potassium channel regulator, Potassium channel subfamily K member 1, Potassium channel subfamily K member 10, Potassium channel subfamily K member 12, Potassium channel subfamily K member 13, Potassium channel subfamily K member 15, Potassium channel subfamily K member 16, Potassium channel subfamily K member 17, Potassium channel subfamily K member 2, Potassium channel subfamily K member 3, Potassium channel subfamily K member 4, Potassium channel subfamily K member 5, Potassium channel subfamily K member 6, Potassium channel subfamily K member 7, Potassium channel subfamily K member 9, Potassium channel tetramerisation domain containing 3, Potassium channel tetramerisation domain containing protein 12, Potassium channel tetramerisation domain containing protein 14, Potassium channel tetramerisation domain containing protein 2, Potassium channel tetramerisation domain containing protein 4, Potassium channel tetramerisation domain containing protein 5, Potassium channel tetramerization domain containing 10, Potassium channel tetramerization domain containing protein 13, Potassium channel tetramerization domain-containing 1, Potassium voltage-gated channel subfamily A member 1, Potassium voltage-gated channel subfamily A member 2, Potassium voltage-gated channel subfamily A member 4, Potassium voltage-gated channel subfamily A member 5, Potassium voltage-gated channel subfamily A member 6, Potassium voltage-gated channel subfamily B member 1, Potassium voltage-gated channel subfamily B member 2, Potassium voltage-gated channel subfamily C member 1, Potassium voltage-gated channel subfamily C member 3, Potassium voltage-gated channel subfamily C member 4, Potassium voltage-gated channel subfamily D member 1, Potassium voltage-gated channel subfamily D member 2, Potassium voltage-gated channel subfamily D member 3, Potassium voltage-gated channel subfamily E member 1, Potassium voltage-gated channel subfamily E member 2, Potassium voltage-gated channel subfamily E member 3, Potassium voltage-gated channel subfamily E member 4, Potassium voltage-gated channel subfamily F member 1, Potassium voltage-gated channel subfamily G member 1, Potassium voltage-gated channel subfamily G member 2, Potassium voltage-gated channel subfamily G member 3, Potassium voltage-gated channel subfamily G member 4, Potassium voltage-gated channel subfamily H member 1, Potassium voltage-gated channel subfamily H member 2, Potassium voltage-gated channel subfamily H member 3, Potassium voltage-gated channel subfamily H member 4, Potassium voltage-gated channel subfamily H member 5, Potassium voltage-gated channel subfamily H member 6, Potassium voltage-gated channel subfamily H member 7, Potassium voltage-gated channel subfamily H member 8, Potassium voltage-gated channel subfamily KQT member 1, Potassium voltage-gated channel subfamily KQT member 2, Potassium voltage-gated channel subfamily KQT member 3, Potassium voltage-gated channel subfamily KQT member 4, Potassium voltage-gated channel subfamily KQT member 5, Potassium voltage-gated channel subfamily S member 1, Potassium voltage-gated channel subfamily S member 2, Potassium voltage-gated channel subfamily S member 3, Potassium voltage-gated channel subfamily V member 2, Potassium voltage-gated channel, subfamily H, member 7, isoform 2, Potassium/sodium hyperpolarization-activated cyclic nucleotide-gated channel 1, Potassium/sodium hyperpolarization-activated cyclic nucleotide-gated channel 2, Potassium/sodium hyperpolarization-activated cyclic nucleotide-gated channel 3, Potassium/sodium hyperpolarization-activated cyclic nucleotide-gated channel 4, Probable mitochondrial import receptor subunit TOM40 homolog, Purinergic receptor P2X5, isoform A, Putative 4 repeat voltage-gated ion channel, Putative chloride channel protein 7, Putative GluR6 kainate receptor, Putative ion channel protein CATSPER2 variant 1, Putative ion channel protein CATSPER2 variant 2, Putative ion channel protein CATSPER2 variant 3, Putative regulator of potassium channels protein variant 1, Putative tyrosine-protein phosphatase TPTE, Ryanodine receptor 1, Ryanodine receptor 2, Ryanodine receptor 3, SH3KBP1 binding protein 1, Short transient receptor potential channel 1, Short transient receptor potential channel 4, Short transient receptor potential channel 5, Short transient receptor potential channel 6, Short transient receptor potential channel 7, Small conductance calcium-activated potassium channel protein 1, Small conductance calcium-activated potassium channel protein 2, isoform b, Small conductance calcium-activated potassium channel protein 3, isoform b, Small-conductance calcium-activated potassium channel SK2, Small-conductance calcium-activated potassium channel SK3, Sodium channel, Sodium channel beta-1 subunit precursor, Sodium channel protein type II alpha subunit, Sodium channel protein type III alpha subunit, Sodium channel protein type IV alpha subunit, Sodium channel protein type IX alpha subunit, Sodium channel protein type V alpha subunit, Sodium channel protein type VII alpha subunit, Sodium channel protein type VIII alpha subunit, Sodium channel protein type X alpha subunit, Sodium channel protein type XI alpha subunit, Sodium- and chloride-activated ATP-sensitive potassium channel, Sodium/potassium-transporting ATPase gamma chain, Sperm-associated cation channel 1, Sperm-associated cation channel 2, isoform 4, Syntaxin-1B1, Transient receptor potential cation channel subfamily A member 1, Transient receptor potential cation channel subfamily M member 2, Transient receptor potential cation channel subfamily M member 3, Transient receptor potential cation channel subfamily M member 6, Transient receptor potential cation channel subfamily M member 7, Transient receptor potential cation channel subfamily V member 1, Transient receptor potential cation channel subfamily V member 2, Transient receptor potential cation channel subfamily V member 3, Transient receptor potential cation channel subfamily V member 4, Transient receptor potential cation channel subfamily V member 5, Transient receptor potential cation channel subfamily V member 6, Transient receptor potential channel 4 epsilon splice variant, Transient receptor potential channel 4 zeta splice variant, Transient receptor potential channel 7 gamma splice variant, Tumor necrosis factor, alpha-induced protein 1, endothelial, Two-pore calcium channel protein 2, VDAC4 protein, Voltage gated potassium channel Kv3.2b, Voltage gated sodium channel beta1B subunit, Voltage-dependent anion channel, Voltage-dependent anion channel 2, Voltage-dependent anion-selective channel protein 1, Voltage-dependent anion-selective channel protein 2, Voltage-dependent anion-selective channel protein 3, Voltage-dependent calcium channel gamma-1 subunit, Voltage-dependent calcium channel gamma-2 subunit, Voltage-dependent calcium channel gamma-3 subunit, Voltage-dependent calcium channel gamma-4 subunit, Voltage-dependent calcium channel gamma-5 subunit, Voltage-dependent calcium channel gamma-6 subunit, Voltage-dependent calcium channel gamma-7 subunit, Voltage-dependent calcium channel gamma-8 subunit, Voltage-dependent L-type calcium channel alpha-1C subunit, Voltage-dependent L-type calcium channel alpha-1D subunit, Voltage-dependent L-type calcium channel alpha-1S subunit, Voltage-dependent L-type calcium channel beta-1 subunit, Voltage-dependent L-type calcium channel beta-2 subunit, Voltage-dependent L-type calcium channel beta-3 subunit, Voltage-dependent L-type calcium channel beta-4 subunit, Voltage-dependent N-type calcium channel alpha-1B subunit, Voltage-dependent P/Q-type calcium channel alpha-1A subunit, Voltage-dependent R-type calcium channel alpha-1E subunit, Voltage-dependent T-type calcium channel alpha-1G subunit, Voltage-dependent T-type calcium channel alpha-1H subunit, Voltage-dependent T-type calcium channel alpha-11 subunit, Voltage-gated L-type calcium channel alpha-1 subunit, Voltage-gated potassium channel beta-1 subunit, Voltage-gated potassium channel beta-2 subunit, Voltage-gated potassium channel beta-3 subunit, Voltage-gated potassium channel KCNA7.

Exemplary GPCRs include but are not limited to Class A Rhodopsin like receptors such as Musc. acetylcholine Vertebrate type 1, Musc. acetylcholine Vertebrate type 2, Musc. acetylcholine Vertebrate type 3, Musc. acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykinin, C5a anaphylatoxin, Fmet-leu-phe, APJ like, Interleukin-8 type A, Interleukin-8 type B, Interleukin-8 type others, C—C Chemokine type 1 through type 11 and other types, C—X—C Chemokine (types 2 through 6 and others), C—X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPR10), Neuropeptide Y (type 1 through 7), Neuropeptide Y, Neuropeptide Y other, Neurotensin, Opioid (type D, K, M, X), Somatostatin (type 1 through 5), Tachykinin (Substance P (NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF, QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory II fam 1 through 13), Prostaglandin (prostaglandin E2 subtype EP1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY1-4,6,11 GPR91, Purinoceptor P2RY5,8,9,10 GPR35,92,174, Purinoceptor P2RY12-14 GPR87 (UDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg-4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas protooncogene & Mas-related (MRGs), GPR45 like, Cysteinyl leukotriene, G-protein coupled bile acid receptor, Free fatty acid receptor (GP40, GP41, GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAT), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GABA-B subtype 1, GABA-B subtype 2, GABA-B like, Orphan GPRC5, Orphan GPCR6, Bride of sevenless proteins (BOSS), Taste receptors (T1R), Class D Fungal pheromone, Fungal pheromone A-Factor like (STE2, STE3), Fungal pheromone B like (BAR, BBR, RCB, PRA), Class E cAMP receptors, Ocular albinism proteins, Frizzled/Smoothened family, frizzled Group A (Fz 1&2&4&5&7-9), frizzled Group B (Fz 3 & 6), frizzled Group C (other), Vomeronasal receptors, Nematode chemoreceptors, Insect odorant receptors, and Class Z Archaeal/bacterial/fungal opsins.

The subject MURPs can be designed to target any cellular proteins including but not limited to cell surface protein, secreted protein, cytosolic protein, and nuclear protein. A target of particular interest is an ion channel.

Ion channels constitute a superfamily of proteins, including the family of potassium channels (K-channels), the family of sodium channels (Na-channels), the family of calcium channels (Ca-channels), the family of Chlorine channels (Cl-channels) and the family of acetylcholine channels. Each of these families contains subfamilies and each subfamily typically contains specific channels derived from single genes. For example, the K-channel family contains subfamilies of voltage-gated K-channels called Kv1.x and Kv3.x. The subfamily Kv 1.x contains the channels Kv1.1, Kv1.2 and Kv1.3, which correspond to the products of single genes and are thus called 'species'. The classification applies to the Na—, Ca—, Cl— and other families of channels as well.

Ion channels can also be classified according to the mechanisms by which the channels are operated. Specifically, the main types of ion channel proteins are characterized by the method employed to open or close the channel protein to either permit or prevent specific ions from permeating the channel protein and crossing a lipid bilayer cellular membrane. One important type of channel protein is the voltage-gated channel protein, which is opened or closed (gated) in response to changes in electrical potential across the cell membrane. The voltage-gated sodium channel 1.6 (Nav1.6) is of particular interest as a therapeutic target. Another type of ion channel protein is the mechanically gated channel, for which a mechanical stress on the protein opens or closes the channel. Still another type is called a ligand-gated channel, which opens or closes depending on whether a particular ligand is bound to the protein. The ligand can be either an extracellular moiety, such as a neurotransmitter, or an intracellular moiety, such as an ion or nucleotide.

Ion channels generally permit passive flow of ions down an electrochemical gradient, whereas ion pumps use ATP to transport against a gradient. Coupled transporters, both antiporters and symporters, allow movement of one ion species against its gradient, powered by the downhill movement of another ion species.

One of the most common types of channel proteins, found in the membrane of almost all animal cells, permits the specific permeation of potassium ions across a cell membrane. In particular, potassium ions permeate rapidly across cell membranes through K$^+$ channel proteins (up to $10^{-8}$ ions per second). Moreover, potassium channel proteins have the ability to distinguish among potassium ions, and other small alkali metal ions, such as Li$^+$ or Na$^+$ with great fidelity. In particular, potassium ions are at least ten thousand times more permanent than sodium ions. Potassium channel proteins typically comprise four (usually identical) subunits, so their cell surface targets are present as tetramers, allowing tetravalent binding of MURPs. One type of subunit contains six long hydrophobic segments (which can be membrane-spanning), while the other types contains two hydrophobic segments.

Another significant family of channels is calcium channel. Calcium channels are generally classified according to their electrophysiological properties as Low-voltage-activated (LVA) or High-voltage-activated (HVA) channels. HVA channels comprises at least three groups of channels, known as L-, N- and P/Q-type channels. These channels have been distinguished one from another electrophysiologically as well as bio-chemically on the basis of their pharmacology and ligand binding properties. For instance, dihydropyridines, diphenyl-alkylamines and piperidines bind to the $\alpha_1$ subunit of the L-type calcium channel and block a proportion of HVA calcium currents in neuronal tissue, which are termed L-type calcium currents. N-type calcium channels are sensitive to omega conopeptides, but are relatively insensitive to dihydropyridine compounds, such as nimodipine and nifedipine. P/Q-type channels, on the other hand, are insensitive to dihydropyridines, but are sensitive to the funnel web spider toxin Aga IIIA. R-type calcium channels, like L-, N-, P- and Q-type channels, are activated by large membrane depolarization, and are thus classified as high voltage-activated (HVA) channels. R-type channels are generally insensitive to dihydropyridines and omega conopeptides, but, like P/Q, L and N channels, are sensitive to the funnel web spider toxin AgaIVA. Immunocytochemical staining studies indicate that these channels are located throughout the brain, particularly in deep midline structures (caudate-putamen, thalamus, hypothalamus, amygdala, cerebellum) and in the nuclei of the ventral midbrain and brainstem. Neuronal voltage-sensitive calcium channels typically consists of a central $\alpha_1$. subunit, an $\alpha_2/\delta$ subunit, a $\beta$ subunit and a 95 kD subunit.

Additional non-limiting examples include Kir (an inwardly rectified potassium channel), Kv (a voltage-gated potassium channel), Nav (a voltage-gated sodium channel), Cav (a voltage-gated calcium channel), CNG (cyclic nucleotide-gated channel), HCN (hyperpolarization-activated channel), TRP (a transient receptor potential channel), ClC (a chloride channel), CFTR (a cystic fibrosis transmembrane conductance regulator, a chloride channel), IP3R (a inositol trisphosphate receptor), RYR (a ryanodine receptor). Other channel types are 2-pore channels, glutamate-receptors (AMPA, NMDA, KA), M2, Connexins and Cys-loop receptors.

A common layout for ion channel proteins, such as Kv1.2, Kv3.1, Shaker, TRPC1 and TRPC5 is to have six membrane-spanning segments, arranged as follows:

N-terminus-S1-E1-S2-X1-S3-E2-S4-X2-S5-E3-S6-C-terminus

Wherein S1-6 are membrane-spanning sequences, E1-3 are extracellular surface loops and X1-2 are intracellular surface loops. The E3 loop is generally the longest of the three extracellular loops and is hydrophilic so it is a good target for drugs and MURPs to bind. The pore-forming part of most channels is a multimeric (e.g. tetrameric or rarely pentameric) complex of membrane-spanning alpha-helices. There is generally a pore loop, which is a region of the protein that loops back into the membrane to form the selectivity filter that determines which ion species can permeate. Such channels are called 'pore-loop' channels.

The ion channels are valuable targets for drug design because they are involved in a broad range of physiological processes. In human, there exist approximately over three hundreds of ion channel proteins, many of which have been implicated in genetic diseases. For example, abbrebrant expression or function of ion channels has been shown to cause a wide arrange of diseases including cardiac, neuronal, muscular, respiratory metabolic diseases. This section focuses on ion channels, but the same concepts and approaches are equally applicable to all membrane proteins, including 7TMs, 1TMs, G-proteins and G-Protein Coupled receptors (GPCRs), etc. Some of the ion channels are GPCRs.

Ion channels typically form large macromolecular complexes that include tightly bound accessory protein subunits and combinatorial use of such subunits contributes to the diversity of ion channels. These accessory proteins can also be the binding targets of the subject MURPs, microproteins and toxins.

The subject MURPs can be designed to bind any of the channels known in the art and to those specifically exemplified herein. MURPs exhibiting a desired ion channel binding capability (encompassing specificity and avidity) can be selected by any recombinant and biochemical (e.g. expression and display) techniques known in the art. For instance, MURPs can be displayed by a genetic package including but not limited to phages and spores, and be subjected to panning against intact cell membranes, or preferably intact cells such as whole mammalian cells. To remove the phage that bind to the other, non-target cell surface molecules, the standard approach was to perform subtraction panning against similar cell lines that had a low or non-detectable level of the target receptor. However, Popkov et al. (J. Immunol. Methods 291:137-151 (2004))

showed that related cell types are not ideal for subtraction because they generally have a reduced but still significant level of the target on their surface, which reduces the number of desired phage clones. This problem occurs even when panning on cells that have been transfected with the gene encoding the target, followed by negative selection/subtraction on the same cell-line which was not transfected, especially when the native target gene was not knocked out. Instead, Popkov et al. showed that the negative selection or subtraction panning works much better if performed with an excess of the same cells that are used for normal panning (positive selection), except that the target has now been blocked with a high-affinity, target-specific inhibitor, such as a small molecule, peptide or an antibody to the target, which makes the active site unavailable. This process is called "negative selection with epitope-masked cells", which is particularly useful in selecting the subject MURPs with a desired ion-channel binding capability.

In a separate embodiment, the present invention provides microproteins, and particularly microproteins exhibiting binding capability towards at least one family of ion channels. The present invention also provides a genetic package displaying such microproteins. Non-limiting ion-channel examples to which the subject microproteins bind are sodium, potassium, calcium, acetylcholine, and chlorine channels. Of particular interest are those microproteins and the genetic packages displaying such microproteins, which exhibit binding capability towards native targets. Native targets are generally natural molecules or fragments, derivatives thereof that the microprotein is known to bind, typically including those known binding targets that have been reported in the literature.

The subject invention also provides a genetic package displaying an ion-channel-binding microprotein which has been modified. The modified microprotein may (a) binds to a different family of channel as compared to the corresponding unmodified microprotein; (b) binds to a different subfamily of the same channel family as compared to the corresponding unmodified microprotein; (c) binds to a different species of the same subfamily of channel as compared to the corresponding unmodified microprotein; (d) the microprotein binds to a different site on the same channel as compared to the corresponding unmodified microprotein; and/or (e) binds to the same site of the same channel but yield a different biological effect as compared to the corresponding unmodified microprotein.

FIGS. 22 and 46 show how microprotein domains or toxins that each bind at different sites of the same ion channel can be combined into a single protein. The two binding sites that these two microproteins bind to can be on two channels from different families, two channels from the same family but a different subfamily, two channels from the same subfamily but a different species (gene product), or two different binding sites on the same channel (species) or they can (simultaneously or not) bind the same binding site on the same channel (species) since the channels are multimeric. The binding modules and domains that bind to sites on the channels can be microprotein domains (natural or non-natural, 2- to 8-disulfide containing), one-disulfide peptides, or linear peptides. These modules can be selected independently and combined, or one can be selected from a library to bind in the presence of one fixed, active binding module. In the latter case, the display library would display multiple modules of which one would contain a library of variants. A typical goal is to select a dimer from this library that has a higher affinity than the active monomer that was the starting point.

In another embodiment, the present invention provides a protein comprising a plurality of ion-channel binding domains, wherein individual domains are microprotein domains that have been modified such that (a) the microprotein domains bind to a different family of channel as compared to the corresponding unmodified microprotein domains; (b) the microprotein domains bind to a different subfamily of the same channel family as compared to the corresponding unmodified microprotein domains; (c) the microprotein domains bind to a different species of the same subfamily as compared to the corresponding unmodified microprotein domains; (d) the microprotein domains bind to a different site on the same channel as compared to the corresponding unmodified microprotein domains; (e) the microprotein domains bind to the same site of the same channel but yield a different biological effect as compared to the corresponding unmodified microprotein domains; and/or (f) the microprotein domains bind to the same site of the same channel and yield the same biological effect as compared to the corresponding unmodified microprotein domains Where desired, the microprotein domains may comprise natural or non-natural sequences. The individual domains can be linked together via a heterologous linker. The individual microprotein domains can bind to the same or different channel family, same or different channel subfamily, same or different species of the same subfamily, same or different site on the same channel.

The subject microproteins can be a toxin. Preferably, the toxin retains in part or in whole its toxicity spectrum. In particular, venomous animals, such as snakes, encounter a range of prey and intruder species and the venom toxins differ in activity for the different receptors of the different species. The venom consists of a large number of related and unrelated toxins, with each toxin having a "spectrum of activity", which can be defined as all of the receptors from all of the species on which that toxin has measurable activity. All of the targets in the 'spectrum of activity' are considered "native targets" and this includes any human targets that the toxin is active against. The native target(s) of a microprotein or toxin include all of the targets that the toxin is reported to inhibit in the literature. The higher the affinity or activity on a target, the more likely that target is the natural, native target, but it is not uncommon for toxins to act on multiple targets within the same species. Native target(s) can be human or non-human receptors that the toxin is active against.

For the toxin to retain the ability to bind to cells after fusion to the display vector, it may be desirable to test both the N-terminus and C-terminus for fusion and to test a variety of fusion sites (i.e., 0, 1, 2, 3, 4, 5, 6 amino acids before the first cysteine or after the last cysteine of the toxin domain, if the toxin domain is a cystein-containing domain) using a synthetic DNA library approach, preferably encoding a library of glycine-rich linkers, which form the smallest amino acid chain, are uncharged and are most likely to be compatible with binding of the toxin to the target. Since the N-terminal amino group and the C-terminal carboxyl groups may be involved in target binding, the library should contain a lysine or a arginine to mimic the positively charged amino group (or fusions to the N-terminus of the toxin) and a glutamate or an aspartate to mimic the negatively charged carboxyl group (for fusions to the C-terminus of the toxin).

The inhibitor(s) that are used to block the target during negative selection can be small molecules, peptides or proteins, and natural or non-natural. In addition to simple subtraction, the choice of the mixture of inhibitors is a valuable tool to control the specificity of the ion channel inhibitors that are being designed. Because there are over three hundreds ion channels in total, with partially overlapping specificities and sequence similarities, and multiple modulatory sites per channel, each having a different effect, the specificity requirement can be complex.

When modifying the activity of a toxin, or when combining two different toxins into a single protein, the two toxins can bind the same channel at the same site and have the same physiologic effect, or the two toxins can bind the same channel at the same site and have a different physiologic effect, or the two toxins can bind to the same channel at a different site, or the two toxins can bind to different channels that belong to the same subfamily (i.e. Kv1.3 and Kv1.2; meaning product of a different gene or 'species'), or the two toxins can bind to different channels that belong to the same family (i.e. both are K-channels), or the two toxins can bind to channels that belong to different families (i.e. K-channels versus Na-channels).

Ion channels typically have many transmembrane segments (24 for sodium channels) and thus offer a number of different, non-competing and non-overlapping binding sites for modulators to alter the activity of the channel in different ways. One approach is to create binders for one site on the same ion channel from existing binders for a different site, even if these sites are unrelated. To achieve this, the existing toxin can be used as a targeting agent for a library of 1-,2-,3-, or 4-disulfide proteins that is separated from the targeting toxin by a flexible linker of 5, 6, 7, 8, 9, 10, 12, 14, 16, 18, 20, 25, 30, 35, 40 or 50 amino acids. It is useful if the affinity of the targeting agent is not too high, so that the affinity of the new library can have a significant contribution to the overall affinity. Another approach is to create new modulators for channels from existing modulators for other channels that are related in sequence or in structure. The conotoxin family, for example, contains sequence-related and structure-related modulators for Ca—, K, Na-channels and nicotinic acetylcholine receptors. It appears feasible to convert a K-channel modulator into a Na-channel modulator using a library of conotoxin-derivatives, or vice versa. For example, Kappa-conotoxins inhibit K-channels, Mu-conotoxins and Delta-conotoxins inhibit Na-channels, Omega-conotoxins inhibit Ca-channels and Alpha-conotoxins inhibit acetylcholine receptors.

The proximity of different binding sites, each with a different effect on channel activity, from the same ion channel makes it attractive to link the inhibitors using flexible linkers, creating a single inhibitor with two domains, each binding at a different site. Or a single protein with two domains that bind at different copies of the same site, yielding a bivalent, high affinity interaction (avidity). This approach has not been taken by natural toxins, presumably because they must act fast and thus stay small in order to have maximal tissue penetration, but for pharmaceuticals the speed of action is less important, making this is an attractive approach.

One can thus create combinatorial libraries of dimeric, trimeric, tetrameric or multimeric toxins/modulators, each native or modified, and directly screen these libraries at the protein level or pan these libraries using genetic packages for improved affinity (avidity, if binding occurs simultaneously at multiple sites) and then characterize the specificity and activity of such multimeric clones by protein expression and purification followed by cell-based activity assays, including patch-clamp assays. The individual modules can be panned and selected separately, in isolation of each other, or they can be designed in each other's presence, such that the new domain is added to a display system as a library that also contain a fixed, active copy that serves as a targeting element for the library and only clones that are significantly better than the fixed, active monomer are selected and characterized.

FIGS. 46 and 47 show some of the monomeric derivatives that can be made from native (natural) toxins, and some of the multimers that can be made to bind at multiple different binding sites of the target. The linkers are shown as glycine-rich rPEG, but the linkers could be any sequence and could also be optimized using molecular libraries followed by panning One can create libraries inside the active, native toxin itself, using a variety of mutagenesis strategies as describes above, or one can expand the existing area of contact with the target by creating libraries on the N-terminal or C-terminal side of the active toxin, hoping to create additional contacts with the target. Such libraries can be based on existing toxins with known activity for that site, or they can be or naive 1-, 2-, 3-, 4-disulfide libraries based on unrelated microprotein scaffolds. These additional contact elements can be added on one or both sides of the active domains, and can be directly adjacent to the existing modulatory domain or they can be separated from it by flexible linkers. The initial multimer or the final, improved multimer can be a homomultimer or a heteromultimer, based on sequence similarity of the domains or based on target specificity of the domains of the multimer. Thus, the monomers that comprise the multimer may bind to the same target sites but have the same or different sequences. With 10-100 different native toxins that are known to bind to each family of channels, and with 2, 3, 4, 5 or 6 domains per clone, display libraries with a huge combinatorial diversity can be created even if one only uses native toxin sequences. Low level synthetic mutagenesis based on amino acid similarity or on phylogenetic substitution rates within the family can be used to create high quality libraries of mutants, of which a very high fraction is expected to retain function, with a high probability of enhanced function in some of the properties of interest.

The binding capability of the subject MURPs, microproteins, or toxins to a given ion channel can be measured in terms of Hill Coefficient. Hill Coefficient indicates the stoichiometry of the binding interaction. A Hill coefficient of 2 indicates that 2 inhibitors bind to each channel. One can also assess the allosteric modulation, which is modulation of activity at one site caused by binding at a distant site.

The biological activity or effect of an ion channel and the ability of the subject MURPs, microproteins or toxins to regulate an ion channel activity can be assessed using a variety of in vitro and in vivo assays. For instance, methods are available in the art for measuring voltage, measuring current, measuring membrane potential, measuring ion flux, e.g., potassium or rubidium, measuring ion concentration, measuring gating, measuring second messengers and transcription levels, and using e.g., voltage-sensitive dyes, radioactive tracers, and patch-clamp electrophysiology. In particular such assays can be used to test for microproteins and toxins that can inhibit or activate an ion channel of interest.

Specifically, potential channel inhibitors or activators can be tested in comparison to a suitable control to examine the extent of modulation. Control samples can also be samples untreated with the candidate activators or inhibitors. Inhibition is present when a given ion channel activity value relative to the control is about 90%, 80%, 70%, 60%, 50%, 40%, 30%, 20%, 10%, or even less. IC50 is a commonly used unit (the concentration of inhibitor that reduces the ion channel's activity by 50%) for determining the inhibitory effect. Similar for IC90. Activation of channels is achieved when the select a given ion channel activity value relative to the control is increased by 10%, 20%, 30%, 40%, 50%, 60%, 70%, 80%, 90%, 100%, 200%, 500%, or more.

Changes in ion flux may be assessed by determining changes in polarization (i.e., electrical potential) of the cell or membrane expressing the channel of interest. For instance, one method is to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., New Engl. J. Med. 336:1575-1595 (1997)). Whole cell currents are conveniently determined using the standard methodology (see, e.g., Hamil et al., Pflugers. Archiv. 391:85 (1981). Other known assays include: radio-labeled rubidium flux assays and fluorescence assays using voltage-sensitive dyes (see, e.g., Vestergarrd-Bogind et al., J. Membrane Biol. 88:67-75 (1988); Daniel et al., J. Pharmacol. Meth. 25:185-193 (1991); Holevinsky et al., J. Membrane Biology 137:59-70 (1994)).

The effects of the candidate MURPs, microproteins, or toxins upon the function of a channel of interest can be measured by changes in the electrical currents or ionic flux or by the consequences of changes in currents and flux. The downstream effect of the candidate proteins on ion flux can be varied. Accordingly, any suitable physiological change can be used to assess the influence of a candidate protein on the test channels. The effects of candidate protein can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$.

Other key biological activities of ion channels are ion selectivity and gating. Selectivity is the ability of some channels to discriminate between ion species, allowing some to pass through the pore while excluding others. Gating is the transition between open and closed states. They can be assessed by any of the methods known in the art or disclosed herein Yet another biological property that the subject MURP, microprotein, or toxin can be selected for is the frequency of opening and closing of the target channels, called Gating Frequency. Gating Frequency is influenced by voltage (in voltage gated channels, which are opened or closed by changes in membrane voltage) and ligand-binding. The transition rate between open and closed states is typically <10 microseconds but can be increased or decreased by other molecules. The flux rate (current) through the pore when it is open is on the order of 10e7 ions per second for ion channels and much less for coupled exchangers. Following opening, some voltage-gated channels enter an inactivated, non-conducting state in which they are refractory to depolarization.

EXAMPLES

Example

Design of a Glycine-Serine Oligomer Based on Human Sequences

The human genome database was searched for sequences that are rich in glycine. Three sequences were identified as suitable donor sequences as shown in Table 5.

TABLE 5

Donor sequences for GRS design A.

| Accession | Sequences | SEQ ID NO: | Amino acid | Protein |
|---|---|---|---|---|
| NP_009060 | GGGSGGGSGSGGGG | 103 | 486-499 | zinc finger protein |
| Q9Y2X9 | GSGSGGGSGG | 104 | 19-31 | zinc finger protein |
| CAG38801 | SGGGGSGGGSGSG | 105 | 7-19 | MAP2K4 |

Based on the sequences in Table 5 we designed a glycine rich sequence that contains multiple repeats of the peptide A with sequence GGGSGSGGGGS (SEQ ID NO: 106). Peptide A can be oligomerized to form structures with the formula (GGGSGSGGGGS)n (SEQ ID NO: 107) where n is between 2 and 40. FIG. 5 shows that all possible 9mer subsequences in oligomers of peptide A are contained in at least one of the proteins listed in Table 3. Thus oligomers of peptide A do not contain human T cell epitopes. Inspection of FIG. 5 reveals that GRS based on oligomers of peptide A can begin and end at any of the positions of peptide A.

Example

Design of Glycine-proline Oligomer Based on Human Sequences

Glycine rich sequences were designed based on sequence GPGGGGGPGGGGGPGGGGPGGGGGGGPGGGGG-PGGG (SEQ ID NO: 108), which represents amino acids 146-182 of the human class 4 POU domain with accession number NP_006228. FIG. 6 illustrates that oligomers of peptide B with sequence GGGGGPGGGGP (SEQ ID NO: 109) can be utilized as GRS. All 9mer subsequences that are contained in peptides with the sequence (GGGGG-PGGGGP)$_n$ (SEQ ID NO: 109) are also contained in the sequence of the POU domain. Thus, such oligomeric sequences do not contain T cell epitopes.

Example

Design of Glycine-glutamic Acid Oligomer

Glycine rich sequences can be designed based on the subsequence GAGGEGGGGEGGGPGG (SEQ ID NO: 110) that is part of the ribosomal protein S6 kinase (accession number BAD92170). For instance, oligomers of peptide C with the sequence GGGGE (SEQ ID NO: 111) will form sequences where most 9mer subsequences will be contained in the sequence of ribosomal protein S6 kinase. Thus, oligomeric GRS of the general structure (GGGGE)$_n$ (SEQ ID NO: 111) bear a very low risk of containing T cell epitopes.

Example

Identification of Human Hydrophilic Glycine-rich Sequences

A data base of human proteins was searched for subsequences that are rich in glycine residues. These subsequences contained at least 50% glycine. Only the following non-glycine residues were allowed to occur in the GRS: ADEHKPRST. 70 subsequences were identified that had a minimum length of 20 amino acids. These subsequences are listed in appendix A. They can be utilized to construct GRS with low immunogenic potential in humans.

Example

Construction of rPEG_J288

The following example describes the construction of a codon optimized gene encoding a URP sequence with 288 amino acids and the sequence $(GSGGEG)_{48}$ (SEQ ID NO: 113). First we constructed a stuffer vector pCW0051 as illustrated in FIG. 40. The sequence of the expression cassette in pCW0051 is shown in FIG. 42. The stuffer vector was based on a pET vector and includes a T7 promoter. The vector encodes a Flag sequence followed by a stuffer sequence that is flanked by BsaI, BbsI, and KpnI sites. The BsaI and BbsI sites were inserted such that they generate compatible overhangs after digestion as illustrated in FIG. 42. The stuffer sequence was followed by a $His_6$ tag (SEQ ID NO: 97) and the gene of green fluorescent protein (GFP). The stuffer sequence contains stop codons and thus *E. coli* cells carrying the stuffer plasmid pCW0051 formed non-fluorescent colonies. The stuffer vector pCW0051 was digested with BsaI and KpnI. A codon library encoding URP sequences of 36 amino acid length was constructed as shown in FIG. 41. The URP sequence was designated rPEG_J36 and had the amino acid sequence $(GSGGEG)_6$ (SEQ ID NO: 114). The insert was obtained by annealing synthetic oligonucleotide pairs encoding the amino acid sequence GSGGEGGSGGEG (SEQ ID NO: 115) as well as a pair of oligonucleotides that encode an adaptor to the KpnI site. The following oligonucleotides were used: pr_LCW0057for: AGGTAGTGGWGGWGARGGWGGWTCYGGWGGA-GAAGG (SEQ ID NO: 116), pr_LCW0057rev: ACCTCCTTCTCCWCCRGAWCCWCCYTCWCCWC-CACT (SEQ ID NO: 117), pr_3KpnIstopperFor: AGGT-TCGTCTTCACTCGAGGGTAC (SEQ ID NO: 118), pr_3KpnIstopperRev: CCTCGAGTGAAGACGA (SEQ ID NO: 119). The annealed oligonucleotide pairs were ligated, which resulted in a mixture of products with varying length that represents the varying number of rPEG_J12 repeats. The product corresponding to the length of rPEG_J36 was isolated from the mixture by agarose gel electrophoresis and ligated into the BsaI/KpnI digested stuffer vector pCW0051. Most of the clones in the resulting library designated LCW0057 showed green fluorescence after induction which shows that the sequence of rPEG_J36 had been ligated in frame with the GFP gene. The process of screening and iterative multimerization of rPEG_J36 sequences is illustrated in FIG. 14. We screened 288 isolates from library LCW0057 for high level of fluorescence. 48 isolates with strong fluorescence were analyzed by PCR to verify the length of the rPEG_J segment and 16 clones were identified that had the expected length of rPEG_J36. This process resulted in a collection of 16 isolates of rPEG_J36, which show high expression and which differ in their codon usage. The isolates were pooled and dimerized using a process outlined in FIG. 40. A plasmid mixture was digested with BsaI/NcoI and a fragment comprising the rPEG_J36 sequence and a part of GFP was isolated. The same plasmid mixture was also digested with BbsI/NcoI and the vector fragment comprising rPEG_J36, most of the plasmid vector, and the remainder of the GFP gene was isolated. Both fragments were mixed, ligated, and transformed into BL21 and isolates were screened for fluorescence. This process of dimerization was repeated two more rounds as outlined in FIG. 14. During each round, we doubled the length of the rPEG_J gene and ultimately obtained a collection of genes that encode rPEG_J288. The amino acid and nucleotide sequence of rPEG_J288 is shown in FIG. 15. It can be seen that the rPEG_J288 module contains segments of rPEG_J36 that differ in their nucleotide sequence despite of having identical amino acid sequence. Thus we minimized internal homology in the gene and as a result we reduced the risk of spontaneous recombination. We cultured *E. coli* BL21 harboring plasmids encoding rPEG_J288 for at least 20 doublings and no spontaneous recombination was observed.

Example

Construction of rPEG_H288

A library of genes encoding a 288 amino acid URP termed rPEG_H288 was constructed using the same procedure that was used to construct rPEG_J288. rPEG_H288 has the amino acid sequence $(GSGGEGGSGGSG)_{24}$ (SEQ ID NO: 120). The flow chart of the construction process in shown in FIG. 14. The complete amino acid sequence as well as the nucleotide sequence of one isolate of rPEG_H288 as given in FIG. 16.

Example

Serum Stability of rPEG_J288

A fusion protein containing the an N-terminal Flag tag and the URP sequence rPEG_J288 fused to the N-terminus of green fluorescent protein was incubated in 50% mouse serum at 37 C for 3 days Samples were withdrawn at various time points and analyzed by SDS PAGE followed by detection using Western analysis. An antibody against the N-terminal flag tag was used for Western detection. Results are shown in FIG. 28, which indicate that a URP sequence of 288 amino acids can be completely stable in serum for at least three days.

Example

Absence of Pre-existing Antibodies to rPEG_J288 in Serum

Existence of antibodies against URP would be an indication of a potential immunogenic response to this glycine rich sequence. To test for the presence of existing antibodies in serum, an URP-GFP fusion was subjected to an ELISA by immobilizing URP-GFP on a support and subsequently incubating with 30% serum. The presence of antibodies bound to URP-GFP were detected using an anti-IgG-horse radish peroxidase antibody and substrate. The data are shown in FIG. 29. The data show, that the fusion protein can be detected by antibodies against GFP or Flag but not by murine serum. This indicates that murine serum does not contain antibodies that contain the URP sequence.

Example

Purification of a Fusion Protein Containing rPEG_J288

We purified a protein with the architecture Flag-rPEG_J288-H6-GFP. The protein was expressed in *E. coli*

BL21 in SB medium. Cultures were induced with 0.5 mM IPTG overnight at 18 C. Cells were harvested by centrifugation. The pellet was re-suspended in TBS buffer containing benzonase and a commercial protease inhibitor cocktail. The suspension was heated for 10 min at 75 C in a water bath to lyze the cells. Insoluble material was removed by centrifugation. The supernatant was purified using immobilized metal ion specificity (IMAC) followed by a column with immobilized anti-Flag antibody. FIG. 43 shows PAGE analysis of the purification process. The process yielded protein with at least 90% purity.

Example

Construction of Fusion Protein Between rPEG_J288 and Interferon-alpha

A gene encoding human interferon alpha was designed using codon optimization for *E. coli* expression. The synthetic gene was fused with a gene encoding rPEG_J288. A His6 tag (SEQ ID NO: 97) was placed at the N-terminus to facilitate detection and purification of the fusion protein. The amino acid sequence of the fusion protein is given in FIG. 44.

Example

Construction of rPEG_J288-G-CSF Fusion

A gene encoding human G-CSF was designed using codon optimization for *E. coli* expression. The synthetic gene was fused with a gene encoding rPEG_J288. A His6 tag (SEQ ID NO: 97) was placed at the N-terminus to facilitate detection and purification of the fusion protein. The amino acid sequence of the fusion protein is given in FIG. 44.

Example

Construction of rPEG_J288-hGH Fusion

A gene encoding human growth hormone was designed using codon optimization for *E. coli* expression. The synthetic gene was fused with a gene encoding rPEG_J288. A His6 tag (SEQ ID NO: 97) was placed at the N-terminus to facilitate detection and purification of the fusion protein. The amino acid sequence of the fusion protein is given in FIG. 44.

Example

Expression of Fusion Proteins Between rPEG_J288 and Human Proteins

The fusion proteins between rPEG_J288 and two human proteins, interferon-alpha and human growth hormone were cloned into a T7expression vector and transformed into *E. coli* BL21. The cells were grown at 37 C to an optical density of 0.5 OD. Subsequently, the cells were cultured at 18 C for 30 min Then 0.5 mM IPTG was added and the cultures were incubated in a shaking incubator at 18 C overnight. Cells were harvested by centrifugation and soluble protein was released using BugBuster (Novagen). Both, insoluble and soluble protein fractions were separated by SDS-PAGE and the fusion proteins were detected by Western using and antibody against the N-terminal His6 tag (SEQ ID NO: 97) for detection. FIG. 45 shows the Western analysis of the two fusion proteins as well as rPEG_J288-GFP as control. All fusion proteins were expressed and the majority of the protein was in the soluble fraction. This is evidence of the high solubility of rPEG_J288 because most attempts at expression of the interferon-alpha and human growth hormone in the cytosol of *E. coli*, that have been reported in the literature, resulted in the formation of insoluble inclusion bodies. FIG. 45 shows that the majority of fusion proteins are expressed as full length proteins, i.e. no fragments that would suggest incomplete synthesis or partial protein degradation were detected.

Example

Construction and Binding of aVEGF Multimer

Libraries of cysteine-constrained peptides were constructed as published [Scholle, M. D., et al. (2005) *Comb Chem High Throughput Screen,* 8: 545-51]. These libraries were panned against human VEGF and two binding modules were indentified consisting of amino acid sequences FTCTNHWCPS (SEQ ID NO: 121) or FQCTRHWCPI (SEQ ID NO: 122). Oligonucleotides encoding the amino acid sequence FTCTNHWCPS (SEQ ID NO: 121) were ligated to a nucleotide sequence encoding the URP sequence rPEG_A36 with the sequence $(GGS)_{12}$ (SEQ ID NO: 123). Subsequently, the fusion sequence was dimerized using restriction enzymes and ligation steps to construct a molecule that contains 4 copies of the VEGF binding module separated by rPEG_A36 fused to GFP. The VEGF binding affinity of fusion proteins containing between zero and four VEGF-binding units were compared in FIG. 30. A fusion protein containing only rPEG_A36 fused to GFP shows no affinity for VEGF. Adding increasing numbers of VEGF binding modules increases affinity of the resulting fusion proteins.

Example

Discovery of 1SS Binding Modules Against Therapeutic Targets

Random peptide libraries were generated according to Scholle, et al. [Scholle, M. D., et al. (2005) *Comb Chem High Throughput Screen,* 8: 545-51] The naïve peptide libraries displayed cysteine-constrained peptides with cysteines spaced by 4 to 10 random residues. The library design is illustrated in the table:

TABLE 6

| Naive 1SS libraries: | | | |
|---|---|---|---|
| LNG0001 | XXXCXXCXXX | $X_3CX_2CX_3$ | NNS NNS NNS TGC NNS NNS TGT NNS NNS NNS (SEQ ID NO: 124) |
| LNG0002 | XXCXXXCXXX | $X_2CX_3CX_3$ | NNS NNS TGC NNS NNS NNS TGT NNS NNS NNS (SEQ ID NO: 125) |

TABLE 6-continued

Naive 1SS libraries:

| ID | Pattern | Formula | Sequence |
|---|---|---|---|
| LNG0003 | XXCXXXXCXX | $X_2CX_4CX_2$ | NNS NNS TGC NNS NNS NNS NNS TGT NNS NNS (SEQ ID NO: 126) |
| LNG0004 | XCXXXXXCXX | $X_1CX_5CX_2$ | NNS TGC NNS NNS NNS NNS NNS TGT NNS NNS (SEQ ID NO: 127) |
| LNG0005 | XCXXXXXXCX | $X_1CX_6X_1$ | NNS TGC NNS NNS NNS NNS NNS NNS TGT NNS (SEQ ID NO: 128) |
| LNG0006 | CXXXXXXXCX | $CX_7CX_1$ | TGC NNS NNS NNS NNS NNS NNS NNS TGT NNS (SEQ ID NO: 129) |
| LNG0007 | CXXXXXXXXC | $CX_8C$ | TGC NNS NNS NNS NNS NNS NNS NNS NNS TGT (SEQ ID NO: 130) |
| LNG0008 | CXXXXXXXXXC | $CX_9C$ | TGC NNS NNS NNS NNS NNS NNS NNS NNS NNS TGT (SEQ ID NO: 131) |
| LNG0009 | CXXXXXXXXXXC | $CX_{10}C$ | TGC NNS NNS NNS NNS NNS NNS NNS NNS NNS NNS TGT (SEQ ID NO: 132) |
| LNG0010 | XXXXXXCXXCXXXXXX | $X_6CX_2CX_6$ | NNS NNS NNS NNS NNS NNS TGC NNS NNS TGT NNS NNS NNS NNS NNS (SEQ ID NO: 133) |
| LNG0011 | XXXXXCXXXCXXXXXX | $X_5CX_3CX_6$ | NNS NNS NNS NNS NNS TGC NNS NNS TGT NNS NNS NNS NNS NNS NNS (SEQ ID NO: 134) |
| LNG0012 | XXXXXCXXXXCXXXXX | $X_5CX_4CX_5$ | NNS NNS NNS NNS NNS TGC NNS NNS NNS TGT NNS NNS NNS NNS NNS (SEQ ID NO: 135) |
| LNG0013 | XXXXCXXXXXCXXXXX | $X_4CX_5CX_5$ | NNS NNS NNS NNS TGC NNS NNS NNS NNS TGT NNS NNS NNS NNS NNS (SEQ ID NO: 136) |
| LNG0014 | XXXXCXXXXXXCXXXX | $X_4CX_6CX_4$ | NNS NNS NNS NNS TGC NNS NNS NNS NNS NNS TGT NNS NNS NNS NNS (SEQ ID NO: 137) |
| LNG0015 | XXXCXXXXXXXCXXXX | $X_3CX_7CX_4$ | NNS NNS NNS TGC NNS NNS NNS NNS NNS NNS NNS TGT NNS NNS NNS (SEQ ID NO: 138) |
| LNG0016 | XXXCXXXXXXXXCXXX | $X_3CX_8CX_3$ | NNS NNS NNS TGC NNS NNS NNS NNS NNS NNS NNS NNS TGT NNS NNS NNS (SEQ ID NO: 139) |
| LNG0017 | XXCXXXXXXXXXCXXX | $X_2CX_9CX_3$ | NNS NNS TGC NNS NNS NNS NNS NNS NNS NNS NNS NNS TGT NNS NNS NNS (SEQ ID NO: 140) |
| LNG0018 | XXCXXXXXXXXXXCXX | $X_2CX_{10}CX_2$ | NNS NNS TGC NNS NNS NNS NNS NNS NNS NNS NNS NNS NNS TGT NNS NNS (SEQ ID NO: 141) |

The libraries were panned against a series of therapeutically relevant targets using the following protocol: Wells on immunosorbent ELISA plates were coated with 5 µg/ml of the target antigen in PBS overnight at 4° C. Coated plates were washed with PBS, and non-specific sites were blocked with Blocking Buffer (PBS containing either 0.5% BSA or 0.5% Ovalbumin) for 2 h at room temperature. The plates were then washed with PBST (PBS containing 0.05% Tween 20), and phage particles at 1-5×10$^{12}$/ml in Binding Buffer (Blocking Buffer containing 0.05% Tween 20) were added to the wells and incubated with shaking for 2 h at room temperature. Wells were then emptied and washed with PBST. Bound phage particles were eluted from the wells by incubation with 100 mM HCl for 10 min at room temperature, transferred to sterile tubes, and neutralized with 1M TRIS base. For infection, log phase *E. Coli* SS320 growing in Super Broth supplemented with 5µg/ml Tetracycline were added to the neutralized phage eluate, and the culture was incubated with shaking for 30min at 37° C. Infected cultures were then transferred to larger tubes containing Super Broth with 5 µg/ml Tetracycline and the cultures were incubated with shaking overnight at 37° C. The overnight cultures were cleared of *E. Coli* by centrifugation, and phage were precipitated from the supernatant following the addition of a solution of 20% PEG and 2.5MNaCl to a final PEG concentration of 4%. Precipitated phage were harvested by centrifugation, and the phage pellet was resuspended in 1 ml PBS, cleared of residual *E. Coli* by centrifugation, and transferred to a fresh tube. Phage concentrations were estimated spectrophotometrically and phage was utilized for the next round of selection. Individual clones were screened for target binding affinity after 3 or 4 rounds of phage panning. Individual plaques from phage clones selected during the panning were picked into Super Broth containing 5 μg/ml Tetracycline and grown overnight with shaking at 37° C. ELISA plates were prepared by coating antigen and control proteins (BSA, Ovalbumin, IgG) at 3 μg/ml in PBS overnight at 4° C. The plates were washed with PBS, and blocked with Blocking Buffer (PBS containing 0.5% BSA) for 2 h at room temperature. Overnight cultures were cleared of *E. coli* by centrifugation and the supernatant was diluted 1:10 in Binding Buffer (Blocking Buffer containing 0.05% Tween 20) and transferred to the ELISA plates after washing with PBST (PBS containing 0.05% Tween 20). The plates were incubated with shaking for 2 h at room temperature. Following washing with PBST, anti-M13-HRP (Pharmacia), 1:5000 dilution in PBS, was added to wells. The plates were incubated with shaking for 30 min at room temperature and washed with PBST, followed by PBS. A substrate solution containing 0.4 mg/ml ABTS and 0.001% $H_2O_2$ in 50 mM phosphate-citrate buffer was added to the wells, and allowed to develop for 40 min after which the plates were read in a plate reader at 405 nm. These ELISA readings allowed the determination of clone specificity, and antigen-specific clones were sequenced commercially via established methods.

TABLE 7

Sequences of EpCAM-specific binding modules

| Sequence | Clone | SEQ ID NO: |
|---|---|---|
| S Y I C H N C L L S | sNG0017S3.021 | 142 |
| L R C W G M L C Y A | sNG0017S3.017 | 143 |
| L R C I G Q I C W R | sNG0017S3.022 | 144 |
| L K C L Y N I C W V | sNG0017S3.024 | 145 |
| R P G M A C S G Q L C W L N S P | sNG0018S3.015 | 146 |
| P H A L Q C Y G S L C W P S H L | sNG0018S3.018 | 147 |
| R A G I T C H G H L C W P I T D | sNG0018S3.019 | 148 |
| R P A L K C I G T L C S L A N P | sNG0018S3.014 | 149 |
| P H G L W C H G S L C H Y P L A | sNG0018S3.012 | 150 |
| P H G L I C A G S I C F W P P P | sNG0018S3.007 | 151 |
| P R N L T C Y G Q I C F Q S Q H | sNG0018S3.011 | 152 |
| P H N L A C Q N S I C V R L P R | sNG0018S3.021 | 153 |
| P H G L T C T N Q I C F Y G N T | sNG0018S3.006 | 154 |
| L F C W G N V C H F | sNG0017S3.006 | 155 |
| L T C W G Q V C F R | sNG0017S3.009 | 156 |
| R C P S R V P W C V | sNG0017S3.011 | 157 |
| Q L V C G F S D S S R L C Y M R | sNG0018S3.009 | 158 |
| L L C Y I T S P G N R L C S P Y | sNG0018S3.022 | 159 |

TABLE 8

Sequences of VEGF-specific binding modules

| Sequence | Clone | SEQ ID NO: |
|---|---|---|
| W E C T Q H W C P S | sNG0025S3.021 | 160 |
| A P F F S C S F G F C R D L Q T | sNG0026S3.035 | 161 |
| T P Y F R C Q F G F C F D S F S | sNG0026S3.045 | 162 |
| N P F F Y C V A G K C V D A P L | sNG0026S3.029 | 163 |
| D M R F L C R H G K C H D L P L | sNG0026S3.034 | 164 |
| P P F F V C S L G K C R D A H L | sNG0026S3.043 | 165 |
| P P Q F Q C V R G K C F D L T F | sNG0026S3.053 | 166 |
| I S T F F C S N G S C V D V P A | sNG0026S3.006 | 167 |
| P P H F R C F N G S C V D L S R | sNG0026S3.051 | 168 |
| N V H F W C H N H K C H D L V S | sNG0026S3.040 | 169 |
| L F F K C D V G H G C Y D I K H | sNG0026S3.038 | 170 |
| L Y F Q C F P N R G C S T L Q P | sNG0026S3.002 | 171 |
| P S F F C S P L L G C R D S L S | sNG0026S3.052 | 172 |
| G T P R C N P F R Q F C A I P S | sNG0026S3.032 | 173 |
| L C L P L G R W C P | sNG0025S3.016 | 174 |
| T S P A C N P F R H F C T L P T | sNG0026S3.058 | 175 |
| Q P P I C N P F R Q L C G I P L | sNG0026S3.046 | 176 |
| V H T F C N P F R Q M C S L P M | sNG0026S3.027 | 177 |
| R M V N C N P F N S W C S L P S | sNG0026S3.001 | 178 |
| S K H M C N P F H S W C G V P L | sNG0026S3.047 | 179 |
| R W P V C N P F L G Y C G I P N | sNG0026S3.056 | 180 |
| S K P T C N V F N S W C S V P L | sNG0026S3.059 | 181 |
| R P P A C N L F L S W C S Y D S | sNG0026S3.004 | 182 |
| G R S V C N P Y K S W C P V R Q | sNG0026S3.011 | 183 |
| A S S C K D S P H F R C L F P L | sNG0026S3.055 | 184 |
| L A N C P N S P G F L C L H A V | sNG0026S3.024 | 185 |
| P F A C P H S S G F R C L Y N I | sNG0026S3.005 | 186 |
| S F T C S L F P S P H C T T L R | sNG0026S3.054 | 187 |
| L R L C T Y G G G K Y D C S S T | sNG0026S3.050 | 188 |
| G S Y C Q Y R P F S S F C N R S | sNG0026S3.048 | 189 |
| C S Y N Q V L G R A C | sNG0025S3.001 | 190 |
| P H C R Q H P L D R W M C S P S | sNG0026S3.057 | 191 |
| S L C S M F G D T P H W N C V P | sNG0026S3.007 | 192 |
| S S C S L F N N T R H W S C T D | sNG0026S3.008 | 193 |

TABLE 9

Sequences of CD28-specific binding modules

| Sequence | ID | SEQ ID NO: |
|---|---|---|
| T T A Y P D C F W C S L F G P P | sNG0028S3.085 | 194 |
| M L D T T I C P W C S L F G P V | sNG0028S3.081 | 195 |
| M L X T T I C P W C S L F G P V | sNG0028S3.018 | 196 |
| E L L L E R C S W C S L F G P P | sNG0028S3.086 | 197 |
| S L S Q Q S C D W C W L F G P P | sNG0028S3.060 | 198 |
| K R L L E C G A L C A L F G P P | sNG0028S3.008 | 199 |
| H T I L T C D S G F C T L F G P | sNG0028S3.012 | 200 |
| N L W H V C H T S L C H S R L A | sNG0028S3.092 | 201 |
| N S F Y L C H S S V C G Q L P S | sNG0028S3.082 | 202 |
| A G F S C E N Y F F C P P K N L | sNG0028S3.016 | 203 |
| S W C T V F G N H D P S C N S R | sNG0028S3.004 | 204 |
| C S S N G R W K A H C | sNG0028S3.076 | 205 |
| L P N M W R V V V P D V Y D R R | sNG0028S3.068 | 206 |

TABLE 10

Sequences of CD28-specific binding modules

| Sequence | ID | SEQ ID NO: |
|---|---|---|
| K H Y C F G P K S W T T C A R G | sNG0030S3.096 | 207 |
| P W C H L C P G S P S R C C Q P | sNG0030S3.091 | 208 |
| P E S K L I S E E D L N G D V S | sNG0030S3.042 | 209 |

TABLE 11

Sequences of Tie1-specific binding modules

| Sequence | ID | SEQ ID NO: |
|---|---|---|
| I W D R V C R M N T C H Q H S H | sNG0032S3.096 | 210 |
| P Y T I F C L H S S C R S S S S | sNG0032S3.087 | 211 |
| D W C L T G P N T L S F C P R R | sNG0032S3.031 | 212 |

TABLE 12

Sequences of DR4-specific binding modules

| Sequence | ID | SEQ ID NO: |
|---|---|---|
| L S T W R C L H D V C W P P L K | sNG0033S3.072 | 213 |

TABLE 13

Sequences of DR5-specific binding modules

| Sequence | ID | SEQ ID NO: |
|---|---|---|
| V Y L T Q C G A Q L C L K R T N | sNG0034S3.039 | 214 |
| P Y L T S C G D R V C L K R P P | sNG0034S3.001 | 215 |
| P Y L S R C G G R I C M H D R L | sNG0034S3.026 | 216 |
| L K L T P C S H G V C M H R L R | sNG0034S3.087 | 217 |
| Y Y L T N C P K G H C L R R V D | sNG0034S3.080 | 218 |
| L Y L H S C S R G I C L S P R V | sNG0034S3.082 | 219 |
| F S C Q S S F P G R R M C E L R | sNG0034S3.040 | 220 |
| H R C S A H G S S S F C P G S | sNG0034S3.029 | 221 |

TABLE 14

Sequences of TrkA-specific binding modules

| Sequence | ID | SEQ ID NO: |
|---|---|---|
| K T W D C R N S G H C V I T F K | sNG0035S3.074 | 222 |
| A T W D C R D H N F S C V R L S | sNG0035S3.089 | 223 |

Example aEpCAM Drug Conjugates

Anti-EpCAM peptides were isolated from random peptide libraries that were generated according to Scholle, et al. [Scholle, M. D., et al. (2005) *Comb Chem High Throughput Screen*, 8: 545-51] The naïve peptide libraries displayed cysteine-constrained peptides with cysteines spaced by 4 to 10 random residues. After three rounds of affinity selection with the above libraries, several EpCAM specific peptide ligands (EpCam1) were isolated (Table 15). The EpCam1 isolates have a conserved cysteine spacing of four amino acids (CXXXXC). EpCam1 peptide ligands were then softly randomized (except cysteine positions) with codons encoding 3-9 residues and moved into a phagemid vector. Phagemid libraries were subsequently affinity selected against EpCAM to isolate peptide ligands optimized for binding (Table 15, EpCam2). EpCam2 ligands contain the conserved CXXXXC cysteine spacing. In addition, the majority of anti-EpCam sequences do not contain a lysine residue, which allows for conjugation to free amine groups outside of the binding sequences. Furthermore, anti-EpCam peptide ligands can be genetically fused to URP sequences (of any length) and multimerized using iterative dimerization. The resulting anti-EpCAM MURPs can be used to specifically target EpCAM with increased affinity over monomer sequences. An example of a tetramer EpCAM-URP amino acid sequence is shown in FIG. 31. This sequence contains only two lysine residues that are located in the N-terminal Flag-tag. The side chains of these lysine residues are particularly suitable for drug conjugation.

TABLE 15

Anti-EpCam sequences

| Name | Sequence |
|---|---|
| EpCam 1 | LRCWGMLCYA (SEQ ID NO: 224) |
| | LRCIGQICWR (SEQ ID NO: 225) |
| | LKCLYNICWV (SEQ ID NO: 226) |
| | LFCWGNVCHF (SEQ ID NO: 227) |
| | LTCWGQVCFR (SEQ ID NO: 228) |
| | RPGMACSGQLCWLNSP (SEQ ID NO: 229) |
| | PHALQCYGSLCWPSHL (SEQ ID NO: 230) |
| | RAGITCHGHLCWPITD (SEQ ID NO: 231) |
| | RPALKCIGTLCSLANP (SEQ ID NO: 232) |
| | PHGLWCHGSLCHYPLA (SEQ ID NO: 233) |
| | PHGLICAGSICFWPPP (SEQ ID NO: 234) |
| | PRNLTCYGQICFQSQH (SEQ ID NO: 235) |
| | PHNLACQNSICVRLPR (SEQ ID NO: 236) |
| | PHGLTCTNQICFYGNT (SEQ ID NO: 237) |
| EpCam 2 | HSLTCYGQICWVSNI (SEQ ID NO: 238) |
| | PTLTCYNQVCWVNRT (SEQ ID NO: 239) |
| | PALRCLGQLCWVTPT (SEQ ID NO: 240) |
| | PGLRCLGTLCWVPNR (SEQ ID NO: 241) |
| | RNLTCWNTVCYAYPN (SEQ ID NO: 242) |
| | RGLKCLGQLCWVSSN (SEQ ID NO: 243) |
| | PTLKCSGQICWVPPP (SEQ ID NO: 244) |
| | RNLECLGNVCSLLNQ (SEQ ID NO: 245) |
| | PTLTCLNNLCWVPPQ (SEQ ID NO: 246) |
| | RGLKCSGHLCWVTPQ (SEQ ID NO: 247) |
| | HGLTCHNTVCWVHHP (SEQ ID NO: 248) |
| | HTLECLGNICWVINQ (SEQ ID NO: 249) |
| | HGLTCYNQICWAPRP (SEQ ID NO: 250) |
| | HGLACYNQLCWVNPH (SEQ ID NO: 251) |
| | RGLACQGNICWRLNP (SEQ ID NO: 252) |
| | RAITCLGTLCWPTSP (SEQ ID NO: 253) |
| | LTLECIGNICYVPHH (SEQ ID NO: 254) |

Example

Random Sequence Addition

Binding modules can be affinity matured, or lengthened, by the addition of URP-like linkers and random sequence to the N-terminus, C-terminus, or both N- and C-terminus of the binding sequence. FIG. 32 shows the addition of naïve cysteine-constrained sequences to an anti-EpCAM binding module. Libraries of random sequence additions can be generated using a single-stranded or double-stranded DNA cloning approaches. Once generated, libraries can be affinity selected against the initial target protein or a second protein. For example, an addition library that contains an anti-EpCAM binding module can be used to select sequences that contain 2 or more binding sites to the target protein.

Example

Construction of a 2SS Buildup Library

A series of oligonucleotides was designed to construct a library based on the VEGF-binding 1SS peptide FTCT-NHWCPS (SEQ ID NO: 121). The oligonucleotides incorporate variations in cysteine distance patterns of the flanking sequences while the VEGF-binding peptide sequence was kept fixed.

```
Forward oligos:
LMS70-1
CAGGCAGCGGGCCCGTCTGGCCCGTGYTTTACTTGTACGAATCATTGGTG

TCCT (SEQ ID NO: 255)

LMS70-2
CAGGCAGCGGGCCCGTCTGGCCCGTGYNNKTTTACTTGTACGAATCATTG

GTGTCCT (SEQ ID NO: 256)

LMS70-3
CAGGCAGCGGGCCCGTCTGGCCCGTGYNNKNNKTTTACTTGTACGAATCA

TTGGTGTCCT (SEQ ID NO: 257)

LMS70-4
CAGGCAGCGGGCCCGTCTGGCCCGTGYNHTNHTNHTTTTACTTGTACGAA

TCATTGGTGTCCT (SEQ ID NO: 258)

LMS70-5
CAGGCAGCGGGCCCGTCTGGCCCGTGYNHTNHTNHTNHTTTTACTTGTAC

GAATCATTGGTGTCCT (SEQ ID NO: 259)

LMS70-6
CAGGCAGCGGGCCCGTCTGGCCCGTGYKMTKMTKMTKMTKMTTTTACTTG

TACGAATCATTGGTGTCC (SEQ ID NO: 260)

Reverse oligos (reverse complemented):
LMS70-1R
ACCGGAACCACCAGACTGGCCRCACGAAGGACACCAATGATTCGTACAA
(SEQ ID NO: 261)

LMS70-2R
ACCGGAACCACCAGACTGGCCRCAMNNCGAAGGACACCAATGATTCGTAC

AA (SEQ ID NO: 262)

LMS70-3R
ACCGGAACCACCAGACTGGCCRCAMNNMNNCGAAGGACACCAATGATTCG

TACAA (SEQ ID NO: 263)

LMS70-4R
ACCGGAACCACCAGACTGGCCRCAADNADNADNCGAAGGACACCAATGAT

TCGTACAA (SEQ ID NO: 264)

LMS70-5R
ACCGGAACCACCAGACTGGCCRCAADNADNADNADNCGAAGGACACCAAT

GATTCGTACAA (SEQ ID NO: 265)

LMS70-6R
ACCGGAACCACCAGACTGGCCRCAAKMAKMAKMAKMAKMCGAAGGACACC

AATGATTCGTACAA (SEQ ID NO: 266)
```

Oligo dilutions

Mixture 1 (from 100 μM stocks): 100 μl 70-6, 33 μl 70-5, 11 μl 70-4, 3.66 μl 70-3, 1.2 μl 70-2, 0.4 μl 70-1. Mixture 2 (from 100 μM stocks): 100 μl 70-6R, 33 μl 70-5R, 11 μl 70-4R, 3.66 μl 70-3R, 1.2 μl 70-2R, 0.4 μl 70-1R PCR Assembly 10.0 μl Template Oligo (5 μM), 10.0 μl 10× Buffer, 2.0 dNTPs (10 mM), 1.0 μl cDNA Polymerase (Clonetech), 77 μl DS $H_2O$. PCR program: 95° C. 1 min, (95° C. 15 sec, 54° C. 30 sec, 68° C. 15 sec)×5, 68° C. 1 min PCR Amplification Primers, 10.0 μl Assembled mixture, 10.0 μl 10× buffer, 2.0 dNTPs (10 mM), 10.0 μl LIBPTF (5 μM), 10.0 μl LIBPTR (5 μM), 1.0 μl cDNA polymerase (Clonetech), 57 μl DS $H_2O$. PCR program: 95° C. 1 min, (95° C. 15 sec, 54° C. 30 sec, 68° C. 15 sec)×25, 68° C. 1 min. The product was purified by Amicon column Y10. The assembled product was digested with SfiI and BstXI and ligated into the phagemid vector pMP003. Ligation was performed over night at 16° C. in a MJ PCR machine. Ligation then was purified by EtOH precipitation. Transformation into fresh competent ER2738 cells by Electroporation.

The resulting library was panned against VEGF as described below. Several isolates were identified that showed improved binding to VEGF relative to the 1SS starting sequence. Binding and expression data are shown in FIG. 38. Sequences and results of Western analysis of buildup clones is shown in FIG. 39.

Example

Phage Panning of Buildup Libraries

First Round Panning:
1) First round, coat 4 wells per library to be screened. Coat the well of a Costar 96-well ELISA plate with 0.25 μg of $VEGF_{121}$ antigen in 25 μl of PBS. Cover the plate with a plate sealer. Coating can be performed overnight at 4° C. or for 1 h at 37° C.
2) After shaking out the coating solution, block the well by adding 150 μl of PBS/BSA 1%. Seal and incubate for 1 h at 37° C.
3) After shaking out the blocking solution, add 50 μl of freshly prepared phage (see library reamplification protocol) to the well. For the first round only, also add 5 μl of Tween 5%. Seal the plate and incubate for 2 h at 37° C.

In the meantime, inoculate 2 ml SB medium plus 2 μl of 5 mg/ml Tetracycline with 2 μl of an ER 2738 cell preparation and allow growth at 250 rpm and 37° C. for 2.5 h. Grow 1 culture for each library that is screened including negative selections. Take all precautions to avoid a contamination of the culture with phage.
4) Shake out the phage solution, add 150 μl of PBS/Tween 0.5% to the well and pipette 5 times vigorously up and down. Wait 5 min, shake out, and repeat this washing step. In the first round, wash in this fashion 5 times, in the second round 10 times, and in the third, fourth and fifth round 15 times.
5) After shaking out the final washing solution, add 50 μl of freshly prepared 10 mg/ml trypsin in PBS, seal, and incubate for 30 min at 37° C. Pipette 10 times vigorously up and down and transfer the eluate (4×50 μl in the first round, 2×50 ml in the second round, 1×50 μl in the subsequent rounds) to the prepared 2-ml *E. coli* culture and incubate at room temperature for 15 min.
6) Add 6 ml of pre-warmed SB medium, 1.6 μl of carbenicillin and 6 μl of 5 mg/ml Tetracycline. Transfer the culture into a 50-ml polypropylene tube.
7) Shake the 8-ml culture at 250 rpm and 37° C. for 1 h, add 2.4 μl 100 mg/ml carbenicillin, and shake for an additional hour at 250 rpm and 37° C.
8) Add 1 ml of VCSM13 helper phage and transfer to a 500-ml polypropylene centrifuge bottle. Add 91 ml of pre-warmed (37° C.) SB medium and 46 μl of 100 mg/ml carbenicillin and 92 μl of 5 mg/ml Tetracycline. Shake the 100-ml culture at 300 rpm and 37° C. for 1½ to 2 h.
9) Add 140 μl of 50 mg/ml kanamycin and continue shaking at 300 rpm and 37° C. overnight.
10) Spin at 4000 rpm for 15 min at 4° C. Transfer the supernatant to a clean 500-ml centrifuge bottle and add 25 ml of 20% PEG-8000/NaCl 2.5M. Store on ice for 30 min.
11) Spin at 9000 rpm for 15 min at 4° C. Discard the supernatant, drain inverted on a paper towel for at least 10 min, and wipe off remaining liquid from the upper part of the centrifuge bottle with a paper towel.
12) Resuspend the phage pellet in 2 ml of PBS/BSA 0.5%/Tween 0.5% buffer by pipetting up and down along the side of the centrifuge bottle and transfer to a 2-ml microcentrifuge tube. Resuspend further by pipetting up and down using a 1-ml pipette tip, spin at full speed in a microcentrifuge for 1 min at 4° C., and pass the supernatant through a 0.2-μm filter into a sterile 2-ml microcentrifuge tube.
13) Continue from step 3) for the next round or store the phage preparation at 4° C. Sodium azide may be added to 0.02% (w/v) for long-term storage. Only freshly prepared phage should be used for each round.

Second Round Panning

Second round, coat 2 wells per library to be screened. Coat the well of a Costar 96-well ELISA plate with 0.25 μg of $VEGF_{121}$ antigen in 25 μl of PBS. Cover the plate with a plate sealer. Coating can be performed overnight at 4° C. or for 1 h at 37° C.

Also block 2 uncoated wells for each library to be used as negative control for the enrichment ratio calculation.

Third Round Panning

Third round, coat 1 well per library to be screened. Coat the well of a Costar 96-well ELISA plate with 0.25 μg of $VEGF_{121}$ antigen in 25 μl of PBS. Cover the plate with a plate sealer. Coating can be performed overnight at 4° C. or for 1 h at 37° C.

Also block 1 uncoated well for each library to be used as negative control for the enrichment ratio calculation.

Example

Solution-based Panning

1. Biotinylate the target protein according to manufacturer.
2. Coat a total of 8 wells (per selection) with 1.0 μg of neutravidin (Pierce) in PBS and incubate overnight at 4° C.
3. Block the wells with SuperBlock (Pierce) for 1 h at room temp. Store plate with blocking buffer until needed (in Step 6).
4. Use 100 nM of biotinylated target protein and add 1012 phage/ml (in PB ST) for a total volume of 100-200 μl using SuperBlock plus Tween 20 0.05%.
5. Tumble phage-target mixture at room temp for at least 1 h.

6. Dilute 100 µl phage-target mix with 700 µl SuperBlock, mix, and add 100 µl to each of 8 neutravidin-coated wells (from Step 3).
7. Incubate for 5 min at room temp.
8. Wash 8× with PBST.
9. Elute phage with 100 µl of 100 mM HCl for 10 min.
10. Neutralize by adding 10 µl of 1M TRIS pH=8.0.
11. Infect cells for plating or amplify phage for a subsequent round of solution panning.

Example

Screening by Phage ELISA for VEGF Positive Clones

1) Add 0.5 ml SB containing 50 µg/ml carbenicillin to 96 deep well plate. Pick one colony and inoculate wells.
2) Shake the plate containing the bacterial cultures at 300 rpm o/n at 37° C.
3) Prepare 4 ng/µl target protein solution in PBS. Add 25 µl (100 ng) of protein to each well and incubate overnight at 4° C.
4) Shake out coated ELISA plates and wash 2× with PBS. Add 150 µl/well PBS+0.5% BSA (blocking buffer). Block for 1 h at RT.
5) Spin down microtube racks (3000 rpm; 20 min).
6) Prepare binding buffer (blocking buffer+0.5% Tween 20). Aliquot 135 µl binding buffer per well in low protein-binding 96 well plate.
7) Shake out wells on ELISA plates and wash 2 times with PBST (PBS+0.5% Tween 20).
8) Dilute 15 µl phage from o/n cultures 1:10 in PBST, mix by pipetting, and transfer 30 µl to each protein-coated well. Incubate 2 h at RT with gentle shaking.
9) Wash plates 6 times with PBST.
10) Add 50 µl antiM13-HRP 1:5000 in binding buffer to the wells. Incubate 30 min with gentle shaking at RT.
11) Wash the plates 4 times with PBST, followed by 2 times with H2O.
12) Prepare 6 ml of ABTS solution (5.88 ml of citrate buffer plus 120 µl ABTS and 2 µl H2O2). Aliquot 50 µl per well on each ELISA plate
13) Incubate at RT and read O.D. at 405 nm using an ELISA plate reader at appropriate time points depending on the signal (up to 1 h)

Example

Dimerization of Binding Modules

Phage displayed libraries of 10e9 to 10e11 cyclic peptides with 4, 5, 6, 7, 8, 9, 10, 11 and 12 randomized or partially randomized amino acids between the disulfide-bonded cystines, and in some cases additional randomized amino acids on the outside of the cystine pair, were created by standard methods Panning of these cyclic peptide libraries against a number of targets, including human VEGF, reliably yielded peptides that bound specifically to hVEGF and not to BSA, Ovalbumin or IgG.

Example

Construction and Panning of a Plexin-based Library

Two libraries were designed based on the Plexin scaffold. The Pfam protein database was used for phylogenetic alignment of naturally occurring plexin domains as shown in FIG. 35. The middle part of plexin scaffold (Cys24-Gly25-Trp26-Cys27) (SEQ ID NO: 267) is conserved in both library designs and served as a crossover region for N- and C-library generation. The randomization schemes of both plexin libraries are shown in FIG. 36. The two libraries were generated by overlapping two library-encoding oligos at the crossover region and using pull-thru PCR followed by restriction cloning (SfiI/BstXI) and cloning into phagemid vector pMP003. The resulting plexin libraries were designated LMP031 (N terminal library) and LMP032 (C terminal library) and each was represented by a complexity of approximately $5 \times 10^8$ independent transformants. For validation, approximately 24 Carb-resistant clones from each unselected library were analyzed by PCR. Clones that gave a correct size fragment (375 bp) were further analyzed by DNA sequencing. Correct full-length plexin sequences were obtained for 50% and 67% of clones derived from LMP031 and LMP032 libraries, respectively.

The two libraries were mixed together at 50/50 ratio and panned in parallel against VEGF, death receptor Dr4, ErbB2, and HGFR immobilized on 96-well ELISA plates. Four rounds of panning were carried out using 1000 ng of protein target in the first round, 500 ng in the second round, 250 ng in the third round, and 100 ng in the fourth round. After the final round of panning, 192 Carb-resistant clones from each selection were analyzed for binding to 100 ng immobilized protein target, human IgG, Ovalbumin, and BSA by phage ELISA using polyclonal anti-M13 Ab conjugated to horseradish peroxidase for detection. The highest percentage of positive clones was obtained for target DR4 (69%), followed by target ErbB2 (53%), HGFR (13%), and BoNT target (1%). Positive clones were further analyzed by PCR and by DNA sequencing. All clones revealed unique sequences and all but one (against DR4) were derived from LMP032 (C terminal library). Sequences of some of the identified target-selective isolates are shown in FIG. 37.

For further analysis, an assortment of selected target-specific binders are first subcloned into protein expression vector pVS001, then produced as soluble microproteins, and finally purified by heat lysis. The purified target-specific microproteins are analysed by protein ELISA to confirm the target recognition, by SDS-PAGE to confirm monomer formation, and by surface plasmon resonance to measure their affinities to target. The best clones are used in the next round of library generation to further improve their properties.

Example

Construction of a Snake Toxin-based Library

Phage displayed libraries of 10e8 to 10e10 of 3 finger toxin (3FT) scaffolds with partially randomized amino acids of fingertip 1 and descending part of finger 2 or fingertip 3 and ascending part of finger 2 were created by standard methods.

Two 3FT scaffolds were used as a template for 3FT library generation (fingers 1 and 2 configuration). The structure of a 3FT scaffold and a multiple sequence alignment of related sequences is shown in FIG. 33. A library was designed such that two surface loops of the toxin are randomized as illustrated in FIG. 34. The library of partially randomized 3FT scaffold was generated by overlapping four library-encoding oligos at the annealing regions and using pull-thru PCR followed by restriction cloning (SfiI/BstXI) into phagemid vector pMP003. The resulting 3FT library was designated LMP041.

Example

Grafting of Binding Peptides into Microprotein Scaffolds—Target-specific Peptides-assisted Randomization The aim here is to use the peptides that have been identified to be specific for target of interest in order to generate 3SSplus target-specific binders. This strategy is illustrated by using VEGF-specific peptide transfer into fingertip 1 of 3FT scaffold and by modifying the AA residues of finger 2, which are in close proximity from target specific sequence to generate high affinity VEGF binders. Phage displayed libraries of 10e8 to 10e10 of 3 finger toxin (3FT) scaffolds with VEGF specific sequence of fingertip 1 and partially randomized descending part of finger 2 was created by standard methods as described in example above except 2 random finger 1 forward primers were replaced by F1-VEGF-specific forward primer encoding the following sequence: P S G P S C H T T N H W P I S A V T C P P (SEQ ID NO: 268).

The focused (VEGF-specific) 3FT scaffold library with partially randomized finger 2 was generated by overlapping four library-encoding oligos at the annealing regions and using pull-thru PCR followed by restriction cloning (SfiI/BstXI) into phagemid vector pMP003. The resulting 3FT library was designated LMP042.

Example

Plasma Half-life of an MURP

The plasma half-life of MURPs can be measured after i.v. or i.p. injection of the MURP into catheterized rats essentially as described by [Pepinsky, R. B., et al. (2001) *J Pharmacol Exp Ther,* 297: 1059-66]. Blood samples can be withdrawn at various time points (5 min, 15 min, 30 min, 1 h, 3 h, 5 h, 1d, 2d, 3d) and the plasma concentration of the MURP can be measured using ELISA. Pharmacokinetic parameters can be calculated using WinNonlin version 2.0 (Scientific Consulting Inc., Apex, N.C.). To analyze the effect of the URP module one can compare on plasma half-life of a protein containing the URP module with the plasma half-life of the same protein lacking the URP module.

Example

Solubility Testing of an MURP

Solubility of MURPs can be determined by concentrating purified samples of MURPs in physiological buffers like phosphate buffered saline to various concentrations in the range of 0.01 mg/ml to 10 mg/ml Samples can be incubated for up to several weeks. Samples where the concentration exceeds the solubility of the MURP show precipitation as indicated by turbidity, which can be measured in an absorbance reader. On can remove precipitated material by centrifugation or filtration and measure the concentration of remaining protein in the supernatant using a protein assay like the Bradford assay of by measuring the absorbance at 280 nm. Solubility studies can be accelerated by freezing the samples at −20C and subsequent thawing. This process frequently leads to the precipitation of poorly soluble proteins.

Example

Serum Binding Activity of MURPs

One can coat MURPs of interest into microtiter plates and control proteins in other wells of the plate. Subsequently, one can add serum samples of interest to the wells for 1 hour. Subsequently, the wells can be washed with a plate washer. Bound serum proteins can be detected by adding antibodies against serum proteins that have been conjugated with enzymes like horse radish peroxidase or alkaline phosphatase for detection. Another way to detect serum binding to MURPs to add the MURP of interest to serum for about 1 hour to allow binding. Subsequently, one can immunoprecipitate the MURP using an antibody against an epitope in the MURP sequence. The precipitated samples can be analyzed by PAGE and optionally by Western to detect any proteins that co-precipitated with the MURP. One can identify the serum proteins that show co-precipitation by mass spectrometry.

What is claimed is:

1. An unstructured recombinant polymer (URPs), wherein the URP comprising at least about 200 contiguous amino acids, and wherein
   (a) the sum of glycine (G), aspartate (D), alanine (A), serine (S), threonine (T), glutamate (E) and proline (P) residues contained in the URP, constitutes more than about 80% of the total amino acids of the URP;
   (b) at least 50% of the amino acids of the URP are not present in secondary structure as determined by Chou-Fasman algorithm;
   (c) the URP has a Tepitope score equal to or less than −5;
   (d) the URP contains only 3, 4, 5, or 6 different types of amino acids; and
   (e) the URP contains greater than 5% glutamic acid and less than 2% lysine or arginine;
   wherein incorporation of the URP into a heterologous protein results in a fusion protein having at least a 2-fold increase in apparent molecular weight of the fusion protein as compared to the protein lacking said URP wherein the apparent molecular weight is approximated by size exclusion chromatography, and wherein the fusion protein exhibits an increased half-life as compared to the protein lacking said URP.

2. The URP of claim 1, wherein upon incorporation of the URP into an N-terminus, a C-terminus, into a loop of the heterologous protein, or between domains of the heterologous protein to create a monomeric fusion protein, said heterologous protein exhibits a serum secretion half-life that is at least two-fold longer as compared to the corresponding protein that is deficient in said URP.

3. The URP of claim 1, wherein the URP comprises a non-natural amino acid sequence.

4. The URP of claim 1, wherein the URP comprises at least 400 contiguous amino acids.

5. The URP of claim 1, wherein the URP comprises at least five types of amino acids selected from the group consisting of glycine (G), aspartate (D), alanine (A), serine (S), threonine (T), glutamate (E) and proline (P).

6. The URP of claim 1, wherein the URP comprises at least six types of amino acids selected from the group consisting of glycine (G), aspartate (D), alanine (A), serine (S), threonine (T), glutamate (E) and proline (P).

7. The URP of claim 1, wherein one type of the amino acids selected from the group consisting of glycine (G), aspartate (D), alanine (A), serine (S), threonine (T), glutamate (E) and proline (P) constitutes at least 20% of the total amino acids of the URP.

8. The URP of claim 7, wherein the one type of amino acid is glutamate (E).

9. The URP of claim 1, wherein any one type of amino acid is no more than 30% of the total amino acids of the URP.

10. The URP of claim 1, wherein the heterologous protein is a pharmaceutically active protein.

11. The URP of claim 1, wherein the heterologous protein comprises one or more modules selected from the group consisting of binding modules, effector modules, multimerization modules, C-terminal modules, and N-terminal modules.

12. The URP of claim 10, wherein the pharmaceutically active protein is selected from the group consisting of cytokines, growth factors, enzymes, receptors, microproteins, hormones, erythopoetin, adenosine deiminase, asparaginase, arginase, interferon, growth hormone, growth hormone releasing hormone, G-CSF, GM-CSM, insulin, hirudin, TNF-receptor, uricase, rasburicase, axokine, RNAse, DNAse, phosphatase, pseudomonas exotoxin, ricin, gelonin, desmoteplase, laronidase, thrombin, blood clotting enzyme, VEGF, protropin, somatropin, alteplase, interleukin, factor VII, factor VIII, factor X, factor IX, dornase, glucocerebrosidase, follitropin, glucagon, thyrotropin, nesiritide, alteplase, teriparatide, agalsidase, laronidase, methioninase.

13. The URP of claim 1, wherein any amino acids of the URP that are not glycine, aspartate, alanine, serine, threonine, glutamate, or proline are not hydrophobic amino acids selected from the group consisting of tryptophan, tyrosine, phenylalanine, methionine, leucine, isoleucine, and valine.

* * * * *

UNITED STATES PATENT AND TRADEMARK OFFICE
CERTIFICATE OF CORRECTION

PATENT NO. : 9,938,331 B2  
APPLICATION NO. : 14/970723  
DATED : April 10, 2018  
INVENTOR(S) : Volker Schellenberger et al.

Page 1 of 1

It is certified that error appears in the above-identified patent and that said Letters Patent is hereby corrected as shown below:

In the Claims

Claim 1 (Column 315, Line 11) reads "(URPs)", which should read "(URP)".

Signed and Sealed this  
Twenty-fourth Day of July, 2018

Andrei Iancu  
*Director of the United States Patent and Trademark Office*